United States Patent
Zhang et al.

(10) Patent No.: US 11,780,900 B2
(45) Date of Patent: *Oct. 10, 2023

(54) GLUCAGON LIKE PEPTIDE 1 (GLP-1) FUSION PEPTIDE COUPLED CYCLIC PEPTIDE TYROSINE TYROSINE CONJUGATES AND USES THEREOF

(71) Applicant: Janssen Sciences Ireland Unlimited Company, Cork (IE)

(72) Inventors: Yue-Mei Zhang, Wellesley, MA (US); Raul Camacho, Philadelphia, PA (US); Martin A. Case, San Diego, CA (US); Ellen Chi, San Diego, CA (US); Suzanne Edavettal, San Diego, CA (US); Wilson Edwards, Cardiff-by-the-Sea, CA (US); Lisa Norquay, Spring House, PA (US); Mark J. Wall, Lansdale, PA (US); Rui Zhang, Belle Mead, NJ (US); Songmao Zheng, Spring House, PA (US)

(73) Assignee: Janssen Sciences Ireland Unlimited Company, Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/733,776

(22) PCT Filed: Apr. 24, 2019

(86) PCT No.: PCT/IB2019/053384
§ 371 (c)(1),
(2) Date: Oct. 22, 2020

(87) PCT Pub. No.: WO2019/207505
PCT Pub. Date: Oct. 31, 2019

(65) Prior Publication Data
US 2021/0253661 A1   Aug. 19, 2021

Related U.S. Application Data

(60) Provisional application No. 62/662,313, filed on Apr. 25, 2018.

(51) Int. Cl.
| | | |
|---|---|---|
| *C07K 14/605* | (2006.01) |
| *A61K 47/66* | (2017.01) |
| *A61P 3/06* | (2006.01) |
| *A61P 5/50* | (2006.01) |
| *C07K 7/64* | (2006.01) |
| *A61P 3/10* | (2006.01) |
| *A61K 47/64* | (2017.01) |
| *A61P 3/04* | (2006.01) |
| *A61K 9/00* | (2006.01) |
| *C07K 14/575* | (2006.01) |
| *A61K 38/00* | (2006.01) |

(52) U.S. Cl.
CPC .......... *C07K 14/605* (2013.01); *A61K 9/0019* (2013.01); *A61K 47/64* (2017.08); *A61K 47/66* (2017.08); *A61P 3/04* (2018.01); *A61P 3/06* (2018.01); *A61P 3/10* (2018.01); *A61P 5/50* (2018.01); *C07K 7/64* (2013.01); *C07K 14/57545* (2013.01); *A61K 38/00* (2013.01); *C07K 2319/30* (2013.01)

(58) Field of Classification Search
CPC ..... C07K 14/605; C07K 14/5755; A61P 3/04; A61P 3/06; A61P 3/10
See application file for complete search history.

(56) References Cited

U.S. PATENT DOCUMENTS

| | | | |
|---|---|---|---|
| 7,166,575 | B2 | 1/2007 | Quay |
| 8,759,295 | B2 | 6/2014 | Ghosh |
| 2006/0094653 | A1 | 5/2006 | Levy |
| 2007/0244041 | A1 | 10/2007 | Larsen |
| 2010/0292172 | A1 | 11/2010 | Ghosh |
| 2013/0040877 | A1 | 2/2013 | Kofoed |
| 2016/0108098 | A1 | 4/2016 | Dock |
| 2018/0117170 | A1 | 5/2018 | Macielag |
| 2018/0127476 | A1 | 5/2018 | Macielag |

FOREIGN PATENT DOCUMENTS

| | | |
|---|---|---|
| JP | 2007-525495 A | 9/2007 |
| JP | 2007-531713 A | 11/2007 |
| JP | 2009-504681 A | 2/2009 |
| JP | 2012-502888 A | 2/2012 |
| JP | 2013-506628 A | 2/2013 |
| WO | 2005/077072 A2 | 8/2005 |
| WO | 2005077094 A2 | 8/2005 |
| WO | 2005/089789 A2 | 9/2005 |
| WO | 2005080424 A2 | 9/2005 |
| WO | 2006059106 A2 | 6/2006 |
| WO | 2007/022123 A2 | 2/2007 |

(Continued)

OTHER PUBLICATIONS

Perfetti et al., Eur. J. Endocr. 143, 717-725,(2000).*

(Continued)

*Primary Examiner* — Gyan Chandra
(74) *Attorney, Agent, or Firm* — Seed IP Law Group LLP

(57) ABSTRACT

The present invention comprises conjugates comprising a glucagon-like peptide 1 (GLP-1) fusion peptide coupled to a cyclic PYY peptide. The invention also relates to pharmaceutical compositions and methods for use thereof. The novel conjugates are useful for preventing, treating or ameliorating diseases and disorders disclosed herein.

27 Claims, 12 Drawing Sheets
Specification includes a Sequence Listing.

(56) References Cited

FOREIGN PATENT DOCUMENTS

| WO | 2007018619 A2 | 2/2007 |
|---|---|---|
| WO | 2008021560 A2 | 2/2008 |
| WO | 2010/031707 A1 | 3/2010 |
| WO | 2011006497 A1 | 1/2011 |
| WO | 2011/039096 A1 | 4/2011 |
| WO | 2017075505 A2 | 5/2017 |
| WO | 2018081370 A1 | 5/2018 |

OTHER PUBLICATIONS

Gutniak et al., New England J. Med. 30 326:1316-1322, (1992).*
International Search Report and Written Opinion dated Jul. 15, 2019 in International patent application No. PCT IB02/053384.
Carlson, et al., "Secretion of Fc-amidated peptide fusion proteins by Chinese hamster ovary cells", BMC Biotechnol., vol. 15, No. 61, p. 1-13, (Jun. 2015).
Batterham et al., "Gut hormone PYY3-36 physiologically inhibits food intake.", Nature, Aug. 8, 2002, pp. 650-654, vol. 418.
Batterham et al., "Inhibition of Food Intake in Obese Subjects by Peptide YY 3-36", The New England Journal of Medicine, vol. 349, No. 10, pp. 941-948, Sep. 2003.
Challis et al., "Acute effects on PYY3-36 on food intake and hypothalamic neuropeptide expression in the mouse," Biochem Biophys Res Commun 311, vol. No. 4, pp. 915-919, Oct. 2003.
Pittner et al., "Effects of PYY[3-36] in rodent models of diabetes and obesity.", International Journal of Obesity, 2004, pp. 963-971, vol. 28.
Vrang et al., "PYY (3-36) reduces food intake and body weight and improves insulin sensitivity in rodent models of diet-induced obesity", Am J Physiol Regul Integr Comp Physiol, 291, pp. R367-R375, 2006.
le Roux et al., "Gut Hormone Profiles Following Bariatric Surgery Favor an Anorectic State, Facilitate Weight Loss, and Improve Metabolic Parameters.", Annals of Surgery, Jan. 2006, pp. 108-114, vol. 243(1).
Kreymann et al., "Glucagon-like Peptide-1 7-36: A Physiological incretin in Man", The Lancet, vol. 2, Issue 8571, pp. 1300-1304, Dec. 1987.
Gutniak et al., "Antidiabetogenic Effect of Glucagon-like Peptide-1 (7-36) amide in Normal Subjects and Patients with Diabetes Mellitus", New England Journal of Medicine, 326, pp. 1316-1322, 1992.
Wettergren et al., "Truncated GLP-1 (proglucagon 78-107-amide) inhibits gastric and pancreatic functions in man", Digestive Diseases and Sciences, vol. 38, Issue 4, pp. 665-673, 1993.
Flint et al., "Glucagon-like Peptide 1 Promotes Satiety and Suppresses Energy Intake in Humans", J. Clin invest, vol. 101, No. 3, pp. 515-520, 1998.
Marso et al., "Liraglutide and Cardiovascular Outcomes in Type 2 Diabetes", New England Journal of Medicine, 375, pp. 311-322, 2016.
Mann et al., "Liraglutide and Renal Outcomes in Type 2 Diabetes", New England Journal of Medicine, 377, pp. 839-848, 2017.
Zhu et al., "The Role of Dipeptidyl Peptidase IV in the Cleavage of Glucagon Family Peptides", Journal of Biological Chemistry, vol. 278, No. 25, pp. 22418-22423, 2003.
Hupe-Sodmann etal., "Characterisation of the processing by human neutral endopeptidase 24.11 of GLP-1(7-36) amide and comparison of the substrate specificity of the enzyme for other glucagon-like peptides", Regulatory Peptides, vol. 58, Issue 3, pp. 149-156, 1995.
Ruiz-Grande et al., "Renal catabolism of human glucagon-like peptides 1 and 2", Canadian Journal of Physiology and Pharmacology, 68(12), pp. 1568-1573, 1990.
Smith et al., "Comparison of Biosequences," Advances in Applied Mathematics, vol. 2, pp. 482-489 (1981).
Needleman et al., "A General Method Applicable to the Search Similarities in the Amino Acid Sequence of Two Proteins," Journal of Molecular Biology, vol. 48, pp. 443-453 (1970).
Pearson et al., "Improved tools for biological sequence comparison," Proceedings of the National Academy of Sciences of the United States of America, vol. 85, pp. 2444-2448 (1988).
Altschul et al. "Basic Local Alignment Search Tool" J. Mol. Biol., vol. 215, pp. 403-410, 1990.
Altschul et al., "Gapped BLAST and PSI-BLAST: A New Generation of Protein Database Search Programs," Nucleic Acids Research, vol. 25, No. 17, pp. 3389-3402 (1997).
Torang et al., "In vivo and in vitro degradation of peptide YY3-36 to inactive peptide YY3-34 in humans," Am. J. Physiol. Regul. Integr. Comp. Physiol., vol. 310, pp. R866-74, 2016.
Merrifield, "Solid Phase Peptide Synthesis. I. The Synthesis of Tetrapeptide", J. Am. Chern Soc, 85,14, pp. 2149-2154, 1963.
Yu et al., "Enhanced Coupling Efficiency in Solid-Phase Peptide Synthesis by Microwave Irradiation.", Journal of Organic Chemistry, Aug. 28, 1992, pp. 4781-4784, vol. 57(18).
Palasek et al., "Limiting racemization and aspartimide formation in microwave-enhanced Fmoc solid phase peptide synthesis," Journal of Peptide Science, vol. 13, No. 3, pp. 143-8, 2007.
Spahr et al., "O-Glycosylation of glycine-serine linkers in recombinant Fc-fusion proteins", mAbs, vol. 6, Issue 4, pp. 904-914, 2014.
Geiser et al., "Clinical Pharmacokinetics of Dulaglutide in Patients with Type 2 Diabetes: Analyses of Data from Clinical Trials", vol. 55, Issue 5, p. 625-634, 2016.
Lecklin et al., "Agonists for neuropeptide Y receptors Y1 and Y5 stimulate different phases of feeding in guinea pigs," Br. J. Pharmacol. 139(8):1433-40 (2003).
Int'l Search Report and Written Opinion dated Feb. 21, 2018 in Int'l Application No. PCT/US2017/058451 (13 pages).
Int'l Search Report and Written Opinion dated Mar. 13, 2018 in Int'l Application No. PCT/US2017/058455 (11 pages).
Andrushchenko et al., "Optimization of the hydrochloric acid concentration used for trifluoroacetate removal from Synthetic peptides" Journal of Peptide Science, vol. 13, pp. 37-43, 2007.
Germain et al., "Analogs of pancreatic polypeptide and peptide YY with a locked PP-fold structure are biologically active," Peptides vol. 39, pp. 6-10, 2013.
Kaiser et al., "Color Test for Detection of Free Terminal Amino Groups in the Solid-Phase Synthesis of Peptides,", Anal. Biochem., 1970, pp. 595-598, vol. 34.
Spahr et al., "Recombinant human lecithin-cholesterol acyltranferase Fc fusion; Analysis of N- and O-linked glycans and identification and elimination of xylose-based O-linked tetrasaccharide core in the linker region", Protein Science, vol. 22, pp. 1739-1753, 2013.
Wen et al., "Discovery and Investigation of O-Xylosylation in Engineered Proteins Containing a (GGGGS)n Linker", Analytical Chemistry, 85, pp. 4805-4812, 2013.
Int'l Search Report and Written Opinion dated Feb. 12, 2018 in Int'l Application No. PCT/US2017/058462. 8 pages.

* cited by examiner ized and released by intestinal endocrine cells. Cleavage of NPY and PYY by the endothelial serine-protease, di-peptidyl peptidase IV (DPP-IV), generates $NPY_{3-36}$ and $PYY_{3-36}$ which are selective ligands for Y2 and Y5 sub-types of the NPY receptor family. PP is mainly found in pancreatic islet cells distinct from those storing insulin, glucagon or somatostatin.

GLUCAGON LIKE PEPTIDE 1 (GLP-1) FUSION PEPTIDE COUPLED CYCLIC PEPTIDE TYROSINE TYROSINE CONJUGATES AND USES THEREOF

CROSS REFERENCE TO RELATED APPLICATIONS

This application is a Section 371 of International Application No. PCT/IB2019/053384, filed Apr. 24, 2019, which published in the English language on Oct. 31, 2019 under International Publication No. WO/2019/207505 A1, which claims priority to U.S. Provisional Application No. 62/662,313, filed Apr. 25, 2018. Each disclosure is incorporated herein by reference in its entirety.

FIELD OF THE INVENTION

The present invention is directed generally to novel glucagon like peptide-1 (GLP-1) fusion peptide coupled cyclic peptide tyrosine tyrosine (PYY) conjugates, which are modulators of the neuropeptide Y2 receptor and the GLP-1 receptor. The invention also relates to pharmaceutical compositions and methods for use thereof. The novel GLP-1 fusion peptide coupled cyclic PYY conjugates are useful for preventing, treating or ameliorating diseases and disorders, such as obesity, type 2 diabetes, the metabolic syndrome, insulin resistance, and dyslipidemia, among others.

REFERENCE TO SEQUENCE LISTING SUBMITTED ELECTRONICALLY

This application contains a sequence listing, which is submitted electronically via EFS-Web as an ASCII formatted sequence listing with a file name "004852_68US3_Sequence_Listing" and a creation date of Oct. 9, 2020 and having a size of 409 kb. The sequence listing submitted via EFS-Web is part of the specification and is herein incorporated by reference in its entirety. In the event of any inconsistency with regard to the structures for SEQ ID NOs:225-262 between the information described herein and the Sequence Listing submitted electronically via EFS-Web with a file name "004852_68US3_Sequence_Listing," the information herein will prevail.

BACKGROUND OF THE INVENTION

Neuropeptide Y (NPY) receptors are activated by a closely related group of peptide agonists termed "NPY family" which have differing affinities for each receptor sub-type. NPY, peptide tyrosine-tyrosine (PYY) and pancreatic polypeptide (PP), all 36 amino acids in length, are agonists for the NPY family of receptors. NPY is a neurotransmitter, synthesized, co-stored and released with norepinephrine and epinephrine. NPY is one of the most abundant and widely distributed peptides in the central nervous system (CNS) of humans and rodents and is expressed in areas of the brain related to feeding and stress. In the peripheral nervous system, NPY-containing neurons are predominantly sympathetic. PYY is predominantly synthe- Five distinct NPY receptors have been identified to date, four of which are understood as relevant to human physiology. The receptors Y1, Y2 and Y5 preferentially bind NPY and PYY, whereas the Y4 receptor preferentially binds PP. The Y2 and Y5 receptors are also potently activated by $NPY_{3-36}$ and $PYY_{3-36}$. In general, the NPY family of ligands possesses variable selectivity for each of the NPY receptor isoforms, with $PYY_{3-36}$ previously reported to have modest-to-robust selectivity for the Y2 isoform. Each of these receptors is coupled to inhibition of adenylate cyclase via pertussis-toxin sensitive Gαi.

PYY is secreted from endocrine L-cells in response to food, and in particular following fat ingestion. $PYY_{1-36}$ predominates in the fasting state, with $PYY_{3-36}$ being the major form found post-prandially in humans, with plasma concentrations negatively correlated with the number of calories consumed. $PYY_{3-36}$ has been demonstrated to reduce food intake in humans, monkeys, rats, rabbits, and mice (Batterham et al., Nature 418(6898):650-4 (2002); Batterham et al., N Engl J Med 349(10):941-8 (2003); Challis et al., Biochem Biophys Res Commun 311(4):915-9 (2003)). The anorexigenic effects of $PYY_{3-36}$ are believed to be Y2-mediated, based on preferential binding at this receptor and loss of feeding efficacy in Y2-deficient mice (Batterham et al., Nature 418(6898): 650-4 (2002)). Intra-arcuate injection of $PYY_{3-36}$ reduces food intake in rats and mice (Batterham et al., Nature 418(6898):650-4 (2002)), suggesting that engagement of hypothalamic Y2 receptors may mediate these effects. Acute effects on feeding have also been shown to translate to dose-dependent effects on body-weight in ob/ob mice, DIO mice and Zucker fa/fa mice (Pittner et al., Int J Obes Relat Metab Disord 28(8):963-71 (2004)). In addition, $PYY_{3-36}$ has also been shown to improve insulin-mediated glucose disposal and insulin sensitivity in DIO rodents (Vrang et al., Am J Physiol Regul Integr Comp Physiol 291(2): R367-75(2006)). Bariatric surgery results in increased circulating PYY-immunoreactivity (le Roux et al., Ann Surg 243(1):108-14(2006)), which appears to play a role in postoperative weight loss.

Given its role in controlling appetite and food intake as well as its anti-secretory and pro-absorptive effects in the gastrointestinal tract in mammals, $PYY_{3-36}$ may be effective in treating obesity and associated conditions as well as in a number of gastrointestinal disorders. However, the therapeutic utility of $PYY_{3-36}$ itself as a treatment agent is limited by its rapid metabolism and resultant short circulating half-life (Torang et al., Am. J. Physiol. Regul. Integr. Comp. Physiol. 310:R866-R874 (2016)).

The incretin hormone, GLP-1 and activation of its receptor (GLP1R), have an array of beneficial effects in glucose metabolism and energy balance in humans including stimulation of glucose-dependent insulin secretion (Kreymann et al., Lancet 2:1300-1304 (1987)), as well as inhibiting glucagon secretion (Gutniak et al., N Engl J Med 326:1316-1322 (1992)), gastric emptying (Wettergren et al. Digestive Diseases Sciences 38:665-673 (1993)), and food intake (Flint et al., JCI 101:515-520 (1998)). GLP1R agonists have also been shown to significantly decrease the risk of cardiovascular and microvascular outcomes (Marso et al., N Engl J Med 375(4):311-322 (2016)) and kidney disease (Mann et al., N Engl J Med 377(9):839-848 (2017) in type 2 diabetic patients. GLP-1 is characterized by a short half-life, which makes the use of GLP-1 impractical as a potential therapeutic. Circulating half-life is limited both by proteolytic liabilities from dipeptidyl peptidase IV (Zhu, L. et al., JBC 278:22418-22423 (2003)) and neutral endopeptidase (Hupe-Sodmann et al., Regul Pept 58(3): 149-156 (1995)), as well as by renal filtration (Ruiz-Grande et al., Can J Physiol Pharmacol 68(12):1568-1573 (1990)).

Thus, it is desirable to obtain a PYY analogue or derivative thereof and/or a GLP-1 analogue or derivative thereof with an improved metabolic stability and pharmacokinetic profile relative to $PYY_{3-36}$ and/or GLP-1, respectively. Such derivatives, with a protracted half-life in vivo, would provide Y2 and/or GLP-1 receptor modulation with greater duration of action, making them suitable as therapeutic agents for subjects in need of such modulation.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

In one general aspect, the invention relates to novel glucagon-like peptide-1 (GLP-1) fusion-coupled cyclic peptide tyrosine tyrosine (PYY) conjugates, which are modulators of the neuropeptide Y2 receptor and GLP-1 receptor.

Provided herein are conjugates comprising a glucagon-like peptide 1 (GLP-1) fusion peptide coupled to a cyclic PYY peptide, wherein the GLP-1 fusion peptide comprises a GLP-1 or GLP-1 variant peptide, a first linker peptide, a hinge-Fc region peptide, and a second linker peptide, wherein the first linker is optionally absent.

In certain embodiments, the cyclic PYY peptide is represented by Formula I or a derivative or pharmaceutically acceptable salt thereof:

Formula I $$Z_4PEZ_7PZ_9EZ_{11}ASPEELNRYYZ_{22}Z_{23}LRZ_{26}YLNZ_{30}$$

[structure of Formula I showing cyclic peptide with (CH$_2$)$_m$—BRIDGE—(CH$_2$)$_n$ linker and $[V_{31}]_qTRZ_{34}Z_{35}Y$—NH$_2$]

wherein
p is 0 or 1;
m is 0, 1, 2, 3, 4, or 5;
n is 1, 2, 3, or 4;
q is 0 or 1; provided that q is 1 only when $Z_{30}$ is absent;
BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;
$Z_4$ is K, A, E, S, or R;
$Z_7$ is A or K;
$Z_9$ is G or K;
$Z_{11}$ is D or K;
$Z_{22}$ is A or K;
$Z_{23}$ is S or K;
$Z_{26}$ is A or H;
$Z_{30}$ is L, W, or absent;
provided that $Z_{30}$ is absent only when q is 1;

$Z_{34}$ is

[two chemical structures of glutamine residues, connected by "or"]

$Z_{35}$ is

[two chemical structures of arginine-like residues with guanidino groups]

-continued

[two more chemical structures of modified arginine-like residues connected by "or"]

wherein the derivative is the compound of Formula I that is modified by one or more processes selected from the group consisting of amidation, acylation, and pegylation.

In certain embodiments, the cyclic PYY peptide is represented by Formula I or the derivative or pharmaceutically acceptable salt thereof, wherein:

p is 0 or 1;

m is 0, 1, 2, 3, 4, or 5;

n is 1, 2, 3, or 4;

q is 0 or 1; provided that q is 1 only when $Z_{30}$ is absent;

BRIDGE is -Ph-CH$_2$—S—, -triazolyl-, —NHC(O)CH$_2$S—, —SCH$_2$C(O)NH$_2$—, —(OCH$_2$CH$_2$)$_2$NHC(O)CH$_2$S, —NHC(O)—, or —CH$_2$S—;

$Z_4$ is K, A, E, S, or R;

$Z_7$ is A or K, wherein the amino side chain of said K is optionally substituted with

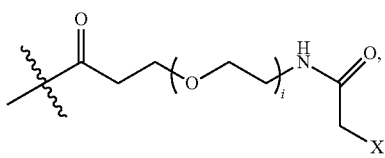

wherein i is an integer of 0 to 24, and X=Br, I or Cl, —C(O)CH$_2$Br, —C(O)CH$_2$I, or —C(O)CH$_2$Cl;

$Z_9$ is G or K, wherein the amino side chain of said K is optionally substituted with

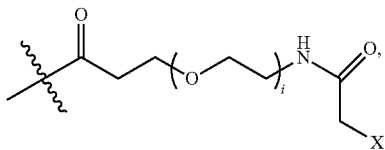

wherein i is an integer of 0 to 24, and X=Br, I or Cl, —C(O)CH$_2$Br, —C(O)CH$_2$I, or —C(O)CH$_2$Cl;

$Z_{11}$ is D or K, wherein the amino side chain of said K is optionally substituted with

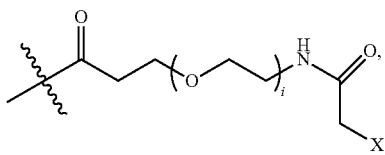

wherein i is an integer of 0 to 24, and X=Br, I or Cl, —C(O)CH$_2$Br, —C(O)CH$_2$I, or —C(O)CH$_2$Cl;

$Z_{22}$ is A or K, wherein the amino side chain of said K is optionally substituted with

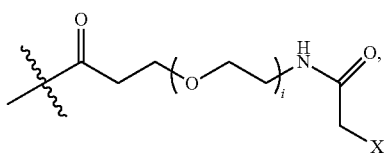

wherein i is an integer of 0 to 24, and X=Br, I or Cl, —C(O)CH$_2$Br, —C(O)CH$_2$I, or —C(O)CH$_2$Cl;

$Z_{23}$ is S or K, wherein the amino side chain of said K is optionally substituted with

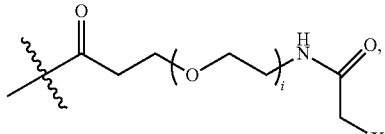

wherein i is an integer of 0 to 24, and X=Br, I or Cl, —C(O)CH$_2$Br, —C(O)CH$_2$I, or —C(O)CH$_2$Cl;

$Z_{26}$ is A or H;

$Z_{30}$ is L;

$Z_{34}$ is

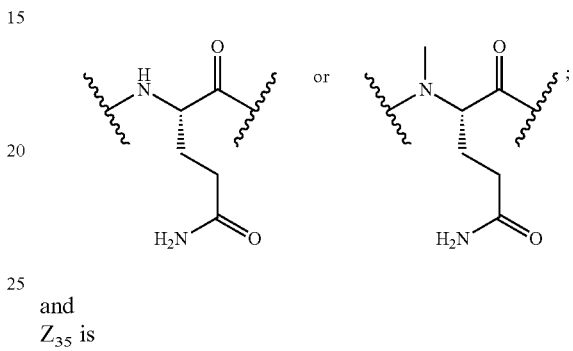

and $Z_{35}$ is

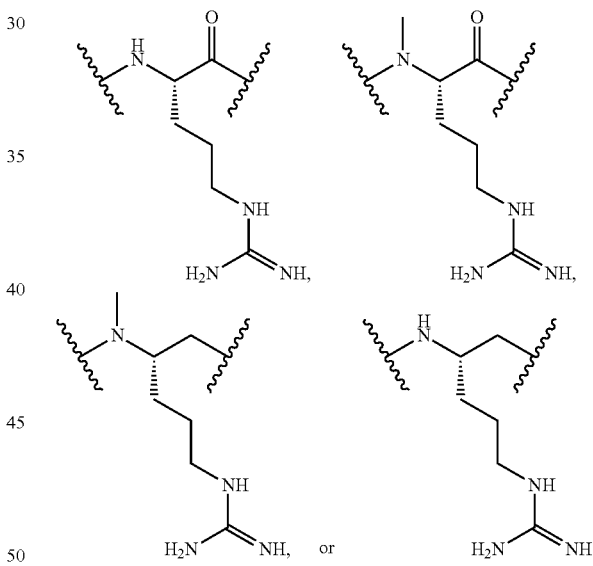

In certain embodiments, the cyclic PYY peptide is represented by Formula I or the derivative or pharmaceutically acceptable salt thereof, wherein:

p is 0 or 1;

m is 0, 1, 2, 3, 4, or 5;

n is 1, 2, or 4;

q is 0 or 1; provided that q may be 1 only when $Z_{30}$ is absent;

BRIDGE is -Ph-CH$_2$—S—, -triazolyl-, —NHC(O)CH$_2$S—, —(OCH$_2$CH$_2$)$_2$NHC(O)CH$_2$S, —NHC(O)—, or —CH$_2$S—;

$Z_4$ is K, A, E, S, or R;

$Z_7$ is A or K, wherein the amino side chain of said K is substituted with —C(O)CH$_2$Br, $Z_9$ is G or K, wherein the amino side chain of said K is substituted with —C(O)CH$_2$Br, $Z_{11}$ is D or K, wherein the amino side chain of said K is substituted with —C(O)CH$_2$Br,
$Z_{22}$ is A or K, wherein the amino side chain of said K is substituted with —C(O)CH$_2$Br,
$Z_{23}$ is S or K, wherein the amino side chain of said K is substituted with —C(O)CH$_2$Br,
$Z_{26}$ is A or H,
$Z_{30}$ is L,
$Z_{34}$ is

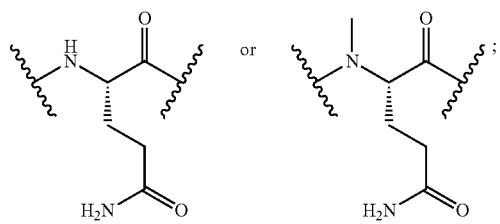 [SMILES: *N[C@@H](CCC(N)=O)C(*)=O ; *C(=O)[C@H](CCC(N)=O)N(*)C]

$Z_{35}$ is

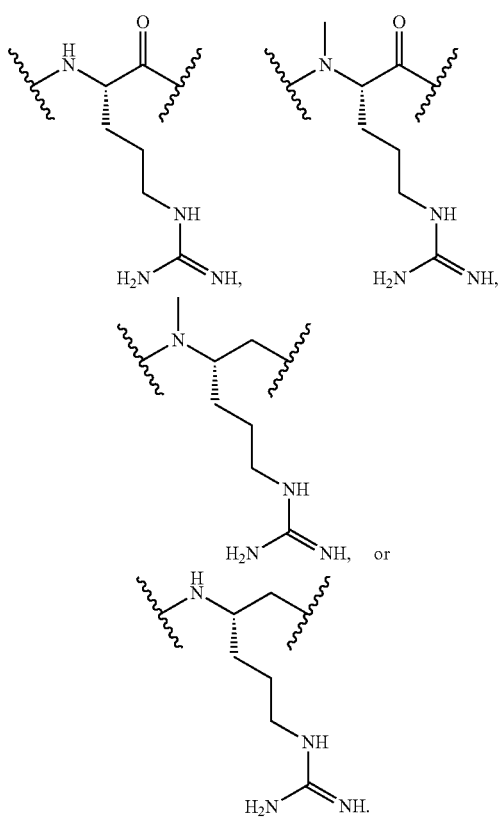

In certain embodiments, the cyclic PYY peptide is selected from the group consisting of SEQ ID NOs:1-54, or a pharmaceutically acceptable salt thereof. In certain embodiments, the cyclic PYY peptide is selected from SEQ ID NO:24, 25, 27, 28, 29, 30, 33, or 34.

In certain embodiments, the GLP-1 fusion peptide is covalently linked to the cyclic PYY peptide at a lysine residue of the cyclic PYY peptide. In certain embodiments, only one of $Z_7$, $Z_9$, $Z_{11}$, $Z_{22}$ and $Z_{23}$ in Formula I is lysine, and the lysine is covalently linked to a cysteine residue in the second linker peptide of the GLP-1 fusion peptide.

In certain embodiments, the GLP-1 peptide of the GLP-1 fusion peptide comprises an amino acid sequence selected from the group consisting of SEQ ID NOs:56-59. In certain embodiments, the first linker peptide of the GLP-1 fusion peptide comprises an amino acid sequence selected from the group consisting of SEQ ID NOs:60-83. In certain embodiments, the hinge-Fc region peptide of the GLP-1 fusion peptide comprises an amino acid sequence selected from the group consisting of SEQ ID NOs:84-90. In certain embodiments, the second linker peptide of the GLP-1 fusion peptide comprises an amino acid sequence selected from the group consisting of SEQ ID NOs:91-112. In certain embodiments, the second linker peptide comprises an amino acid sequence of SEQ ID NO:93, 94, 95, 106 or 111.

Also provided are conjugates comprising a glucagon-like peptide 1 (GLP-1) fusion peptide coupled to a cyclic PYY peptide, wherein the GLP-1 fusion peptide comprises an amino acid sequence selected from the group consisting of SEQ ID NOs:113-224 and 267-274, and wherein the cyclic PYY peptide comprises an amino acid sequence selected from SEQ ID NO:24, 25, 27, 28, 29, 30, 33, or 34. In certain embodiments, the GLP-1 fusion peptide comprises an amino acid sequence of SEQ ID NO:113 or SEQ ID NO:136. In certain embodiments, a cysteine residue between amino acid residues 287 to 289 of SEQ ID NO:113 or SEQ ID NO:136, preferably the cysteine residue 288 of SEQ ID NO:113 or SEQ ID NO:136 is covalently linked to a lysine residue at residue 7, 9, 11, 22, or 23 of the cyclic PYY peptide, preferably the lysine residue 11 of the cyclic PYY peptide, directly or via a chemical linker.

Also provided are conjugates comprising a glucagon-like peptide 1 (GLP-1) fusion peptide coupled to a cyclic PYY peptide, wherein the conjugate comprises a sequence selected from the group consisting of SEQ ID NOs:225-262 or a pharmaceutically acceptable salt thereof.

Also provided are methods of producing the conjugates of the invention. The methods comprise reacting an electrophile, preferably bromoacetamide or maleimide, introduced onto a sidechain of the cyclic PYY peptide, preferably the sidechain of a lysine residue of the cyclic PYY peptide, with the sulfhydryl group of a cysteine residue of the second linker peptide (e.g., the carboxy-terminal linker peptide) of a GLP-1 fusion peptide, thereby creating a covalent linkage between the cyclic PYY peptide and the GLP-1 fusion peptide.

Also provided are pharmaceutical compositions comprising the conjugates of the invention and a pharmaceutically acceptable carrier.

Also provided are methods for treating or preventing a disease or disorder in a subject in need thereof, wherein said disease or disorder is obesity, type I or type II diabetes, metabolic syndrome, insulin resistance, impaired glucose tolerance, hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and/or eczema. The methods comprise administering to the subject in need thereof an effective amount of a pharmaceutical composition of the invention.

Also provided are methods of reducing at least one of food intake or body weight in a subject in need thereof. The methods comprise administering to the subject in need thereof an effective amount of a pharmaceutical composition of the invention.

Also provided are methods of modulating Y2 receptor activity or GLP-1 receptor activity in a subject in need thereof. The methods comprise administering to the subject in need thereof an effective amount of a pharmaceutical composition of the invention.

In certain embodiments, the pharmaceutical composition is administered via an injection.

Also provided are kits comprising the compounds of the invention, preferably further comprising a liraglutide and a device for injection.

Also provided are methods of producing the pharmaceutical compositions of the invention. The methods comprise combining the conjugate with a pharmaceutically acceptable carrier to obtain the pharmaceutical composition.

Further aspects, features, and advantages of the present invention will be better appreciated upon a reading of the following detailed description of the invention and claims.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 1A shows a graph demonstrating ex vivo human plasma stability of GLP-1 fusion peptides GF32 (SEQ ID NO 144) (▲), GF36 (148) (Δ), GF33 (145) (▼), GF39 (151) (∇), GF34 (146) (◎), GF35 (147) (●), GF37 (149) (○), GF40 (152) (◇), and a dulaglutide control (◆) incubated in human plasma at 37° C. for 7 days. FIG. 1B shows a graph demonstrating ex vivo human plasma stability of GF40 (SEQ ID NOs:152) (▲) and GF34 (SEQ ID NO:146) (●), and their corresponding GLP-1 fusion peptide coupled cyclic PYY peptide conjugates SEQ ID NO:248 (Δ) and SEQ ID NO:262 (○), and another GLP-1 fusion peptide GF41 (SEQ ID NO:153) (▼) incubated in human plasma ex vivo at 37° C. for 7 days along with a dulaglutide control (◇).

FIGS. 2A and 2B show graphs of food intake (FIG. 2A) and percentage body weight loss (FIG. 2B) in DIO mice treated with dulaglutide, compound 1 (GF1 (SEQ ID NO:113)) (0.3 nmol/kg), and compound 2 (SEQ ID NO:225) (0.3 nmol/kg). Mice were dosed by subcutaneous injection with vehicle (white circles), dulaglutide (white squares), compound 1 (black squares), or compound 2 (black circles), and body weight and food intake were recorded for 3 days.

FIGS. 3A and 3B show graphs of food intake (FIG. 3A) and percentage body weight loss (FIG. 3B) in DIO mice treated with dulaglutide, compound 3 (GF24 (SEQ ID NO:136)) (0.3 nmol/kg), and compound 4 (SEQ ID NO:229) (0.3 nmol/kg). Mice were dosed by subcutaneous injection with vehicle (white circles), dulaglutide (white squares), compound 3 (black squares), or compound 4 (black circles), and body weight and food intake were recorded for 3 days.

FIG. 4A shows a graph of glucose levels over time in DIO mice treated with dulaglutide, compound 4 (SEQ ID NO:229) and compound 2 (SEQ ID NO:225) at 0.3 nmol/kg and 1.0 nmol/kg. FIG. 4B shows a graph of NET AUC relative to baseline in DIO mice treated with dulaglutide, compound 4 (SEQ ID NO:229), and compound 2 (SEQ ID NO:225) at 0.3 nmol/kg and 1.0 nmol/kg. Mice were dosed by subcutaneous injection with vehicle (black circles), dulaglutide (white/black squares), compound 4 (white/black triangles), or compound 2 (white/black circles, dotted line). All compounds were dosed at 0.3 or 1.0 nmol/kg. After an 18 hour fast, mice were dosed with 1 g/kg dextrose for an intraperitoneal glucose tolerance test (IGPTT).

FIGS. 5A and 5B show graphs of food intake (FIG. 5A) and percentage body weight loss (FIG. 5B) in DIO mice treated with dulaglutide, GF41 (SEQ ID NO:153) (0.3 nmol/kg), and GF40 (SEQ ID NO:152) (0.3 nmol/kg). Mice were dosed by subcutaneous injection with vehicle (white circles), dulaglutide (white squares), SEQ ID NO:153 (black squares), or SEQ ID NO:152 (black circles), and body weight and food intake were recorded for 3 days.

FIGS. 6A and 6B show graphs of food intake (FIG. 6A) and percentage body weight loss (FIG. 6B) in DIO mice treated with dulaglutide and GF19 (SEQ ID NO:131) (0.3 nmol/kg). Mice were dosed by subcutaneous injection with vehicle (white circles), dulaglutide (white squares), or SEQ ID NO:131 (black squares), and body weight and food intake were recorded for 3 days.

FIG. 7A shows a graph of glucose levels over time in DIO mice treated with dulaglutide, compound 4 (SEQ ID NO:229) and compound 3 (GF24 (SEQ ID NO:136)) at 0.3 nmol/kg. FIG. 7B shows a graph of NET AUC relative to baseline in DIO mice treated with dulaglutide, compound 4 (SEQ ID NO:229), and compound 3 (GF24 (SEQ ID NO:136)) at 0.3 nmol/kg. Mice were dosed by subcutaneous injection with vehicle (black circles), dulaglutide (white squares), compound 4 (white circles), or compound 3 (black squares, dotted line). All compounds were dosed at 0.3 nmol/kg. After an 18 hour fast, mice were dosed with 1 g/kg dextrose for an intraperitoneal glucose tolerance test (IGPTT).

FIGS. 8A and 8B show graphs of percent food intake change (FIG. 8A) and percentage body weight change (FIG. 8B). Open squares represent observed individual data for dulaglutide. Solid squares represent observed individual data for compound 4. The curved lines represent best-fit curves based on the exposure-response nonlinear regression for dulaglutide (gray curve) and compound 4 (black curve). The gray vertical line represents dulaglutide mean (±standard deviation) day 3 HGE concentrations at 0.3 nmol/kg in all analyzed studies: ≈0.32 (±0.15) nM.

DETAILED DESCRIPTION OF THE INVENTION

Figure 1A:
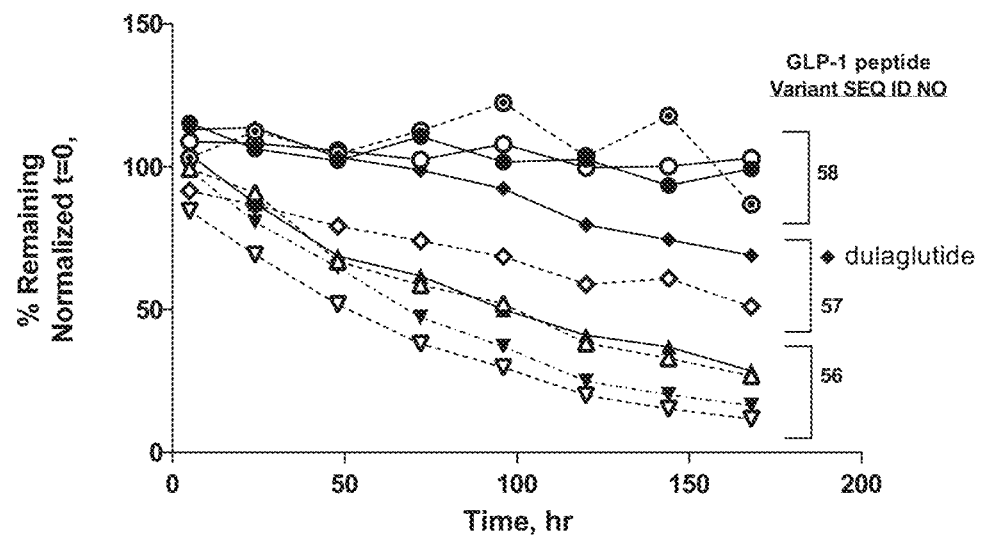
FIGS. 1A-1B show ex vivo human plasma stability of GLP-1 fusion peptide moieties.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., GLP-1 peptide, linker peptides, hinge-Fc region peptides, cyclic $PYY_{3-36}$ peptide sequences), refer to two or more sequences or subsequences that are the same or have a specified percentage of amino acid residues or nucleotides that are the same, when compared and aligned for maximum correspondence, as measured using one of the following sequence comparison algorithms or by visual inspection using methods known in the art in view of the present disclosure.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al., J. Mol. Biol. 215: 403-410 (1990) and Altschul et al., Nucleic Acids Res. 25: 3389-3402 (1997), respectively. Software for performing BLAST analyses is publicly available through the National Center for Biotechnology Information.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The term "administering" with respect to the methods of the invention, means a method for therapeutically or prophylactically preventing, treating or ameliorating a syndrome, disorder or disease as described herein by using a conjugate or compound of the invention or a form, composition or medicament thereof. Such methods include administering an effective amount of said conjugate, compound, a form, composition or medicament thereof at different times during the course of a therapy or concurrently in a combination form. The methods of the invention are to be understood as embracing all known therapeutic treatment regimens.

The term "effective amount" means that amount of active conjugate, compound or pharmaceutical agent that elicits the biological or medicinal response in a tissue system, animal or human, that is being sought by a researcher, veterinarian, medical doctor, or other clinician, which includes preventing, treating or ameliorating a syndrome, disorder, or disease being treated, or the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

As used herein the term "coupled" refers to the joining or connection of two or more objects together. When referring to chemical or biological compounds, coupled can refer to a covalent connection between the two or more chemical or biological compounds. By way of a non-limiting example, a glucagon-like peptide-1 (GLP-1) fusion peptide of the invention can be coupled with a cyclic PYY peptide of interest to form a GLP-1 fusion peptide coupled cyclic PYY peptide conjugate. In certain embodiments, a GLP-1 fusion peptide of the invention can be covalently coupled with a cyclic PYY peptide of the invention through at least one linker. A GLP-1 fusion peptide coupled cyclic PYY peptide conjugate can be formed through specific chemical reactions designed to conjugate the GLP-1 fusion peptide to the cyclic PYY peptide. By way of an example, the GLP-1 fusion peptide coupled cyclic PYY peptide conjugate can be formed through a conjugation reaction. The conjugation reaction can, for example, comprise reacting an electrophilic group (e.g., a bromoacetamide or a maleimide) with the sulfhydryl group of a cysteine residue on a peptide of interest (e.g., the GLP-1 fusion peptide). The electrophilic group can, for example, be introduced onto a sidechain of an amino acid residue of a cyclic PYY peptide. The reaction of the electrophilic group with the sulfhydryl group results in the formation of a covalent thioether bond.

As used herein, the term "peptide linker" or "linker peptide" refers to a chemical module containing one or more amino acids that links a GLP-1 peptide to a hinge-Fc region peptide or that links a hinge-Fc-region peptide to a cyclic PYY peptide to form a GLP-1 fusion peptide coupled cyclic PYY peptide conjugate. The GLP-1 fusion peptide can, for example, comprise a first linker peptide and a second linker peptide.

As used herein, the term "chemical linker" refers to a chemical module not containing any amino acid that links the cyclic PYY peptide to a GLP-1 fusion peptide. In certain embodiments, the cyclic PYY peptide comprises a chemical linker. The chemical linker for the cyclic PYY peptide can, for example, include, but is not limited to, a hydrocarbon linker, a polyethylene glycol (PEG) linker, a polypropylene glycol (PPG) linker, a polysaccharide linker, a polyester linker, a linker containing an acyl group, a hybrid linker consisting of PEG and an embedded heterocycle, and a hydrocarbon chain. The chemical linker can, for example, be first covalently connected to the cyclic PYY peptide, then covalently connected to the GLP-1 fusion peptide, preferably to the second linker peptide of the GLP-1 fusion peptide.

As used herein, the term "conjugate" refers to a peptide (e.g., a GLP-1 fusion peptide) covalently coupled to another pharmaceutically active moiety (e.g., a cyclic PYY peptide). The term "conjugated to" refers to a peptide of the invention covalently linked to or covalently connected to another pharmaceutically active moiety, preferably a therapeutic peptide, directly or indirectly via a linker. By way of a non-limiting example, the peptide can be a GLP-1 fusion peptide of the invention and the other pharmaceutically active moiety can be a therapeutic peptide, such as a cyclic PYY peptide of interest.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

Glucagon-Like Peptide-1 (GLP-1) Fusion Peptides

In one general aspect, the invention relates to a glucagon-like peptide 1 (GLP-1) fusion peptide. GLP-1 fusion peptides comprise a GLP-1 or GLP-1 variant peptide, a first linker peptide (e.g., an amino (N)-terminal linker), a hinge-Fc region peptide, and a second linker peptide (e.g., a carboxy (C)-terminal linker).

Glucagon-Like Peptide-1 or GLP-1 Variant Peptide

Glucagon-like peptide 1 (GLP-1) is an insulin secretagogue synthesized in the intestine and released in response to the intake of food. It is secreted primarily in two forms, GLP-1-(7-37) and GLP-1-(7-36)NH$_2$, both of which bind to a specific GLP-1 receptor (GLP-1R) on the pancreatic beta-cell and augment glucose-stimulated insulin secretion.

Numerous GLP-1 analogs and derivatives are known and can be referred to herein as "GLP-1 variants." These GLP-1 variant peptides can include the Exendins, which are peptides found in the venom of the Gila monster. These Exendins have sequence homology to native GLP-1 and can bind the GLP-1 receptor and initiate the signal transduction cascade response for the activities attributed to GLP-1 (7-37).

GLP-1 and GLP-1 variant peptides have been shown to act in a variety of manners, which can include, but are not limited to, stimulating insulin release, lowering glucagon secretion, inhibiting gastric emptying, and enhancing glucose utilization.

GLP-1R belongs to the class B family of 7-transmembrane-spanning, heterotrimeric G-protein-coupled receptors and is expressed in a wide range of tissues including, but not limited to, α-, β-, and δ-cells of the pancreatic islets, heart, kidney, stomach, intestine, nodose ganglion neurons of the vagus nerve, and several regions of the central nervous system (CNS) including the hypothalamus and brainstem. The GLP-1R can couple to $G\alpha_s$, $G\alpha_q$, $G\alpha_i$, and $G\alpha_o$ (Montrose-Rafizadeh et al., Endocrinology 140:1132-40 (1999); Hallbrink et al., Biochim Biophys Acta 1546:79-86 (2001)) leading to increases in intracellular calcium, adenylate cyclase, and phospholipase C, and activation of PKA, PKC, PI-3K, Epac2, and MAPK signal transduction pathways (Drucker et al., PNAS 84:3434-8 (1987); Wheeler et al., Endocrinology 133:57-62 (1993); and Holz et al., JBC 270:17749-57 (1995)).

Provided herein are GLP-1 fusion peptides that comprise a first component, wherein the first component is a GLP-1 or GLP-1 variant peptide. As used herein, the terms "GLP-1 peptide," "GLP-1 variant peptide," "GLP-1 peptide variant," and "GLP-1 or GLP-1 variant peptide" are used interchangeably. The GLP-1 or GLP-1 variant peptide can comprise one of the sequences provided in Table 1. The GLP-1 or GLP-1 variant peptide sequence can be chosen based on at least one of the following criteria: (i) expression yield, (ii) in vitro stability, (iii) in vitro potency, (iv) the retention of in vitro potency after chemical conjugation with the cyclic PYY peptide, (v) lack of serine xylosylation or potential for serine xylosylation, and (vi) properties of the GLP-1 fusion peptide coupled cyclic PYY peptide conjugate (e.g., in vivo stability and in vivo potency (i.e., whether the GLP-1 or GLP-1 variant peptide and cyclic PYY peptide are capable of having agonist activity on GLP-1 and Y2 receptor, respectively)).

The GLP-1 or GLP-1 variant peptides that make up the first component of the GLP-1 fusion peptide are intended to encompass peptides that have sufficient homology and functionality to the native GLP-1. The GLP-1 or GLP-1 variant peptides are designed to be capable of binding to the GLP-1 receptor on β-cells in the pancreas, resulting in the same signaling pathway and exhibiting the same or similar insulinotropic activity as when the native GLP-1 binds the GLP-1 receptor on the β-cells in the pancreas.

TABLE 1

Glucagon-like peptide-1 and variants thereof

| GLP-1 or GLP-1 Variant Peptide | Peptide Sequence | SEQ ID NO: |
|---|---|---|
| (A8S, A30E) GLP-1(7-36) | HSEGTFTSDVSSYLEGQAAKEFIEWLVKGR | 56 |
| (A8G, G22E, R36G) GLP-1 (7-37) | HGEGTFTSDVSSYLEEQAAKEFIAWLVKGGG | 57 |
| Exendin 4 (1-39) | HGEGTFTSDLSKQMEEEAVRLFIEWLKNGGPSSGAPPPS | 58 |
| Exendin 4 (1-28) | HGEGTFTSDLSKQMEEEAVRLFIEWLKN | 59 |

First Linker Peptide: Amino-Terminal Linker (N-Terminal Linker)

Provided herein are GLP-1 fusion peptides that comprise a second component, wherein the second component is a first linker peptide (i.e., an amino-terminal linker peptide). The first linker peptide can comprise one of the sequences provided in Table 2. The first linker peptide sequence can be chosen based on at least one of the following criteria: (i) expression yield, (ii) in vitro potency, (iii) in vitro stability, (iv) lack of serine xylosylation or potential for serine xylosylation, and (v) properties of the GLP-1 fusion peptide coupled cyclic PYY peptide conjugate (e.g., in vivo stability and in vivo potency (i.e., whether the GLP-1 or GLP-1 variant peptide and cyclic PYY peptide are capable of having agonist activity on GLP-1 and Y2 receptor, respectively)).

In certain embodiments, the GLP-1 fusion peptides do not comprise a second component, wherein the second component is a first linker peptide.

TABLE 2

First linker peptides (N-terminal linker peptide)

| Linker 1 | Peptide Sequence | SEQ ID NO |
|---|---|---|
| 1-1 | GGGGAGGGGAGGGGAA | 60 |
| 1-2 | GGGGGGGGGGGGGGGA | 61 |
| 1-3 | APAPAPAPAPAPAPAPAPAPA | 62 |
| 1-4 | APAPAPAPAPAPAPAPAPAPAPA | 63 |
| 1-5 | APAPAP | 64 |
| 1-6 | ASAPAPAPAPAPGS | 65 |
| 1-7 | ASAPAPAPAPAPAPAPAPAPGS | 66 |
| 1-8 | ASGGGGSGGGGS | 67 |
| 1-9 | ASGGGGSGGGGSGGGGSGGGGS | 68 |
| 1-10 | ASGGGGSGGGGSGGGGSGGGGSGGGGSGGGGSGGGGSGGGGS | 69 |
| 1-11 | GGGGAGGGGAGGGGA | 70 |
| 1-12 | GGGGAGGGGAGGGGAGGGGA | 71 |
| 1-13 | GGGGAGGGGAGGGGAGGGGAA | 72 |
| 1-14 | GGGGAGGGGAGGGGAGGGGAGGGGAA | 73 |
| 1-15 | GGGGGG | 74 |
| 1-16 | GGGGHGGGGHGGGGHA | 75 |

TABLE 2-continued

First linker peptides (N-terminal linker peptide)

| Linker 1 | Peptide Sequence | SEQ ID NO |
|---|---|---|
| 1-17 | GGGGHGGGGHGGGGHGGGGHA | 76 |
| 1-18 | GGGGHGGGGHGGGGHGGGGHGGGGHA | 77 |
| 1-19 | GGGGPGGGGPGGGGPA | 78 |
| 1-20 | GGGGPGGGGPGGGGPGGGGPA | 79 |
| 1-21 | GGGGPGGGGPGGGGPGGGGPGGGGPA | 80 |
| 1-22 | GGGGSGGGGSGGGGSA | 81 |
| 1-23 | PAPAPAPAPAPAPAPAPAPAP | 82 |
| 1-24 | PAPAPAPAPAPAPAPAPAPA | 83 |

Hinge-Fc Region Peptide

In certain embodiments, the GLP-1 fusion peptides comprise a third component, wherein the third component is a hinge-Fc region peptide. The hinge-Fc region peptide can confer greater circulating half-life of the therapeutic peptides through increased molecular weight and reduced glomerular filtration, in addition to FcRn receptor recycling. In certain embodiments, the hinge-Fc region peptide can be derived from human IgG4 Fc region. Human IgG4 Fc region has reduced ability to bind FcγR and complement factors compared to other IgG sub-types. Preferably, the Fc region contains human IgG4 Fc region having substitutions that eliminate effector function. Thus, a GLP-1 fusion peptide further comprises a Fc region having a modified human IgG4 Fc region containing one or more of the following substitutions: substitution of proline for glutamate at residue 233, alanine or valine for phenylalanine at residue 234 and alanine or glutamate for leucine at residue 235 (EU numbering, Kabat et al., *Sequences of Proteins of Immunological Interest*, 5$^{th}$Ed. U.S. Dept. of Health and Human Services, Bethesda, Md., NIH Publication no. 91-3242 (1991)). Removing the N-linked glycosylation site in the IgG4 Fc region by substituting Ala for Asn at residue 297 (EU numbering) is another way to ensure that residual effector activity is eliminated.

In certain embodiments, the GLP-1 fusion peptides of the invention exist as a monomer or a dimer. In preferred embodiments, the GLP-1 fusion peptide exists as a dimer. In certain embodiments, wherein the GLP-1 fusion peptide exists as a dimer, the dimer is a homodimer, i.e., the dimer comprises two GLP-1 fusion peptides having the same sequence. In certain embodiments, wherein the GLP-1 fusion peptide exists as a dimer, the dimer is a heterodimer, i.e., the dimer comprises two GLP-1 fusion peptides having different sequences.

Preferably, the GLP-1 fusion peptides of the invention exist as dimers joined together by disulfide bonds and various non-covalent interactions. Thus, the Fc portion useful for the antibody of the invention can be human IgG4 Fc region containing a substitution, such as serine to proline at position at 228 (EU numbering), that stabilizes heavy chain dimer formation and prevents the formation of half-IgG4 Fc chains. In certain embodiments the native sequence of amino acids N-terminal to the hinge disulfides can be included. The x-ray crystal structure of the human IgG4 suggests that these amino acids can form a structure that predisposes upstream structures in opposite orientations in space. Such predisposition is advantageous in maintaining spatial separation of upstream elements such as the GLP-1 fusion peptides. In other embodiments the native amino acids N-terminal to the hinge disulfides can be omitted.

In certain embodiments, a hybrid human IgG2a hinge fused to the human PAA Fc was used to explore the impact on GLP-1 fusion peptide potency and stability.

In another embodiment, the C-terminal Lys residue in the heavy chain is removed, as commonly seen in recombinantly produced monoclonal antibodies.

The hinge-Fc region peptides can comprise one of the sequences provided in Table 3. The hinge-Fc region peptide sequence can be chosen based on at least one of the following criteria: (i) in vitro stability, (ii) in vitro potency, and (iii) properties of the GLP-1 fusion peptide coupled cyclic PYY peptide conjugate (e.g., in vivo stability and in vivo potency (i.e., whether the GLP-1 or GLP-1 variant peptide and cyclic PYY peptide are capable of having agonist activity on GLP-1 and Y2 receptor, respectively)).

TABLE 3

Hinge-Fc Region Peptides

| Hinge-Fc region | Peptide Sequence | SEQ ID NO |
|---|---|---|
| Hinge-Fc region-1 | ESKYGPPCPPCPAPEAAGGPSVFLFPPKPKDTLMISRTPEVTCVVVDVS QEDPEVQFNWYVDGVEVHNAKTKPREEQFNSTYRVVSVLTVLHQD WLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYS RLTVDKSRWQEGNVFSCSVMHEALHNHYTQKSLSLSLG | 84 |
| Hinge-Fc region-2 | GPPCPPCPAPEAAGGPSVFLFPPKPKDTLMISRTPEVTCVVVDVSQEDP EVQFNWYVDGVEVHNAKTKPREEQFNSTYRVVSVLTVLHQDWLNG KEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTV DKSRWQEGNVFSCSVMHEALHNHYTQKSLSLSLG | 85 |
| Hinge-Fc region-3 | CPPCPAPEAAGGPSVFLFPPKPKDTLMISRTPEVTCVVVDVSQEDPEV QFNWYVDGVEVHNAKTKPREEQFNSTYRVVSVLTVLHQDWLNGKE YKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDK SRWQEGNVFSCSVMHEALHNHYTQKSLSLSLGK | 86 |

TABLE 3-continued

Hinge-Fc Region Peptides

| Hinge-Fc region | Peptide Sequence | SEQ ID NO |
|---|---|---|
| Hinge-Fc region-4 | CPPCPAPEAAGGPSVFLFPPKPKDTLMISRTPEVTCVVVDVSQEDPEV QFNWYVDGVEVHNAKTKPREEQFNSTYRVVSVLTVLHQDWLNGKE YKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDK SRWQEGNVFSCSVMHEALHNHYTQKSLSLSLG | 87 |
| Hinge-Fc region-5 | GPPCPPCPAPEAAGGPSVFLFPPKPKDTLMISRTPEVTCVVVDVSQEDP EVQFNWYVDGVEVHNAKTKPREEQFNSTYRVVSVLTVLHQDWLNG KEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTV DKSRWQEGNVFSCSVMHEALHNHYTQKSLSLSLGK | 88 |
| Hinge-Fc region-6 | ESKYGPPCPPCPAPEAAGGPSVFLFPPKPKDTLMISRTPEVTCVVVDVS QEDPEVQFNWYVDGVEVHNAKTKPREEQFNSTYRVVSVLTVLHQD WLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYS RLTVDKSRWQEGNVFSCSVMHEALHNHYTQKSLSLSLGK | 89 |
| Hinge-Fc region-7 | ERKCCVECPPCPAPEAAGGPSVFLFPPKPKDTLMISRTPEVTCVVVDV SQEDPEVQFNWYVDGVEVHNAKTKPREEQFNSTYRVVSVLTVLHQD WLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYS RLTVDKSRWQEGNVFSCSVMHEALHNHYTQKSLSLSLG | 90 |

Also provided herein are hinge-Fc region platform peptides, wherein the hinge-Fc region platform peptides comprise a hinge-Fc region peptide and at least one of a first linker peptide, which is connected to the amino-terminal end of the hinge-Fc region peptide, and a second linker peptide, which is connected to the carboxy-terminal end of the hinge-Fc region peptide. The hinge-Fc region peptide can, for example, be an amino acid sequence selected from the group consisting of SEQ ID NOs:84-90; the first linker peptide can, for example, be an amino acid sequence selected from the group consisting of SEQ ID NOs:60-83; and the second linker peptide can, for example, be an amino acid sequence selected from the group consisting of SEQ ID NOs:91-112. In certain embodiments, the hinge-Fc region peptide comprises SEQ ID NO:84 and the first linker peptide comprises SEQ ID NO:60. In certain embodiments, the hinge-Fc region peptide comprises SEQ ID NO:84 and the second linker peptide comprises SEQ ID NO:93, 94, 95, 106, or 111. In certain embodiments, the hinge-Fc region peptide comprises SEQ ID NO:84; the first linker peptide comprises SEQ ID NO:60; and the second linker peptide comprises SEQ ID NO:93, 94, 95, 106, or 111.

Second Linker Peptide: Carboxy-Terminal Linker (C-Terminal Linker)

Provided herein are GLP-1 fusion peptides that comprise a fourth component, wherein the fourth component is a second linker peptide (i.e., a carboxy-terminal linker peptide). The second linker peptide can comprise one of the sequences provided in Table 4. The second linker peptide sequence can be chosen based on at least one of the following criteria: (i) expression yield, (ii) in vitro potency, (iii) in vitro stability, (iv) lack of serine xylosylation or potential for serine xylosylation, (v) conjugation yield, and (vi) properties of the GLP-1 fusion peptide coupled cyclic PYY peptide conjugate (e.g., in vivo stability and in vivo potency (i.e., whether the GLP-1 or GLP-1 variant peptide and cyclic PYY peptide are capable of having agonist activity on GLP-1 and Y2 receptor, respectively)).

In addition, the second linker peptide sequence can be chosen based on its ability to undergo specific, effective conjugation to the cyclic PYY peptide. In this context, specificity refers to preferential conjugation at the engineered cysteine residues in the C-terminal region of the second linker over conjugation at any other part of the fusion protein. Examples of strategies to maximize specificity include (i) the introduction of amino acids adjacent to the engineered cysteine residues to increase the nucleophilicity of the sulfhydryl side-chain and enhance their reactivity, (ii) inclusion of the engineered cysteine residues in an amino acid sequence that has previously demonstrated enhanced selectivity in thiol-electrophile conjugations, and (iii) the incorporation of amino acids with anionic or cationic side-chains that respectively electrostatically attract cationic or anionic disulfide reducing agents for the specific liberation of reactive thiols for conjugation. Examples of strategies to maximize conjugation efficiency include (i) the introduction of like charges, either anionic or cationic, at any part of the second linker peptide in order to cause mutual electrostatic repulsion of the second linker peptides, and, thus, reduce disulfide formation between the engineered cysteine residues, (ii) the incorporation of amino acids that enhance rigidity of the linker, (iii) the incorporation of amino acids that increase the flexibility of the linker, and (iv) the incorporation of amino acids with anionic or cationic side-chains that electrostatically predispose the cyclic PYY peptide for efficient conjugation.

TABLE 4

Second linker peptide (C-terminal linker peptide)

| Linker 2 | Peptide Sequence | SEQ ID NO |
|---|---|---|
| 2-1 | ASGSAPAPAPEEEPCA | 91 |

TABLE 4-continued

Second linker peptide (C-terminal linker peptide)

| Linker 2 | Peptide Sequence | SEQ ID NO |
|---|---|---|
| 2-2 | GGGAPAPAPEEEPCA | 92 |
| 2-3 | APAPAPAPAPAPCPEEP | 93 |
| 2-4 | APAPAPAPAPAPCP | 94 |
| 2-5 | GGGGAGGGGAGGGGACA | 95 |
| 2-6 | GGGGAYCAKYDGCYGELDFWCQ | 96 |
| 2-7 | GGGGAYSAKYDGCYGELDFWGQ | 97 |
| 2-8 | AAACPEEE | 98 |
| 2-9 | AAAEEPCA | 99 |
| 2-10 | APAPAPAPCAPRRR | 100 |
| 2-11 | APAPEEPCA | 101 |
| 2-12 | ASGSAPAPAPAPCEEE | 102 |
| 2-13 | ASGSAPAPAPAPCPEEP | 103 |
| 2-14 | ASGSGGGSGGGSCA | 104 |
| 2-15 | GGGGGGGGGGGGGGGCA | 105 |
| 2-16 | GGGGSGGGGSCA | 106 |
| 2-17 | ASGSPPPPPPEPEPCA | 107 |

TABLE 4-continued

Second linker peptide (C-terminal linker peptide)

| Linker 2 | Peptide Sequence | SEQ ID NO |
|---|---|---|
| 2-18 | ASGSAPAPAPAPCPEPE | 108 |
| 2-19 | ASGSGGGGSGGGGSCA | 109 |
| 2-20 | ASGSAPAPAPAPAEEEPCA | 110 |
| 2-21 | GGGGSGGGGSGGGGSCA | 111 |
| 2-22 | ASGSGGGGSGGGGSEEEACA | 112 |

GLP-1 Fusion Peptides

Provided herein are GLP-1 fusion peptides that comprise a first, a second, a third, and a fourth component as described previously, wherein the second component can be optionally absent. The first component is a GLP-1 or GLP-1 variant peptide, the second component is a first linker peptide, the third component is a hinge-Fc region peptide, and the fourth component is a second linker peptide. The GLP-1 fusion peptide can comprise one of the sequences provided in Table 5. The GLP-1 fusion peptide sequence can be chosen based on at least one of the following criteria: (i) expression yield, (ii) in vitro potency, (iii) in vitro stability, (iv) lack of serine xylosylation, (v) conjugation yield, and (vi) properties of the GLP-1 fusion peptide coupled cyclic PYY peptide conjugate (e.g., in vivo stability and in vivo potency (i.e., whether the GLP-1 or GLP-1 variant peptide and cyclic PYY peptide are capable of having agonist activity on GLP-1 receptor and Y2 receptor, respectively)).

TABLE 5

GLP-1 fusion peptides

| GLP-1 Fusion (GF) | Peptide Sequence | SEQ ID NO: |
|---|---|---|
| GF1 | HGEGTFTSDVSSYLEEQAAKEFIAWLVKGGGGGGGAGGGGAGGGGAAESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAPAPAPAPAPAPCP | 113 |
| GF2 | HGEGTFTSDVSSYLEEQAAKEFIAWLVKGGGGGGGGGGGGGGGGGGAESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAPAPAPAPAPAPCP | 114 |
| GF3 | HGEGTFTSDVSSYLEEQAAKEFIAWLVKGGGAPAPAPAPAPAPAPAPAPAPAGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAPAPAPAPAPAPCPGF | 115 |
| GF4 | HGEGTFTSDLSKQMEEEAVRLFIEWLKNGGGGAGGGGAGGGGAAESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAPAPAPAPAPAPCP | 116 |
| GF5 | HGEGTFTSDLSKQMEEEAVRLFIEWLKNGGGGGGGGGGGGGGGGAESKYGPPCPPCPAPEAAGGPSVFLFPPKPKDTLMISRTPEVTCVVVDVSQEDPEVQFNWYVD | 117 |

TABLE 5-continued

GLP-1 fusion peptides

| GLP-1 Fusion (GF) | Peptide Sequence | SEQ ID NO: |
|---|---|---|
| | GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKS LSLSLGAPAPAPAPAPAPCP | |
| GF6 | HGEGTFTSDLSKQMEEEAVRLFIEWLKNAPAPAPAPAPAPAPAPAPAPAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGAPAPAPAPAPAPCP | 118 |
| GF7 | HGEGTFTSDLSKQMEEEAVRLFIEWLKNAPAPAPAPAPAPAPAPAPAPAPAG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGAPAPAPAPAPAPCP | 119 |
| GF8 | HGEGTFTSDVSSYLEEQAAKEFIAWLVKGGGGGGGGAGGGGAGGGGAAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGGAGGGGAGGGGACA | 120 |
| GF9 | HGEGTFTSDVSSYLEEQAAKEFIAWLVKGGGGGGGGGGGGGGGGGGGAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGGAGGGGAGGGGACA | 121 |
| GF10 | HGEGTFTSDVSSYLEEQAAKEFIAWLVKGGGAPAPAPAPAPAPAPAPAPAPA PAGPPCPPCPAPEAAGGPSVFLFPPKPKDTLMISRTPEVTCVVVDVSQEDPEVQF NWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVMHEALHN HYTQKSLSLSLGGGGAGGGGAGGGGACA | 122 |
| GF11 | HGEGTFTSDLSKQMEEEAVRLFIEWLKNGGGGAGGGGAGGGGAAESKYGPPC PPCPAPEAAGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKS LSLSLGGGGGAGGGGAGGGGACA | 123 |
| GF12 | HGEGTFTSDLSKQMEEEAVRLFIEWLKNGGGGGGGGGGGGGGGGAESKYGPPC PPCPAPEAAGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKS LSLSLGGGGGAGGGGAGGGGACA | 124 |
| GF13 | HGEGTFTSDLSKQMEEEAVRLFIEWLKNAPAPAPAPAPAPAPAPAPAPAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGGAGGGGAGGGGACA | 125 |
| GF14 | HGEGTFTSDLSKQMEEEAVRLFIEWLKNAPAPAPAPAPAPAPAPAPAPAPAG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGGAGGGGAGGGGACA | 126 |
| GF15 | HGEGTFTSDVSSYLEEQAAKEFIAWLVKGGGGGGGAGGGGAGGGGAAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGGAYCAKYDGCYGELDFWCQ | 127 |

TABLE 5-continued

GLP-1 fusion peptides

| GLP-1 Fusion (GF) | Peptide Sequence | SEQ ID NO: |
|---|---|---|
| GF16 | HGEGTFTSDLSKQMEEEAVRLFIEWLKNAPAPAPAPAPAPAPAPAPAPAPAG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGGAYCAKYDGCYGELDFWCQ | 128 |
| GF17 | HGEGTFTSDVSSYLEEQAAKEFIAWLVKGGGGGGGAGGGGAGGGGAAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGGAYSAKYDGCYGELDFWGQ | 129 |
| GF18 | HGEGTFTSDLSKQMEEEAVRLFIEWLKNAPAPAPAPAPAPAPAPAPAPAPAG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGGAYSAKYDGCYGELDFWGQ | 130 |
| GF19 | HGEGTFTSDVSSYLEEQAAKEFIAWLVKGGGGGGGAGGGGAGGGGAAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGAPAPAPEEEPCA | 131 |
| GF20 | HGEGTFTSDVSSYLEEQAAKEFIAWLVKGGGGGGGGGGGGGGGGGGGAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGAPAPAPEEEPCA | 132 |
| GF21 | HGEGTFTSDLSKQMEEEAVRLFIEWLKNGGGGAGGGGAGGGGAAESKYGPPC PPCPAPEAAGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKS LSLSLGGGGAPAPAPEEEPCA | 133 |
| GF22 | HGEGTFTSDLSKQMEEEAVRLFIEWLKNGGPSSGAPPPSGGGGAGGGGAGGGG AAESKYGPPCPPCPAPEAAGGPSVFLFPPKPKDTLMISRTPEVTCVVVDVSQEDP EVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYPSDI AVEWESNGQPENNYKTTPPVLDSDGSFFLYSRLTVDKSRWQEGNVFSCSVMHE ALHNHYTQKSLSLSLGGGGAPAPAPEEEPCA | 134 |
| GF23 | HGEGTFTSDLSKQMEEEAVRLFIEWLKNGGPSSGAPPPSGGGGGGGGGGGGG GAESKYGPPCPPCPAPEAAGGPSVFLFPPKPKDTLMISRTPEVTCVVVDVSQEDP EVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYPSDI AVEWESNGQPENNYKTTPPVLDSDGSFFLYSRLTVDKSRWQEGNVFSCSVMHE ALHNHYTQKSLSLSLGGGGAPAPAPEEEPCA | 135 |
| GF24 | HGEGTFTSDVSSYLEEQAAKEFIAWLVKGGGGGGGAGGGGAGGGGAAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGAPAPAPAPAPAPCPEEP | 136 |
| GF25 | HGEGTFTSDVSSYLEEQAAKEFIAWLVKGGGGGGGGGGGGGGGGGGGAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGAPAPAPAPAPAPCPEEP | 137 |
| GF26 | HGEGTFTSDVSSYLEEQAAKEFIAWLVKGGGAPAPAPAPAPAPAPAPAPAES KYGPPCPPCPAPEAAGGPSVFLFPPKPKDTLMISRTPEVTCVVVDVSQEDPEVQF NWYVDGVEVHNAKTKPREEQFNSTYRVVSVLTVLHQDWLNGKEYKCKVSNK | 138 |

TABLE 5-continued

GLP-1 fusion peptides

| GLP-1 Fusion (GF) | Peptide Sequence | SEQ ID NO: |
|---|---|---|
| | GLPSSIEKTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVMHEALHN HYTQKSLSLSLGAPAPAPAPAPAPCPEEP | |
| GF27 | HGEGTFTSDVSSYLEEQAAKEFIAWLVKGGGAPAPAPAPAPAPAPAPAPAPAPA PAGPPCPPCPAPEAAGGPSVFLFPPKPKDTLMISRTPEVTCVVVDVSQEDPEVQF NWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVMHEALHN HYTQKSLSLSLGAPAPAPAPAPAPCPEEP | 139 |
| GF28 | HGEGTFTSDLSKQMEEEAVRLFIEWLKNGGGGAGGGGAGGGGAAESKYGPPC PPCPAPEAAGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKS LSLSLGAPAPAPAPAPAPCPEEP | 140 |
| GF29 | HGEGTFTSDLSKQMEEEAVRLFIEWLKNGGGGGGGGGGGGGGAESKYGPPC PPCPAPEAAGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKS LSLSLGAPAPAPAPAPAPCPEEP | 141 |
| GF30 | HGEGTFTSDLSKQMEEEAVRLFIEWLKNAPAPAPAPAPAPAPAPAPAPAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGAPAPAPAPAPAPCPEEP | 142 |
| GF31 | HGEGTFTSDLSKQMEEEAVRLFIEWLKNAPAPAPAPAPAPAPAPAPAPAPAG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGAPAPAPAPAPAPCPEEP | 143 |
| GF32 | HSEGTFTSDVSSYLEGQAAKEFIEWLVKGRASGGGGSGGGGSCPPCPAPEAAGG PSVFLFPPKPKDTLMISRTPEVTCVVVDVSQEDPEVQFNWYVDGVEVHNAKTK PREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVL DSDGSFFLYSRLTVDKSRWQEGNVFSCSVMHEALHNHYTQKSLSLSLGKASGS APAPAPEEEPCA | 144 |
| GF33 | HSEGTFTSDVSSYLEGQAAKEFIEWLVKGRASAPAPAPAPAPGSCPPCPAPEAA GGPSVFLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLGKAS GSAPAPAPEEEPCA | 145 |
| GF34 | HGEGTFTSDLSKQMEEEAVRLFIEWLKNGGPSSGAPPPSASGGGGSGGGGSCPP CPAPEAAGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQKSLS LSLGKASGSAPAPAPEEEPCA | 146 |
| GF35 | HGEGTFTSDLSKQMEEEAVRLFIEWLKNGGPSSGAPPPSASAPAPAPAPGSCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGKASGSAPAPAPEEEPCA | 147 |
| GF36 | HSEGTFTSDVSSYLEGQAAKEFIEWLVKGRASGGGGSGGGGSGPPCPPCPAPEA AGGPSVFLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLSLGKA SGSAPAPAPEEEPCA | 148 |

TABLE 5-continued

GLP-1 fusion peptides

| GLP-1 Fusion (GF) | Peptide Sequence | SEQ ID NO: |
|---|---|---|
| GF37 | HGEGTFTSDLSKQMEEEAVRLFIEWLKNGGPSSGAPPPSASGGGGSGGGGSGPP CPPCPAPEAAGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSI EKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQK SLSLSLGKASGSAPAPAPEEEPCA | 149 |
| GF38 | HSEGTFTSDVSSYLEGQAAKEFIEWLVKGRASGGGGSGGGGSGGGGSGGGGSC PPCPAPEAAGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKS LSLSLGKASGSAPAPAPEEEPCA | 150 |
| GF39 | HSEGTFTSDVSSYLEGQAAKEFIEWLVKGRASAPAPAPAPAPAPAPAPAPAPGS CPPCPAPEAAGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSI EKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQK SLSLSLGKASGSAPAPAPEEEPCA | 151 |
| GF40 | HGEGTFTSDVSSYLEEQAAKEFIAWLVKGGGASGGGGSGGGGSCPPCPAPEAA GGPSVFLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLGKAS GSAPAPAPEEEPCA | 152 |
| GF41 | HGEGTFTSDVSSYLEEQAAKEFIAWLVKGGGASGGGGSGGGGSGGGGSGGGG SCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGKASGSAPAPAPEEEPCA | 153 |
| GF42 | HGEGTFTSDLSKQMEEEAVRLFIEWLKNGGPSSGAPPPSASGGGGSGGGGSCPP CPAPEAAGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQKSLS LSLGKASGSAPAPEPEPEPCA | 154 |
| GF43 | HGEGTFTSDLSKQMEEEAVRLFIEWLKNGGPSSGAPPPSASAPAPAPAPAPGSCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGKASGSAPAPEPEPEPCA | 155 |
| GF44 | HGEGTFTSDVSSYLEEQAAKEFIAWLVKGGGASGGGGSGGGGSCPPCPAPEAA GGPSVFLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLGKAS GSAPAPEPEPEPCA | 156 |
| GF45 | HGEGTFTSDLSKQMEEEAVRLFIEWLKNGGPSSGAPPPSASGGGGSGGGGSCPP CPAPEAAGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQKSLS LSLGKASGSAPAPAPCEEE | 157 |
| GF46 | HGEGTFTSDLSKQMEEEAVRLFIEWLKNGGPSSGAPPPSASAPAPAPAPAPGSCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGKASGSAPAPAPCEEE | 158 |
| GF47 | HGEGTFTSDLSKQMEEEAVRLFIEWLKNGGPSSGAPPPSASGGGGSGGGGSGPP CPPCPAPEAAGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSI EKTISKAKGQPREPQVYTLPPSQEEMTKNQVSLTCLVKGFYPSDIAVEWESNGQ | 159 |

TABLE 5-continued

GLP-1 fusion peptides

| GLP-1 Fusion (GF) | Peptide Sequence | SEQ ID NO: |
|---|---|---|
| | PENNYKTTPPVLDSDGSFFLYSRLTVDKSRWQEGNVFSCSVMHEALHNHYTQK SLSLSLGKASGSAPAPAPAPCEEE | |
| GF48 | HGEGTFTSDVSSYLEEQAAKEFIAWLVKGGGASGGGGSGGGGSCPPCPAPEAA GGPSVFLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLGKAS GSAPAPAPAPCEEE | 160 |
| GF49 | HGEGTFTSDLSKQMEEEAVRLFIEWLKNGGPSSGAPPPSASGGGGSGGGGSCPP CPAPEAAGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQKSLS LSLGKASGSAPAPAPAPCPEEP | 161 |
| GF50 | HGEGTFTSDLSKQMEEEAVRLFIEWLKNGGPSSGAPPPSASAPAPAPAPAPGSCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGKASGSAPAPAPAPCPEEP | 162 |
| GF51 | HGEGTFTSDLSKQMEEEAVRLFIEWLKNGGPSSGAPPPSASGGGGSGGGGSGPP CPPCPAPEAAGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSI EKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQK SLSLSLGKASGSAPAPAPAPCPEEP | 163 |
| GF52 | HGEGTFTSDVSSYLEEQAAKEFIAWLVKGGGASGGGGSGGGGSCPPCPAPEAA GGPSVFLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLGKAS GSAPAPAPAPCPEEP | 164 |
| GF53 | HGEGTFTSDVSSYLEEQAAKEFIAWLVKGGGASAPAPAPAPAPGSCPPCPAPEA AGGPSVFLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLSLGKA SGSAPAPAPEEEPCA | 165 |
| GF54 | HGEGTFTSDVSSYLEEQAAKEFIAWLVKGGGASAPAPAPAPAPAPAPAPAPG SCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGKASGSAPAPAPEEEPCA | 166 |
| GF55 | HGEGTFTSDLSKQMEEEAVRLFIEWLKNGGPSSGAPPPSCPPCPAPEAAGGPSVF LFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGKASGSAPAP APEEEPCA | 167 |
| GF56 | HGEGTFTSDLSKQMEEEAVRLFIEWLKNGGPSSGAPPPSGGGGGGCPPCPAPEA AGGPSVFLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLSLGKA SGSAPAPAPEEEPCA | 168 |
| GF57 | HGEGTFTSDLSKQMEEEAVRLFIEWLKNGGPSSGAPPPSAPAPAPCPPCPAPEAA GGPSVFLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLGKAS GSAPAPAPEEEPCA | 169 |

TABLE 5-continued

GLP-1 fusion peptides

| GLP-1 Fusion (GF) | Peptide Sequence | SEQ ID NO: |
|---|---|---|
| GF58 | HGEGTFTSDLSKQMEEEAVRLFIEWLKNGGPSSGAPPPSASGGGGSGGGGSCPP CPAPEAAGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQKSLS LSLGKAPAPEEPCA | 170 |
| GF59 | HGEGTFTSDLSKQMEEEAVRLFIEWLKNGGPSSGAPPPSASGGGGSGGGGSCPP CPAPEAAGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQKSLS LSLGKAAAEEPCA | 171 |
| GF60 | HGEGTFTSDLSKQMEEEAVRLFIEWLKNGGPSSGAPPPSASGGGGSGGGGSCPP CPAPEAAGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQKSLS LSLGKAPAPAPAPCAPRRR | 172 |
| GF61 | HGEGTFTSDLSKQMEEEAVRLFIEWLKNGGPSSGAPPPSASGGGGSGGGGSCPP CPAPEAAGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQKSLS LSLGKAAACPEEE | 173 |
| GF62 | HGEGTFTSDLSKQMEEEAVRLFIEWLKNGGPSSGAPPPSASGGGGSGGGGSCPP CPAPEAAGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQKSLS LSLGKASGSGGGGSGGGGSCA | 174 |
| GF63 | HGEGTFTSDVSSYLEEQAAKEFIAWLVKGGGAPAPAPAPAPAPAPAPAPAPAES KYGPPCPPCPAPEAAGGPSVFLFPPKPKDTLMISRTPEVTCVVVDVSQEDPEVQF NWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVMHEALHN HYTQKSLSLSLGKASGSAPAPAPEEEPCA | 175 |
| GF64 | HGEGTFTSDLSKQMEEEAVRLFIEWLKNGGPSSGAPPPSAPAPAPAPAPAPAP APAPAESKYGPPCPPCPAPEAAGGPSVFLFPPKPKDTLMISRTPEVTCVVVDVSQ EDPEVQFNWYVDGVEVHNAKTKPREEQFNSTYRVVSVLTVLHQDWLNGKEY KCKVSNKGLPSSIEKTISKAKGQPREPQVYTLPPSQEEMTKNQVSLTCLVKGFYP SDIAVEWESNGQPENNYKTTPPVLDSDGSFFLYSRLTVDKSRWQEGNVFSCSV MHEALHNHYTQKSLSLSLGKASGSAPAPAPEEEPCA | 176 |
| GF65 | HGEGTFTSDLSKQMEEEAVRLFIEWLKNAPAPAPAPAPAPAPAPAPAPAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGKASGSAPAPAPEEEPCA | 177 |
| GF66 | HGEGTFTSDLSKQMEEEAVRLFIEWLKNGGPSSGAPPPSGGGGSGGGGSGGGGS AESKYGPPCPPCPAPEAAGGPSVFLFPPKPKDTLMISRTPEVTCVVVDVSQEDPE VQFNWYVDGVEVHNAKTKPREEQFNSTYRVVSVLTVLHQDWLNGKEYKCKV SNKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEA LHNHYTQKSLSLSLGKASGSAPAPAPEEEPCA | 178 |
| GF67 | HGEGTFTSDLSKQMEEEAVRLFIEWLKNGGGGSGGGGSGGGGSAESKYGPPCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGKASGSAPAPAPEEEPCA | 179 |
| GF68 | HGEGTFTSDVSSYLEEQAAKEFIAWLVKGGGGGGGGGGGGGGGGGGGAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG | 180 |

TABLE 5-continued

GLP-1 fusion peptides

| GLP-1 Fusion (GF) | Peptide Sequence | SEQ ID NO: |
|---|---|---|
| | QPENNYKTTPPVLDSDGSFFLYSRLTVDKSRWQEGNVFSCSVMHEALHNHYTQKSLSLSLGGGGAPAPAPEEEPCA | |
| GF69 | HGEGTFTSDVSSYLEEQAAKEFIAWLVKGGGGGGGGGGGGGGGGGGGAESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKAPAPEEPCA | 181 |
| GF70 | HGEGTFTSDVSSYLEEQAAKEFIAWLVKGGGGGGGAGGGGAGGGGAAESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKAPAPEEPCA | 182 |
| GF71 | HGEGTFTSDLSKQMEEEAVRLFIEWLKNGGPSSGAPPPSGGGGGGGGGGGGGGGAESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKAPAPEEPCA | 183 |
| GF72 | HGEGTFTSDLSKQMEEEAVRLFIEWLKNGGPSSGAPPPSGGGGAGGGGAGGGGAAESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKAPAPEEPCA | 184 |
| GF73 | HGEGTFTSDVSSYLEEQAAKEFIAWLVKGGGGGGGSGGGGSGGGGSAERKCCVECPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAPAPAPAPAPCP | 185 |
| GF74 | HGEGTFTSDVSSYLEEQAAKEFIAWLVKGGGGGGGAGGGGAGGGGAAERKCCVECPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAPAPAPAPAPCP | 186 |
| GF75 | HGEGTFTSDVSSYLEEQAAKEFIAWLVKGGGGGGGAGGGGAGGGGAGGGGAGGGGAAGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAPAPAPAPAPCP | 187 |
| GF76 | HGEGTFTSDVSSYLEEQAAKEFIAWLVKGGGGGGGPGGGGPGGGGPGGGGPAESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAPAPAPAPAPCP | 188 |
| GF77 | HGEGTFTSDVSSYLEEQAAKEFIAWLVKGGGGGGGHGGGHGGGHGGGHAESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAPAPAPAPAPCP | 189 |
| GF78 | HGEGTFTSDVSSYLEEQAAKEFIAWLVKGGGGGGGAGGGGAGGGGAGGGGAAESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAPAPAPAPAPCP | 190 |

TABLE 5-continued

GLP-1 fusion peptides

| GLP-1 Fusion (GF) | Peptide Sequence | SEQ ID NO: |
|---|---|---|
| GF79 | HGEGTFTSDVSSYLEEQAAKEFIAWLVKGGGASGGGGSGGGGSGGGGSGGGG SGGGGSGGGGSGGGGSGGGGSCPPCPAPEAAGGPSVFLFPPKPKDTLMISRTPE VTCVVVDVSQEDPEVQFNWYVDGVEVHNAKTKPREEQFNSTYRVVSVLTVLH QDWLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSRWQ EGNVFSCSVMHEALHNHYTQKSLSLSLGKASGSAPAPAPEEEPCA | 191 |
| GF80 | HGEGTFTSDLSKQMEEEAVRLFIEWLKNGGPSSGAPPPSASGGGGSGGGGSCPP CPAPEAAGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQKSLS LSLGKGGGGSGGGGSCA | 192 |
| GF81 | HGEGTFTSDVSSYLEEQAAKEFIAWLVKGGGGGGGGAGGGGAGGGGAAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGKGGGAPAPAPEEEPCA | 193 |
| GF82 | HGEGTFTSDVSSYLEEQAAKEFIAWLVKGGGGGGGGAGGGGAGGGGAAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGKASGSAPAPAPEEEPCA | 194 |
| GF83 | HGEGTFTSDVSSYLEEQAAKEFIAWLVKGGGGGGGGGGGGGGGGGGGAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGKASGSAPAPAPEEEPCA | 195 |
| GF84 | HGEGTFTSDVSSYLEEQAAKEFIAWLVKGGGGGGGGGGGGGGGGGGGAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGKGGGAPAPAPEEEPCA | 196 |
| GF85 | HGEGTFTSDVSSYLEEQAAKEFIAWLVKGGGGGGGGPGGGGPGGGGPAERKCC VECPPCPAPEAAGGPSVFLFPPKPKDTLMISRTPEVTCVVVDVSQEDPEVQFNW YVDGVEVHNAKTKPREEQFNSTYRVVSVLTVLHQDWLNGKEYKCKVSNKGLP SSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYT QKSLSLSLGAPAPAPAPAPCP | 197 |
| GF86 | HGEGTFTSDVSSYLEEQAAKEFIAWLVKGGGGGGGHGGGHGGGHAERKCC VECPPCPAPEAAGGPSVFLFPPKPKDTLMISRTPEVTCVVVDVSQEDPEVQFNW YVDGVEVHNAKTKPREEQFNSTYRVVSVLTVLHQDWLNGKEYKCKVSNKGLP SSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYT QKSLSLSLGAPAPAPAPAPCP | 198 |
| GF87 | HGEGTFTSDVSSYLEEQAAKEFIAWLVKGGGGGGGGPGGGGPGGGGPGGGGPG GGGPAGPPCPPCPAPEAAGGPSVFLFPPKPKDTLMISRTPEVTCVVVDVSQEDPE VQFNWYVDGVEVHNAKTKPREEQFNSTYRVVSVLTVLHQDWLNGKEYKCKV SNKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEA LHNHYTQKSLSLSLGAPAPAPAPAPCP | 199 |
| GF88 | HGEGTFTSDVSSYLEEQAAKEFIAWLVKGGGGGGGHGGGHGGGHGGGH GGGHAGPPCPPCPAPEAAGGPSVFLFPPKPKDTLMISRTPEVTCVVVDVSQED PEVQFNWYVDGVEVHNAKTKPREEQFNSTYRVVSVLTVLHQDWLNGKEYKC KVSNKGLPSSIEKTISKAKGQPREPQVYTLPPSQEEMTKNQVSLTCLVKGFYPSD IAVEWESNGQPENNYKTTPPVLDSDGSFFLYSRLTVDKSRWQEGNVFSCSVMH EALHNHYTQKSLSLSLGAPAPAPAPAPCP | 200 |
| GF89 | HGEGTFTSDVSSYLEEQAAKEFIAWLVKGGGGGGGSGGGGSGGGGSAERKCC VECPPCPAPEAAGGPSVFLFPPKPKDTLMISRTPEVTCVVVDVSQEDPEVQFNW YVDGVEVHNAKTKPREEQFNSTYRVVSVLTVLHQDWLNGKEYKCKVSNKGLP SSIEKTISKAKGQPREPQVYTLPPSQEEMTKNQVSLTCLVKGFYPSDIAVEWESN | 201 |

TABLE 5-continued

GLP-1 fusion peptides

| GLP-1 Fusion (GF) | Peptide Sequence | SEQ ID NO: |
|---|---|---|
| | GQPENNYKTTPPVLDSDGSFFLYSRLTVDKSRWQEGNVFSCSVMHEALHNHYT QKSLSLSLGAPAPAPAPAPCPEEP | |
| GF90 | HGEGTFTSDVSSYLEEQAAKEFIAWLVKGGGGGGGPGGGGPGGGGPAERKCC VECPPCPAPEAAGGPSVFLFPPKPKDTLMISRTPEVTCVVVDVSQEDPEVQFNW YVDGVEVHNAKTKPREEQFNSTYRVVSVLTVLHQDWLNGKEYKCKVSNKGLP SSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYT QKSLSLSLGAPAPAPAPAPCPEEP | 202 |
| GF91 | HGEGTFTSDVSSYLEEQAAKEFIAWLVKGGGGGGGHGGGGHGGGGHAERKCC VECPPCPAPEAAGGPSVFLFPPKPKDTLMISRTPEVTCVVVDVSQEDPEVQFNW YVDGVEVHNAKTKPREEQFNSTYRVVSVLTVLHQDWLNGKEYKCKVSNKGLP SSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYT QKSLSLSLGAPAPAPAPAPCPEEP | 203 |
| GF92 | HGEGTFTSDVSSYLEEQAAKEFIAWLVKGGGGGGGAGGGGAGGGGAAERKCC VECPPCPAPEAAGGPSVFLFPPKPKDTLMISRTPEVTCVVVDVSQEDPEVQFNW YVDGVEVHNAKTKPREEQFNSTYRVVSVLTVLHQDWLNGKEYKCKVSNKGLP SSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYT QKSLSLSLGAPAPAPAPAPCPEEP | 204 |
| GF93 | HGEGTFTSDVSSYLEEQAAKEFIAWLVKGGGGGGGGPGGGGPGGGGPGGGGPG GGGPAGPPCPPCPAPEAAGGPSVFLFPPKPKDTLMISRTPEVTCVVVDVSQEDPE VQFNWYVDGVEVHNAKTKPREEQFNSTYRVVSVLTVLHQDWLNGKEYKCKV SNKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEA LHNHYTQKSLSLSLGAPAPAPAPAPCPEEP | 205 |
| GF94 | HGEGTFTSDVSSYLEEQAAKEFIAWLVKGGGGGGGGHGGGGHGGGGHGGGGH GGGGHAGPPCPPCPAPEAAGGPSVFLFPPKPKDTLMISRTPEVTCVVVDVSQED PEVQFNWYVDGVEVHNAKTKPREEQFNSTYRVVSVLTVLHQDWLNGKEYKC KVSNKGLPSSIEKTISKAKGQPREPQVYTLPPSQEEMTKNQVSLTCLVKGFYPSD IAVEWESNGQPENNYKTTPPVLDSDGSFFLYSRLTVDKSRWQEGNVFSCSVMH EALHNHYTQKSLSLSLGAPAPAPAPAPCPEEP | 206 |
| GF95 | HGEGTFTSDVSSYLEEQAAKEFIAWLVKGGGGGGGGAGGGGAGGGGAGGGGA GGGGAAGPPCPPCPAPEAAGGPSVFLFPPKPKDTLMISRTPEVTCVVVDVSQED PEVQFNWYVDGVEVHNAKTKPREEQFNSTYRVVSVLTVLHQDWLNGKEYKC KVSNKGLPSSIEKTISKAKGQPREPQVYTLPPSQEEMTKNQVSLTCLVKGFYPSD IAVEWESNGQPENNYKTTPPVLDSDGSFFLYSRLTVDKSRWQEGNVFSCSVMH EALHNHYTQKSLSLSLGAPAPAPAPAPCPEEP | 207 |
| GF96 | HGEGTFTSDVSSYLEEQAAKEFIAWLVKGGGGGGGPGGGGPGGGGPGGGGPA ESKYGPPCPPCPAPEAAGGPSVFLFPPKPKDTLMISRTPEVTCVVVDVSQEDPEV QFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIAV EWESNGQPENNYKTTPPVLDSDGSFFLYSRLTVDKSRWQEGNVFSCSVMHEAL HNHYTQKSLSLSLGAPAPAPAPAPCPEEP | 208 |
| GF97 | HGEGTFTSDVSSYLEEQAAKEFIAWLVKGGGGGGGHGGGGHGGGGHGGGGH AESKYGPPCPPCPAPEAAGGPSVFLFPPKPKDTLMISRTPEVTCVVVDVSQEDPE VQFNWYVDGVEVHNAKTKPREEQFNSTYRVVSVLTVLHQDWLNGKEYKCKV SNKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEA LHNHYTQKSLSLSLGAPAPAPAPAPCPEEP | 209 |
| GF98 | HGEGTFTSDVSSYLEEQAAKEFIAWLVKGGGGGGGAGGGGAGGGGAGGGGA AESKYGPPCPPCPAPEAAGGPSVFLFPPKPKDTLMISRTPEVTCVVVDVSQEDPE VQFNWYVDGVEVHNAKTKPREEQFNSTYRVVSVLTVLHQDWLNGKEYKCKV SNKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEA LHNHYTQKSLSLSLGAPAPAPAPAPCPEEP | 210 |
| GF99 | HGEGTFTSDVSSYLEEQAAKEFIAWLVKGGGPAPAPAPAPAPAPAPAPAPES KYGPPCPPCPAPEAAGGPSVFLFPPKPKDTLMISRTPEVTCVVVDVSQEDPEVQF NWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVMHEALHN HYTQKSLSLSLGAPAPAPAPAPCP | 211 |

TABLE 5-continued

GLP-1 fusion peptides

| GLP-1 Fusion (GF) | Peptide Sequence | SEQ ID NO: |
|---|---|---|
| GF100 | HGEGTFTSDVSSYLEEQAAKEFIAWLVKGGGPAPAPAPAPAPAPAPAPAAES KYGPPCPPCPAPEAAGGPSVFLFPPKPKDTLMISRTPEVTCVVVDVSQEDPEVQF NWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVMHEALHN HYTQKSLSLSLGAPAPAPAPAPAPCPEEP | 212 |
| GF101 | HGEGTFTSDVSSYLEEQAAKEFIAWLVKGGGPAPAPAPAPAPAPAPAPAPES KYGPPCPPCPAPEAAGGPSVFLFPPKPKDTLMISRTPEVTCVVVDVSQEDPEVQF NWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVMHEALHN HYTQKSLSLSLGAPAPAPAPAPCPEEP | 213 |
| GF102 | ESKYGPPCPPCPAPEAAGGPSVFLFPPKPKDTLMISRTPEVTCVVVDVSQEDPEV QFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIAV EWESNGQPENNYKTTPPVLDSDGSFFLYSRLTVDKSRWQEGNVFSCSVMHEAL HNHYTQKSLSLSLGGGGAPAPAPEEEPCA | 214 |
| GF103 | HGEGTFTSDVSSYLEEQAAKEFIAWLVKGGGGGGGAGGGGAGGGGAESKYGP PCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGAPAPAPEEEPCA | 215 |
| GF104 | HGEGTFTSDLSKQMEEEAVRLFIEWLKNGGGGSGGGGSGGGGSAESKYGPPCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGKGGGAPAPAPEEEPCA | 216 |
| GF105 | HGEGTFTSDLSKQMEEEAVRLFIEWLKNGGGGSGGGGSGGGGSAESKYGPPCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGGGGAPAPAPEEEPCA | 217 |
| GF106 | HGEGTFTSDLSKQMEEEAVRLFIEWLKNGGGGSGGGGSGGGGSAESKYGPPCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGGGGGGGGGGGGGGCA | 218 |
| GF107 | HGEGTFTSDLSKQMEEEAVRLFIEWLKNGGGGSGGGGSGGGGSAESKYGPPCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGGGGAGGGGAGGGACA | 219 |
| GF108 | HGEGTFTSDLSKQMEEEAVRLFIEWLKNGGGGSGGGGSGGGGSAESKYGPPCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGAPAPAPAPAPCP | 220 |
| GF109 | HGEGTFTSDLSKQMEEEAVRLFIEWLKNGGGGSGGGGSGGGGSAESKYGPPCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGAPAPAPAPAPCPEEP | 221 |

TABLE 5-continued

GLP-1 fusion peptides

| GLP-1 Fusion (GF) | Peptide Sequence | SEQ ID NO: |
|---|---|---|
| GF110 | HGEGTFTSDLSKQMEEEAVRLFIEWLKNGGGGAGGGGAGGGGAAESKYGPPC PPCPAPEAAGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKS LSLSLGKGGGAPAPAPEEEPCA | 222 |
| GF111 | HGEGTFTSDLSKQMEEEAVRLFIEWLKNGGGGAGGGGAGGGGAAESKYGPPC PPCPAPEAAGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKS LSLSLGGGGGGGGGGGGGGGGCA | 223 |
| GF112 | HGEGTFTSDVSSYLEEQAAKEFIAWLVKGGGGGGGAGGGGAGGGGAAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGGGGGGGGGGGGGCA | 224 |
| GF113 | HGEGTFTSDVSSYLEEQAAKEFIAWLVKGGGGGGGGAGGGGAGGGGAAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGGSGGGGSCA | 267 |
| GF114 | HGEGTFTSDLSKQMEEEAVRLFIEWLKNGGGGAGGGGAGGGGAAESKYGPPC PPCPAPEAAGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKS LSLSLGGGGGSGGGGSCA | 268 |
| GF115 | HGEGTFTSDVSSYLEEQAAKEFIAWLVKGGGGGGGGAGGGGAGGGGAAESKYG PPCPPCPAPEAAGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGGGGGSGGGGSGGGGSCA | 269 |
| GF116 | HGEGTFTSDLSKQMEEEAVRLFIEWLKNGGGGAGGGGAGGGGAAESKYGPPC PPCPAPEAAGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKS LSLSLGGGGGSGGGGSGGGGSCA | 270 |
| GF117 | HGEGTFTSDLSKQMEEEAVRLFIEWLKNGGGGSGGGGSGGGGSAESKYGPPCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGGGGSGGGGSCA | 271 |
| GF118 | HGEGTFTSDLSKQMEEEAVRLFIEWLKNGGPSSGAPPPSGGGGSGGGGSGGGGS AESKYGPPCPPCPAPEAAGGPSVFLFPPKPKDTLMISRTPEVTCVVVDVSQEDPE VQFNWYVDGVEVHNAKTKPREEQFNSTYRVVSVLTVLHQDWLNGKEYKCKV SNKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEA LHNHYTQKSLSLSLGGGGGSGGGGSCA | 272 |
| GF119 | HGEGTFTSDLSKQMEEEAVRLFIEWLKNGGGGSGGGGSGGGGSAESKYGPPCP PCPAPEAAGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGGGGSGGGGSGGGGSCA | 273 |
| GF120 | HGEGTFTSDLSKQMEEEAVRLFIEWLKNGGPSSGAPPPSGGGGSGGGGSGGGGS AESKYGPPCPPCPAPEAAGGPSVFLFPPKPKDTLMISRTPEVTCVVVDVSQEDPE VQFNWYVDGVEVHNAKTKPREEQFNSTYRVVSVLTVLHQDWLNGKEYKCKV SNKGLPSSIEKTISKAKGQPREPQVYTLPPSQEEMTKNQVSLTCLVKGFYPSDIA | 274 |

TABLE 5-continued

GLP-1 fusion peptides

| GLP-1 Fusion (GF) | Peptide Sequence | SEQ ID NO: |
|---|---|---|
| | VEWESNGQPENNYKTTPPVLDSDGSFFLYSRLTVDKSRWQEGNVFSCSVMHEA LHNHYTQKSLSLSLGGGGGSGGGGSGGGGSCA | |

Cyclic PYY Peptides $PYY_{3-36}$ is an endogenous hormone secreted by L cells in the distal gut that acts as an agonist of the Y2 receptor to inhibit food intake. Given its role in controlling appetite and food intake as well as its anti-secretory and pro-absorptive effects in the gastrointestinal tract in mammals, $PYY_{3-36}$ may be effective in treating obesity and associated conditions as well as in a number of gastrointestinal disorders. However, the therapeutic utility of $PYY_{3-36}$ itself as a treatment agent is limited by its rapid metabolism and short circulating half-life. Thus, the present invention is generally directed to modified $PYY_{3-36}$ conjugates, which extend the half-life of the $PYY_{3-36}$ peptide and reduces the metabolism of the peptide in vivo.

In certain embodiments of the invention, the modified $PYY_{3-36}$ peptides are cyclic PYY peptides. The terms "cyclic PYY peptide," "cyclic $PYY_{3-36}$ analog," and "cyclic $PYY_{3-36}$ peptide analog" can be used interchangeably. Examples of cyclic PYY peptides that can be used in the conjugates of the present invention are described in U.S. patent application Ser. No. 15/794,231, filed on Oct. 26, 2017, and U.S. patent application Ser. No. 15/794,171, filed on Oct. 26, 2017, the contents of both applications are hereby incorporated by reference in their entireties.

As used herein, the term "NTSC-PYY" is intended to describe N-terminus-to-side-chain cyclic analogues of PYY.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated. For convenience in describing the molecules of this invention, conventional and non-conventional abbreviations for various amino acids (both single and three-letter codes) and functional moieties are used. These abbreviations are familiar to those skilled in the art, but for clarity are listed as follows: A=Ala=alanine; R=Arg=arginine; N=Asn=asparagine; D=Asp=aspartic acid; βA=βAla=beta-alanine; C=Cys=cysteine; hC=hCys=homocysteine; E=Glu=glutamic acid; Q=Gln=glutamine; G=Gly=glycine; H=His=histidine; I=Ile=isoleucine; L=Leu=leucine; K=Lys=lysine; Nle=norleucine; F=Phe=phenylalanine; P=Pro=proline; S=Ser=serine; T=Thr=threonine; W=Trp=tryptophan; Y=Tyr=tyrosine and V=Val=valine.

For convenience, the amino acid residue numbering convention used in naming the NTSC-PYY peptides of the present invention follows that of $hPYY_{3-36}$. Specific amino acid replacements that have been introduced into the NTSC-PYY peptides, relative to the native residues at the corresponding positions in $hPYY_{3-36}$, are indicated by the appropriate amino acid code, followed by the position of the substitution. Thus, "S4" in the NTSC-PYY peptide refers to a peptide in which serine has replaced the corresponding native lys4 residue of $hPYY_{3-36}$. Similarly, "hC31" in the NTSC-PYY peptide refers to a peptide in which homocysteine has replaced the corresponding native val31 residue of $hPYY_{3-36}$. Additional amino acid replacements occurring within NTSC-PYY peptides are described according to this convention and will be recognized as such by one skilled in the art.

Also, for convenience, the naming convention used for the NTSC-PYY peptides of the present invention incorporates the amino acid residues involved in the cycle along with the linking group(s) between them in a left-to-right direction, starting from the N-terminal residue involved in the cycle. In all cases, the N-terminal amino acid residue of the cycle links by way of its α-amino functionality to the linking group, which in turn connects to the side chain residue of the amino acid at position 31 of the NTSC-PYY peptide. Thus, "cyclo-(I3-m-COPhCH$_2$-hC31)" is used to describe the cycle of an NTSC-PYY peptide in which the α-amino functionality of Ile3 is acylated with a meta-toluic acid residue, whose methyl group is further linked by way of a thioether bond to the side chain of a hCys31 residue. Similarly, "cyclo-(K4-CO(CH$_2$)$_2$NHCOCH$_2$-hC31)" is used to describe the cycle of an NTSC-PYY peptide, in which the native Ile3 residue has been deleted and whose (now N-terminal) α-amino functionality of lys4 is acylated by a 3-acetamidopropanoyl group, whose acetamido methylene carbon is connected to the side chain of a hCys31 residue by way of a thioether bond.

Lysine residues can be incorporated at various positions of the $hPYY_{3-36}$ sequence to provide a convenient functional handle for further derivatization. The lysine residues can be modified to be coupled to the GLP-1 fusion peptide indirectly. In an indirect coupling to the GLP-1 fusion peptide, the lysine residue can be modified to comprise a chemical linker which will allow for the cyclic PYY peptide to be coupled to the GLP-1 fusion peptide. One skilled in the art will recognize that related orthologues could also be effectively employed as such and are contemplated herein.

The term "K(PEG24-AcBr)" represents a lysinyl residue whose side chain ε-amino group has been acylated by N-bromoacetyl-75-amino-4,7,10,13,16,19,22,25,28,31,34, 37,40,43,46,49,52,55,58,61,64,67,70,73-tetracosaoxapentaheptacontanoic acid via its 1-carboxylic acid functionality.

The term "K(PEG12-AcBr)" represents a lysinyl residue whose side chain ε-amino group has been acylated by N-bromoacetyl-39-amino-4,7,10,13,16,19,22,25,28,31,34, 37-dodecaoxanonatriacontanoic acid via its 1-carboxylic acid functionality.

The term "K(PEG6-AcBr)" represents a lysinyl residue whose side chain ε-amino group has been acylated by N-bromoacetyl-3-[(17-amino-3,6,9,12,15-pentaoxaheptadec-1-yl)oxy]-propanoic acid via its 1-carboxylic acid functionality.

The term "K(PEG8-triazolyl-CH$_2$CH$_2$CO-PEG4-AcBr)" represents a lysinyl residue whose side chain ε-amino group has been acylated by 27-[4-[2-[3-[2-[2-[3-(N-bromoacetylamino)propoxy]ethoxy]ethoxy]propylaminocarbonyl]

ethyl]tetrazol-1-yl]-4,7,10,13,16,19,22,25-octaoxaheptacosanoic acid via its 1-carboxylic acid functionality.

Many of the compounds/conjugates of the present invention incorporate a reduced amide bond between the C-terminal residue of the sequence, Y36, and its adjacent residue, R35. This reduced amide linkage is represented by the term, "psi-(R35,Y36)".

Various amino acid residues comprising certain sequences of the present invention contain α-amino groups that have been methylated. Thus, the terms, "N-Me-Q34" or "N-Me-R35" represent α-N-methylated glutamine at position 34 of a sequence, and α-N-methylated arginine at position 35 of a sequence, respectively.

The term, "N-Me-Q34,psi-(R35,Y36)" in a sequence description refers to a sequence containing both an α-methyl glutamine residue at position 34, as well as a reduced amide bond between residues R35 and Y36.

Similarly, the term, "N-Me-R35, psi-(R35,Y36)" in a sequence description refers to a sequence containing both an α-methyl arginine residue at position 35, as well as a reduced amide bond between this residue and Y36.

Examples of cyclic PYY peptides are provided in Table 6.

TABLE 6

Cyclic PYY peptides

| SEQ ID NO: | Cyclic PYY Peptide Name |
|---|---|
| 1 | [cyclo-(βA2-COCH₂-hC31), K(PEG12-AcBr)11, psi-(35R, 36Y)]-PYY2-36 |
| 2 | [cyclo-(I3-CO(CH₂)₂triazolyl-Nle31), K(AcBr)11, N-Me-R35]-PYY3-36 |
| 3 | [cyclo-(I3-CO(CH₂)₂triazolyl-Nle31), K(AcBr)11, psi-(R35Y36)]-PYY3-36 |
| 4 | [cyclo-(G2-E31), S4, K(AcBr)11, psi-(R35, Y36)]-PYY2-36 |
| 5 | [cyclo-(βA2-COCH₂-hC31), K(PEG6-AcBr)11, psi-(R35, Y36)]-PYY2-36 |
| 6 | [cyclo-(βA2-COCH₂-hC31), K(AcBr)11, psi-(R35, Y36)]-PYY2-36 |
| 7 | [cyclo-(I3-COCH₂-C31), K(PEG12-AcBr)11, psi-(R35, Y36)]-PYY3-36 |
| 8 | [cyclo-(βA2-COCH₂-hC31), K(PEG12-AcBr)11, (N-Me)Q34, psi-(R35, Y36)]-PYY2-36 |
| 9 | [cyclo-(βA2-COCH₂-hC31), K(PEG12-AcBr)11, N-Me-R35, psi-(R35, 36Y)]-PYY2-36 |
| 10 | [cyclo-(βA2-COCH₂-hC31), R4, K(PEG12-AcBr)11, W30, psi-(R35, Y36)]-PYY2-36 |
| 11 | [cyclo-(I3-COCH₂CH₂NHCOCH₂-C31), R4, K(PEG12-AcBr)11, W30, psi-(R35, Y36)]-PYY3-36 |
| 12 | [cyclo-(K4-OEG-COCH₂-C31), K(PEG12-AcBr)11, psi-(R35 ,Y36)]-PYY4-36 |
| 13 | [cyclo-(I3-COCH₂CH₂triazolyl-Nle31), K(PEG12-AcBr)11, psi-(R35, Y36)]-PYY3-36 |
| 14 | [cyclo-(I3-m-CO-benzyl-hC31), K(PEG8-triazolyl-CH₂CH₂CO-PEG4-AcBr)11, psi-(R35, Y36)]-PYY3-36 |
| 15 | [cyclo-(βA2-COCH₂-hC31), K(PEG12-AcBr)23, psi-(R35, Y36)]-PYY2-36 |
| 16 | [cyclo-(βA2-COCH₂-hC31), K(PEG12-AcBr)22, psi-(R35, Y36)]-PYY2-36 |
| 17 | [cyclo-(βA2-COCH₂-hC31), K(PEG12-AcBr)7, psi-(R35, Y36)]-PYY2-36 |
| 18 | [cyclo-(G2-COCH₂-C30), K(AcBr)11, psi-(R35, Y36)]-PYY2-36 |
| 19 | [cyclo-(G2-COCH₂-C30), K(PEG12-AcBr)11, N-Me-R35]-PYY2-36 |
| 20 | [cyclo-(βA2-COCH₂-C30), K(PEG12-AcBr)11, N-Me-R35]-PYY2-36 |
| 21 | [cyclo-(G2-COCH₂-hC30), K(PEG12-AcBr)11, N-Me-R35]-PYY2-36 |
| 22 | [cyclo-(βA2-COCH₂-hC31), K(PEG12-AcBr)11, N-Me-R35]PYY2-36 |
| 23 | [cyclo-(G2-COCH₂-hC30), K(PEG12-AcBr)11, psi-(R35, Y36)]-PYY2-36 |
| 24 | [cyclo-(G2-E30), S4, K(AcBr)11, psi-(R35, Y36)]-PYY2-36 |
| 25 | [cyclo-(βA2-COCH₂-hC31), K(PEG24-AcBr)11, psi-(R35, Y36)]-PYY2-36 |
| 26 | [cyclo-(G2-COCH₂-hC31), K(AcBr)11, psi-(R35-Y36)]-PYY2-36 |
| 27 | [cyclo-(G2-COCH₂-C30), K(AcBr)11, N-Me-R35]-PYY2-36 |
| 28 | [cyclo-(βA2-COCH₂-C30), K(AcBr)11, N-Me-R35]-PYY2-36 |
| 29 | [cyclo-(βA2-COCH₂-C30), K(AcBr)11, psi-(R35, Y36)]-PYY2-36 |
| 30 | [cyclo-(G2-COCH₂-C30), K(AcBr)11, psi-(R35, Y36)]-PYY2-36 |
| 31 | [cyclo-(βA2-COCH₂-hC31), psi-(R35, Y36)]-PYY2-36 |
| 32 | [cyclo-(βA2-COCH₂-hC31), K(AcBr)11, N-Me-R35]-PYY2-36 |
| 33 | [cyclo-(G2-E30), S4, K(AcBr)11, N-Me-R35]-PYY2-36 |
| 34 | [cyclo-(γAba2-COCH₂-hC30), K(AcBr)11, N-Me-R35]-PYY2-36 |
| 35 | [cyclo-(I3-COCH₂-hC30), K(AcBr)11, N-Me-R35]-PYY3-36 |
| 36 | [cyclo-(I3-COCH₂-hC30), K(AcBr)11, psi-(R35, Y36)]]-PYY3-36 |
| 37 | [cyclo-(I3-COCH₂-C30), K(AcBr)11, N-Me-R35]-PYY3-36 |
| 38 | [cyclo-(I3-COCH₂-C30), K(AcBr)11, psi-(R35, Y36)]]-PYY3-36 |
| 39 | [cyclo-(I3-COCH₂-hC30), K(AcBr)11, psi-(R35, Y36)]]-PYY3-36 |
| 40 | [cyclo-(G2-COCH₂-hC31), K(AcBr)11, N-Me-R35]-PYY2-36 |
| 41 | [cyclo-(G2-COCH₂-hC31), K(AcBr)11, psi-(R35, Y36)]]-PYY2-36 |
| 42 | [cyclo-(γAba2-COCH₂-C30), K(AcBr)11, N-Me-R35]-PYY2-36 |
| 43 | [cyclo-(γAba2-COCH₂-C30), K(AcBr)11, psi-(R35, Y36)]-PYY2-36 |
| 44 | [cyclo-(γAba2-COCH₂-hC31), K(AcBr)11, N-Me-R35]-PYY2-36 |
| 45 | [cyclo-(γAba2-COCH₂-hC31), K(AcBr)11, psi-(R35, Y36]-PYY2-36 |
| 46 | [cyclo-(γAba2-COCH₂-C31), K(AcBr)11, N-Me-R35]-PYY2-36 |
| 47 | [cyclo-(γAba2-COCH₂-C31), K(AcBr)11, psi-(R35, Y36]-PYY2-36 |
| 48 | [cyclo-(δAva2-COCH₂-hC31), K(AcBr)11, N-Me-R35]-PYY2-36 |
| 49 | [cyclo-(δAva2-COCH₂-hC31), K(AcBr)11, psi-(R35, Y36]-PYY2-36 |
| 50 | [cyclo-(δAva2-COCH₂-C31), K(AcBr)11, N-Me-R35]-PYY2-36 |
| 51 | [cyclo-(δAva2-COCH₂-C31), K(AcBr)11, psi-(R35, Y36]-PYY2-36 |
| 52 | [cyclo-(βA2-COCH₂-C31), K(AcBr)11, N-Me-R35]-PYY2-36 |
| 53 | [cyclo-(βA2-COCH₂-C31), K(AcBr)11, psi-(R35, Y36]-PYY2-36 |
| 54 | [cyclo-(γAba2-COCH₂-hC31), K(AcBr)11, psi-(R35, Y36]-PYY2-36 |

Also provided herein are N-terminus to side chain cyclic analogues of PYY exhibiting at least 70%, 75% 80%, 85%, 90%, 95%, or 99% sequence identity to human PYY$_{3-36}$ (hPYY$_{3-36}$). As an example of a method for determination of the sequence identity between two analogues the two peptides

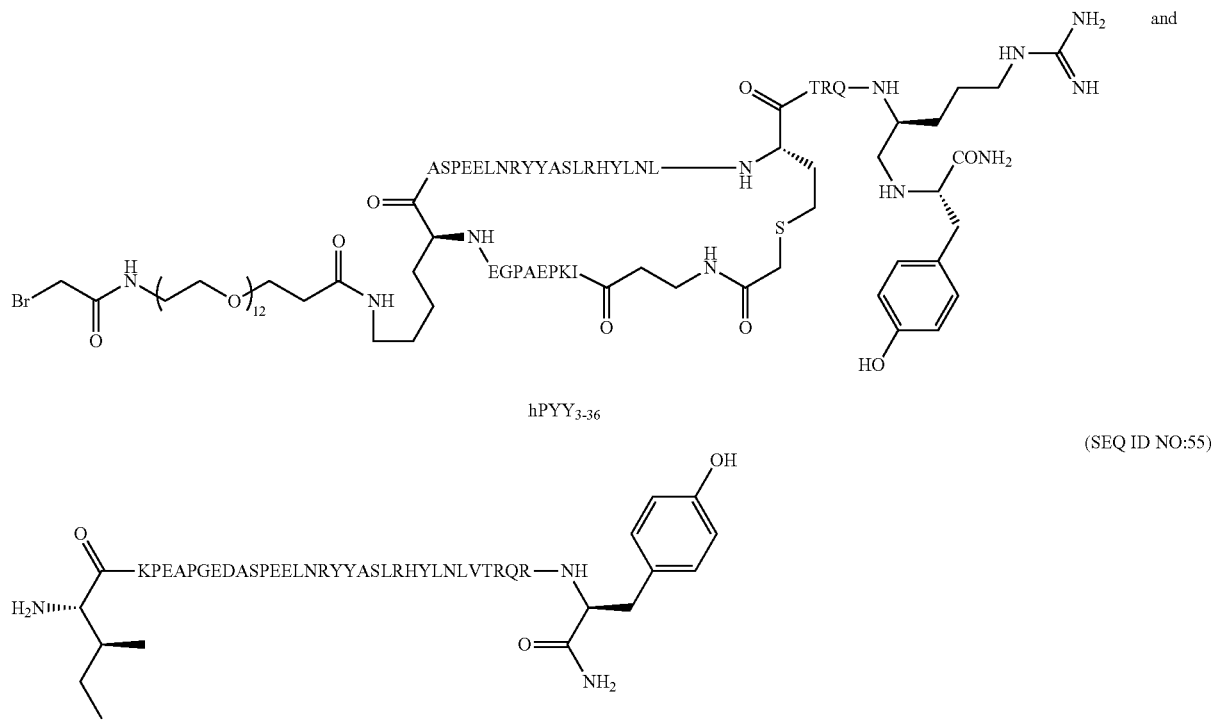

are aligned. The sequence identity of the analogue relative to hPYY$_{3-36}$ is given by the total number of aligned residues minus the number of different residues (i.e. the number of aligned identical residues) divided by the total number of residues in hPYY$_{3-36}$. In this example the different residues are D11 which has been exchanged for a substituted K11, followed by V31 which has been exchanged for hC31, and finally R35 has been decarbonylated. Accordingly, in said example the sequence identity is (34-3)/34×100.

Conjugates

In another general aspect, the invention relates to a conjugate comprising a GLP-1 fusion peptide of the invention covalently conjugated to a cyclic PYY peptide, in a site-specific manner, such that the GLP-1 fusion peptide coupled cyclic PYY peptide has an extended/increased half-life compared to the GLP-1 or GLP-1 variant peptide or cyclic PYY peptide alone. The invention also relates to pharmaceutical compositions and methods for use thereof. The conjugates are useful for preventing, treating, or ameliorating diseases or disorders, such as obesity, type 2 diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, among others.

In certain embodiments, the GLP-1 fusion peptide of the invention comprises at least one cysteine residue that is capable of being conjugated to the cyclic PYY peptide. In certain embodiments, the GLP-1 fusion peptide comprises an amino acid sequence selected from the group consisting of SEQ ID NOs:113-224 and 267-274. In certain embodiments, the GLP-1 fusion comprises an amino acid sequence selected from SEQ ID NO:113 or 136. In certain embodiments, the at least one cysteine residue is comprised in the second linker peptide of the GLP-1 fusion peptide. In certain embodiments, the cysteine residue is located between resides 287 and 289 of the GLP-1 fusion peptide of SEQ ID NO:113 or SEQ ID NO:136, preferably the cysteine residue is located at residue 288 of the GLP-1 fusion. In certain embodiments, the GLP-1 fusion peptide is covalently linked to a lysine residue at residue 7, 9, 11, 22, or 23 of the cyclic PYY peptide, preferably the lysine residue 11. In certain embodiments, the GLP-1 fusion peptide is covalently linked directly to the cyclic PYY peptide, or indirectly to the cyclic PYY peptide via a chemical linker on the cyclic PYY peptide.

In certain embodiments, the cyclic PYY peptide can comprise a chemical linker. The chemical linker can be modified chemically (e.g., an electrophilic group can be added to the linker) to allow for the conjugation of the GLP-1 fusion peptide to the cyclic PYY chemical linker. The chemical linker can, for example, include, but is not limited to, a peptide linker, a hydrocarbon linker, a polyethylene glycol (PEG) linker, a polypropylene glycol (PPG) linker, a polysaccharide linker, a polyester linker, a linker containing an acyl group, a hybrid linker consisting of PEG and an embedded heterocycle, or a hydrocarbon chain. The PEG linkers can, for example, comprise 2-24 PEG units.

Methods of conjugating GLP-1 fusion peptides of the invention with the cyclic PYY peptides of the invention are known in the art. Briefly, the GLP-1 fusion peptides of the invention can be reduced with a reducing agent (e.g., 1,3,5-triaza-7-phosphaadamantane (PTA)), purified (e.g., by desalting chromatography), and conjugated with the cyclic PYY peptide (e.g., by providing the reduced GLP-1 fusion peptide under conditions that allow for conjugation). During the conjugation reaction, the electrophilic leaving group of the cyclic PYY peptide is displaced and a covalent bond forms between the GLP-1 fusion peptide and the cyclic PYY peptide to form a GLP-1 fusion peptide coupled cyclic PYY peptide conjugate. After the conjugation reaction, the conjugate can be purified by ion exchange chromatography or hydrophobic interaction chromatography (HIC) with a final purification step of protein A adsorption. In certain embodiments, the GLP-1 fusion peptides of the invention can be purified prior to being reduced utilizing HIC methods. For more detailed description of the conjugation methods, see, e.g., Example 2.

Provided herein are conjugates comprising a glucagon-like peptide 1 (GLP-1)-fusion peptide coupled to a cyclic PYY peptide, wherein the GLP-1 fusion peptide comprises a GLP-1 peptide, a first linker peptide, a hinge-Fc region peptide, and a second linker peptide, wherein the first linker peptide is optionally absent.

In certain embodiments, the cyclic PYY peptide is represented by Formula I or a derivative or pharmaceutically acceptable salt thereof:

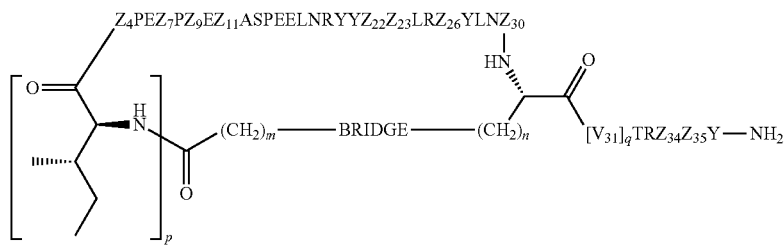

Formula I wherein
p is 0 or 1;
m is 0, 1, 2, 3, 4, or 5;
n is 1, 2, 3, or 4;
q is 0 or 1; provided that q is 1 only when $Z_{30}$ is absent;
BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;
$Z_4$ is K, A, E, S, or R;
$Z_7$ is A or K;
$Z_9$ is G or K;
$Z_{11}$ is D or K;
$Z_{22}$ is A or K;
$Z_{23}$ is S or K;
$Z_{26}$ is A or H;
$Z_{30}$ is L, W, absent,
provided that $Z_{30}$ is absent only when q is 1;
$Z_{34}$ is

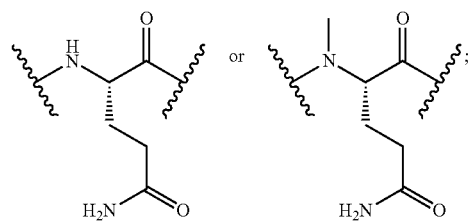 [SMILES: *N[C@@H](CCC(N)=O)C(*)=O ; *C(=O)[C@H](CCC(N)=O)N(*)C]

$Z_{35}$ is

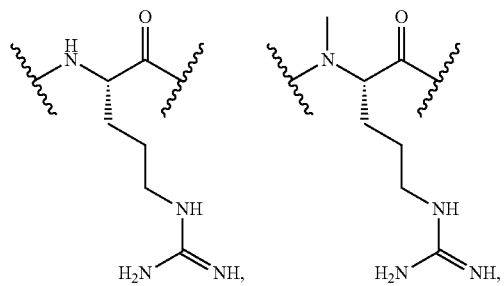

-continued

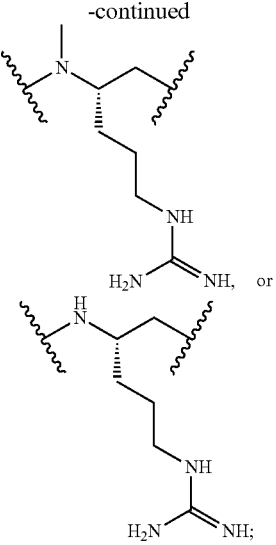

wherein the derivative is the compound of Formula I that is modified by one or more processes selected from the group consisting of amidation, acylation, and pegylation.

In certain embodiments, the cyclic PYY peptide is represented by Formula I or the derivative or pharmaceutically acceptable salt thereof, wherein:
p is 0 or 1;
m is 0, 1, 2, 3, 4, or 5;

n is 1, 2, 3, or 4;

q is 0 or 1; provided that q is 1 only when $Z_{30}$ is absent;

BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;

$Z_4$ is K, A, E, S, or R;

$Z_7$ is A or K, wherein the amino side chain of said K is optionally substituted with

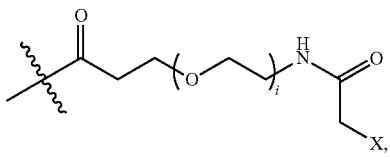

wherein i is an integer of 0 to 24, and X=Br, I or Cl, —C(O)CH$_2$Br, —C(O)CH$_2$I, or —C(O)CH$_2$Cl;

$Z_9$ is G or K, wherein the amino side chain of said K is optionally substituted with

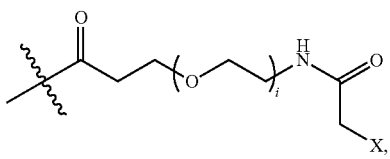

wherein i is an integer of 0 to 24, and X=Br, I or Cl, —C(O)CH$_2$Br, —C(O)CH$_2$I, or —C(O)CH$_2$Cl;

$Z_{11}$ is D or K, wherein the amino side chain of said K is optionally substituted with

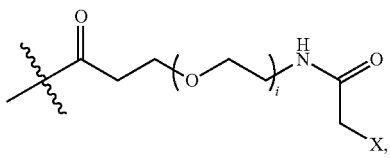

wherein i is an integer of 0 to 24, and X=Br, I or Cl, —C(O)CH$_2$I, —C(O)CH$_2$Cl or —C(O)CH$_2$Br;

$Z_{22}$ is A or K, wherein the amino side chain of said K is optionally substituted with

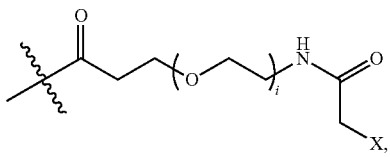

wherein i is an integer of 0 to 24, and X=Br, I or Cl, —C(O)CH$_2$Br, —C(O)CH$_2$I, or —C(O)CH$_2$Cl;

$Z_{23}$ is S or K; wherein the amino side chain of said K is optionally substituted with

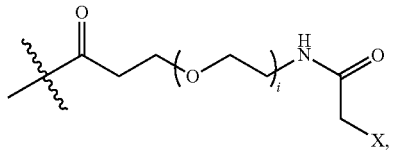

wherein i is an integer of 0 to 24, and X=Br, I or Cl, —C(O)CH$_2$Br, —C(O)CH$_2$I, or —C(O)CH$_2$Cl;

$Z_{26}$ is A or H;

$Z_{30}$ is L, W, absent, provided that $Z_{30}$ is absent only when q is 1;

$Z_{34}$ is

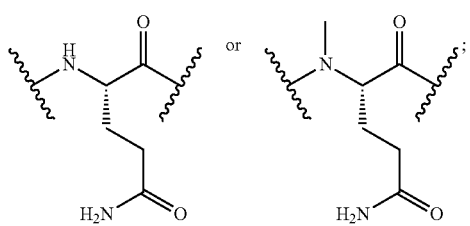 [SMILES: *N[C@@H](CCC(N)=O)C(*)=O ; *C(=O)[C@H](CCC(N)=O)N(*)C]

$Z_{35}$ is

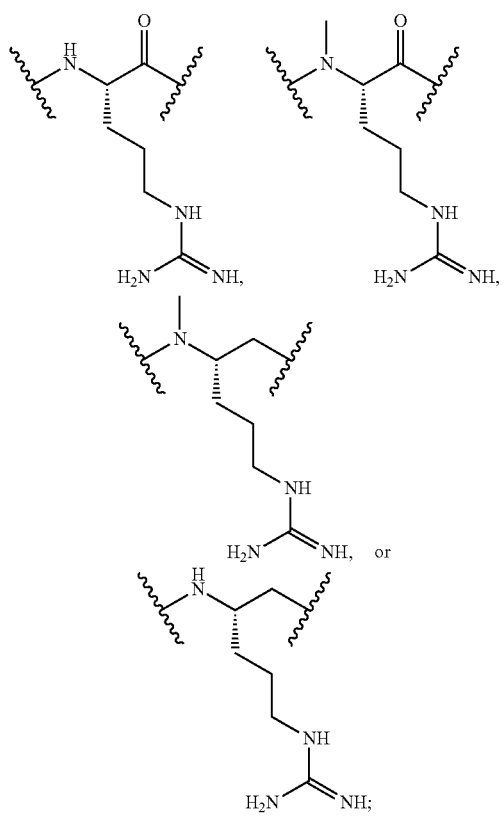

wherein X is an electrophilic group and the Br, Cl, or I of the X electrophilic group is displaced in the conjugation reaction to form the GLP-1 fusion peptide coupled cyclic PYY peptide conjugate.

In certain embodiments, the cyclic PYY peptide is represented by Formula I or the derivative or pharmaceutically acceptable salt thereof, wherein:

p is 0 or 1;
m is 0, 1, 2, 3, or 5;
n is 1, 2, or 4;
q is 0 or 1; provided that q is 1 only when $Z_{30}$ is absent;
BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;
$Z_4$ is K, A, E, S, or R;
$Z_7$ is A or K, wherein the amino side chain of said K is substituted with

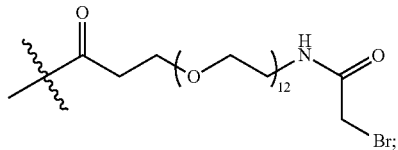

$Z_9$ is G or K;
$Z_{11}$ is D or K, wherein the amino side chain of said K is optionally substituted with

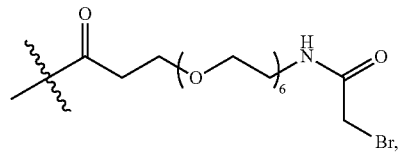

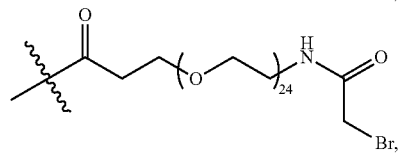

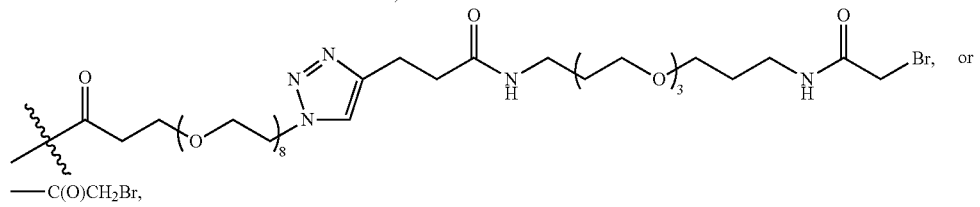

—C(O)CH$_2$Br, $Z_{22}$ is A or K, wherein the amino side chain of said K is substituted with

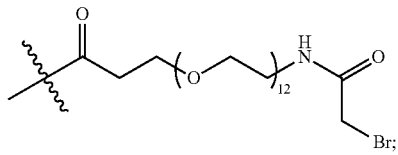

$Z_{23}$ is S or K, wherein the amino side chain of said K is substituted with

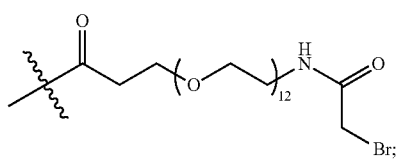

$Z_{26}$ is A or H;
$Z_{30}$ is L;
$Z_{34}$ is

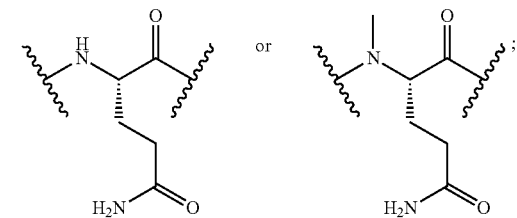 [SMILES: *N[C@@H](CCC(N)=O)C(*)=O ; *C(=O)[C@H](CCC(N)=O)N(*)C]

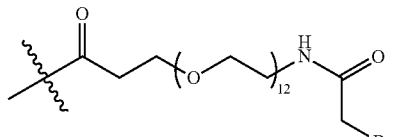

$Z_{35}$ is

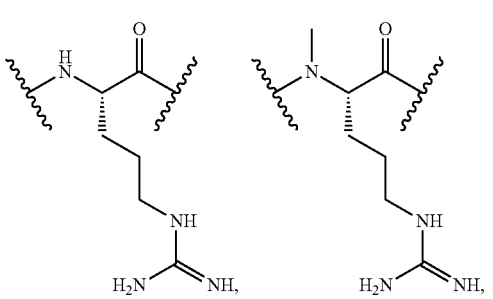

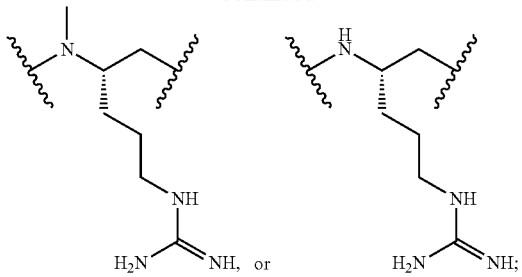

wherein the Br is displaced in the conjugation reaction to form the GLP-1 fusion peptide coupled cyclic PYY peptide conjugate.

In certain embodiments, a conjugate comprises a GLP-1 fusion peptide conjugated to a cyclic PYY peptide, wherein the cyclic PYY peptide is selected from the group consisting of SEQ ID NOs:1-54. In a preferred embodiment, the conjugate comprises a GLP-1 fusion peptide conjugated to a cyclic PYY peptide, wherein the cyclic PYY peptide is selected from SEQ ID NO:24, 25, 27, 28, 29, 30, 33, or 34.

In certain embodiments, the GLP-1 fusion peptide is covalently linked to the cyclic PYY peptide at a lysine residue of the cyclic PYY peptide via a chemical linker on the lysine residue. The chemical linker can, for example, comprise a linker selected from C(O)CH2, polyethylene glycol (PEG)8-triazolyl-CH2CH2CO-PEG4, a PEG chain of 2-24 PEG units, a linker containing an acyl group, or an alkyl chain containing 2-10 carbon atoms.

A GLP-1 fusion peptide according to an embodiment of the invention can be conjugated to a cyclic PYY peptide at one or more amino acid positions of the cyclic PYY peptide, such as amino acid residue 4, 7, 9, 10, 11, 13, 14, 15, 16, 17, 18, 19, 20, 21, 22, 23, 24, 26, 30, or 31 of the cyclic PYY peptide using methods known in the art. The amino acid residue numbering follows that of hPYY$_{3-36}$. In certain embodiments, only one of $Z_7$, $Z_9$, $Z_{11}$, $Z_{22}$ and $Z_{23}$ in Formula I is lysine, and the lysine is covalently linked to a cysteine residue in the second linker peptide of the GLP-1 fusion peptide. In a preferred embodiment, a GLP-1 fusion peptide according to an embodiment of the invention is conjugated to a cyclic PYY peptide at residue 11 of the cyclic PYY peptide, wherein residue 11 is a lysine. In another preferred embodiment, an electrophile, such as bromoacetamide or maleimide, is introduced onto a sidechain of a cyclic PYY peptide, such as the amino side chain of a lysine at residue 11 of the cyclic PYY peptide, and the electrophile reacts site specifically with the sulfhydryl group of the cysteine residue of the second linker peptide of the GLP-1 fusion peptide, preferably the second linker peptide of the GLP-1 fusion peptide is SEQ ID NO:93, 94, 95, 106, or 111, thereby creating a covalent linkage between the cyclic PYY peptide and the GLP-1 fusion peptide. More preferably, the cyclic PYY peptide is selected from SEQ ID NO:24, 25, 27, 28, 29, 30, 33, or 34. In one embodiment, the electrophile is introduced onto the sidechain of a cyclic PYY directly. In another embodiment, the electrophile is introduced onto the sidechain of a cyclic PYY indirectly via a chemical linker.

In certain embodiments, the cysteine residue of the second linker peptide of the GLP-1 fusion peptide is reduced by contacting the GLP-1 fusion peptide with an excess of an azaphosphine reducing agent, whereby the reduced cysteine residue is reacted with the electrophile. The azaphosphine reducing agent is 1,3,5-triaza-7-phosphatricyclo[3.3.1.1]decane (PTA) or a derivative thereof.

Also provided are pharmaceutical compositions comprising the conjugates of the invention and further comprising a pharmaceutically acceptable carrier.

Non-limiting examples of GLP-1 fusion peptide coupled cyclic PYY peptide conjugates are provided in Table 7.

TABLE 7

GLP-1 fusion peptide coupled cyclic PYY peptide conjugates

| GLP-1 Fusion (GF) | GLP-1 fusion SEQ ID NO: | Cyclic PYY Peptide | GLP-1 fusion peptide coupled cyclic PYY peptide conjugate SEQ ID NO: |
|---|---|---|---|
| GF1 | SEQ ID NO: 113 | SEQ ID NO: 27 | SEQ ID NO: 225 |
| GF1 | SEQ ID NO: 113 | SEQ ID NO: 28 | SEQ ID NO: 226 |
| GF1 | SEQ ID NO: 113 | SEQ ID NO: 29 | SEQ ID NO: 227 |
| GF1 | SEQ ID NO: 113 | SEQ ID NO: 30 | SEQ ID NO: 228 |
| GF24 | SEQ ID NO: 136 | SEQ ID NO: 27 | SEQ ID NO: 229 |
| GF24 | SEQ ID NO: 136 | SEQ ID NO: 28 | SEQ ID NO: 230 |
| GF24 | SEQ ID NO: 136 | SEQ ID NO: 29 | SEQ ID NO: 231 |
| GF24 | SEQ ID NO: 136 | SEQ ID NO: 30 | SEQ ID NO: 232 |
| GF70 | SEQ ID NO: 182 | SEQ ID NO: 27 | SEQ ID NO: 233 |
| GF11 | SEQ ID NO: 123 | SEQ ID NO: 27 | SEQ ID NO: 234 |
| GF28 | SEQ ID NO: 140 | SEQ ID NO: 27 | SEQ ID NO: 235 |
| GF67 | SEQ ID NO: 179 | SEQ ID NO: 27 | SEQ ID NO: 236 |
| GF27 | SEQ ID NO: 139 | SEQ ID NO: 27 | SEQ ID NO: 237 |
| GF23 | SEQ ID NO: 135 | SEQ ID NO: 27 | SEQ ID NO: 238 |
| GF54 | SEQ ID NO: 166 | SEQ ID NO: 27 | SEQ ID NO: 239 |
| GF63 | SEQ ID NO: 175 | SEQ ID NO: 27 | SEQ ID NO: 240 |
| GF64 | SEQ ID NO: 176 | SEQ ID NO: 27 | SEQ ID NO: 241 |
| GF22 | SEQ ID NO: 134 | SEQ ID NO: 27 | SEQ ID NO: 242 |
| GF49 | SEQ ID NO: 161 | SEQ ID NO: 27 | SEQ ID NO: 243 |
| GF34 | SEQ ID NO: 146 | SEQ ID NO: 25 | SEQ ID NO: 244 |
| GF35 | SEQ ID NO: 147 | SEQ ID NO: 27 | SEQ ID NO: 245 |
| GF65 | SEQ ID NO: 177 | SEQ ID NO: 27 | SEQ ID NO: 246 |
| GF45 | SEQ ID NO: 157 | SEQ ID NO: 27 | SEQ ID NO: 247 |
| GF40 | SEQ ID NO: 152 | SEQ ID NO: 27 | SEQ ID NO: 248 |
| GF40 | SEQ ID NO: 152 | SEQ ID NO: 33 | SEQ ID NO: 249 |
| GF40 | SEQ ID NO: 152 | SEQ ID NO: 24 | SEQ ID NO: 250 |
| GF19 | SEQ ID NO: 131 | SEQ ID NO: 27 | SEQ ID NO: 251 |
| GF8 | SEQ ID NO: 120 | SEQ ID NO: 27 | SEQ ID NO: 252 |
| GF34 | SEQ ID NO: 146 | SEQ ID NO: 34 | SEQ ID NO: 253 |
| GF42 | SEQ ID NO: 154 | SEQ ID NO: 27 | SEQ ID NO: 254 |
| GF59 | SEQ ID NO: 171 | SEQ ID NO: 27 | SEQ ID NO: 255 |
| GF60 | SEQ ID NO: 172 | SEQ ID NO: 27 | SEQ ID NO: 256 |
| GF61 | SEQ ID NO: 173 | SEQ ID NO: 27 | SEQ ID NO: 257 |
| GF63 | SEQ ID NO: 175 | SEQ ID NO: 28 | SEQ ID NO: 258 |
| GF63 | SEQ ID NO: 175 | SEQ ID NO: 29 | SEQ ID NO: 259 |
| GF40 | SEQ ID NO: 152 | SEQ ID NO: 28 | SEQ ID NO: 260 |
| GF40 | SEQ ID NO: 152 (monomer) | SEQ ID NO: 27 | SEQ ID NO: 261 |
| GF34 | SEQ ID NO: 146 | SEQ ID NO: 27 | SEQ ID NO: 262 |

Half-Life Extending Moieties

In addition to the GLP-1 fusion peptide, the conjugates of the invention can incorporate one or more other moieties for extending the half-life of the pharmaceutical active moiety (e.g., the cyclic PYY peptide), for example via covalent interaction. Exemplary other half-life extending moieties include, but are not limited to, albumin, albumin variants, albumin-binding proteins and/or domains, transferrin and fragments and analogues thereof. Additional half-life extending moieties that can be incorporated into the conjugates of the invention include, for example, polyethylene glycol (PEG) molecules, such as PEG5000 or PEG20,000, and the like, polylysine, octane, carbohydrates (dextran, cellulose, oligo- or polysaccharides) for desired properties. These moieties can be direct fusions with the protein scaffold coding sequences and can be generated by standard cloning and expression techniques. Alternatively, well known chemical coupling methods can be used to attach the moieties to recombinantly and chemically produced conjugates of the invention.

A pegyl moiety can, for example, be added to the peptide molecules of the invention by incorporating a cysteine residue to the C-terminus of the molecule and attaching a pegyl group to the cysteine using well known methods.

Peptide molecules of the invention incorporating additional moieties can be compared for functionality by several well-known assays. For example, the biological or pharmacokinetic activities of a therapeutic peptide of interest, alone or in a conjugate according to the invention, can be assayed using known in vitro or in vivo assays and compared.

Pharmaceutical Compositions

In another general aspect, the invention relates to a pharmaceutical composition, comprising the conjugates and compounds of the invention and a pharmaceutically acceptable carrier. The term "pharmaceutical composition" as used herein means a product comprising a conjugate of the invention together with a pharmaceutically acceptable carrier. Conjugates and compounds of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in a conjugated peptide pharmaceutical composition can be used in the invention.

Pharmaceutically acceptable acidic/anionic salts for use in the invention include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methyl sulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, chloroprocaine, choline, cyclohexylamine, diethanolamine, ethylenediamine, lithium, L-lysine, magnesium, meglumine, N-methyl-D-glucamine, piperidine, potassium, procaine, quinine, sodium, triethanolamine, or zinc.

In some embodiments of the invention, pharmaceutical formulations are provided comprising the conjugates of the invention in an amount from about 0.001 mg/ml to about 100 mg/ml, from about 0.01 mg/ml to about 50 mg/ml, or from about 0.1 mg/ml to about 25 mg/ml. The pharmaceutical formulation can have a pH from about 3.0 to about 10, for example from about 3 to about 7, or from about 5 to about 9. The formulation can further comprise at least one ingredient selected from a buffer system, preservative(s), tonicity agent(s), chelating agent(s), stabilizer(s) and surfactant(s).

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carriers can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of isotonic agents include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

The pharmaceutical composition of the invention can comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid can be present either in its free base form or in its salt form. Any stereoisomer (i.e., L, D, or a mixture thereof) of the amino acid base can be present. The amino acid base can be present individually or in the combination with other amino acid bases, in a concentration from about 0.01 mg/ml to about 50 mg/ml, for example from about 0.1 mg/ml to about 20 mg/ml. Pharmaceutical compositions comprising each one of these specific amino acid bases constitute alternative embodiments of the invention.

The pharmaceutically-acceptable salts of the conjugates of the invention include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups can be quaternized with, for example, alkyl halides.

The pharmaceutical compositions of the invention can be administered by any means that accomplish their intended purpose. Examples include administration by parenteral, subcutaneous, intravenous, intramuscular, intraperitoneal, transdermal, buccal or ocular routes. Administration can be by the oral route. Suitable formulations for parenteral administration include aqueous solutions of the active conjugates in water-soluble form, for example, water-soluble salts, acidic solutions, alkaline solutions, dextrose-water solutions, isotonic carbohydrate solutions and cyclodextrin inclusion complexes. In certain embodiments, the conjugates of the invention are administered peripherally.

The present invention also encompasses a method of making a pharmaceutical composition comprising mixing a pharmaceutically acceptable carrier with any of the conjugates of the present invention. Additionally, the present invention includes pharmaceutical compositions made by mixing one or more pharmaceutically acceptable carriers with any of the conjugates of the present invention.

Furthermore, the conjugates of the present invention can have one or more polymorph or amorphous crystalline forms and as such are intended to be included in the scope of the invention. In addition, the conjugates can form solvates, for example with water (i.e., hydrates) or common organic solvents. As used herein, the term "solvate" means a physical association of the conjugates of the present invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the conjugates of the present invention. Thus, in the methods of treatment of the present invention, the term "administering" shall encompass the means for treating, ameliorating or preventing a syndrome, disorder or disease described herein with the conjugates of the present invention or a polymorph or solvate thereof, which would obviously be included within the scope of the invention albeit not specifically disclosed.

In another embodiment, the invention relates to the conjugates of the invention for use as a medicament.

The present invention includes within its scope prodrugs of the conjugates of this invention. In general, such prodrugs will be functional derivatives of the conjugates which are readily convertible in vivo into the required conjugate. Thus, in the methods of treatment of the present invention, the term "administering" shall encompass the treatment of the various disorders described with the conjugate specifically disclosed or with a conjugate which may not be specifically disclosed, but which converts to the specified conjugate in vivo after administration to the patient. Conventional procedures for the selection and preparation of suitable prodrug derivatives are described, for example, in "Design of Prodrugs," Ed. H. Bundgaard, Elsevier, 1985.

Furthermore, it is intended that within the scope of the present invention, any element, in particular when mentioned in relation to the conjugates of the invention, shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively 12C, $^{13}C$ and $^{14}C$ and $^{16}O$ and $^{18}O$. The isotopes can be radioactive or non-radioactive. Radiolabeled conjugates of the invention may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Some conjugates of the present invention can exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the conjugates according to this invention have at least one stereo center, they can accordingly exist as enantiomers or diastereomers. It is to be understood that all such isomers and mixtures thereof are encompassed within the scope of the present invention.

Where the processes for the preparation of the conjugates according to the invention give rise to mixture of stereoisomers, these isomers can be separated by conventional techniques such as preparative chromatography. The conjugates can be prepared in racemic form, or individual enantiomers can be prepared either by enantiospecific synthesis or by resolution. The conjugates can, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The conjugates can also be resolved by formation of diastereomeric esters or amides, followed by chromatographic separation and removal of the chiral auxiliary. Alternatively, the conjugates can be resolved using a chiral column via high performance liquid chromatography (HPLC) or SFC. In some instances, rotamers of conjugates can exist which are observable by 1H NMR leading to complex multiplets and peak integration in the 1H NMR spectrum.

During any of the processes for preparation of the conjugates of the present invention, it can be necessary and/or desirable to protect sensitive or reactive groups on any of the molecules concerned. This can be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, each of which is herein incorporated by reference in its entirety for all purposes. The protecting groups can be removed at a convenient subsequent stage using methods known from the art.

Methods of Use

The present invention is directed to a method for preventing, treating or ameliorating a Y2 receptor mediated syndrome and/or a GLP-1 receptor mediated syndrome, disorder or disease in a subject in need thereof comprising administering to the subject in need thereof an effective amount of a conjugate, compound, or pharmaceutical composition of the invention.

The present invention also provides a method for preventing, treating, delaying the onset of, or ameliorating a disorder, disease, or condition or any one or more symptoms of said disorder, disease, or condition in a subject in need thereof, comprising administering to the subject in need thereof an effective amount of a conjugate, compound, or pharmaceutical composition of the invention.

According to particular embodiments, the disease disorder, or condition is selected from obesity, type I or II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and/or eczema.

According to particular embodiments, a therapeutically effective amount refers to the amount of therapy which is sufficient to achieve one, two, three, four, or more of the following effects: (i) reduce or ameliorate the severity of the disease, disorder, or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

As used herein, the terms "treat," "treating," and "treatment" are all intended to refer to an amelioration or reversal of at least one measurable physical parameter related the disease, disorder, or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

In one embodiment, the invention provides a method for preventing, treating, delaying the onset of, or ameliorating obesity, or any one or more symptoms of obesity in a subject in need thereof, the method comprising administering to the subject in need thereof an effective amount of a conjugate, compound, or pharmaceutical composition of the invention.

In one embodiment, the invention provides a method for reducing body weight in a subject in need thereof, the method comprising administering to the subject in need thereof an effective amount of a conjugate, compound, or pharmaceutical composition of the invention.

In some embodiments, the body weight of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to the body weight of a subject prior to administration of any of the conjugates, compounds, pharmaceutical compositions, forms, or medicaments of the invention described herein, or compared to control subjects not receiving any of the conjugates, compounds, compositions, forms, medicaments, or combinations of the invention described herein.

In some embodiments, the reduction in body weight is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of preventing, treating, delaying the onset of, or ameliorating a syndrome, disorder or disease, or any one or more symptoms of said syndrome, disorder, or disease in a subject in need thereof, wherein said syndrome, disorder or disease is selected from obesity, type I or type II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, comprising administering to the subject in need thereof an effective amount of a conjugate, compound, or pharmaceutical composition of the invention.

As used herein, metabolic syndrome refers to a subject having any one or more of the following: high blood sugar (e.g., high fasting blood sugar), high blood pressure, abnormal cholesterol levels (e.g., low HDL levels), abnormal triglyceride levels (e.g., high triglycerides), a large waistline (i.e., waist circumference), increased fat in the abdominal area, insulin resistance, glucose intolerance, elevated C-reactive protein levels (i.e., a proinflammatory state), and increased plasma plasminogen activator inhibitor-1 and fibrinogen levels (i.e., a prothrombotic state).

The present invention provides a method of reducing food intake in a subject in need thereof, the method comprising administering to the subject in need thereof an effective amount of a conjugate, compound, or pharmaceutical composition of the invention. In some embodiments, food intake of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to food intake of a subject prior to administration of any of the conjugates, compounds, compositions, forms, medicaments, or combinations of the invention described herein, or compared to control subjects not receiving any of the conjugates, compounds, compositions, forms, medicaments, or combinations of the invention described herein.

In some embodiments, the reduction in food intake is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of reducing glycated hemoglobin (A1C) in a subject in need thereof, the method comprising administering to the subject in need thereof an effective amount of a conjugate, compound, or pharmaceutical composition of the invention. In some embodiments, A1C of a subject is reduced, for example, by between about 0.001% and about 0.01%, between about 0.01% and about 0.1%, between about 0.1% and about 0.2%, between about 0.2% and about 0.3%, between about 0.3% and about 0.4%, between about 0.4% and about 0.5%, between about 0.5% and about 1%, between about 1% and about 1.5%, between about 1.5% and about 2%, between about 2% and about 2.5%, between about 2.5% and about 3%, between about 3% and about 4%, between about 4% and about 5%, between about 5% and about 6%, between about 6% and about 7%, between about 7% and about 8%, between about 8% and about 9%, or between about 9% and about 10% relative to the A1C of a subject prior to administration of any of the conjugates, compounds, compositions, forms, medicaments, or combinations of the invention described herein, or compared to control subjects not receiving any of the conjugates, compounds, compositions, forms, medicaments, or combinations of the invention described herein.

In other embodiments, methods are provided for reducing fasting blood glucose levels in a subject in need thereof, the methods comprising administering to the subject in need thereof an effective amount of a conjugate, compound, or pharmaceutical composition of the invention. Fasting blood glucose levels may be reduced to less than about 140 to about 150 mg/dL, less than about 140 to about 130 mg/dL, less than about 130 to about 120 mg/dL, less than about 120 to about 110 mg/dL, less than about 110 to about 100 mg/dL, less than about 100 to about 90 mg/dL, or less than about 90 to about 80 mg/dL, relative to the fasting blood glucose levels of a subject prior to administration of any of the conjugates, compounds, compositions, forms, medicaments, or combinations of the invention described herein, or compared to control subjects not receiving any of the conjugates, compounds, compositions, forms, medicaments, or combinations of the invention described herein.

The present invention provides a method of modulating Y2 receptor activity and GLP-1 receptor activity in a subject in need thereof, the method comprising administering to the subject in need thereof an effective amount of a conjugate, compound, or pharmaceutical composition of the invention. As used herein, "modulating" refers to increasing or decreasing receptor activity.

In some embodiments, an effective amount of a conjugate or compound of the invention or a form, composition or medicament thereof is administered to a subject in need thereof once daily, twice daily, three times daily, four times daily, five times daily, six times daily, seven times daily, or eight times daily. In other embodiments, an effective amount of a conjugate or compound of the invention or a form, composition or medicament thereof is administered to a subject in need thereof once every other day, once per week, twice per week, three times per week, four times per week, five times per week, six times per week, two times per month, three times per month, or four times per month.

Another embodiment of the invention comprises a method of preventing, treating, delaying the onset of, or ameliorating a disease, disorder or syndrome, or one or more symptoms of any of said diseases, disorders, or syndromes in a subject in need thereof, the method comprising administering to the subject in need thereof an effective amount of a conjugate, compound, or pharmaceutical composition of the invention in a combination therapy. In certain embodiments, the combination therapy is a second therapeutic agent. In certain embodiments, the combination therapy is a surgical therapy.

As used herein, the term "in combination," in the context of the administration of two or more therapies to a subject, refers to the use of more than one therapy.

As used herein, combination therapy refers to administering to a subject in need thereof one or more additional therapeutic agents, or one or more surgical therapies, concurrently with an effective amount of a conjugate or compound of the invention or a form, composition or medicament thereof. In some embodiments, the one or more additional therapeutic agents or surgical therapies can be administered on the same day as an effective amount of a conjugate of the invention, and in other embodiments, the one or more additional therapeutic agents or surgical therapies may be administered in the same week or the same month as an effective amount of a conjugate or compound of the invention.

The present invention also contemplates preventing, treating, delaying the onset of, or ameliorating any of the diseases, disorders, syndromes, or symptoms described herein in a subject in need thereof with a combination therapy that comprises administering to the subject in need thereof an effective amount of a conjugate, compound, or pharmaceutical composition of the invention, in combination with any one or more of the following therapeutic agents: a dipeptidyl peptidase-4 (DPP-4) inhibitor (e.g., sitagliptin, saxagliptin, linagliptin, alogliptin, etc.); a GLP-1 receptor agonist (e.g., short-acting GLP-1 receptor agonists such as exenatide and lixisenatide; intermediate-acting GLP-1 receptor agonists such as liraglutide; long-acting GLP-1 receptor agonists such as exenatide extended-release, albiglutide, dulaglutide); a sodium-glucose co-transporter-2 (SGLT-2) inhibitors (e.g., canaglifozin, dapaglifozin, empaglifozin, etc.); bile acid sequestrants (e.g., colesevelam, etc.); dopamine receptor agonists (e.g., bromocriptine quick-release); biguanides (e.g., metformin, etc.); insulin; oxyntomodulin; sulfonylureas (e.g., chlorpropamide, glimepiride, glipizide, glyburide, glibenclamide, glibornuride, glisoxepide, glyclopyramide, tolazamide, tolbutamide, acetohexamide, carbutamide, etc.); and thiazolidinediones (e.g., pioglitazone, rosiglitazone, lobeglitazone, ciglitazone, darglitazone, englitazone, netoglitazone, rivoglitazone, troglitazone, etc.). In some embodiments, the dose of the additional therapeutic agent(s) is reduced when given in combination with a conjugate or compound of the invention. In some embodiments, when used in combination with a conjugate or compound of the invention, the additional therapeutic agent(s) can be used in lower doses than when each is used singly.

The present invention contemplates preventing, treating, delaying the onset of, or ameliorating any of the diseases, disorders, syndromes, or symptoms described herein in a subject in need thereof, with a combination therapy that comprises administering to the subject in need thereof an effective amount of a conjugate, compound, or pharmaceutical composition of the invention in combination with a surgical therapy. In certain embodiments, the surgical therapy can be bariatric surgery (e.g., gastric bypass surgery, such as Roux-en-Y gastric bypass surgery; sleeve gastrectomy; adjustable gastric band surgery; biliopancreatic diversion with duodenal switch; intragastric balloon; gastric plication; and combinations thereof).

In embodiments in which the one or more additional therapeutic agents or surgical therapies is administered on the same day as an effective amount of a conjugate or compound of the invention, the conjugate or compound of the invention may be administered prior to, after, or simultaneously with the additional therapeutic agent or surgical therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

EMBODIMENTS

The invention provides also the following non-limiting embodiments.

Embodiment 1 is a conjugate comprising a glucagon-like peptide (GLP-1)-fusion peptide coupled to a cyclic PYY peptide, wherein the GLP-1 fusion peptide comprises a GLP-1 peptide, a first linker peptide, a hinge-Fc region peptide, and a second linker peptide, wherein the first linker peptide is optionally absent.

Embodiment 2 is the conjugate of embodiment 1, wherein the cyclic PYY peptide is represented by Formula I or a derivative or pharmaceutically acceptable salt thereof:

wherein p is 0 or 1;

m is 0, 1, 2, 3, 4, or 5;

n is 1, 2, 3, or 4;

q is 0 or 1; provided that q is 1 only when $Z_{30}$ is absent;

BRIDGE is -Ph-$CH_2$—S—, -triazolyl-, —NHC(O)$CH_2$S—, —S$CH_2$C(O)NH—, —(O$CH_2CH_2$)$_2$NHC(O)$CH_2$S, —NHC(O)—, or —$CH_2$S—;

$Z_4$ is K, A, E, S, or R;

$Z_7$ is A or K;

$Z_9$ is G or K;

$Z_{11}$ is D or K;

$Z_{22}$ is A or K;

$Z_{23}$ is S or K;

$Z_{26}$ is A or H;

$Z_{30}$ is L, W, or absent, provided that $Z_{30}$ is absent only when q is 1;

$Z_{34}$ is $Z_{35}$ is

-continued

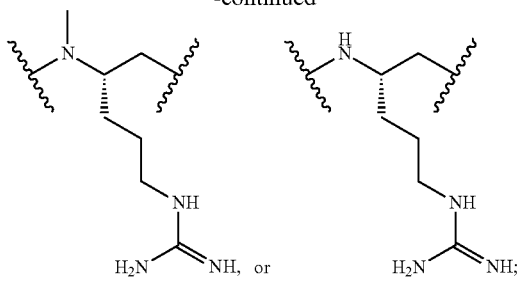

wherein the derivative is the compound of Formula I that is modified by one or more processes selected from the group consisting of amidation, acylation, and pegylation.

Embodiment 3 is the conjugate of embodiment 2, wherein the cyclic PYY peptide is represented by Formula I or the derivative or pharmaceutically acceptable salt thereof, wherein:
p is 0 or 1;
m is 0, 1, 2, 3, 4, or 5;
n is 1, 2, 3, or 4;
q is 0 or 1; provided that q is 1 only when $Z_{30}$ is absent;
BRIDGE is -Ph-CH$_2$—S—, -triazolyl-, —NHC(O)CH$_2$S—, —SCH$_2$C(O)NH$_2$—, —(OCH$_2$CH$_2$)$_2$NHC(O)CH$_2$S, —NHC(O)—, or —CH$_2$S—;
$Z_4$ is K, A, E, S, or R;
$Z_7$ is A or K, wherein the amino side chain of said K is optionally substituted with

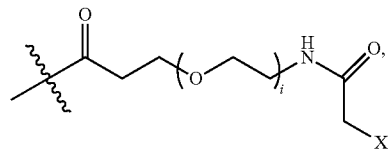

wherein i is an integer of 0 to 24, and X=Br, I or Cl, —C(O)CH$_2$Br, —C(O)CH$_2$I, or —C(O)CH$_2$Cl;
$Z_9$ is G or K, wherein the amino side chain of said K is optionally substituted with

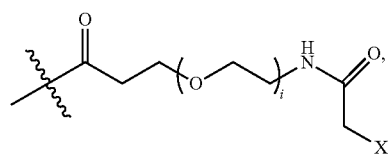

wherein i is an integer of 0 to 24, and X=Br, I or Cl, —C(O)CH$_2$Br, —C(O)CH$_2$I, or —C(O)CH$_2$Cl;
$Z_{11}$ is D or K, wherein the amino side chain of said K is optionally substituted with

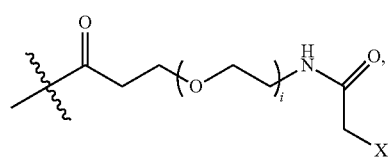

wherein i is an integer of 0 to 24, and X=Br, I or Cl, —C(O)CH$_2$Br, —C(O)CH$_2$I, or —C(O)CH$_2$Cl;

$Z_{22}$ is A or K, wherein the amino side chain of said K is optionally substituted with

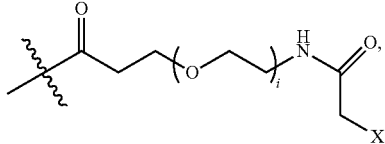

wherein i is an integer of 0 to 24, and X=Br, I or Cl, —C(O)CH$_2$Br, —C(O)CH$_2$I, or —C(O)CH$_2$Cl;
$Z_{23}$ is S or K, wherein the amino side chain of said K is optionally substituted with

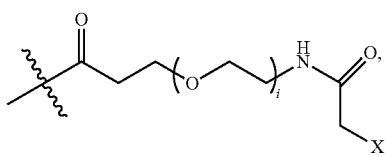

wherein i is an integer of 0 to 24, and X=Br, I or Cl, —C(O)CH$_2$Br, —C(O)CH$_2$I, or —C(O)CH$_2$Cl;
$Z_{26}$ is A or H;
$Z_{30}$ is L;
$Z_{34}$ is

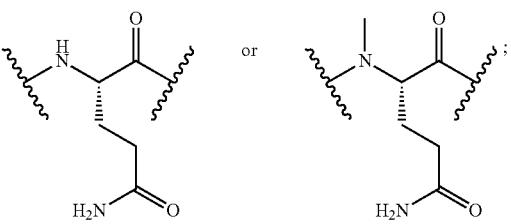 [SMILES: *N[C@@H](CCC(N)=O)C(*)=O ; *C(=O)[C@H](CCC(N)=O)N(*)C]

and
$Z_{35}$ is

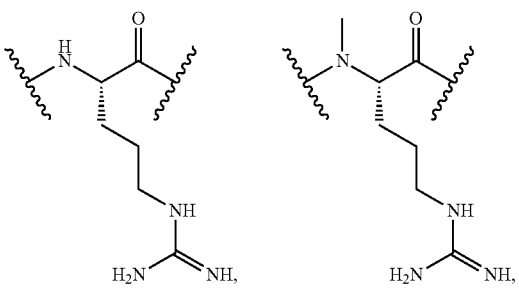

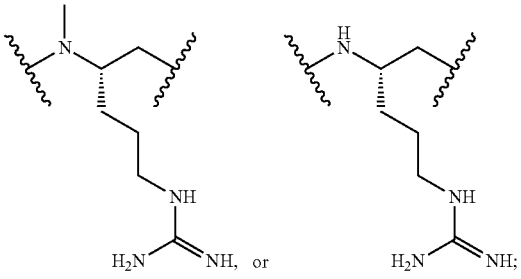

wherein X is an electrophilic group and the Br, Cl, or I of the X electrophilic group is displaced in the conjugation reaction to form the GLP-1 fusion peptide coupled cyclic PYY peptide conjugate.

Embodiment 4 is the conjugate of embodiment 2, wherein the cyclic PYY peptide is represented by Formula I or the derivative or pharmaceutically acceptable salt thereof, wherein:

p is 0 or 1;

m is 0, 1, 2, 3, or 5;

n is 1, 2, or 4;

q is 0 or 1; provided that q may be 1 only when $Z_{30}$ is absent;

BRIDGE is -Ph-CH$_2$—S—, -triazolyl-, —NHC(O)CH$_2$S—, —SCH$_2$C(O)NH$_2$—, —(OCH$_2$CH$_2$)$_2$NHC(O)CH$_2$S, —NHC(O)—, or —CH$_2$S—;

$Z_4$ is K, A, E, S, or R;

$Z_7$ is A or K, wherein the amino side chain of said K is substituted with

—C(O)CH$_2$Br, $Z_9$ is G or K, wherein the amino side chain of said K is substituted with —C(O)CH$_2$Br, $Z_{11}$ is D or K, wherein the amino side chain of said K is substituted with —C(O)CH$_2$Br, $Z_{22}$ is A or K, wherein the amino side chain of said K is substituted with —C(O)CH$_2$Br, $Z_{23}$ is S or K, wherein the amino side chain of said K is substituted with —C(O)CH$_2$Br, $Z_{26}$ is A or H;

$Z_{30}$ is L;

$Z_{34}$ is

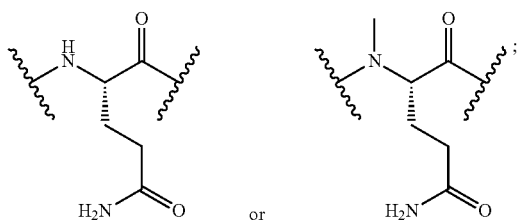 [SMILES: *N[C@@H](CCC(N)=O)C(*)=O ; *C(=O)[C@H](CCC(N)=O)N(*)C]

and $Z_{35}$ is

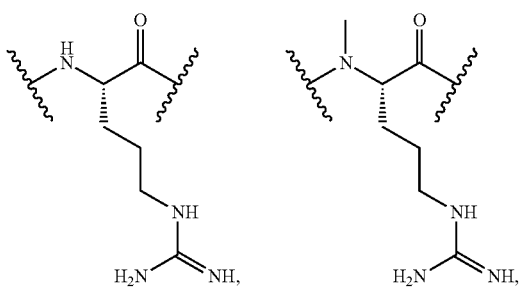

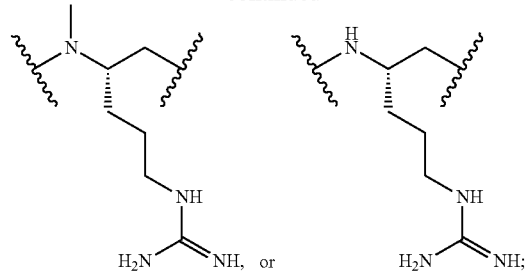

wherein the Br is displaced in the conjugation reaction to form the GLP-1 fusion peptide coupled cyclic PYY peptide conjugate.

Embodiment 5 is the conjugate of embodiment 1 or 2, wherein the cyclic PYY peptide is selected from the group consisting of SEQ ID NOs:1-54, or a pharmaceutically acceptable salt thereof.

Embodiment 6 is the conjugate of embodiment 5, wherein the cyclic PYY peptide is selected from SEQ ID NO: 24, 25, 27, 28, 29, 30, 33, or 34, or a pharmaceutically acceptable salt thereof.

Embodiment 7 is the conjugate of any one of embodiments 1-6, wherein the GLP-1 fusion peptide is covalently linked to the cyclic PYY peptide at a lysine residue of the cyclic PYY peptide.

Embodiment 8 is the conjugate of embodiment 7, wherein the cyclic PYY peptide comprises a chemical linker.

Embodiment 9 is the conjugate of embodiment 8, wherein the chemical linker comprises one selected from the group consisting of C(O)CH$_2$, polyethylene glycol (PEG)$_8$-triazolyl-CH$_2$CH$_2$CO-PEG4, a PEG chain of 2-24 PEG units, a linker containing an acyl group, and an alkyl chain containing 2-10 carbon atoms.

Embodiment 10 is the conjugate of any one of embodiments 7-9, wherein only one of $Z_7$, $Z_9$, $Z_{11}$, $Z_{22}$ and $Z_{23}$ in Formula I is lysine, and the lysine is covalently linked to a cysteine residue of the second linker peptide of the GLP-1 fusion peptide.

Embodiment 11 is the conjugate of embodiment 10, wherein $Z_{11}$ in Formula I is lysine.

Embodiment 12 is the conjugate of any one of embodiments 1-11, wherein the GLP-1 peptide comprises an amino acid sequence selected from the group consisting of SEQ ID NOs:56-59.

Embodiment 13 is the conjugate of embodiment 12, wherein the GLP-1 peptide comprises the amino acid sequence of SEQ ID NO:57.

Embodiment 14 is the conjugate of any one of embodiments 1-13, wherein the first linker peptide comprises an amino acid sequence selected from the group consisting SEQ ID NOs:60-83.

Embodiment 15 is the conjugate of embodiment 14, wherein the first linker peptide comprises the amino acid sequence of SEQ ID NO:60.

Embodiment 16 is the conjugate of any one of embodiments 1-15, wherein the hinge-Fc region peptide comprises an amino acid sequence selected from the group consisting of SEQ ID NOs:84-90.

Embodiment 17 is the conjugate of embodiment 16, wherein the hinge-Fc region peptide comprises an amino acid sequence of SEQ ID NO:84 or SEQ ID NO:85.

Embodiment 18 is the conjugate of any one of embodiments 1-17, wherein the second linker peptide comprises an amino acid sequence selected from the group consisting of SEQ ID NOs:93-112.

Embodiment 19 is the conjugate of embodiment 18, wherein the second linker peptide comprises the amino acid sequence of SEQ ID NO:93, 94, 95, 106, or 111.

Embodiment 20 is a conjugate comprising a glucagon-like peptide 1 (GLP-1) fusion peptide coupled to a cyclic PYY peptide, wherein the GLP-1 fusion peptide comprises an amino acid sequence selected from the group consisting of SEQ ID NOs:113-224 and 267-274, and wherein the cyclic PYY peptide comprises an amino acid sequence selected from SEQ ID NO:24, 25, 27, 28, 29, 30, 33, or 34.

Embodiment 21 is the conjugate of embodiment 20, wherein the GLP-1 fusion peptide comprises the amino acid sequence of SEQ ID NO:113.

Embodiment 22 is the conjugate of embodiment 20, wherein the GLP-1 fusion peptide comprises the amino acid sequence of SEQ ID NO:136.

Embodiment 23 is the conjugate of embodiment 21 or 22, wherein a cysteine residue between residues 287 to 289 of the GLP-1 fusion peptide is covalently linked to a lysine residue at residue 7, 9, 11, 22, or 23 of the cyclic PYY peptide.

Embodiment 24 is the conjugate of embodiment 23, wherein the cysteine residue is at residue 288 of the GLP-1 fusion peptide.

Embodiment 25 is the conjugate of any one of embodiments 20-24, wherein the lysine residue is at residue 11 of the cyclic PYY peptide.

Embodiment 26 is the conjugate of any one of embodiments 20-25, wherein the GLP-1 fusion peptide is covalently linked to the cyclic PYY peptide via a chemical linker on the cyclic PYY peptide.

Embodiment 27 is the conjugate of embodiment 26, wherein the chemical linker is selected from the group consisting of $C(O)CH_2$, polyethylene glycol (PEG)8-triazolyl-$CH_2CH_2CO$-PEG4, a PEG chain of 2-24 PEG units, a linker containing an acyl group, or an alkyl chain containing 2-10 carbon atoms.

Embodiment 28 is a conjugate comprising a glucagon-like peptide 1 (GLP-1) fusion peptide coupled to a cyclic PYY peptide, wherein the conjugate comprises a sequence selected from the group consisting of SEQ ID NOs:225-262 or a pharmaceutically acceptable salt thereof.

Embodiment 29 is the conjugate of any one of embodiments 1-28, wherein the GLP-1 fusion peptide is a monomer.

Embodiment 30 is the conjugate of any one of embodiments 1-28, wherein the GLP-1 fusion peptide is a dimer.

Embodiment 31 is a method of producing the conjugate of any one of embodiments 1-30, comprising reacting an electrophile, preferably bromoacetamide or maleimide, introduced onto a sidechain of the cyclic PYY peptide, preferably the amino sidechain of a lysine residue of the cyclic PYY peptide, with the sulfhydryl group of the cysteine residue of the second linker peptide of the GLP-1 fusion peptide, thereby creating a covalent linkage between the cyclic PYY peptide and the GLP-1 fusion peptide.

Embodiment 32 is the method of embodiment 31, wherein the cysteine residue of the second linker peptide of the GLP-1 fusion peptide is reduced by contacting the GLP-1 fusion peptide with an excess of an azaphosphine reducing agent, whereby the reduced cysteine residue is reacted with the electrophile.

Embodiment 33 is the method of embodiment 32, wherein the azaphosphine reducing agent is 1,3,5-triaza-7-phosphatricyclo[3.3.1.1] decane (PTA) or a derivative thereof.

Embodiment 34 is a pharmaceutical composition comprising the conjugate of any one of embodiments 1-30 and a pharmaceutically acceptable carrier.

Embodiment 35 is a method for treating or preventing obesity in a subject in need thereof, comprising administering to the subject in need thereof an effective amount of the pharmaceutical composition of embodiment 34.

Embodiment 36 is the method of embodiment 35, wherein administration of the effective amount of the pharmaceutical composition to the subject in need thereof results in a reduction in body weight of about 5% to about 10%, about 10% to about 15%, about 15% to about 20%, or about 20% to about 25% as compared to the body weight of the subject prior to administration of the pharmaceutical composition.

Embodiment 37 is a method for treating or preventing a disease or disorder in a subject in need thereof, wherein said disease or disorder is obesity, type I or type II diabetes, metabolic syndrome, insulin resistance, impaired glucose tolerance, hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and/or eczema, the method comprising administering to the subject in need thereof an effective amount of the pharmaceutical composition of embodiment 34.

Embodiment 38 is the method of embodiment 37, wherein said disease or disorder is obesity.

Embodiment 39 is the method of embodiment 37, wherein said disease or disorder is type I diabetes.

Embodiment 40 is the method of embodiment 37, wherein said disease or disorder is type II diabetes Embodiment 41 is the method of embodiment 37, wherein said disease or disorder is metabolic syndrome.

Embodiment 42 is the method of embodiment 37, wherein said disease or disorder is a renal disease.

Embodiment 43 is the method of embodiment 37, wherein said disease or disorder is non-alcoholic steatohepatitis (NASH).

Embodiment 44 is the method of embodiment 37, wherein said disease or disorder is non-alcoholic fatty liver disease (NAFLD).

Embodiment 45 is a method of reducing at least one of food intake or body weight in a subject in need thereof, the method comprising administering to the subject in need thereof an effective amount of the pharmaceutical composition of embodiment 34.

Embodiment 46 is the method of embodiment 45, wherein administration of the effective amount of the pharmaceutical composition to the subject in need thereof results in a reduction in food intake of about 5% to about 10%, about 10% to about 15%, about 15% to about 20%, about 20% to about 25%, about 25% to about 30%, about 30% to about 35%, about 35% to about 40%, about 40% to about 45%, or about 45% to about 50% as compared to the food intake of the subject prior to administration of the pharmaceutical composition.

Embodiment 47 is a method of modulating Y2 receptor activity and GLP-1 receptor activity in a subject in need thereof, the method comprising administering to the subject in need thereof an effective amount of the pharmaceutical composition of embodiment 34.

Embodiment 48 is the method of any one of embodiments 35-47, wherein the pharmaceutical composition is administered via an injection.

Embodiment 49 is the method of embodiment 48, wherein the injection is delivered subcutaneously, intramuscularly, intraperitoneally, or intravenously.

Embodiment 50 is the method of any one of embodiments 35-49, wherein the pharmaceutical composition is administered in a combination with a second therapeutic agent.

Embodiment 51 is the method of any one of embodiments 35-50, wherein the pharmaceutical composition is administered daily, weekly, or monthly to the subject in need thereof.

Embodiment 52 is the method of embodiment 51, wherein the pharmaceutical composition is administered once, twice, three, four, five, or six times per day.

Embodiment 53 is the method of embodiment 51, wherein the pharmaceutical composition is administered once, twice, three, four, five, or six times per week.

Embodiment 54 is the method of embodiment 51, wherein the pharmaceutical composition is administered once, twice, three, or four times per month.

Embodiment 55 is a kit comprising the conjugate of any one of embodiments 1-30 or a pharmaceutical composition of embodiment 34, preferably the kit further comprising an injection device.

Embodiment 56 is a method of producing a pharmaceutical composition comprising the conjugate of any one of embodiments 1-30, comprising combining the conjugate with a pharmaceutically acceptable carrier to obtain the pharmaceutical composition.

Embodiment 57 is an isolated hinge-Fc region platform peptide, wherein the hinge-Fc region platform peptide comprises a hinge-Fc region peptide, which preferably comprises an amino acid sequence selected from the group consisting of SEQ ID NOs:84-90, a first linker peptide, which preferably comprises an amino acid sequence selected from the group consisting of SEQ ID NOs:60-83 and the first linker peptide is optionally missing, and a second linker peptide comprising an amino acid sequence selected from SEQ ID NOs:91-112, wherein the first linker peptide is connected to the amino-terminal end of the hinge-Fc region peptide and the second linker peptide is connected to the carboxy-terminal end of the hinge-Fc region peptide.

Embodiment 58 is the isolated hinge-Fc region platform peptide of embodiment 57, wherein the hinge-Fc region peptide comprises an amino acid sequence of SEQ ID NO:84.

Embodiment 59 is the isolated hinge-Fc region platform peptide of embodiment 57 or 58, wherein the first linker peptide comprises an amino acid sequence of SEQ ID NO:60.

Embodiment 60 is the isolated hinge-Fc region platform peptide of any one of embodiments 57-59, wherein the second linker peptide comprises an amino acid sequence of SEQ ID NO:93, 94, 95, 106, or 111.

Embodiment 61 is a conjugate comprising the hinge-Fc region platform peptide linked covalently to a target peptide at the second linker peptide.

Embodiment 62 is the conjugate of embodiment 61, wherein the target peptide is a cyclic PYY peptide represented by Formula I or a derivative or pharmaceutically acceptable salt thereof:

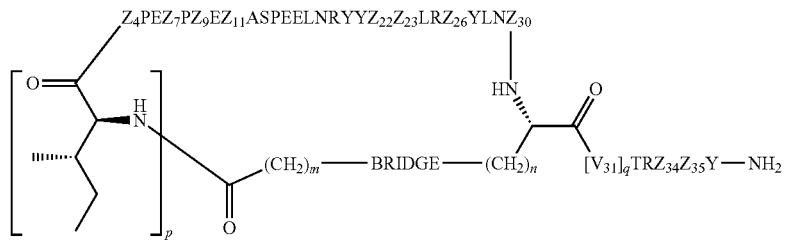

Formula I wherein p is 0 or 1;

m is 0, 1, 2, 3, 4, or 5;

n is 1, 2, 3, or 4;

q is 0 or 1; provided that q is 1 only when $Z_{30}$ is absent;

BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;

$Z_4$ is K, A, E, S, or R;

$Z_7$ is A or K;

$Z_9$ is G or K;

$Z_{11}$ is D or K;

$Z_{22}$ is A or K;

$Z_{23}$ is S or K;

$Z_{26}$ is A or H;

$Z_{30}$ is L, W, or absent, provided that $Z_{30}$ is absent only when q is 1;

$Z_{34}$ is

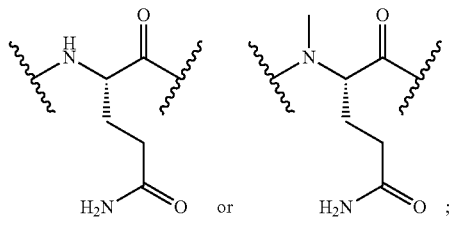 [SMILES: *N[C@@H](CCC(N)=O)C(*)=O ; *C(=O)[C@H](CCC(N)=O)N(*)C]

$Z_{35}$ is

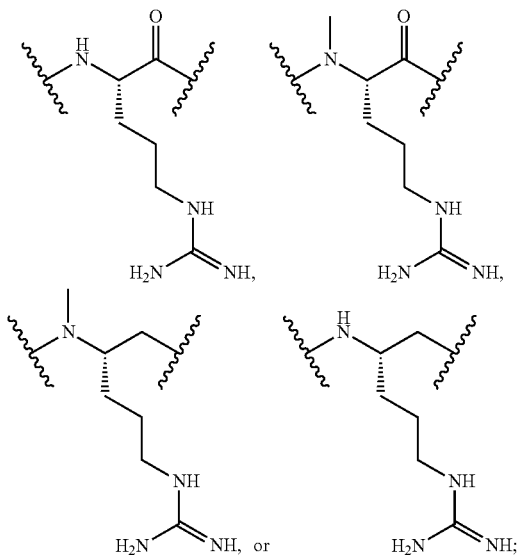

wherein the derivative is the compound of Formula I that is modified by one or more processes selected from the group consisting of amidation, acylation, and pegylation.

Embodiment 63 is a method of producing a conjugate of the hinge-Fc region platform peptide with a target peptide, comprising creating a covalent linkage between the second linker peptide and the target peptide.

EXAMPLES

Synthesis

Compounds or conjugates of the present invention can be synthesized in accordance with general synthetic methods known to those who are skilled in the art. The following description of the synthesis is for exemplary purposes and is in no way meant to be a limit of the invention.

The NTSC cyclic PYY (NTSC-PYY) analogues or derivatives of this invention can be synthesized by a variety of known, conventional procedures for the formation of successive peptide linkages between amino acids, and are preferentially carried out by solid phase peptide synthesis (SPPS), as generally described by Merrifield (J. Am. Chem. Soc., 85:2149-2154 (1963)), using an automated peptide synthesizer, traditional bench synthesis, or a combination of both approaches. Conventional procedures for peptide synthesis involve the condensation between the free amino group of one amino acid residue, whose other reactive functionalities have been suitably protected, and the free carboxyl group of another amino acid, whose reactive functionalities have also been suitably protected. Examples of condensation agents typically utilized for peptide bond formation include diisopropylcarbodiimide (DIC) with or without 1-hydroxybenztriazole (HOBT) or ethyl cyano(hydroxyimino)acetate (Oxyma Pure), 2-(1H-benzotriazol-1-yl)-1,1,3,3-tetramethylaminium hexafluorophosphate (HBTU), 2-(1H-7-azabenztriazol-1-yl)-1,1,3,3-tetramethylaminium hexafluorophosphate (HATU), 2-(6-chloro-1H-benztriazol-1-yl)-1,1,3,3-tetramethylaminium hexafluorophosphate (HCTU), 1-cyano-2-ethoxy-2-oxoethylideneaminooxy-tris-pyrrolidino-phosphonium hexafluorophosphate (PyOxim), 2-(1H-benzotriazol-1-yl)-1,3,3-tetramethylaminium tetrafluoroborate (TBTU) bromo-tris-pyrrolidino-phosphonium hexafluorophosphate (Py-BroP), and the like.

The automated peptide synthetic methodology may be carried out at room temperature (rt), or at elevated temperatures, preferably through the application of microwave heating, as described by Yu (J. Org. Chem., 57:4781-4784 (1992)) and as more recently refined by Palasek (J. Pept. Sci., 13:143-148 (2007)).

Compounds of the present invention (C-terminal amides) can be conveniently prepared using N-α-FMOC (9-fluroenylmethyloxycarbonyl) protected amino acid methodology, whereby the carboxy terminus of a suitably protected N-α-FMOC protected amino acid is coupled onto a conventional solid phase resin using a suitable coupling agent. Suitable conventional, commercially-available solid phase resins include Rink amide MBHA resin, Rink amide AM resin, Tentagel S RAM Resin, FMOC-PAL-PEG PS resin, SpheriTide Rink amide resin, ChemMatrix Rink resin, Sieber amide resin, TG Sieber resin and the like. The resin-bound FMOC-amino acid may then be deprotected by exposure to 20% piperidine in either N,N-dimethylformamide (DMF) or 1-methyl-2-pyrrolidone (NMP), treatment of which serves to selectively remove the FMOC protecting group. Additional FMOC-protected amino acids are then subsequently coupled and deprotected sequentially, thereby generating the desired resin-bound protected peptide. In certain instances, it may be necessary to utilize an orthogonally reactive protecting group for another amine in the peptide sequence that would withstand the FMOC deprotection conditions. Protecting groups such 4-methyltrityl (Mtt) or 4-methoxytrityl (Mmt), both removable by 1% trifluoroacetic acid (TFA)/dichloromethane (DCM) treatments, or preferably allyloxycarbonyl (alloc; removable by Pd(PPh$_3$)$_4$ (tetrakis(triphenylphosphine)palladium(0))/PhSiH$_3$ (phenylsilane) treatment), 1-(4,4-dimethyl-2,6-dioxocyclohex-1-yliden)ethyl (Dde; removable by treatment with 2-3% hydrazine/DMF) and 1-(4,4-dimethyl-2,6-dioxocyclohex-1-yliden)-3-methylbutyl (ivDde; removable by treatment with 2-3% hydrazine/DMF) can be used effectively in such instances.

In conventional peptide synthetic methodologies, reactive side chains of alpha amino acids are generally protected throughout the synthesis with suitable protecting groups to render them inert to the coupling and deprotection protocols. While multiple protecting groups for amino acid side chains are known in the art, herein the following protecting groups are most preferred: tert-butyl (t-Bu) for serine, threonine, glutamic acid, aspartic acid and tyrosine; trityl (Trt) for asparagine, glutamine, cysteine, homocysteine and histidine; tert-butyloxycarbonyl (Boc) for tryptophan and the ε-amino group of lysine; and 2,2,4,6,7-pentamethyldihydrobenzofuran-5-sulfonyl (Pbf) for arginine. These protecting groups are removed upon strong acid treatment, such as with high concentrations of trifluoroacetic acid (TFA).

Upon completion of the SPPS, the resin-bound, side chain-protected peptide is deprotected and concomitantly cleaved from the resin using a cleavage cocktail that consists predominantly of (TFA) along with various combinations of carbocation scavengers, such as triisopropylsilane (TIPS), water, phenol and anisole. The crude solid peptide is then isolated by precipitation of the peptide/cocktail filtrate with cold ether. In the special case of Sieber resin-bound protected peptides, cleavage of the protected peptide from the resin can be advantageously affected upon repeated treatment with 1-2% TFA in DCM without causing side chain deprotections. Once isolated, further manipulations of the protected peptide may be carried out in solution phase reactions. Finally, the protected peptide can be globally deprotected using a separate treatment with the cleavage cocktail and precipitated as described above. The crude peptide thus obtained is then dissolved at low concentration (ca., <4 mg/mL) in a largely aqueous (aq) solvent system containing an organic co-solvent such as acetonitrile or ethanol. Upon raising the pH of the solution to a >5, the peptide then undergoes an intramolecular cyclization reaction to form the corresponding crude NTSC PYY analogue of the present invention. NTSC PYY analogues thus formed can be purified using purification techniques generally known in the art. A preferable method of peptide purification used herein is reverse phase high performance liquid chromatography (HPLC). Purified peptides are then characterized by liquid chromatography/mass spectrometry (LC/MS).

General schemes and methods for producing the cyclic PYY peptides of the invention are described in U.S. patent application Ser. No. 15/794,231, filed on Oct. 26, 2017, and U.S. patent application Ser. No. 15/794,171, filed on Oct. 26, 2017. The contents of both applications are hereby incorporated by reference in their entireties.

It is understood that the following examples and embodiments described herein are for illustrative purposes only and that various modifications or changes in light thereof will be suggestive to persons skilled in the art and are to be included within the spirit and purview of this application and the scope of the appended claims. All publications, patents, and patent applications cited herein are hereby incorporate by reference in their entirety for all purposes.

Example 1: Expression and Purification of Glucagon-Like Peptide 1 (GLP-1) Fusion Peptides from Transiently Transfected Mammalian Cells The DNA constructs for the GLP-1 fusion peptides were generated by cloning synthesized gene fragments into the pCDNA3.1 derived mammalian expression vector using different designed endonuclease restriction enzymes. The synthesized gene fragments were designed to comprise DNA sequences encoding one or all of the following components of the fusion protein (from N-terminus to the C-terminus): GLP-1 peptide or GLP-1 variant peptide, a first linker peptide, a hinge-Fc region peptide, and a second linker peptide, which contains the Cys for conjugation to the cyclic PYY peptide.

GLP-1 fusion proteins were expressed in ExpiCHO-S™ cells (ThermoFisher Scientific; Waltham, Mass., Cat #A29127) by transient transfection of the cells with purified plasmid DNA of a fusion protein expression construct following manufacturer's recommendations. Briefly, ExpiCHO-S™ cells were maintained in suspension in ExpiCHO™ expression medium (ThermoFisher Scientific, Cat #A29100) in a shaking incubator set at 37° C., 8% $CO_2$ and 125 RPM. The cells were passaged and diluted to $6.0\times10^6$ cells per ml, maintaining cell viability at 98% or better. Transient transfections were done using the ExpiFectamine™ CHO transfection kit (ThermoFisher Scientific Cat #A29131). For each ml of diluted cells to be transfected, one microgram of plasmid DNA was used and diluted into OptiPRO™ SFM complexation medium. ExpiFectamine™ CHO reagent was used at a 1:3 ratio (v/v, DNA:reagent) and also diluted into OptiPRO™. The diluted DNA and transfection reagent were combined for one minute, allowing DNA/lipid complex formation, and then added to the cells. After overnight incubation, ExpiCHO™ feed and ExpiFectamine™ CHO enhancer were added to the cells. Cells were cultured with shaking at 37° C. for five days prior to harvesting the culture supernatants.

Culture supernatants from the transiently transfected ExpiCHO-S™ cells were harvested by clarifying through centrifugation (30 min, 6000 rpm) followed by filtration (0.2µ PES membrane, Corning; Corning, N.Y.). Large scale transfections (5 to 20 liters) were first concentrated 10-fold using a Pall Centramate Tangential Flow Filtration system. 10×DPBS, pH7.2 was added to the supernatant to a 1× final concentration prior to loading onto an equilibrated (DPBS, pH 7.2) HiTrap MabSelect Sure Protein A column (GE Healthcare; Little Chalfont, United Kingdom) at a relative concentration of ~20 mg protein per ml of resin, using an AKTA FPLC chromatography system. After loading, the column was washed sequentially with 10 column volumes of DPBS, pH7.2. In some instances, additional washes of 20 column volumes of 100 mM Tris, 2.5M NaCl, 50 mM Sodium caprylate, pH 9 and 10 column volumes of DPBS, pH7.2 were included. The protein was eluted with 10 column volumes of 0.1 M sodium (Na)-Acetate, pH 3. Protein fractions were neutralized immediately by elution into tubes containing 2.0 M Tris, pH 7 at 20% the elution fraction volume. Peak fractions were pooled, and the pH adjusted to ~7 with additional Tris, if necessary. The purified protein was filtered (0.2µ) and the concentration was determined by absorbance at 280 nm on a BioTek Synergy™ HTM spectrophotometer. The quality of the purified protein was assessed by SDS-PAGE and analytical size exclusion HPLC (Dionex™ HPLC system). The endotoxin level was measured using a turbidometric LAL assay (Pyrotell®-T, Associates of Cape Cod; Falmouth, Mass.).

Alternately, GLP-1 fusion proteins were expressed in Expi293F cells (ThermoFisher Scientific, Cat #A14527) by transient transfection of the cells with purified plasmid DNA of a fusion protein expression construct following the manufacturer's recommendations. Briefly, Expi293F cells were maintained in suspension in Expi293™ expression medium (ThermoFisher Scientific, Cat #A1435101) in a shaking incubator set at 37° C., 8% $CO_2$ and 125 RPM. The cells were passaged and diluted to $2.5\times10^6$ cells per ml, maintaining cell viability at 95% or better. Transient transfections were done using the ExpiFectamine™ 293 transfection kit (ThermoFisher Scientific Cat #A14525). For each ml of diluted cells to be transfected, one microgram of plasmid DNA was used and diluted into OptiMEM™ SFM complexation medium. ExpiFectamine™ 293 reagent was used at a 1:2.6 ratio (v/v, DNA:reagent), was diluted into OptiMEM™, and was allowed to incubate for 5 minutes at room temperature. The diluted DNA and transfection reagent were combined for twenty minutes, allowing DNA/lipid complex formation, and then added to the cells. After overnight incubation, Expi293™ feed and ExpiFectamine™ 293 enhancer were added to the cells. Cells were cultured with shaking at 37° C. for four days prior to harvesting the culture supernatants.

Culture supernatants from the transiently transfected Expi293F cells were harvested by clarifying through centrifugation (30 min, 6000 rpm) followed by filtration (0.2µ PES membrane, Corning). 10×DPBS, pH7.2 was added to the supernatant to a 1× final concentration prior to loading onto an equilibrated (DPBS, pH 7.2) HiTrap MabSelect Sure Protein A column (GE Healthcare) at a relative concentration of ~20 mg protein per ml of resin, using an AKTA FPLC chromatography system. After loading, the column was washed with 10 column volumes of DPBS, pH7.2. The protein was eluted with 10 column volumes of 0.1 M Na-Acetate, pH 3. Protein fractions were neutralized immediately by elution into tubes containing 2.0 M Tris, pH 7 at 20% the elution fraction volume. Peak fractions were pooled, and the pH was adjusted to ~5.5 with additional Tris, if necessary. The purified protein was filtered (0.2µ) and the concentration was determined by absorbance at 280 nm on a BioTek Synergy™ HTM spectrophotometer. The quality of the purified protein was assessed by SDS-PAGE and analytical size exclusion HPLC (Dionex™ HPLC system). The endotoxin level was measured using a turbidometric LAL assay (Pyrotell®-T, Associates of Cape Cod).

GLP-1 fusion proteins with a first linker peptide comprising the amino acid sequence of SEQ ID NO:61, which is a polyglycine linker, expressed at a low level and had low purification yields. Thus, the use of polyglycine for the first linker peptides was disfavored in this experiment when engineering GLP-1 fusion proteins.

GLP-1 fusion proteins with a second linker peptide comprising the amino acid sequence of SEQ ID NO:100 were truncated and determined to not be the expected molecular weight when analyzed by mass spectrometry. Thus, the use of a second linker peptide of SEQ ID NO:100 was disfavored in this experiment when engineering GLP-1 fusion proteins.

Additionally, when preparing GLP-1 fusion peptide constructs, the carboxy-terminal lysine of the hinge-Fc region peptide (i.e., the human IgG4) was deleted from the final construct to avoid potential proteolytic liability.

Example 2: Production of GLP-1 Fusion Peptide Coupled Cyclic PYY Peptide Conjugates Reduction of GLP-1 Fusion Proteins
Method A
The purified GLP-1 fusion proteins are a mixture of the recombinant proteins with the engineered second linker peptides containing at least one cysteine residue in each linker, of which is either intramolecularly disulfide bonded to the other cysteine or to adventitious cysteine residues in the cytosol or the growth medium. To such a heterogeneous GLP-1 fusion protein solution (5-12 mg/mL in TrisOAc, pH 5.4-6.4) was added an excess amount of a phosphine reducing reagent 1,3,5-triaza-7-phosphaadamantane (PTA, 15-40 equiv.) followed by addition of 100 mM EDTA (final concentration 1-2 mM). The resulting reaction mixture was gently agitated at room temperature until reduction of the targeted cysteine residues was complete (4-16 h). The liberated cysteines and remaining PTA were removed by desalting chromatography.

Method B
To a heterogeneous GLP-1 fusion protein solution (5-15 mg/mL in TrisOAc, pH 5.0-6.5) was added an excess amount of a phosphine reducing reagent Tris(2-carboxyethyl)phosphine (TCEP, 4-25 equiv.) followed by addition of 100 mM EDTA (final concentration 1 mM). The resulting reaction mixture was gently agitated at room temperature overnight and then applied to a desalting column equilibrated with TrisOAc (pH 7.0). The fully reduced GLP-1 fusion protein (hinge disulfide bonds broken) was treated with dehydroascorbic acid (DHAA, 10 eq.) for 2 hours, after which time the reduced GLP-1 fusion peptide was oxidized to give a full GLP-1 fusion peptide with engineered cysteines on the second linker peptide fully uncapped.

Preparation of GLP-1 Fusion Peptide Coupled Cyclic PYY Peptide Conjugates
A solution of reduced GLP-1 fusion peptides in TrisOAc (3-10 mg/mL, pH 5.5) was added to a solution of cyclic PYY peptide (2.6 to 3.0 eq. 10-15 mg/mL) in deionized water. To protect the reactive thiols against metal-catalyzed oxidation, a 100 mM EDTA solution was added to the reaction mixture until the concentration of EDTA was 1 mM. The pH of the reaction solution was raised to pH 8.0-8.2 by dropwise addition of Tris buffer (1M, pH 9.1). The reaction proceeded 3-7 hours at room temperature and then 18 hours at 5° C. LCMS indicated that conjugation was complete and GLP-1 fusion cyclic PYY peptide conjugate formation was greater than 95%. The reaction was directly subjected to protein A purification to remove excess cyclic PYY peptides or quenched by addition of 5 equivalents of cysteines (to cap remaining reactive cyclic PYY peptides). The resulting crude conjugate was purified by hydrophobic interaction chromatography (HIC) immediately followed by adsorption on protein A. Elution of the conjugate (sodium acetate, pH 3.5) and subsequent neutralization with Tris buffer to pH 7-7.5 afforded the final product. Alternatively, the HIC-purified conjugate can be exchanged to desired buffer by PD-10 column without further protein A polishing if it has been done prior to HIC purification.

Conjugation reaction can also be carried out at low temperature (5° C.) and monitored by LCMS (~48 hr).

In some cases, the reactive cysteines in the second linker peptides of GLP-1 fusion proteins are capped by bromoacetamides to form stable thioether bonds. These acetamide-modified GLP-1 fusion proteins were prepared as follows: To a GLP-1 fusion protein solution (5-12 mg/mL in TrisOAc, pH 5.4-6.4) was added an excess amount of a phosphine reducing reagent 1,3,5-triaza-7-phosphaadamantane (PTA, 15-20 equiv.) followed by addition of 100 mM EDTA (final concentration 1-2 mM). The resulting reaction mixture was gently agitated at room temperature for 18 hours. A 15-20 equiv. of bromoacetamides was added to the GLP-1 fusion peptide solution and the pH value of the reaction mixture was adjusted to pH 7.5-8.1 by Tris buffer (1M, pH 9.1). After 2 hours, the reaction mixture was purified by hydrophobic interaction chromatography (HIC) immediately followed by protein A polishing.

Table 8 provides isolated yields of selected GLP-1 fusion peptide coupled cyclic PYY peptide conjugates. It was observed that when the first linker peptide was an AP linker, as in GLP-1 fusion peptide 64 (GF64), and the second linker peptide was a $G_4A$ linker, as in GLP-1 fusion peptide 8 (GF8), the isolated yields of GLP-1 coupled cyclic PYY peptide conjugates were poor.

TABLE 8

Isolated yields of selected GLP-1 coupled cyclic PYY peptide conjugates

| SEQ ID NO | GLP-1 Fusion | Isolated Yield |
| --- | --- | --- |
| 241 | GF64 | 8% |
| 238 | GF23 | 11% |
| 234 | GF70 | 9% |
| 229 | GF24 | 35% |
| 225 | GF1 | 30% |
| 248 | GF40 | 17% |
| 252 | GF8 | 7% |
| 246 | GF65 | 9% |
| 254 | GF42 | 10% |
| 235 | GF28 | 8% |
| 251 | GF19 | 5% |

Example 3: GLP-1 Fusion Peptide Coupled Cyclic PYY Peptide Conjugate Characterization Analytical characterization of GLP-1 fusion peptide coupled cyclic PYY peptide conjugates was performed using (i) hydrophobic interaction chromatography (HIC), (ii) intact mass measurement by LC-ESIMS, (iii) size-exclusion chromatography (SEC). Results of the analytical characterization of the GLP-1 fusion peptide coupled cyclic PYY peptide conjugates and conjugation method are shown in Table 9.

TABLE 9

Analytical data for GLP-1 coupled cyclic PYY peptide conjugates.

| SEQ ID NO: | Reduction Method | MS (Da) Calc'd | MS (Da) Found | aHIC purity % | aSEC purity % |
|---|---|---|---|---|---|
| SEQ ID NO: 229 | Method A | 74002 | 74000 | 100 | 100 |
| SEQ ID NO: 225 | Method A | 73292 | 73291 | 100 | 100 |
| SEQ ID NO: 227 | Method A | 73261 | 73261 | 100 | 100 |
| SEQ ID NO: 228 | Method A | 73233 | 73231 | 99.5 | 98.4 |
| SEQ ID NO: 252 | Method A | 73014 | 73012 | 99.3 | 100 |
| SEQ ID NO: 235 | Method A | 73964 | 73068 | 100 | 100 |
| SEQ ID NO: 251 | Method A | 73541 | 73547 | 100 | 100 |
| SEQ ID NO: 228 | Method B | 73233 | 73231 | 100 | 97.2 |
| SEQ ID NO: 232 | Method A | 73942 | 73962 | 100 | 100 |
| SEQ ID NO: 244 | Method A | 73926 | 73926 | 100 | 100 |
| SEQ ID NO: 253 | Method A | 74010 | 74010 | 100 | 100 |
| SEQ ID NO: 249 | Method A | 71978 | 71983 | 95 | 95 |
| SEQ ID NO: 239 | Method A | 74571 | 74573 | 100 | 100 |
| SEQ ID NO: 238 | Method A | 75203 | 75205 | 90 | 96 |
| SEQ ID NO: 242 | Method A | 75287 | 75290 | 95 | 100 |
| SEQ ID NO: 236 | Method A | 74117 | 74119 | 95 | 97 |
| SEQ ID NO: 252 | Method A | 73016 | 73013 | 97 | 100 |
| SEQ ID NO: 234 | Method A | 72978 | 72974 | 100 | 90 |
| SEQ ID NO: 226 | Method A | 73319 | 73327 | 100 | 100 |
| SEQ ID NO: 248 | Method B | 72180 | 72182 | 100 | 100 |
| SEQ ID NO: 260 | Method B | 72034 | 72038 | 100 | 100 |
| SEQ ID NO: 247 | Method A | 73926 | 73927 | 100 | 100 |
| SEQ ID NO: 254 | Method A | 73978 | 73978 | 100 | 96 |
| SEQ ID NO: 258 | Method A | 75656 | 75656 | 98 | 100 |
| SEQ ID NO: 241 | Method A | 77374 | 77376 | 100 | 100 |
| SEQ ID NO: 246 | Method A | 75590 | 75594 | 92 | 100 |
| SEQ ID NO: 234 | Method A | 72860 | 72866 | 100 | 100 |
| SEQ ID NO: 230 | Method A | 74044 | 74042 | 100 | 100 |
| SEQ ID NO: 245 | Method A | 74636 | 74625 | 96 | 100 |
| SEQ ID NO: 244 | Method A | 76212 | 76201 | 86 | 98 |
| SEQ ID NO: 243 | Method A | 74057 | 74049 | NA | NA |
| SEQ ID NO: 259 | Method A | 75600 | 75604 | 100 | 100 |
| SEQ ID NO: 240 | Method A | 75627 | 75630 | 100 | 100 |
| SEQ ID NO: 261 (Monomer) | Method B | 67976 | 67976 | 80 | NA |

Example 4: In Vitro Assays

Conjugates were screened for functional activity and in vitro potency in cell-based assays measuring intracellular cAMP using the Lance competitive cAMP immunoassay (Perkin Elmer, Waltham, Mass.) according to the kit instructions. Clonal HEK293 cells stably expressing mouse or human GLP-1R or NPY2 receptors (Y2R) were used in the assays. Cells expressing GLP1R were thawed and suspended in HBSS, 5 mM HEPES, 0.1% BSA, 0.5 mM IBMX. Cells were mixed with the kit anti-cAMP antibody and added to the conjugates serially diluted with HBSS, 5 mM HEPES, 0.1% BSA in 384-well white opti-plates. Following a 10-minute incubation at room temperature, the immunoassay detection mix was added. The assay plate was read as a TR-FRET assay on an Envision plate reader (excitation 320 nm, emission 615 nm and 665 nm) and the data was used to calculate compound $EC_{50}$ values using Prism statistical software (GraphPad Software San Diego).

To determine compound activity at the Y2R receptor, HEK293 cells expressing Y2R were cultured in DMEM-high glucose media (Cellgro) supplemented with 10% fetal bovine serum, 1% L-glutamine, 1% sodium pyruvate, 1% penicillin/streptomycin and 600 ug/ml G418 and plated overnight in 384 well plates in media without G418. On the day of the assay, the cell growth media was removed from the cells and 6 µl of the conjugate (2×) in 5 mM HEPES, 500 uM IBMX and 0.1% BSA in HBSS was added. Next, 6 µl of stimulation buffer containing forskolin (2×, 5 uM final concentration) and LANCE cAMP antibody (1:100) was added to the cells. After incubation for 25 minutes at room temperature, 12 µl of detection mix was added, and cAMP concentrations were quantified in the LANCE cAMP immunoassay.

Data Analysis

Data from the Envision plate reader were expressed as relative fluorescence units (RFU) calculated as (615 nm/665 nm)×10,000. All samples were measured in triplicate. The unknown cAMP concentrations within each well were interpolated from the reference standards of known cAMP concentrations included within each plate. Parameters such as $EC_{50}$, $Log(EC_{50})$, HillSlope (nH), top, and bottom, were derived by plotting cAMP concentration values over log compound concentrations fitted with 4-P model using a non-linear weighted least squares application.

TABLE 10 in vitro data for GLP-1 fusion peptide coupled cyclic PYY conjugates.

| Conjugate | | Human GLP1R | Human Y2R |
|---|---|---|---|
| Compound 4 (SEQ ID NO: 229) | Mean $EC_{50}$ | 0.069 | 0.014 |
| | SEM | 0.007 | 0.001 |
| | 95% CL of mean | (0.051, 0.087) | (0.010, 0.017) |
| Compound 2 (SEQ ID NO: 225) | Mean $EC_{50}$ | 0.078 | 0.009 |
| | SEM | 0.009 | 0.001 |
| | 95% CL of mean | (0.054, 0.102) | (0.006, 0.012) |
| Dulaglutide | Mean $EC_{50}$ | 0.035 | — |
| | SEM | 0.003 | |
| | 95% CL of mean | (0.028, 0.042) | |
| GLP 7-36 | Mean $EC_{50}$ | 0.013 | — |
| | SEM | 0.001 | |
| | 95% CL of mean | (0.012, 0.014) | |
| Exendin 4 | Mean $EC_{50}$ | 0.008 | — |
| | SEM | 0.001 | |
| | 95% CL of mean | (0.007, 0.009) | |
| PYY3-36 | Mean $EC_{50}$ | — | 0.021 |
| | SEM | | 0.001 |
| | 95% CL of mean | | (0.017, 0.024) |

TABLE 11

GLP-1R and NPYR2 in vitro potency for GLP-1 fusion peptides and GLP-1 fusion cyclic PYY conjugates

| SEQ ID NO | Human GLP1R $EC_{50}$ (nM) | Human Y2R $EC_{50}$ (nM) |
|---|---|---|
| 113 | 0.062 | na |
| 120 | 0.066 | na |
| 123 | 0.167 | na |
| 131 | 0.050 | na |
| 131 | 0.106 | na |
| 134 | 0.076 | na |
| 134 | 0.142 | na |
| 135 | 0.079 | na |
| 135 | 0.138 | na |
| 136 | 0.068 | na |
| 136 | 0.126 | na |
| 139 | 0.054 | na |
| 140 | 0.144 | na |
| 140 | 0.202 | na |
| 146 | 0.130 | na |
| 152 | 0.207 | na |
| 153 | 0.049 | na |
| 166 | 0.035 | na |
| 166 | 0.053 | na |
| 175 | 0.042 | na |
| 176 | 0.052 | na |
| 176 | 0.069 | na |

TABLE 11-continued

GLP-1R and NPYR2 in vitro potency for GLP-1 fusion peptides and GLP-1 fusion cyclic PYY conjugates

| SEQ ID NO | Human GLP1R EC$_{50}$ (nM) | Human Y2R EC$_{50}$ (nM) |
| --- | --- | --- |
| 177 | 0.051 | na |
| 177 | 0.054 | na |
| 179 | 0.171 | na |
| 179 | 0.301 | na |
| 225 | 0.078 | 0.009 |
| 226 | 0.064 | 0.014 |
| 227 | 0.061 | 0.005 |
| 228 | 0.051 | 0.004 |
| 229 | 0.069 | 0.014 |
| 230 | 0.043 | 0.023 |
| 232 | 0.058 | 0.065 |
| 233 | 0.103 | 0.010 |
| 234 | 0.140 | 0.009 |
| 235 | 0.193 | 0.010 |
| 236 | 0.229 | 0.009 |
| 238 | 0.523 | 0.019 |
| 239 | 0.042 | 0.006 |
| 240 | 0.036 | 0.007 |
| 241 | 0.121 | 0.006 |
| 242 | 0.285 | 0.011 |
| 262 | 0.985 | 0.012 |
| 246 | 0.078 | 0.003 |
| 247 | 0.350 | 0.040 |
| 248 | 0.264 | 0.018 |
| 249 | 0.148 | 0.143 |
| 250 | 0.213 | 0.010 |
| 251 | 0.062 | 0.015 |
| 252 | 0.080 | 0.009 |
| 253 | 0.567 | 0.077 |
| 254 | 0.39 | 0.022 |
| 258 | 0.036 | 0.007 |
| 259 | 0.059 | 0.004 |
| Extendin4 | 0.008 | na |
| GLP-1 7-36 | 0.013 | na |
| Dulaglutide | 0.035 | na |
| PYY3-36 | na | 0.021 |

Comparing GLP-1R potencies of SEQ ID NO 135, 134, 146, and 176 with SEQ ID NO 238, 242, 262, 253, and 241 showed that GLP-1 fusion peptides with Exendin 4 (1-39) (SEQ ID NO:58) lost GLP-1R potency following conjugation with PYY peptides. Work with GLP-1 fusion peptides with Exendin 4 (1-39) (SEQ ID NO:58) was disfavored in this experiment based on these results.

Human NPY2R primary screening assay: The method used to screen the NPY2R potency of GLP-1 fusion peptide coupled cyclic PYY peptide conjugates in vitro was a cell-based assay designed to measure inhibition of forskolin induced cAMP produced by adenylate cyclase through modulation of the human NPY2R Gi-protein coupled receptor. The forskolin induced cAMP production in human NPY2R transfected CHO-K1 cells (DiscoverX) was reduced through activation of NPY2R by PYY analogs and controls in a dose dependent manner and measured in a FRET based competitive cAMP immunoassay.

Cells were removed from cryopreservation and thawed in a 37° C. water bath, added to 40 mL of 1×DPBS, pH7.2 (Gibco), and filtered through a cell strainer. Cells were centrifuged at 450×g for 5 minutes, and supernatants were aspirated. The cell pellet was re-suspended in DMEM/high glucose, 10% HIFBS, 1% Pen/Strep, 1% L-Glutamine, 1% Na Pyruvate at a density of 0.125×10$^6$ cells/ml. Cells were dispensed at 40 µL/well to a collagen coated white 384 well plate to a final 5000 cells/well, and incubated at 37° C., 5% CO$_2$ for 16 to 24 hours. Cells in the assay plate were washed twice by adding 80 µL/well 1×DPBS and decanting the supernatant. Dilutions of samples and controls were prepared in 1×HBSS, 5 mM HEPES, 0.002 mM forskolin, 0.1% BSA, 0.5 mM 3-Isobutyl-1-methylxanthine (IBMX), and 20 µL/well of each sample were added to designated wells and incubated shaking at room temperature for 30 minutes. Then 20 cAMP detection reagent mix was added to each assay plate, and incubated shaking at room temperature for 2 to 24 hours. Plates were read on a plate reader. All samples were measured in quadruplicate. Data were analyzed by plotting raw LANCE cAMP values over log compound concentrations fitted with 4-P model using a non-linear weighted least squares application within R environment.

Human GLP-1R primary screening assay: The method used to screen the GLP-1R potency of GLP-1 fusion proteins and GLP-1 fusion peptide coupled cyclic PYY peptide conjugates in vitro was a cell-based assay designed to measure cAMP production through modulation of the human GLP-1R Gs-protein coupled receptor. Following concentration dependent activation of GLP-1R by GLP-1 fusion peptides and GLP-1 fusion peptide coupled cyclic PYY peptide conjugates, the cAMP accumulation in human GLP-1R transfected HEK cells was measured in a TRFRET based competitive cAMP assay.

Human GLP-1R transfected HEK cells were thawed the day of the assay, resuspended in 1×HBSS, 5 mM HEPES, 0.1% BSA, and 1 mM IBMX at 0.5×10$^6$ cells/ml, and 10 µl was added to each well of a 384-well plate (5000 cells/well). Samples were diluted in 1×HBSS, 5 mM HEPES, 0.1% BSA and added at 10 µL/well of the assay plate and incubated at room temperature for 30 minutes. The cAMP detection reagent was added at 20 µL/well. Plates were incubated at room temperature for 2 hours, then read on a plate reader. All samples were measured in quadruplicate. Data were analyzed by plotting raw LANCE cAMP values over log compound concentrations fitted with 4-P model using a non-linear weighted least squares application within R environment.

Example 5: Xylose Analysis on GLP-1 Fusion Peptides and GLP-1 Fusion Peptide Coupled Cyclic PYY Conjugates Sample preparation: To prepare samples for peptide mapping, each protein molecule (1 mg/ml): GLP-1 fusion peptide coupled cyclic PYY conjugate (SEQ ID NO:244), GF40 (SEQ ID NO:152), and GF34 (SEQ ID NO:146) was diluted 1:4 in 8 M Guanidine/HCl buffered at pH 8.0. To these samples an aliquot of 1 M DTT (Sigma 43816-10ML, BioUltra) was added to reach a final concentration of 25 mM; the samples were then incubated for 1 hour at 37° C. Alkylation was performed using either iodoacetamide (Sigma, A3221-10VL) or N-Methylmaleimide (NEM) (Sigma, E3876). Freshly prepared 1 M alkylating agent was added to reach approximately 50 mM, and the samples were incubated for 60 minutes at room temperature in the dark. The alkylation reaction was then quenched by adding 15 µl of 1 M DTT for every 400 ul of reaction mixture (Sigma 43816-10ML, BioUltra). The sample was desalted using Zeba Spin Desalting columns (Thermo, cat. #89833) according to the manufacturer's protocol in 50 mM Tris, 1 mM CaCl$_2$, pH=8.0. The samples were digested with trypsin (Promega sequencing grade, V511A) for 4 hours at 37° C. following the addition of 1 µl of 1 µg/µL of trypsin reconstituted in 50 mM acetic acid (supplied with the lyophilized trypsin). The trypsin digestion was quenched by adding 0.6 µl of 100% TFA to a 60 µL aliquot of the digested protein. The samples were resuspended into micro vials and placed in an autosampler set at 4° C. for LC/MS analysis.

Liquid chromatography and mass spectrometry: 2 µg (~10 µl) of digested protein was injected into an Agilent AdvanceBio Peptide Map Micro Bore Rapid Resolution Column (1×150 mm, 2.7 µm, part no: 863600-911) using an Agilent Infinity 1290 UHPLC (Agilent Technologies, part nos: G1330B, G4226A, G4220A, G4212A) at a flow rate of 0.1 mL/min. The column temperature was maintained at 65° C. Mass spectrometry grade HPLC solvents (0.1% Formic acid and B: 100% ACN in 0.1% Formic acid) were purchased from VWR (part no: LC 452-1, LC 441-1). The proteolytic peptides were eluted from the column using a 50-minute gradient of 2 to 40% ACN in 0.1% FA. The column effluent was introduced into an Orbitrap Q-Exactive Mass spectrometer (Thermofisher Scientific) via a heated electrospray ionization probe (HESI) using a positive spray voltage of 3.5 kV, sheath gas of 20 (arb. units), auxiliary gas of 7 (arb. units), ion transfer tube at 299° C. and vaporizer at 100° C. Data dependent acquisition was performed by sequentially dissociating the top 5 most abundant peptide ions observed in the full MS scan. Mass analysis was performed with the precursor scan set to Orbitrap detection, 70,000 resolving power, mass range 150-2000 m/z, Automatic Gain Control (AGC) Target of 1.0e6, maximum injection time 50 milli-seconds. 1 microscan spectra was acquired in profile mode. The precursor decision criteria were monoisotopic precursor selection peptides, charge state: 2-7, dynamic exclusion: 6.0 seconds and precursor intensity threshold of 5e4. Precursor peptides were isolated by the quadrupole with an isolation window of 1.6 m/z was sent to the collision cell. A normalized collision energy of 28 (arb. units) results was used for high energy collisional dissociation (HCD) of the peptide ions. Product ions were transferred to the orbitrap for mass analysis with orbitrap settings are 17,500 resolving power, 200-2000 m/z range, AGC target of 5e5, maximum injection time 100 milliseconds, 1 microscan of spectra acquired in centroid mode.

Data Analysis: Raw LC-MS/MS data were subjected to database searches using Byonic software (Ver. 2.15.7) (Protein Metrics). The following parameters were used for data searches: precursor ion mass tolerance, 8 ppm; product ion mass tolerance, 20 ppm for HCD spectra; variable modification include cysteine carbamidomethylation, or N-Methylmaleimide (NEM), cysteine DTT adduct formation, cysteine peptide YY (PYY) conjugates were included when present, deamidation of asparagine, serine xylose, and serine and threonine O-glycosylation of 78 mammalian O-linked glycans from the Byonic glycan library. A fully-tryptic specificity search with a maximum of two missed cleavages was chosen for all searches. The protein false discovery rate (FDR) was set at 1%. The protein database contained the amino acid sequence of each protein. All Byonic search results were processed in Bylogic software (Ver. 2.15.296) (Protein Metrics), peptides were filtered with a minimum Byonic score of 15, Max alt run Score/Primary rank Score of 0.99, with a maximum precursor m/z error of 8 ppm and XIC area window of 2 minutes. Serine xylosylation-level was reported by accounting for all peptide XIC peak areas of isoforms constituting the linker region. The xylosylation at each serine residue was then calculated as a sum fraction of the total XIC peak area. Database searches were also performed using Andromeda search engine in MaxQuant software version 1.6.1 (MaxPlank Institute) to obtain PTM site-localization probabilities. The masses corresponding to a fully cyclized PYY and trypsin cleaved PYY structures were obtained using BIOVIA draw software. The data is reported in Table 12.

TABLE 12

Xylose modification

| Serine Position in Molecule** | Site-Localization by MS/MS | | | % Xylosylation | | |
|---|---|---|---|---|---|---|
| | NO: 244 | NO: 146 | NO: 152 | NO: 244 | NO: 146 | NO: 152 |
| 41 (33) | YES | YES | YES | 9 | 5* | 0.12 |
| 46 (38) | YES | YES | ND | 7.4* | 5* | NQ |
| 51 (43) | YES | YES | ND | 7.4* | 5* | NQ |

Xylose modification in linker serines: site identification and modification levels
ND = not detected by MS/MS; NQ = not quantified; NA = linker serine position is not applicable for molecule; **NO: SEQ ID NO: Parenthesis indicate site numbering for SEQ ID NO:152.

Table 12 summarizes the site-specific xylosylation identified and quantified using the peak integration in Bylogic where % XIC based of the peak/peaks of interest (putative modifications, i.e., serine xylosylation) was normalized to the sum of all the species contributing to site-specific xylosylation according to the following equation:

% XIC of modification=(XIC of modified peptide/ ΣXIC of peptide counterparts)×100

All three molecules investigated consist of the same first linker peptide, $AS(G_4S)_2$, connecting the GLP-1 peptide and hinge-Fc region peptide. However, due to the differences in the GLP-1 fusion peptide found in SEQ ID NO:152 (GF40) and GLP-1 fusion peptide found in both SEQ ID NO:244 and 146 (GF34), the position of three serine residues in SEQ ID NO:152 differs from SEQ ID NO:244 and 146 as shown in Table 12. Analysis of the peptides demonstrated three site-specific serine residue xylosylation events at Ser-41, Ser-46, Ser-51 in SEQ ID NO:244 and 146 and a serine residue xylosylation event at Ser-33 in SEQ ID NO:152. Quantification of the site-specific xylosylation was feasible only to a limited extent as most xylosylated peptides species co-eluted during reversed phase liquid chromatography. For example, in SEQ ID NO:244, Ser-41 was ~9%, while Ser-46 and Ser-51 was ~7%. Similarly, all three sites of SEQ ID NO:146 were xylosylated at ~5%. The xylosylation of SEQ ID NO:152 was found to occur to a lesser extent ~0.1%.

The $G_4S$ linker regions of therapeutic proteins have shown to be susceptible to xylosylation with xylosylation levels varying based on the linker length (Wen et al., "The propensity for xylosylation in $(G_4S)_n$ linkers occurs when n>2," Anal. Chem. 85:4805-12 (2013); Sphar et al., Protein Sci. 22:1739-53 (2013), Sphar et al., mAbs 6:904-14 (2014)). The first linker peptide, the $AS(G_4S)_2$ linker, found in all three molecules shows xylosylation in all or some serine residues, and based on these data the use of serine containing first linker peptides was disfavored in this experiment when preparing GLP-1 fusion peptide constructs.

Example 6: Ex Vivo Human Plasma Stability of GLP-1 Fusion Peptide

Fresh whole blood from 4 normal human donors with sodium heparin anticoagulant was received the day of setting up the stability samples. The fresh whole blood was processed for plasma by centrifuging at 3500 RPM for 15 minutes and plasma was then isolated. Plasma from all four donors was combined, filtered through a 0.2µ filter, and warmed to 37° C. Samples were spiked with GLP-1 fusion peptides and GLP-1 fusion peptide coupled cyclic PYY conjugate Dual Agonist (DA) analogs at 20 nM, and the time zero sample was immediately collected and stored at −80° C. until analyzed. Samples were incubated at 37° C. and collected at designated time points and stored at −80° C. until analyzed. On the day of analysis, the time zero and subsequent time point samples were thawed and analyzed together in a functional cell-based bioassay.

The method used to detect and quantitate levels of bioactive GLP-1 fusion peptide and GLP-1 fusion peptide coupled cyclic PYY conjugate DA analogs in human plasma samples was a cell-based bioassay designed to measure cAMP production through modulation of the human GLP-1R G-protein coupled receptor. Following concentration dependent activation of GLP-1R by GLP-1 fusion proteins and GLP-1 fusion peptide coupled cyclic PYY peptide conjugates, the cAMP accumulation in human GLP-1R transfected HEK cells was measured in a TRFRET based competitive cAMP assay. Human GLP-1R transfected HEK cells were thawed the day of the assay, resuspended in 1×HBSS, 5 mM HEPES, 0.1% BSA, and 1 mM IBMX at $0.5 \times 10^6$ cells/ml, and 10 μl was added to each well of a 384-well plate (5000 cells/well). Stability samples were thawed and diluted to 20% plasma in assay buffer comprised of 1×HBSS, 5 mM HEPES, 0.1% BSA, 5 mM EDTA, protease inhibitor, and subsequent dilutions were made in assay buffer with 20% normal human plasma. Reference standards of known concentrations for each compound were prepared in assay buffer with 20% normal human plasma. Standards and samples were added at 10 μL/well to each assay plate and incubated at room temperature for 30 minutes. The cAMP detection reagent was added at 20 μL/well. Plates were incubated at room temperature for 2 hours, then read on a plate reader.

All samples were measured in quadruplicate. The compound reference standard curves were generated with transformed concentration to log, nonlinear fit, with log v. response (variable slope), and $EC_{10}$ and $EC_{90}$ values were determined for upper and lower quantitative assay limits. The concentrations of the stability samples for each compound were extrapolated from the corresponding reference standard curve. The percent remaining bioactivity of each stability sample was determined relative to the corresponding time zero sample and reported as % starting plasma concentration over the 168-hour time course. % starting plasma concentration=[Ave stability sample]/[Ave Time zero]×100.

Results: GLP-1 fusion peptides SEQ ID NOs:144 (GF32), 148 (GF36), 145 (GF33), 151 (GF39), 146 (GF34), 147 (GF35), 149 (GF37), 152 (GF40), and a dulaglutide control were incubated in human plasma ex vivo at 37° C. for 7 days and functional stability was measured in an in vitro GLP-1R cAMP functional assay (FIG. 1A). GLP-1 fusion proteins with GLP-1 peptide SEQ ID NO:58 (Exendin 4 (1-39)) showed the greatest stability followed by SEQ ID NO:57 ((A8G, G22E, R36G) GLP-1 (7-37)) and the Dulaglutide control, with SEQ ID NO:56 ((A8S, A30E) GLP-1 (7-36)) having been the least stable. Work with Fc fusion proteins with GLP-1 peptide SEQ ID NO:56 was disfavored in this experiment based on these results.

Figure 1B:
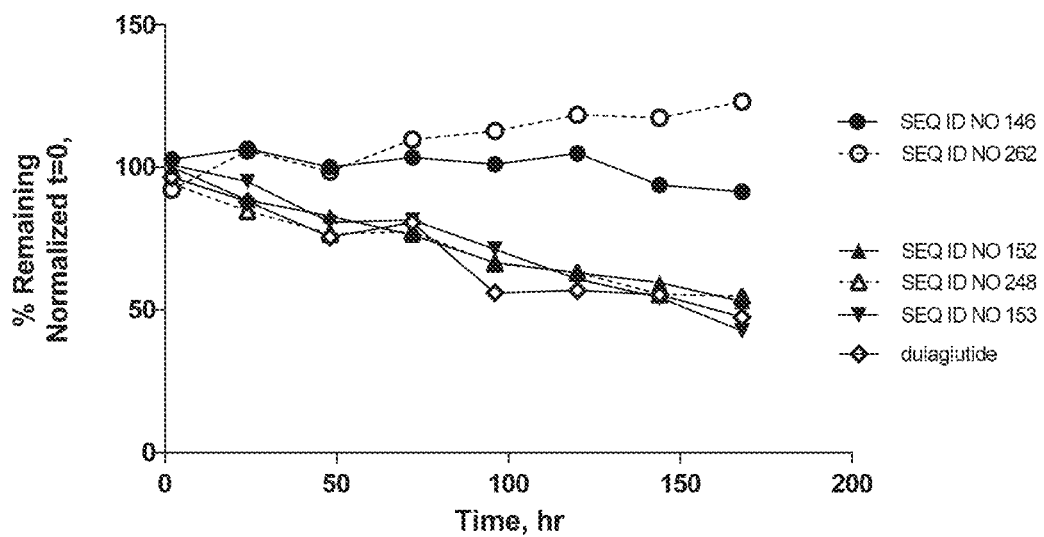
Figure 2A:
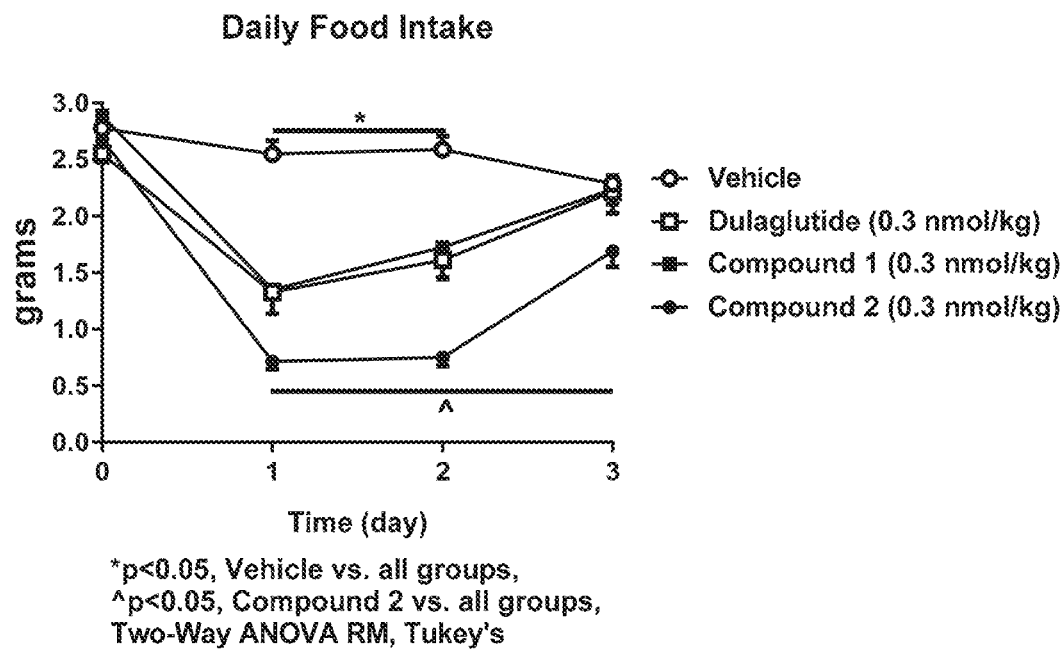
FIGS. 2A-2B show food intake and body weight loss in DIO mice.
Figure 2B:
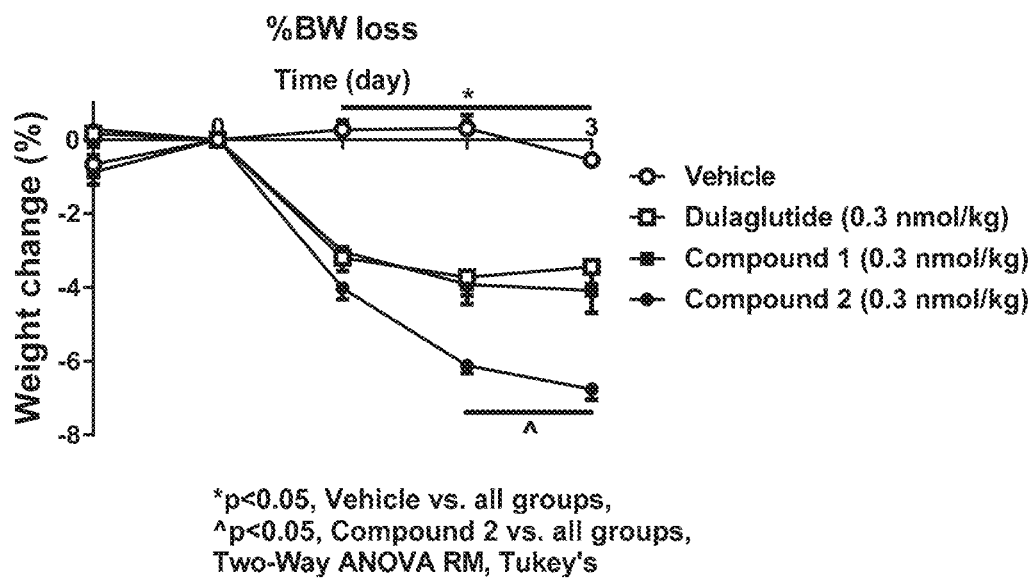
Figure 3A:
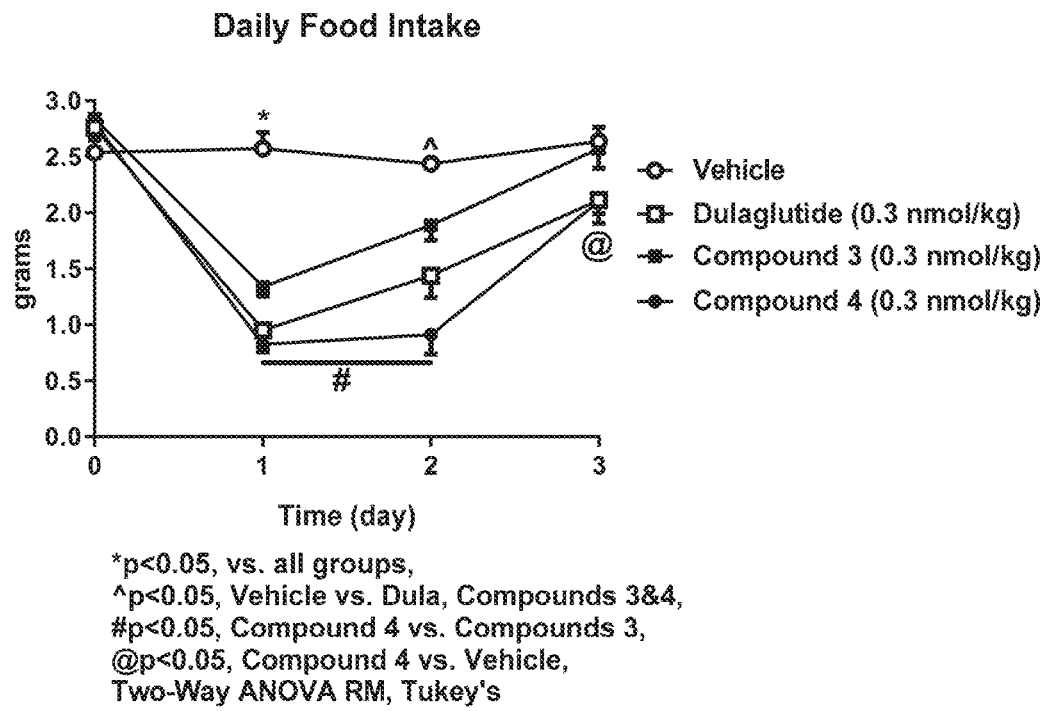
FIGS. 3A-3B show food intake and body weight loss in DIO mice.
Figure 3B:
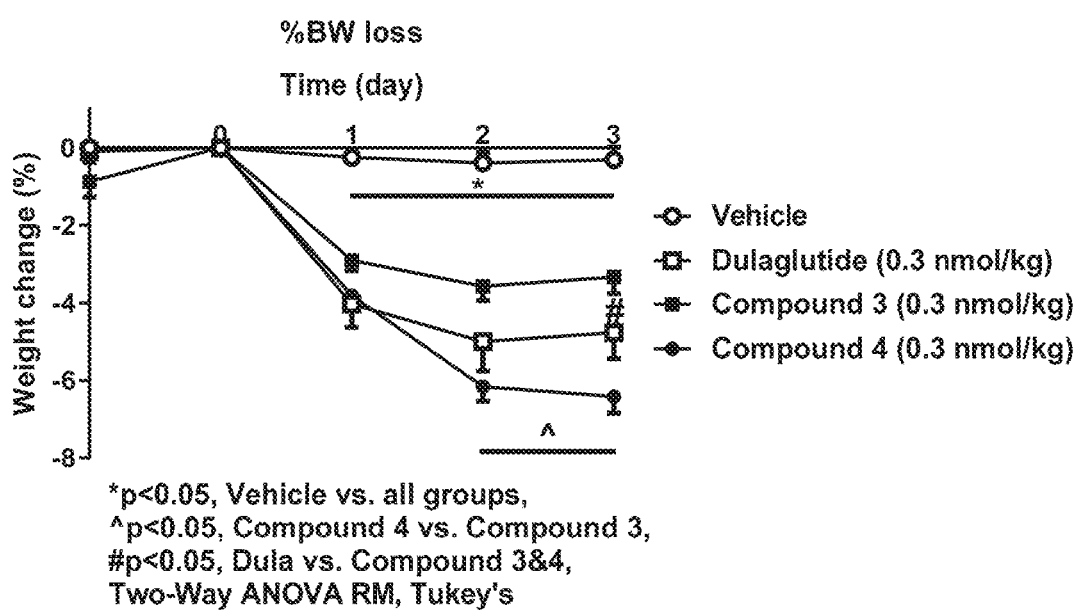
Figure 4A:
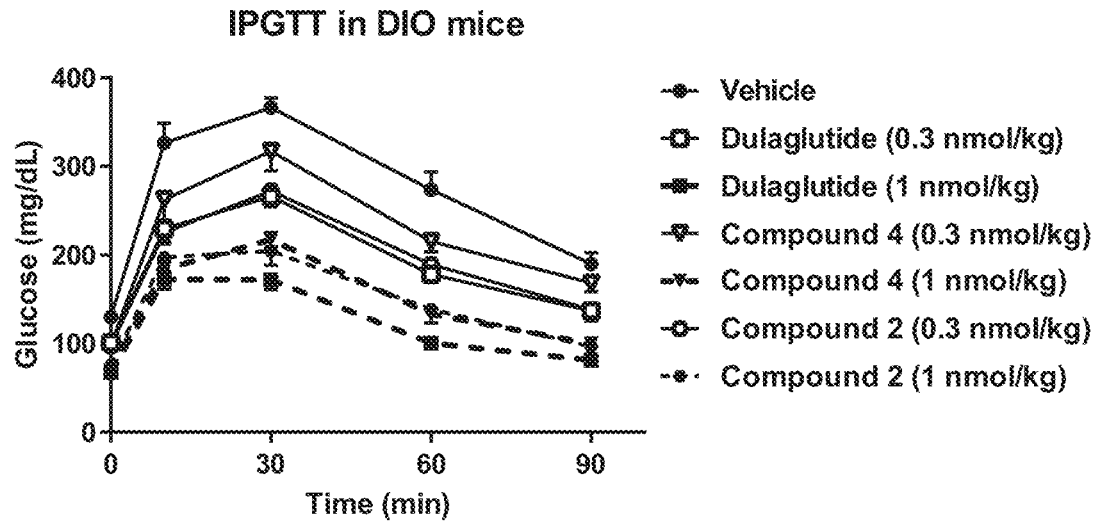
FIGS. 4A-4B show IPGTT in DIO mice.
Figure 4B:
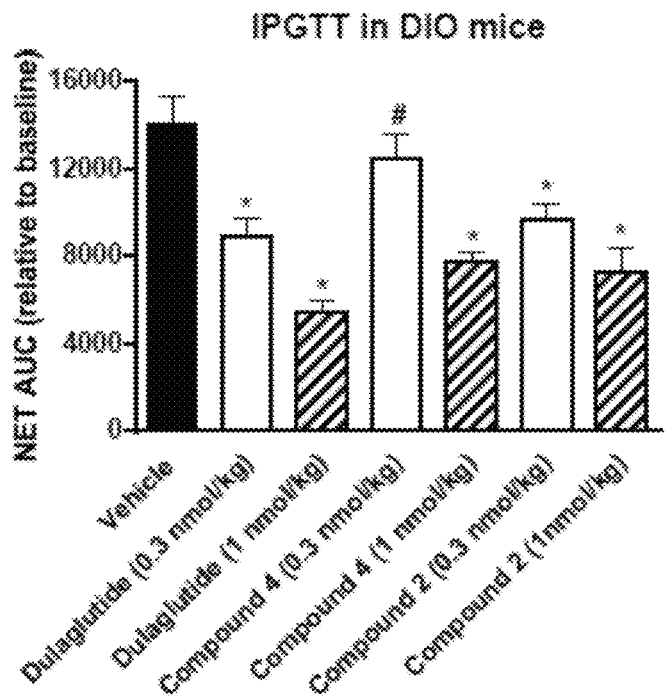
Figure 5A:
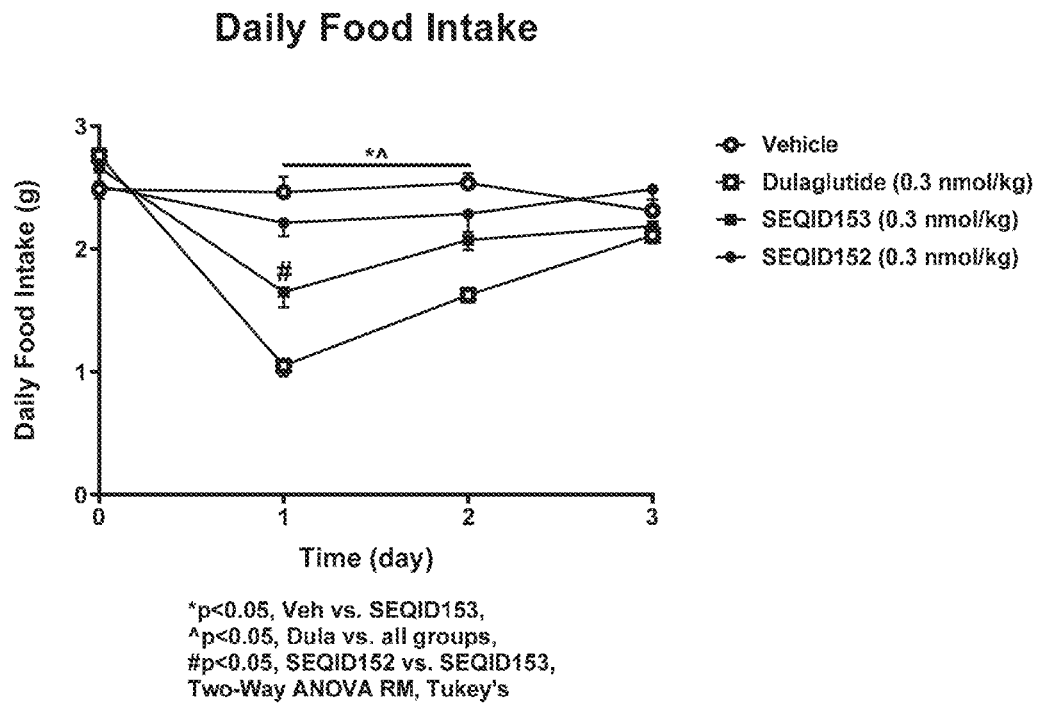
FIGS. 5A-5B show food intake and body weight loss in DIO mice.
Figure 5B:
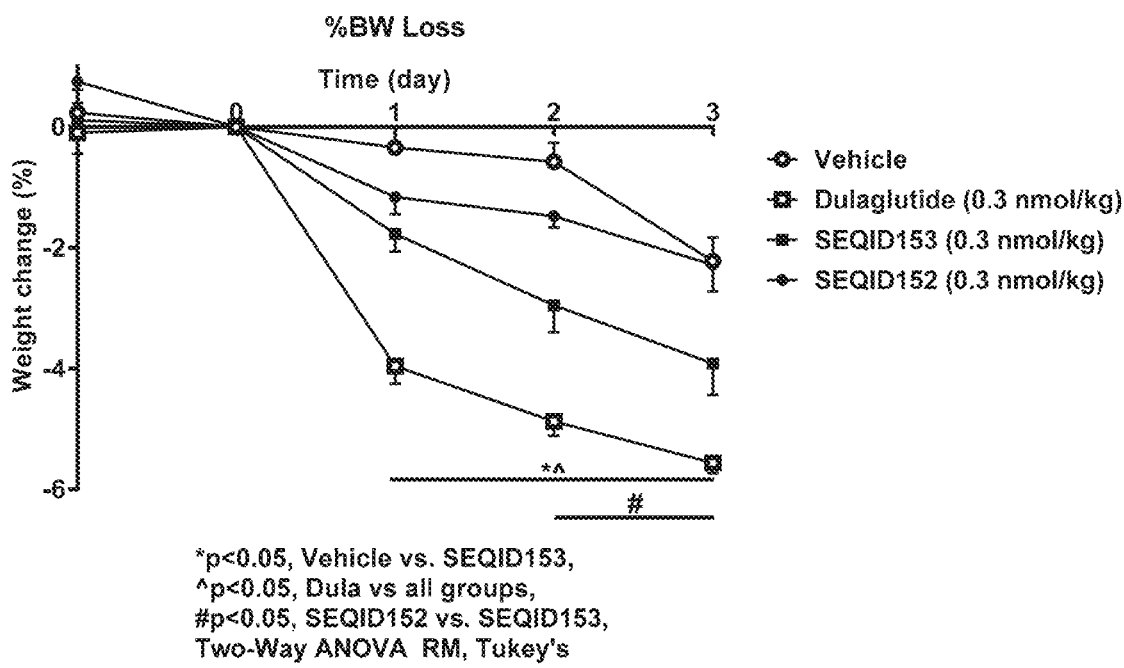

GLP-1 fusion peptides SEQ ID NO:152 (GF40) and 146 (GF34), and their corresponding GLP-1 fusion peptide coupled cyclic PYY peptide conjugates SEQ ID NO:248 and 262, and another GLP-1 fusion peptide SEQ ID NO:153 (GF41) were incubated in human plasma ex vivo at 37° C. for 7 days along with a dulaglutide control. Functional stability was measured in an in vitro GLP-1R cAMP functional assay (FIG. 1B). Stability of the GLP-1 fusion peptide coupled cyclic PYY peptide conjugates were comparable to the corresponding unconjugated fusion proteins, demonstrating conjugation of the PYY peptide did not impact the GLP-1 peptide stability. GLP-1 fusion peptide SEQ ID NO:146 (GF34) and GLP-1 fusion peptide coupled cyclic PYY peptide conjugate SEQ ID NO:262 had the greatest stability, and SEQ ID NOs:152 (GF40), 248, and 153 (GF41) had similar stability to the Dulaglutide control.

Example 7: In Vivo Mouse Stability Assay

Methods

LCMS Method: Plasma samples were processed by immuno-affinity capture using an anti-human Fc antibody, followed by trypsin digestion, and analyzed by reversed phase LC-MS/MS analysis on a triple quadrupole mass spectrometer. The peptide on the N terminus of GLP-1, namely HGE (HGEGTFTSDVSSYLEEQAAK (SEQ ID NO:263) for GLPD30 and HGEGTFTSDLSK (SEQ ID NO:264) for GLPD31) was monitored as a surrogate of molecules containing active GLP1. A peptide located on Fc, namely VVS (VVSVLTVLHQDWLNGK (SEQ ID NO:265)), was monitored as a surrogate of total Fc level. A peptide located on the cyclic PYY peptide, YYA (YYASLR (SEQ ID NO:266)), was monitored as a surrogate of the PYY level. The calibration standard curve and quality control samples were prepared by spiking the reference standard in plasma and processed using the same procedure at the same time as the test samples.

Results

Plasma exposure levels of the intact GLP-1 fusion peptide moiety N terminus post 72 hours administration in mice was measured in an LCMS assay and reported as the percent of the HGE N terminal GLP-1 fusion peptide moiety sequence level relative to the Fc level (HGE % of Fc). The results in Table 13 demonstrate that the first linker peptide of SEQ ID NOs:62 and 66, which comprise an AP repeat, were less stable than the first linker peptide of SEQ ID NO:60, which comprises a $G_4A$ repeat. Work with GLP-1 fusion peptides with first linker peptides comprising AP repeats was disfavored in this experiment based on these results.

TABLE 13

In vivo mouse stability of GLP-1 fusion peptides and GLP-1 fusion peptide coupled cyclic PYY peptide conjugates

| SEQ ID NO | GLP-1 or GLP-1 variant peptide SEQ ID NO | First linker peptide SEQ ID NO | Hinge-Fc Region SEQ ID NO | in vivo mouse 72 hour HGE % of Fc |
|---|---|---|---|---|
| 135 | 58 | 60 | 84 | 36 |
| 134 | 58 | 60 | 84 | 36 |
| 176 | 58 | 62 | 89 | 14 |
| 241 | 58 | 62 | 89 | 17 |
| 140 | 59 | 60 | 84 | 60, 56 |
| 177 | 59 | 62 | 89 | 9 |
| 246 | 59 | 62 | 89 | 7 |
| 233 | 57 | 60 | 89 | 6 |
| 131 | 57 | 60 | 84 | 12, 12, 14 |
| 136 | 57 | 60 | 84 | 12, 12 |
| 120 | 57 | 60 | 84 | 9 |
| 113 | 57 | 60 | 84 | 10, 9 |
| 259 | 57 | 62 | 89 | 3 |
| 258 | 57 | 62 | 89 | 3 |
| 175 | 57 | 62 | 89 | 3 |
| 240 | 57 | 62 | 89 | BQL |
| 166 | 57 | 66 | 86 | 4 |
| 239 | 57 | 66 | 86 | BQL |

BQL = below quantitative limits

Acute and Sub-Chronic Pharmacodynamics Studies in DIO Mice

All rodents used in these studies were maintained in accordance with the protocols approved by the Institutional Animal Care & Use Committee (IACUC) at Janssen R&D, Spring House, Pa. Animals were housed on a 12-hour light/12-hour dark cycle at standard temperature and humidity conditions with ad libitum access to food and water (unless noted otherwise). Twenty-week-old male DIO (on 60% kcal % high fat diet for 15 weeks) C57BL/6T mice (Taconic Laboratory) that were individually housed were used. Animals were randomized into groups based on body weight. For intraperitoneal (IP) glucose tolerance tests (IP-GTT), mice were dosed with vehicle, dulaglutide (Eli Lilly; purchased from Myoderm, Norristown, Pa.), or compounds 1-4 (SEQ ID NO:113, SEQ ID NO:225, SEQ ID NO:136, SEQ ID NO:229, respectively) (n=8/group). Twenty-four hours later (after an overnight fast), mice were dosed IP with dextrose (1 g/kg). Blood glucose was measured at indicated times with a One Touch Ultra glucometer (LifeScan), and plasma insulin (Meso Scale Discovery) was measured at 0 and 10 minutes. For acute food intake (FI) and weight loss (WL) studies, individually housed DIO mice were dosed with vehicle, dulaglutide, or compounds, and food and body weights were measured for 3 days (n=8/group). Data are shown in FIGS. 2A-2B, 3A-3B, and 4A-4B. The data in FIGS. 2A-2B, 3A-3B, and 4A-4B demonstrate that GLP-1 fusion peptides have desirable GLP-1R efficacy and have enhanced efficacy when conjugated with cyclic PYY peptide SEQ ID NO:27. From the data in FIGS. 5A-5B and 6A-6B, it was determined that the upper hinge of the GLP-1 fusion peptide contributes to GLP-1R potency.

Example 8: In Vivo Studies with Cynomolgus Monkey

Methods
Efficacy Study

Monkeys were selected and randomized into groups for compound treatment based on their baseline (average of 3 days before day 0) food intake (primary—weighted 80%) and body weight (secondary—weighted 20%) measured during run-in and vehicle treatment. The study lasted 9 weeks, 2 weeks of acclimatization/training, 3 weeks of vehicle treatment every 3 days (Q3D) and baseline food intake measurement, 12 days of treatment (5 doses, Q3D) and 2 weeks of washout. Animals were dosed 7 times with vehicle and 5 times with one of the test articles (at 0.5 mL/kg dosing volume) Q3D at approximately 8 AM. The doses of each group were as follows: dulaglutide (0.0125 mg/kg, n=11), compound 4 (high dose; 0.0148 mg/kg, n=11), compound 4 (low dose; 0.0074 mg/kg, n=6). Caloric intake was measured daily, and body weight was measured Q3D.

Exposure-Response Analysis

Two analytical methods were used to measure the concentrations of compound 4 and dulaglutide from in vivo plasma samples in Cynomolgus monkey.

Ligand binding assay (LBA) exposure analysis for compound 4 and dulaglutide in Cynomolgus monkey was performed by a fit-for-purpose electrochemiluminescent immunoassay (ECLIA) method using a Meso Scale Discovery (MSD) Sector Imager S600 (Meso Scale Diagnostics, Rockville, Md. USA). The format to measure active GLP-1 for both compound 4 and dulaglutide is described as follows: the analyte was captured with a GLP-1 N-terminal (7-17) specific mAb (Biotin-anti-GLP1 (7-37, 7-36, amide, free NT) mAb) and detected with an anti-human Fc specific mAb (SulfoTag-R10). Raw data regression was performed in Watson LIMS™ software (Thermo Fischer Scientific, Waltham, Mass. USA) using a 5-parameter logistic fit with 1/F2 standard curve weighting.

The LC-MS/MS analysis for compound 4 and dulaglutide in Cynomolgus monkey was also done by a bottom-up trypsin assay for quantitation of individual parts of the molecules. For the trypsin assay, the analyte was purified from plasma samples using immuno-affinity capture by an anti-human Fc antibody, followed by trypsin digestion and analysis by reversed phase LC-MS/MS on a SCIEX Triple Quad™ 5500 LC-MS/MS System (CIEX, Concord, Ontario, Canada). A stable isotope [13C6, 15N4-arginine] and [13C6, 15N2-lysine] labeled human IgG4 (Sigma, Catalog number MSQC7) was used as an internal standard and added at the beginning of immuno-affinity capture step. The peptide on the N-terminus of GLP-1, namely HGE (HGEGTFTSDVS-SYLEEQAAK) (SEQ ID NO:263) was monitored as a surrogate of molecules containing active GLP-1, as the HGE peptide is essential for its activity.

Results

Dual agonists according to embodiments of the application contains a GLP-1 fusion (GF) peptide covalently linked to a cyclic PYY peptide. The dual agonists are comprised of a recombinant Glucagon-like peptide-1 (GLP-1) peptide or GLP-1 variant peptide fused to a hinge-Fc region through a first linker peptide (N-terminal linker peptide) and a cyclic PYY peptide chemically conjugated to a target cysteine contained within the second linker peptide (C-terminal linker peptide) of the recombinant GLP-1 fusion (GF) peptide. Each component of the dual agonist was selected empirically based on several key parameters, which included, but was not limited to, potency at each receptor, stability, post translational modifications, conjugation production yields, and biophysical properties.

Figure 10A:
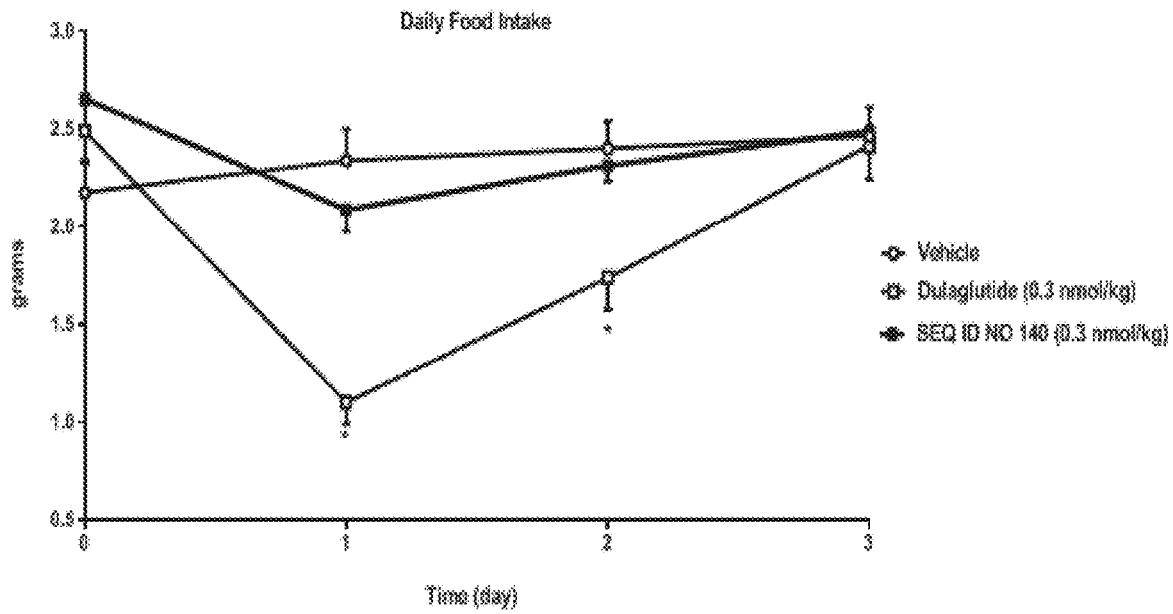
FIGS. 10A-10B show food intake (FI) in grams (FIG. 10A) and % body weight (BW) change (FIG. 10B) in DIO mice treated with vehicle, dulaglutide (0.3 nmol/kg), or SEQ ID NO:140 (0.3 nmol/kg). One day prior to the study, DIO mice were weighed and grouped by body weight. Mice were dosed by subcutaneous injection (2 mL/kg) with vehicle (white circles), dulaglutide (white squares), or SEQ ID NO 140 (black squares), and BW and FI were recorded for the following 3 days.
Figure 10B:
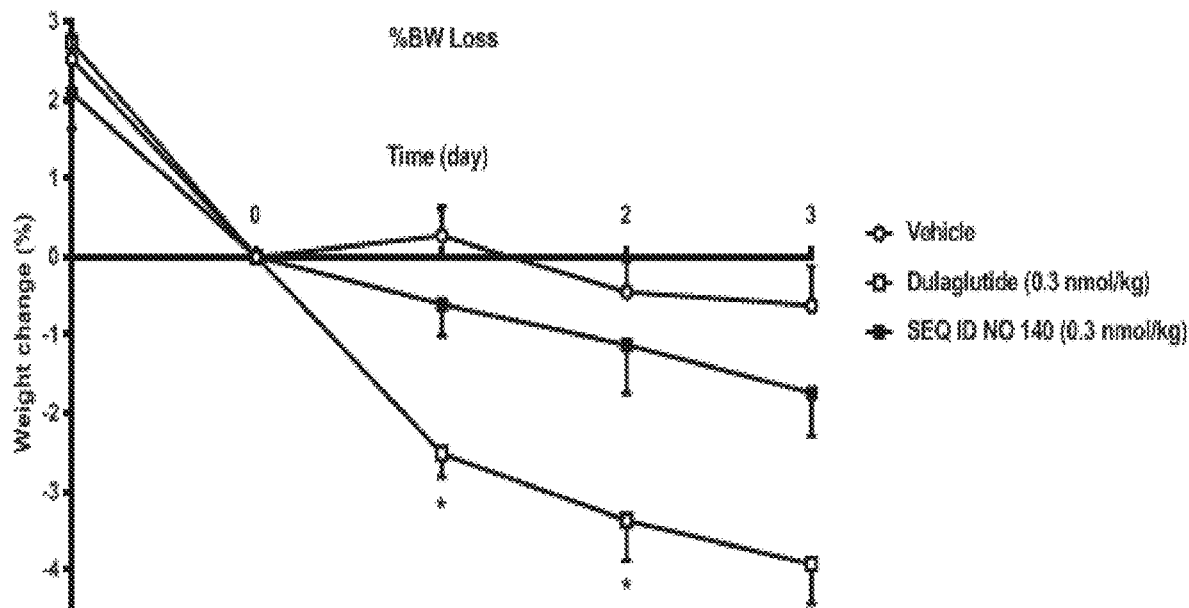

The GLP-1 peptide variant SEQ ID NO:57 was selected as a GLP-1 peptide variant. GLP-1 peptide-1 variant SEQ ID NO:56 was less potent in vivo and was less stable in ex vivo human plasma stability studies (FIG. 1A), thus was disfavored in this experiment. GLP-1 peptide variant SEQ ID NO:58 unexpectedly lost GLP-1R potency when conjugated to cyclic PYY peptides (Table 11), see, e.g., GLP-1R potencies of SEQ ID NO:135, 134, 146, and 176 with SEQ ID NO:238, 242, 262, 253, and 241 showed that GLP-1 fusion peptides with Exendin 4 (1-39) (SEQ ID NO:58) lost or had significantly reduced GLP-1R potency following conjugation with some PYY peptides. Work with GLP-1 fusion peptides with Exendin 4 (1-39) (SEQ ID NO:58) was disfavored in this experiment based on these results. GLP-1 peptide variant SEQ ID NO:58 additionally contains an NG deamidation liability motif. SEQ ID NO:59 formed an NG deamidation liability motif at the GLP-1 peptide/first linker peptide interface when glycine was the first amino acid in the first linker peptide. Additionally, GF28 (SEQ ID NO:140), which contained GLP-1 peptide SEQ ID NO:59, had less potency than dulaglutide for both food intake (FI) and % body weight (BW) change (FIG. 10A and FIG. 10B, respectively).

Figure 12:
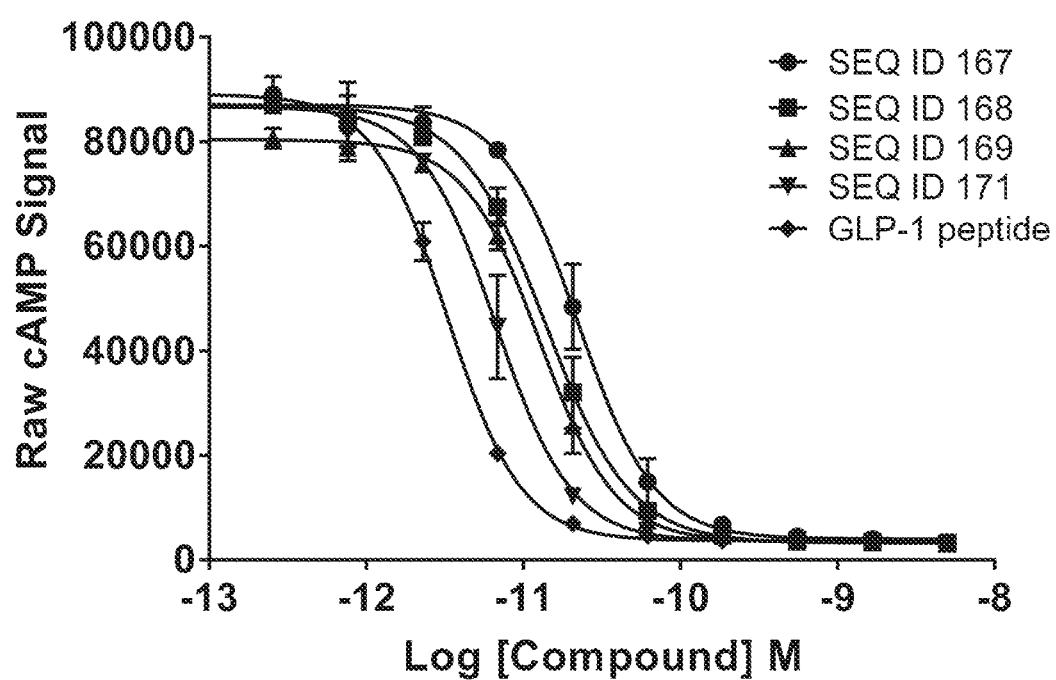
FIG. 12 shows a graph demonstrating the results of a human GLP-1R primary screening assay comparing the GLP-1 peptide (SEQ ID NO:58) with different length first linker peptides (N-terminal linker peptides). SEQ ID NO:171 containing the longest first linker peptide (SEQ ID NO:67) (▼), was the most potent, followed by GLP-1 fusion peptides with shorter first linker peptides, i.e., SEQ ID NO 169 with first linker peptide SEQ ID NO 64 (▲) and SEQ ID NO 168 with first linker peptide SEQ ID NO 74 (■). SEQ ID NO 167, which does not have an intervening first linker peptide between the GLP peptide and the hinge-Fc peptide (●) was the least potent. GLP-1 peptide (♦) was included as an assay control.

SEQ ID NO:60, was selected as the first linker peptide (N-terminal linker peptide). GLP-1 fusion proteins containing the first peptide linker, SEQ ID NO:61, had a low expression and purification yields and were disfavored in this experiment for producing the desired amount of GLP-1 fusion peptide coupled cyclic PYY peptide conjugate. First linker peptides containing AP repeats had poor yields when the second terminal peptide was a $G_4A$ repeat (see, e.g., Example 2 and Table 8) and were less stable in vivo compared with SEQ ID NO:60 (see, e.g., Table 13). Work with AP repeat linkers was disfavored in this experiment based on these results. Shorter linkers resulted in reduced potency (see, e.g., SEQ ID NO:152 in FIG. 5, SEQ ID NO:140 in FIGS. 10A-10B, and FIG. 12 comparing the potencies for GLP-1 fusion peptides comprising the same GLP-1 peptide (SEQ ID NO:58) with different length first linker peptides). Thus, work with shorter linkers was disfavored in this experiment based on these results. Use of serine containing linkers was disfavored in this experiment based on the propensity of serine residues to be xylosylated (see, e.g., Table 12).

Figure 6A:
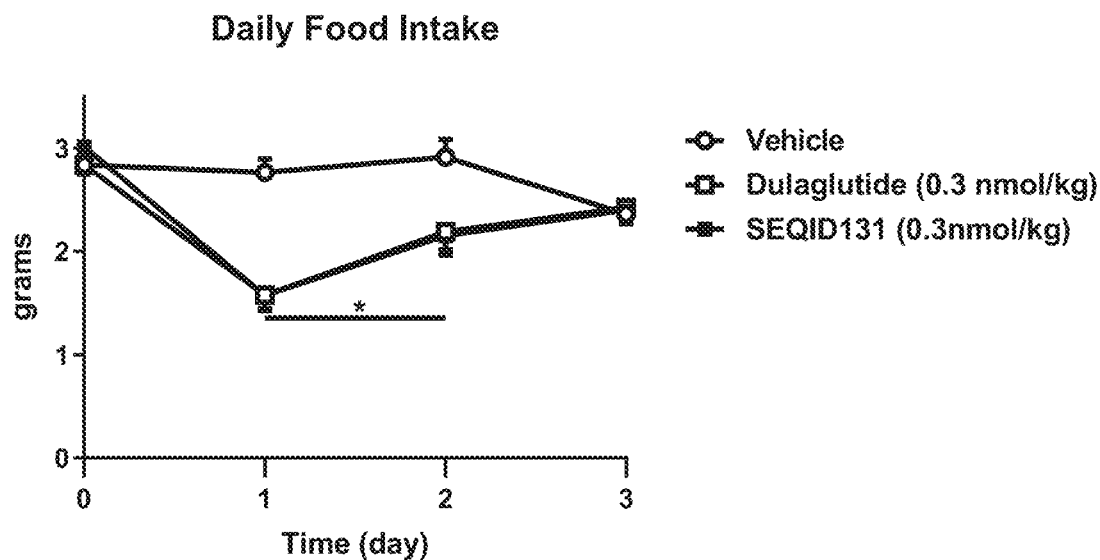
FIGS. 6A-6B show food intake and body weight loss in DIO mice.
Figure 6B:
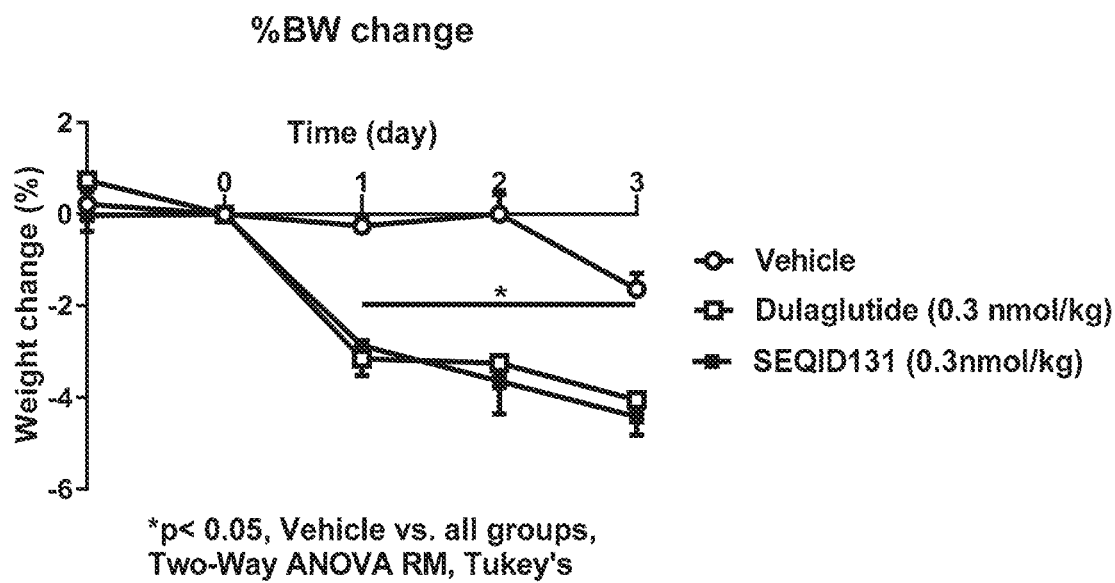
Figure 7A:
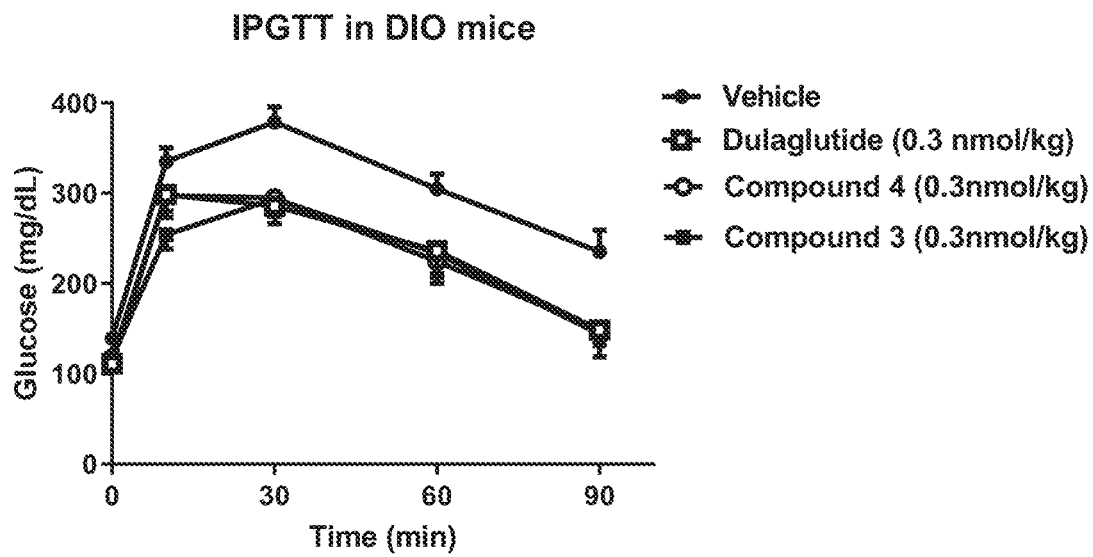
FIGS. 7A-7B show IPGTT in DIO mice.
Figure 7B:
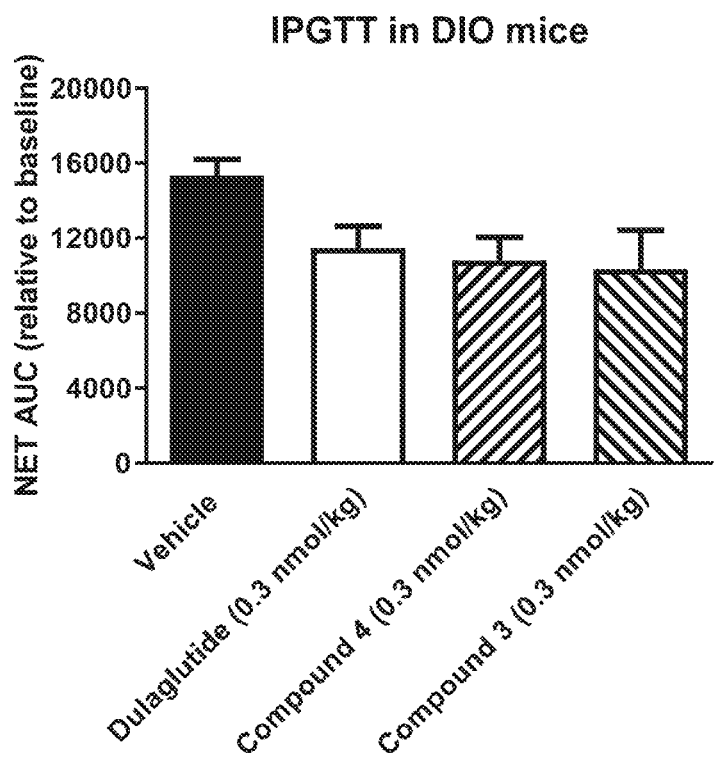

The GLP-1 fusion peptide, GF19 (SEQ ID NO:131), which contained the GLP-1 variant peptide, SEQ ID NO:57, the first linker peptide, SEQ ID NO:60, and the hinge-Fc region peptide, SEQ ID NO:84, demonstrated potency that was comparable to dulaglutide for both food intake (FI) and % body weight (BW) change (see, e.g., FIG. 6A and FIG. 6B, respectively).

GLP-1 fusion peptides GF1 (SEQ ID NO:113, compound 1), GF19 (SEQ ID NO:131), and GF24 (SEQ ID NO:136, compound 3) all demonstrated comparable efficacy to dulaglutide for food intake and % body weight change (see, e.g., FIGS. 2A-2B, FIGS. 6A-6B, and FIGS. 3A-3B, respectively). GF1 (SEQ ID NO:113, compound 1) and GF24 (SEQ ID NO:136, compound 3) also demonstrated comparable efficacy to dulaglutide on glucose tolerance (FIGS. 4A-4B and FIGS. 7A-7B).

Figure 11A:
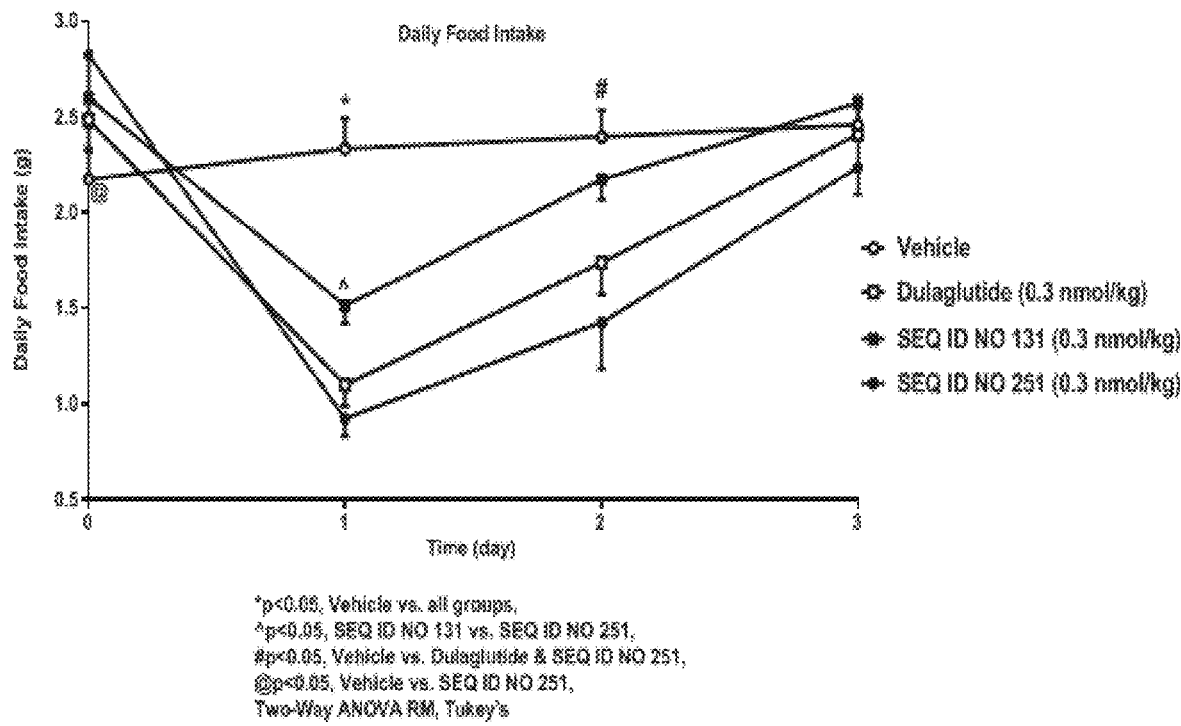
FIGS. 11A-11B show food intake (FI) in grams (FIG. 11A) and % body weight (BW) change (FIG. 11B) in DIO mice treated with vehicle, dulaglutide (0.3 nmol/kg), SEQ ID NO:131 (0.3 nmol/kg), or SEQ ID NO:251 (0.3 nmol/kg). One day prior to the study, DIO mice were weighed and grouped by body weight. Mice were dosed by subcutaneous injection (2 mL/kg) with vehicle (white circles), dulaglutide (white squares), SEQ ID NO 131 (black squares), or SEQ ID NO 251 (black circles), and BW and FI were recorded for the following 3 days.
Figure 11B:
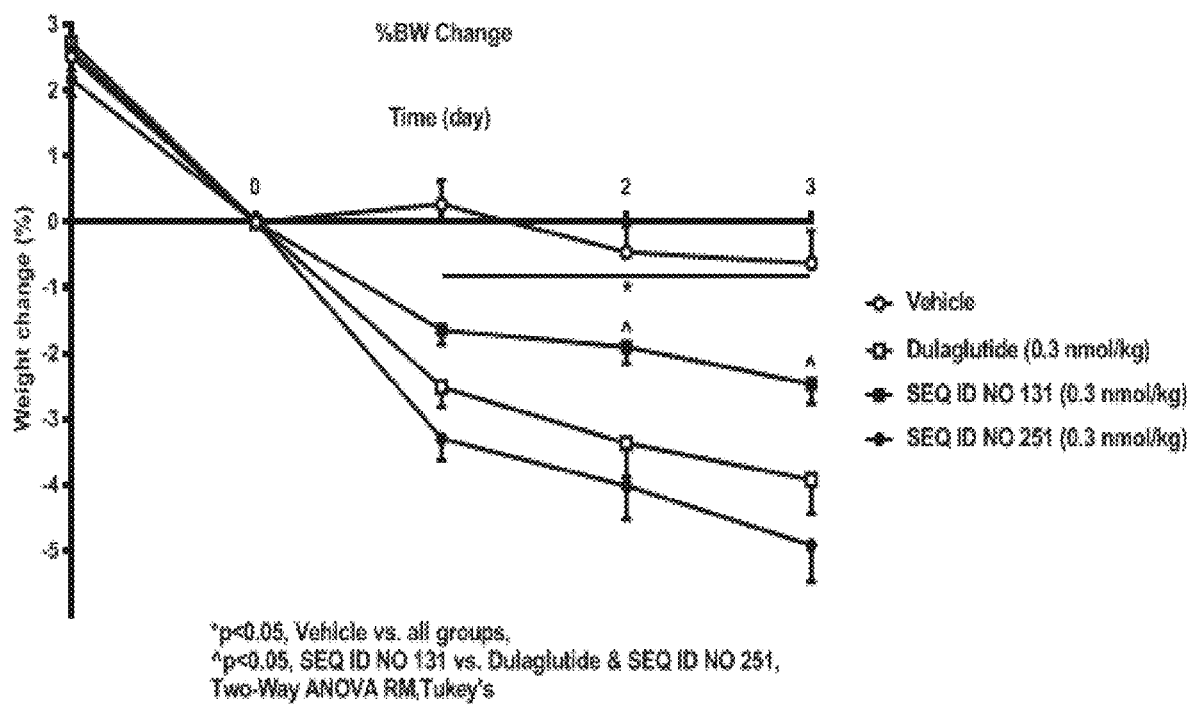

However, when a GLP-1 fusion peptide coupled cyclic PYY peptide conjugate, SEQ ID NO:251, was made by conjugating a cyclic PYY peptide (SEQ ID NO:27) to the second linker peptide, SEQ ID NO:92, of GF19 (SEQ ID NO:131), there was no additional pharmacology for food intake or % body weight change compared to dulaglutide (FIG. 11A and FIG. 11B, respectively). Additional second linker peptides were tested but were disfavored in this experiment, at least for the following reasons: (a) SEQ ID NO:95 had low production yields when the first linker peptide was an AP repeat, (b) SEQ ID NO:100 was truncated during recombinant expression, (c) hinge Fc region peptides with no second linker peptide, which comprise the target cysteine for PYY peptide conjugation at the C-terminal end of the hinge Fc region peptide, were truncated during protein expression, indicating that a second linker peptide was needed to produce intact protein amenable to PYY peptide conjugation, (d) serine containing second linker peptides had the potential to be xylosylated, and (e) shorter second linker peptides conjugated less efficiently with lower purity.

While GLP-1 fusion peptide coupled cyclic PYY peptide conjugate, SEQ ID NO:225 (compound 2), with the second linker peptide, SEQ ID NO:94, showed significantly greater potency than dulaglutide for both FI and % BW change (see, e.g., FIGS. 2A and 2B, respectively), it surprisingly had significant protein loss during 2-week storage at 4° C. in a high concentration liquid formulation. The comparable GLP-1 fusion peptide coupled cyclic PYY peptide conjugate, SEQ ID NO:229, with the second linker peptide, SEQ ID NO:93, was stable and maintained protein levels in high concentration liquid formulation during two-week storage at 4° C. and 40° C. (Table 14). The second linker peptide was the only difference between these two molecules, and, thus, SEQ ID NO:93 was selected as the second linker peptide in this experiment.

TABLE 14

Protein stability in high concentration liquid formulation during two-week storage at 4° C. and 40° C.

| SEQ ID NO: | Final concentration time = 0 at 4° C. | Final concentration time = 2 weeks at 4° C. | Final concentration time = 2 weeks at 40° C. |
| --- | --- | --- | --- |
| 225 | 52.6 mg/mL | 14.0 mg/mL | 52.8 mg/mL |
| 229 | 51.4 mg/mL | 48.5 mg/mL | 52.9 mg/mL |

Several modifications are required for cyclic PYY peptide functional activity, to confer in vivo stability required for an agent with extended half-life, and to enable linkage to GLP-1 fusion peptides while retaining potency. Synthetic peptide chemistry was employed to make cyclic PYY peptides, which incorporate these modifications, and the cyclic PYY peptides where chemically conjugated to GLP-1 fusion peptides to generate GLP-1 fusion peptide coupled cyclic PYY peptide conjugates.

Cyclic PYY peptides were selected to conjugate to GLP-1 fusion peptides to explore and compare modifications for PYY peptide potency and stability. The PYY peptide was cyclized to stabilize multiple sites of proteolysis along the peptide backbone.

Cyclic PYY peptides were selected to conjugate to GLP-1 fusion peptides to explore the spacing and size of the N- to C-terminal linkage of the cyclic PYY peptides, and the effects on potency and stability. These cyclic PYY peptides contained variations in the number of carbons in the cycle and varied the positions of the cysteine and homo cysteines used to selectively link the N-terminus to the C-terminus. See, for example, a) βA2 linked to hCys31 SEQ ID NO:25
b) βA2 linked to Cys30 SEQ ID NOs:28 and 29
c) G2 linked to Cys30 SEQ ID NOs:27 and 30
d) γAba2 linked to hCys31 SEQ ID NO:34

N-Me arginine substituted at position 35 (N-MeR35) (SEQ ID NOs:27, 28, 33, and 34) and a reduced amide bond between positions 35 and 36 (psi35,36) (SEQ ID NOs: 24, 25, 29, and 30) were compared for their ability to stabilize the amidated C-terminal tyrosine at position 36 in the cyclic PYY peptide and retain potency (see, e.g., U.S. Patent Publication No. 2018/0117170, which is incorporated herein by reference in its entirety). In certain instances, the N-Me35 modification resulted in reduced potency compared to the psi35,36 modification, (see, e.g., U.S. Patent Publication. No. 2018/0117170), Table 3, which shows that SEQ ID NO:102 with the psi35,36 modification was approximately 12-fold more potent for the human Y2 receptor than SEQ ID NO: 122 with the N-Me35 modification).

Unpredictably, the potency of the N-MeR35 modification in the GLP-1 fusion peptide coupled cyclic PYY peptide conjugate, SEQ ID 229, which contains the cyclic PYY peptide, SEQ ID 27, was equal to or greater compared with the psi35,36 modification in SEQ ID NO:232, which contains the cyclic PYY peptide, SEQ ID NO:30 (Table 11).

Cyclic PYY peptide, SEQ ID NO:27, was selected as the PYY peptide in this experiment based on potency and stability, along with the determination that the combination of components resulted in a lower cost of goods and ease of reagent sourcing. The natural amino acid glycine on the N-terminus linked to the cysteine at position 30 near the C-terminus had potency and stability that was comparable to the highest levels of potency and stability achieved for any cyclic PYY peptide tested when the cyclic PYY peptide was conjugated with the GLP-1 fusion peptide. The cysteine at position 30 was selected over homo cysteine at position 31 because cyclic PYY peptide SEQ ID NO:27 had sufficient potency and stability. Therefore, the more expensive and less readily available unnatural amino acids were not required in this experiment. N-MeR35 used to stabilize the C-terminal amidated tyrosine at position 36 is a less expensive and more readily available reagent than the costly psi35,36 modification. This eliminates the need for a custom component and provides the same stability and potency.

Additionally, it was determined that a PEG spacer was not required for potency, and, also unexpectedly, a PEG spacer was not required for in vivo PYY stability. This was unexpected, as it was determined that mAb-cyclic PYY peptide conjugates with the PEG spacer had increased in vivo stability (see, e.g., U.S. Patent Publication No. 2018/0117170, Table 4, which shows the percent remaining of the intact compound relative to the amount of total human mAb levels in blood samples from mice collected at 48 hours post administration. Compound 1, containing a 12×PEG spacer, had 90.8% remaining at 48 hours; compound 2, containing a 6×PEG spacer, had 65.6% remaining at 48 hours; and compound 3, without a PEG spacer, had only 51% remaining at 48 hours). This result eliminated the need for the PEG component that would have increased the manufacturing cost of goods.

SEQ ID NO:229, which contained GLP-1 fusion peptide SEQ ID NO:136 with the addition of two stable cyclic PYY peptides, SEQ ID NO:27, was selected as the GLP-1 fusion peptide coupled cyclic PYY peptide conjugate in this experiment. SEQ ID NO:229 exhibited additional pharmacodynamic efficacy from Y2R engagement relative to SEQ ID NO:136 (with GLP1R engagement only) for both FI and BW (FIGS. 3A-3B), while exhibiting GLP1R potency comparable to dulaglutide and SEQ ID NO:136 on glucose tolerance (FIGS. 4A-4B and 7A-7B).

Figure 8A:
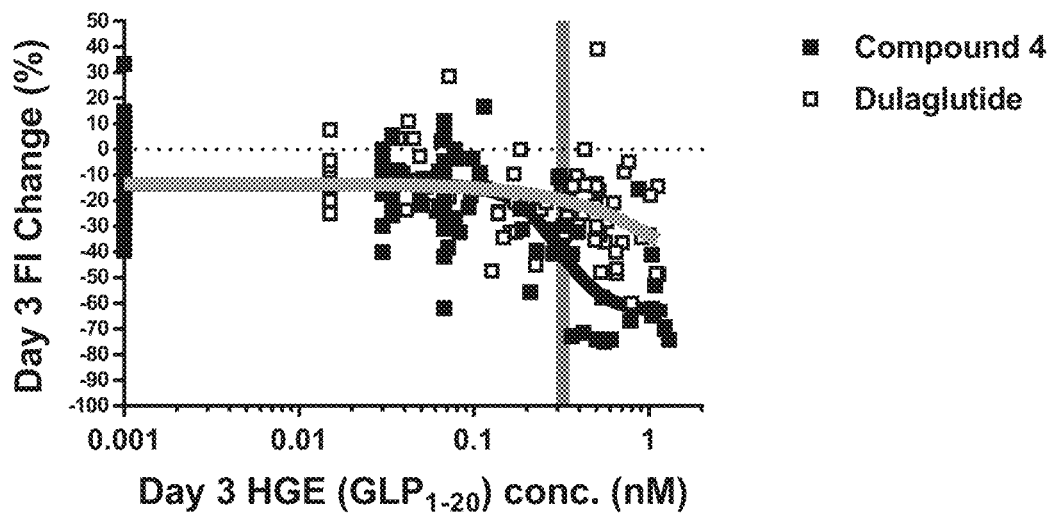
FIGS. 8A-8B show exposure-response analysis of compound 4 (SEQ ID NO:229) or dulaglutide on food intake and weight change after a single dose in DIO mice.
Figure 8B:
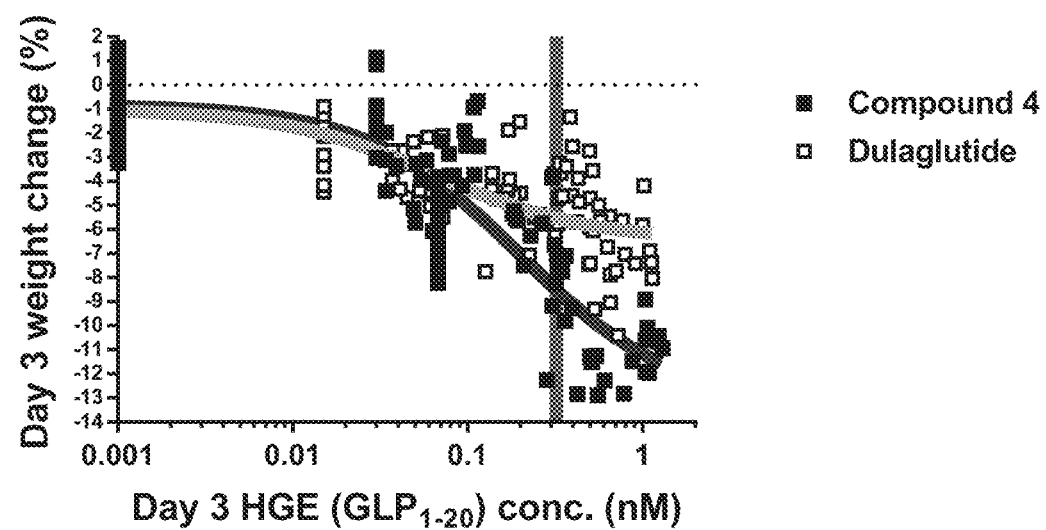

The effects of dulaglutide and SEQ ID NO:229 (compound 4) on FI and BW were compared in DIO mice. Based on integrated exposure-response nonlinear regression analysis of available studies (6 studies for compound 4 and 7 studies for dulaglutide; doses 0.03-1.0 nmol/kg), at a dose resulting in clinically relevant active GLP-1 (HGE) exposures on day 3 (single subcutaneous dose of 0.3 nmol/kg), compound 4 demonstrated additional pharmacology relative to dulaglutide, through Y2R engagement by the cyclic PYY peptides of the conjugate, in reducing FI and BW (FIGS. 8A-8B) at matched active GLP1 (HGE) exposures. At matched HGE concentrations of dulaglutide at 0.3 nmol/kg (single SC dose), based on exposure-response nonlinear regression by compound 4 (SEQ ID NO:229), the calculated FI and % BW change were about 2.1 and 1.5-fold greater than dulaglutide, respectively.

Figure 9A:
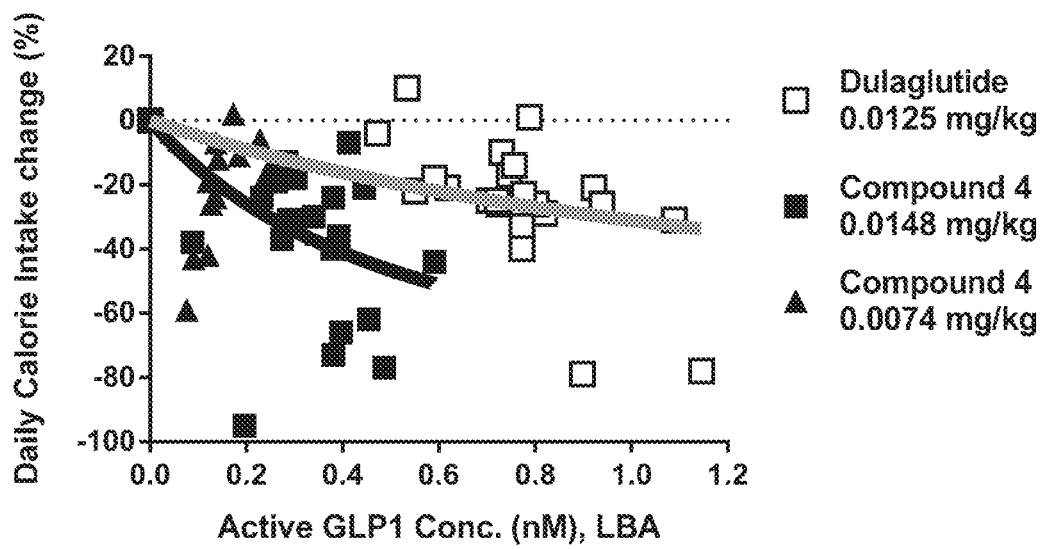
FIGS. 9A-9B show exposure-response analysis of compound 4 (black symbols) or dulaglutide (white squares) for effect on calorie intake in overweight cynomolgus monkeys on day 9 (pre-dose) and day 12 (pre-dose) after repeat (4, Q3D) subcutaneous (SC) dosing. Active GLP-1 concentrations were measured by both ligand binding assay (LBA) (FIG. 9A) and LC-MS/MS HE assays (FIG. 9B). The curved lines represent best-fit curves based on the exposure-response nonlinear regression for dulaglutide (gray curve) and compound 4 (black curve). Data from compound 4 dosed at 0.0074 mg/kg was not included in the exposure-response analysis but is included in the graph only. Daily calorie intake % change was calculated relative to baseline, which was defined as the average of days −2 to 0.
Figure 9B:
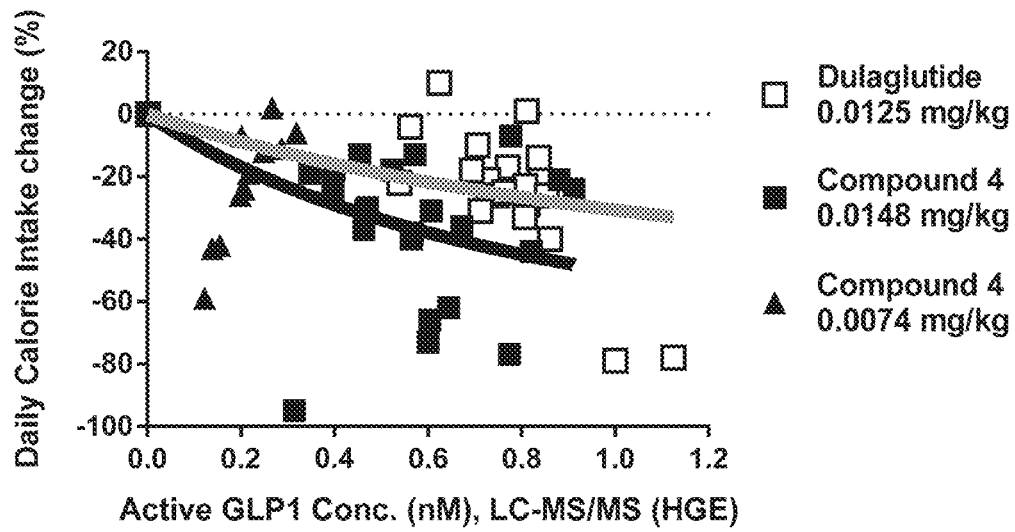

In overweight cynomolgus monkeys, individual PK and caloric intake based exposure-response analysis (FIGS. 9A-9B) suggested at clinically relevant dulaglutide exposures (1-2 nM bracketing the $C_{trough}$ and $C_{max}$ at steady state after QW SC dosing of 1.5 mg in T2DM patients [Geiser et al., *Clin Pharmacokinet* 55(5): (2016)]), compound 4 resulted in ~1.7 to 2-fold (95% Confidence Interval: 1.3 to 3.3, PK based on ligand binding assay [LBA], FIG. 9A), or ~1.5 to 1.6-fold (95% Confidence Interval: 1.0 to 2.8, PK based on LC-MS/MS HE, FIG. 9B) greater caloric intake percent reduction compared to dulaglutide at matched active GLP-1 exposures, demonstrating additional pharmacology from the cyclic PYY peptides of compound 4.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

All documents cited herein are incorporated by reference.

Exemplary GLP-1 fusion cyclic PYY peptide conjugates thereof of the invention include:

SEQ ID NO: 225

Name: GLP-1 fusion-[Cyclo-(G2-COCH$_2$-C30), K(Ac)11, N-Me-R35]-PYY2-36 homodimer conjugate Structure:

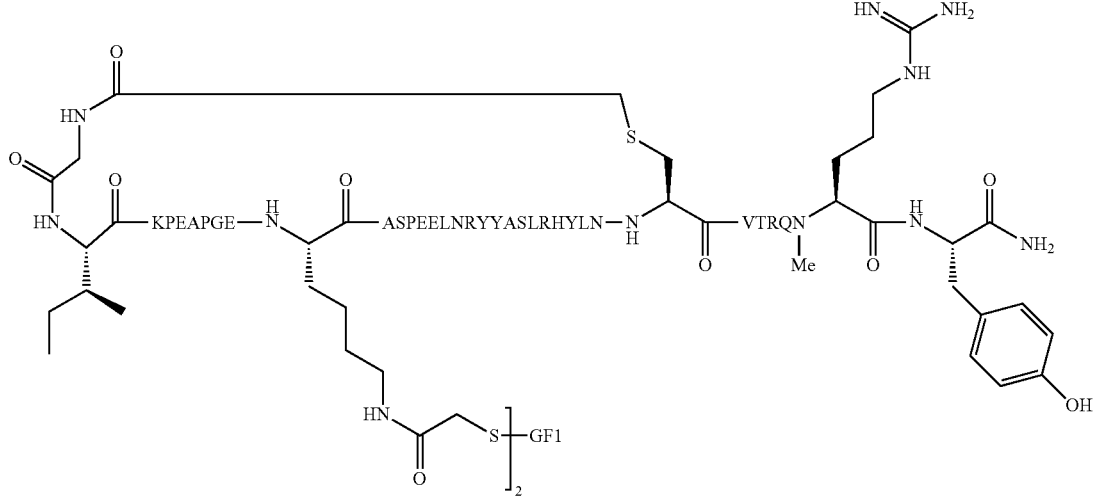

SEQ ID NO: 226
Name: GLP-1 fusion-[Cyclo-(βA2-COCH₂-C30), K(Ac)11, N-Me-R35]-PYY2-36 homodimer conjugate
Structure:
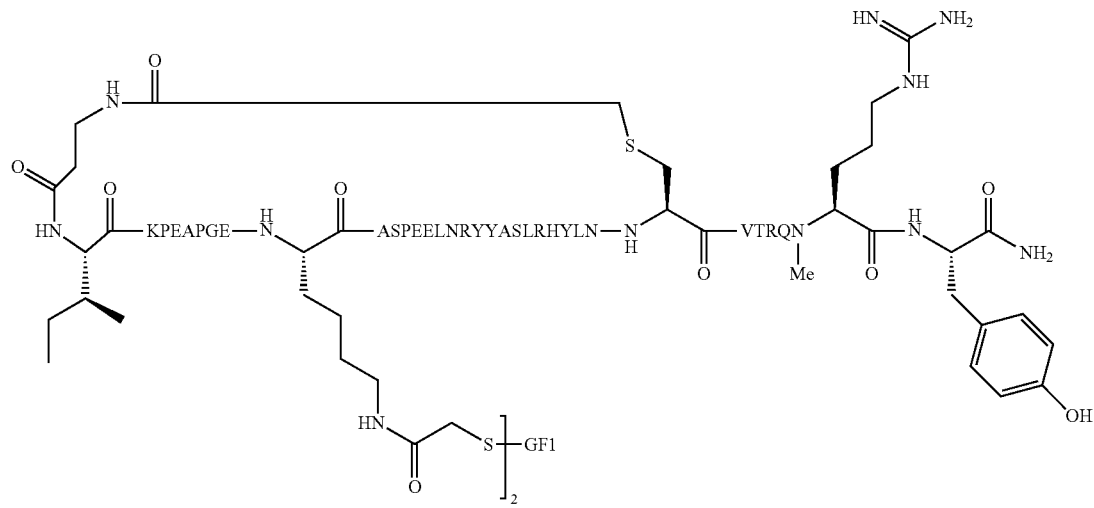
SEQ ID NO: 227
Name: GLP-1 fusion-[Cyclo-(βA2-COCH₂-C30), K(Ac)11, psi-(R35, Y36)]-PYY2-36 homodimer conjugate
Structure:
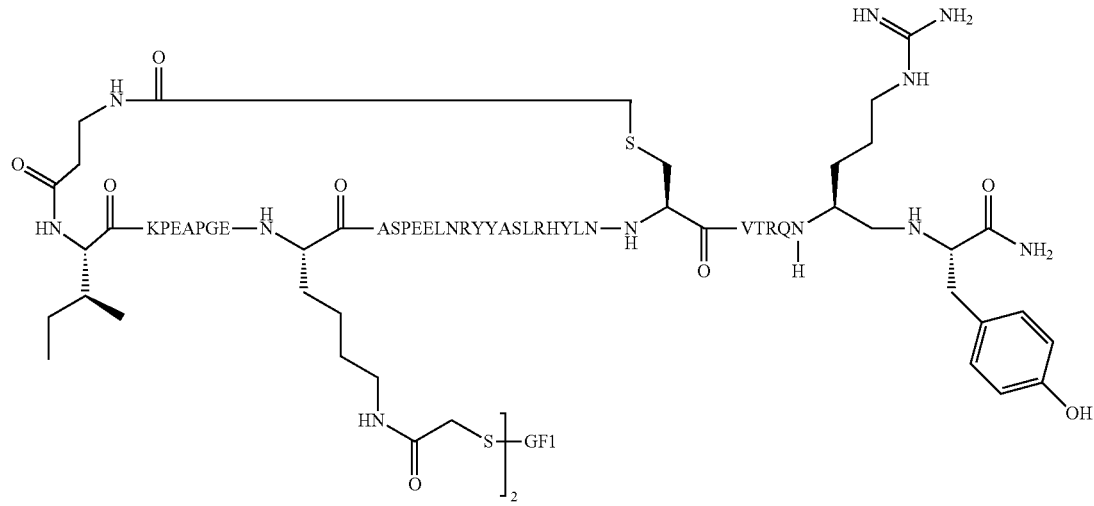

SEQ ID NO: 228
Name: GLP-1 fusion-[Cyclo-(βA2-COCH₂-C30), K(Ac)11, N-Me-R35]-PYY2-36 homodimer conjugate
Structure:
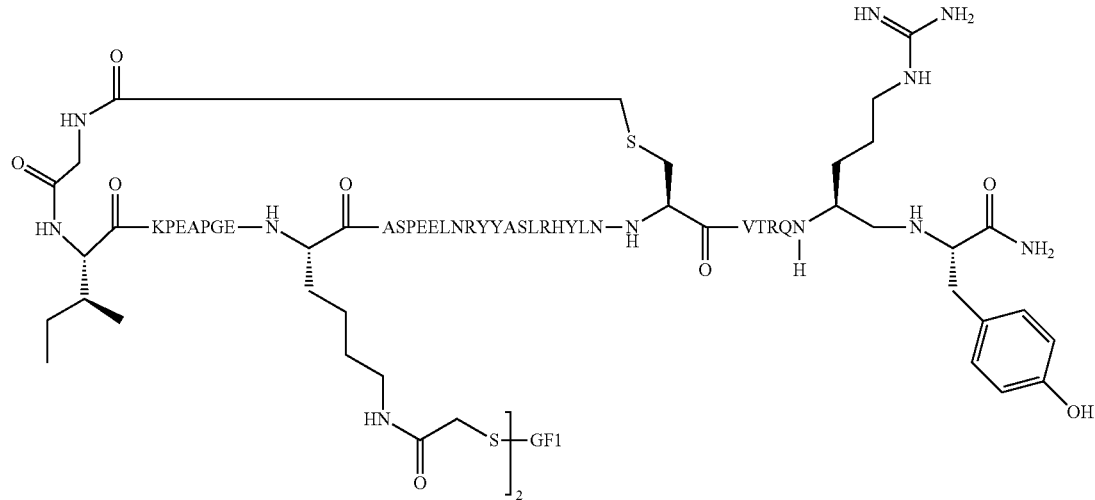
SEQ ID NO: 229
Name: GLP-1 fusion-[Cyclo-(G2-COCH₂-C30), K(Ac)11, N-Me-R35]-PYY2-36 homodimer conjugate
Structure:
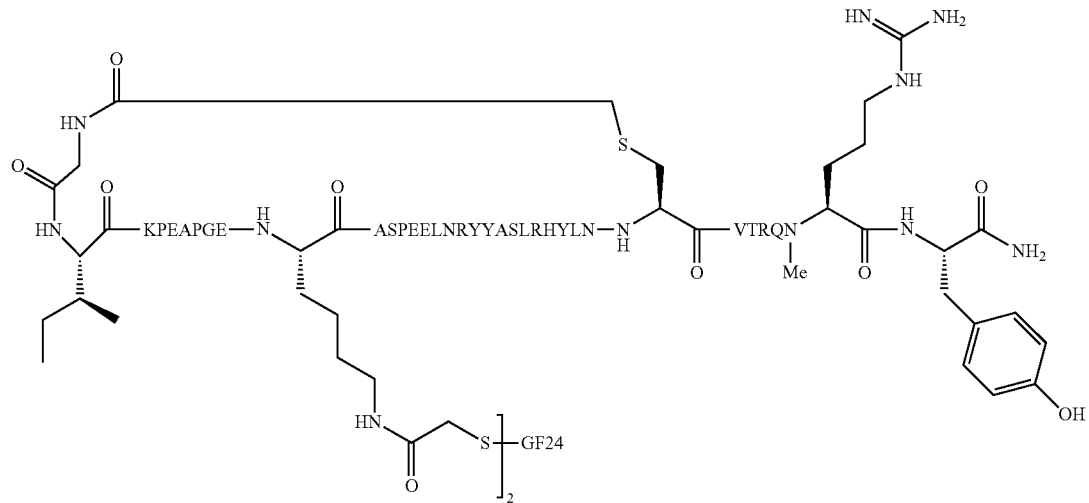

SEQ ID NO: 230
Name: GLP-1 fusion-[Cyclo-(βA2-COCH₂-C30), K(Ac)11, N-Me-R35]-PYY2-36 homodimer conjugate
Structure:
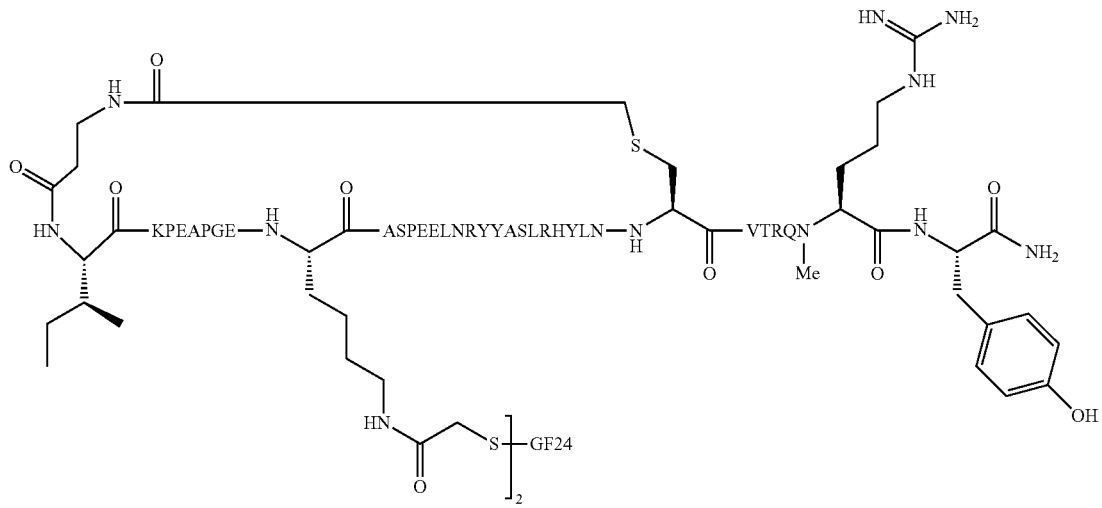
SEQ ID NO: 231
Name: GLP-1 fusion-[Cyclo-(βA2-COCH₂-C30), K(Ac)11, psi-(R35, Y36)]-PYY2-36 homodimer conjugate
Structure:
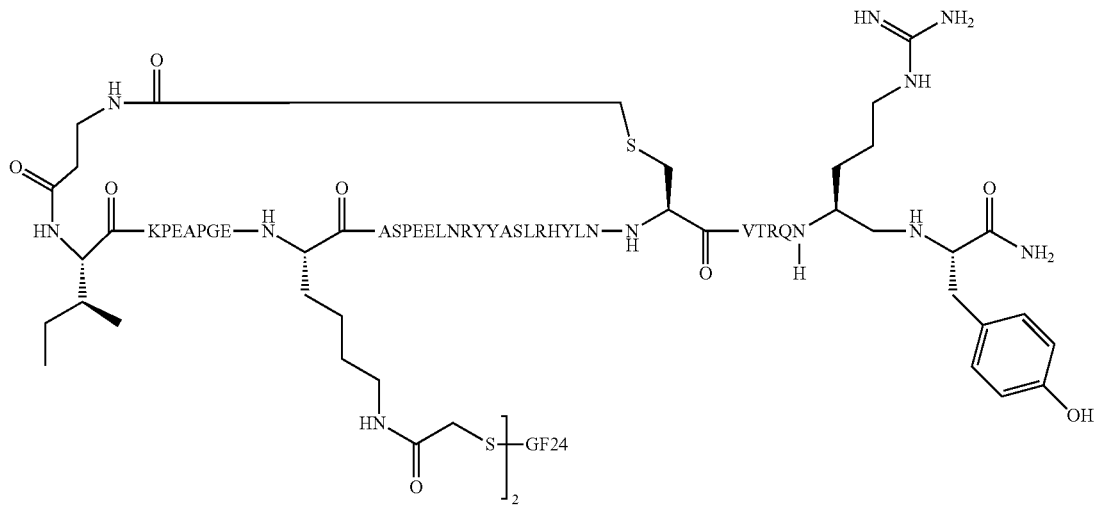

SEQ ID NO: 232
Name: GLP-1 fusion-[Cyclo-(G2-COCH$_2$-C30), K(Ac)11, psi-(R35, Y36)]-PYY2-36 homodimer conjugate
Structure:
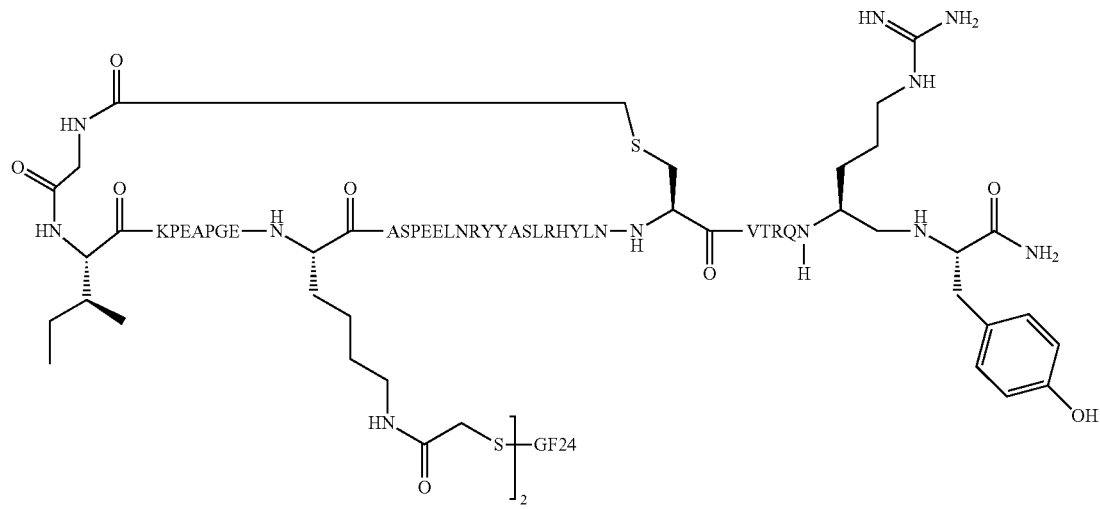
SEQ ID NO: 233
Name: GLP-1 fusion-[Cyclo-(G2-COCH$_2$-C30), K(Ac)11, N-Me-R35]-PYY2-36 homodimer conjugate
Structure:
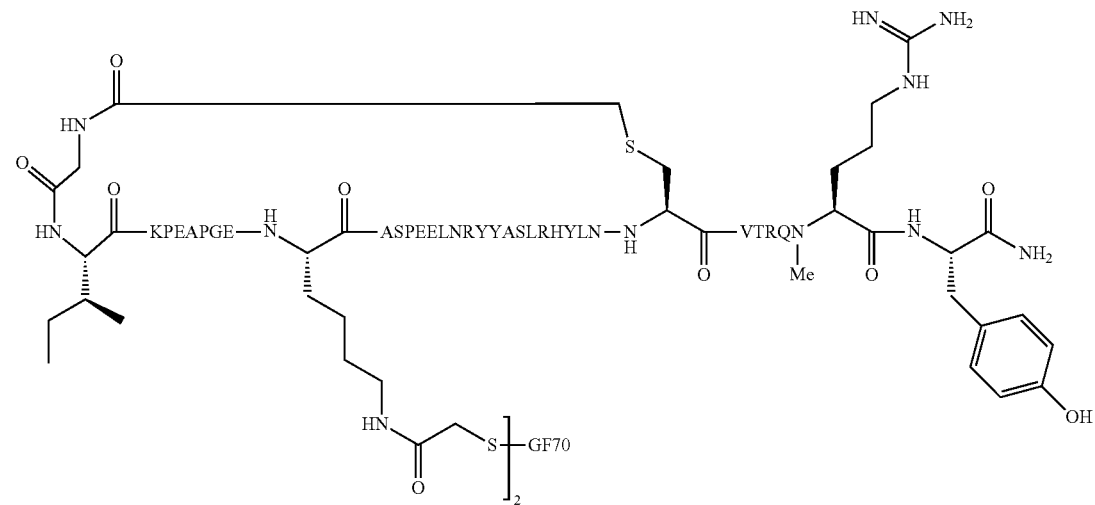

SEQ ID NO: 234
Name: GLP-1 fusion-[Cyclo-(G2-COCH$_2$-C30), K(Ac)11, N-Me-R35]-PYY2-36 homodimer conjugate
Structure:
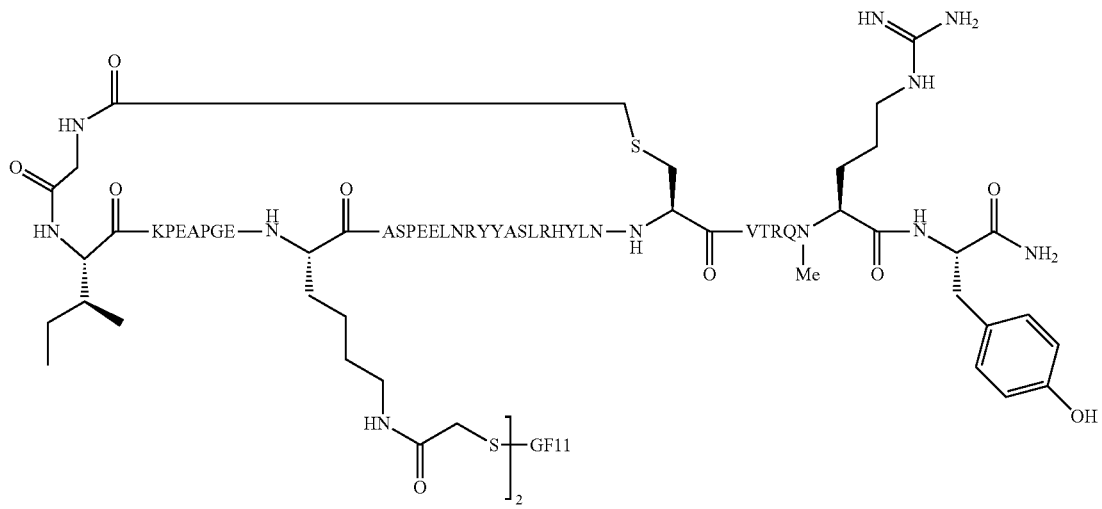
SEQ ID NO: 235
Name: GLP-1 fusion-[Cyclo-(G2-COCH$_2$-C30), K(Ac)11, N-Me-R35]-PYY2-36 homodimer conjugate
Structure:
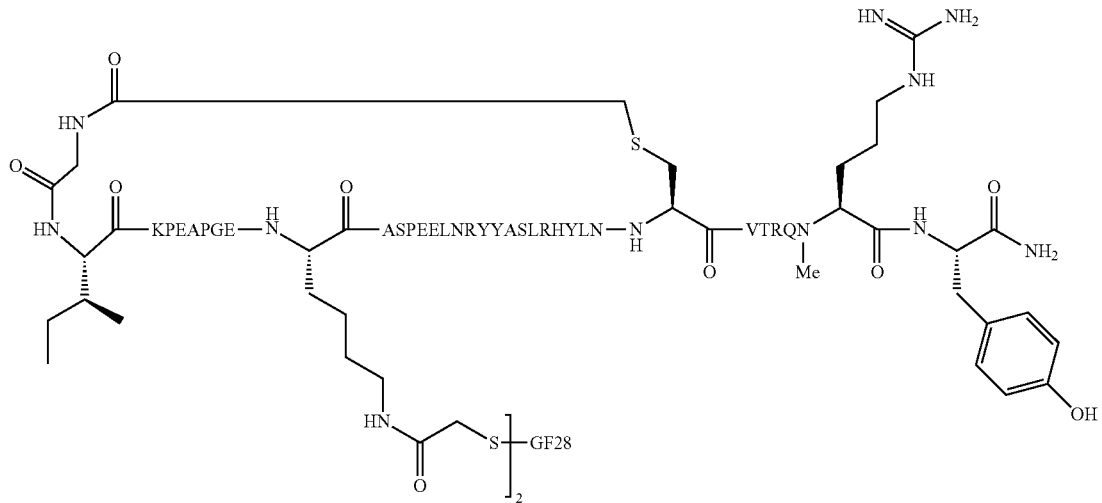

SEQ ID NO: 236
Name: GLP-1 fusion-[Cyclo-(G2-COCH₂-C30), K(Ac)11, N-Me-R35]-PYY2-36 homodimer conjugate
Structure:
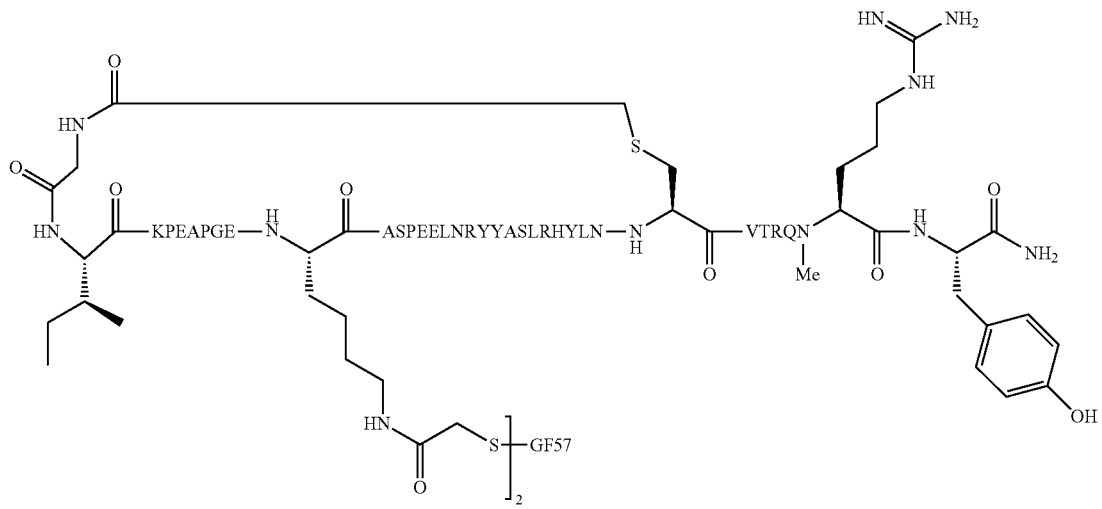
SEQ ID NO: 237
Name: GLP-1 fusion-[Cyclo-(G2-COCH₂-C30), K(Ac)11, N-Me-R35]-PYY2-36 homodimer conjugate
Structure:
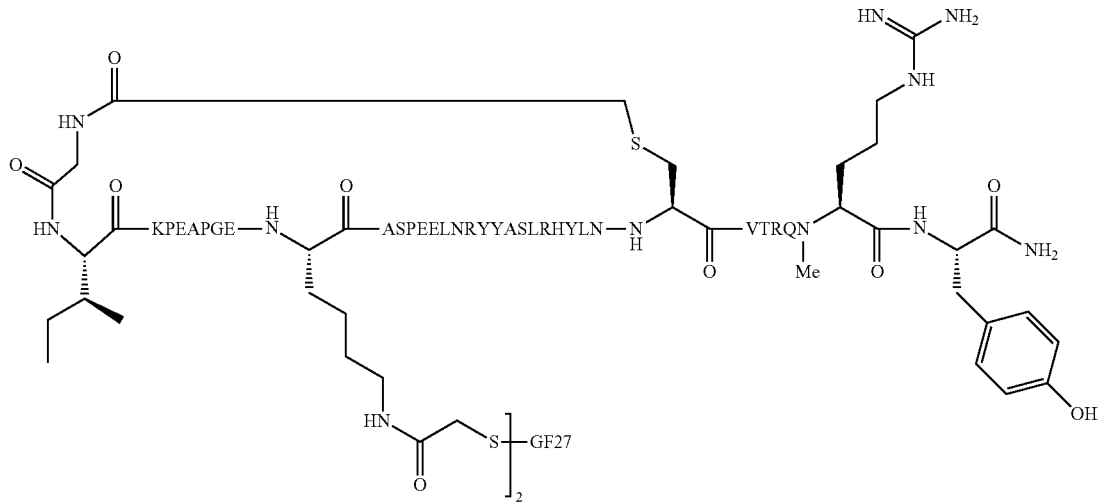

SEQ ID NO: 238
Name: GLP-1 fusion-[Cyclo-(G2-COCH₂-C30), K(Ac)11, N-Me-R35]-PYY2-36 homodimer conjugate
Structure:
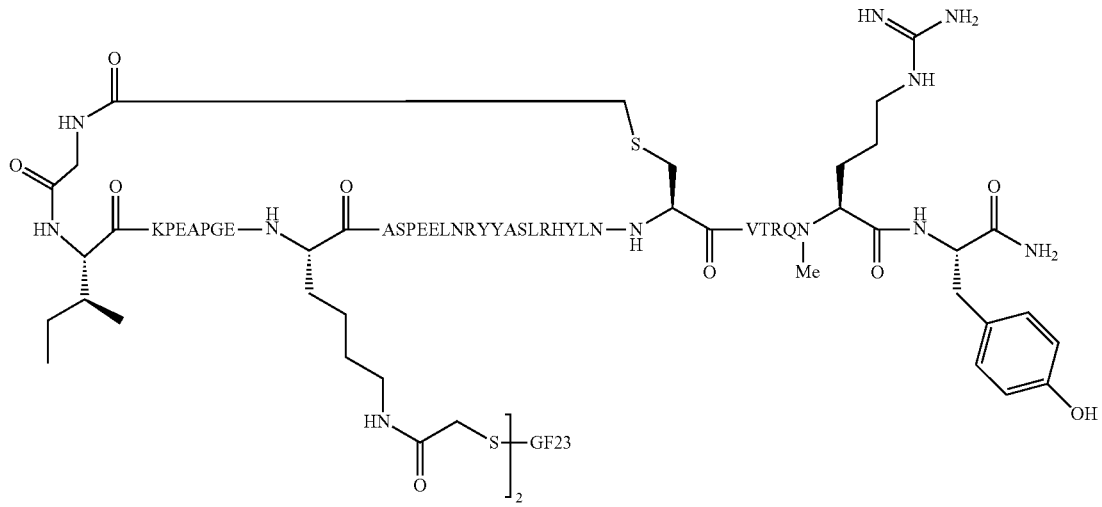
SEQ ID NO: 239
Name: GLP-1 fusion-[Cyclo-(G2-COCH₂-C30), K(Ac)11, N-Me-R35]-PYY2-36 homodimer conjugate
Structure:
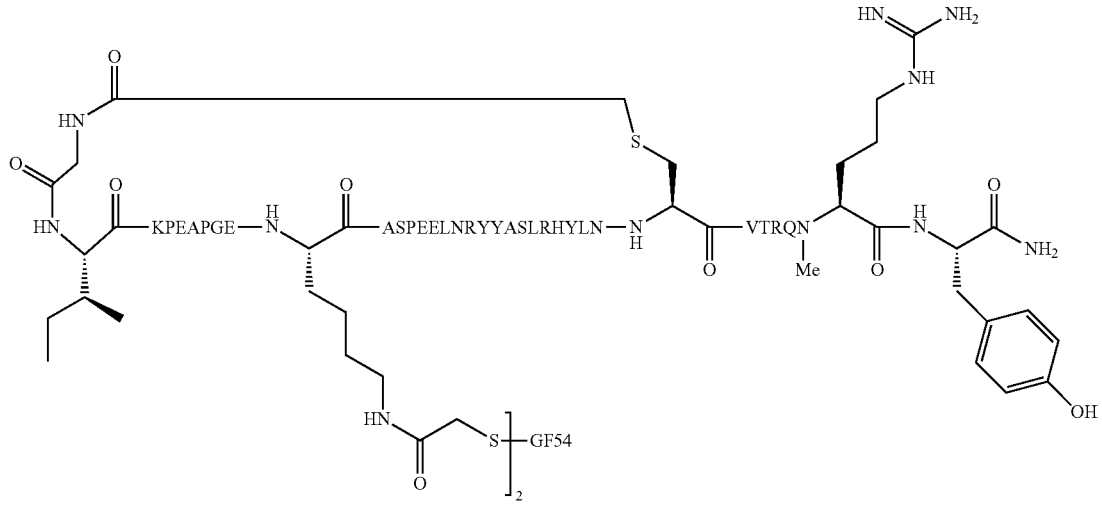

SEQ ID NO: 240
Name: GLP-1 fusion-[Cyclo-(G2-COCH₂-C30), K(Ac)11, N-Me-R35]-PYY2-36 homodimer conjugate
Structure:
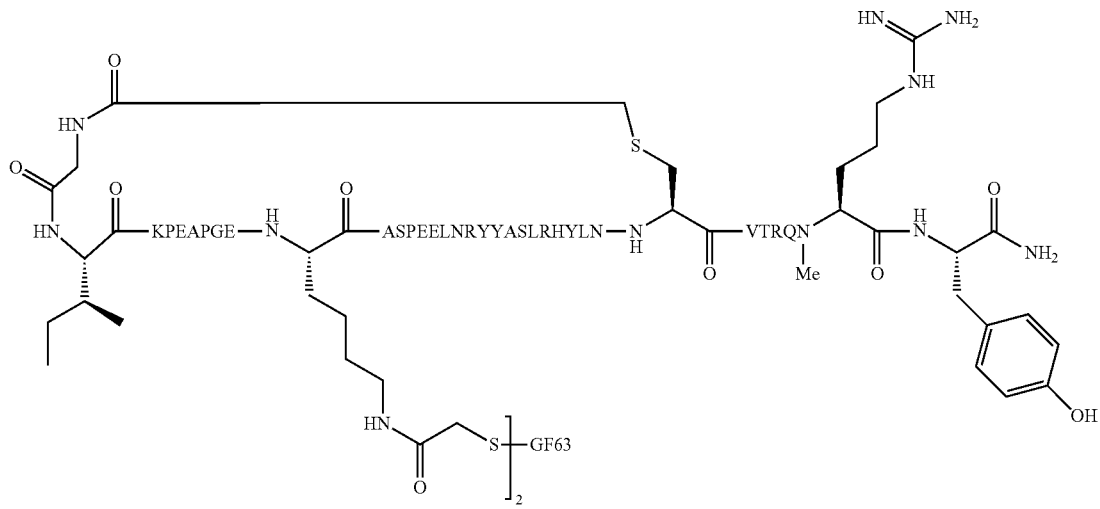
SEQ ID NO: 241
Name: GLP-1 fusion-[Cyclo-(G2-COCH₂-C30), K(Ac)11, N-Me-R35]-PYY2-36 homodimer conjugate
Structure:
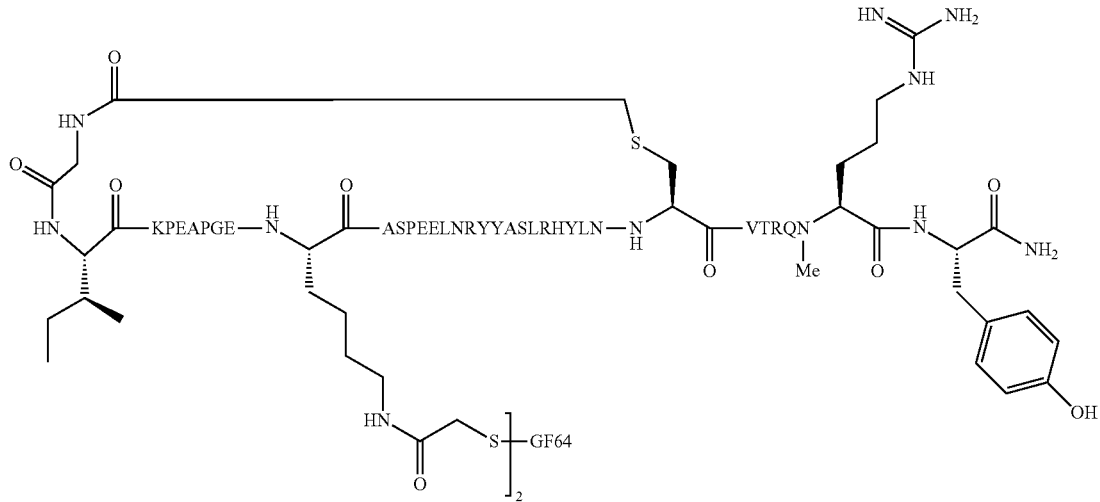

SEQ ID NO: 242
Name: GLP-1 fusion-[Cyclo-(G2-COCH₂-C30), K(Ac)11, N-Me-R35]-PYY2-36 homodimer conjugate
Structure:
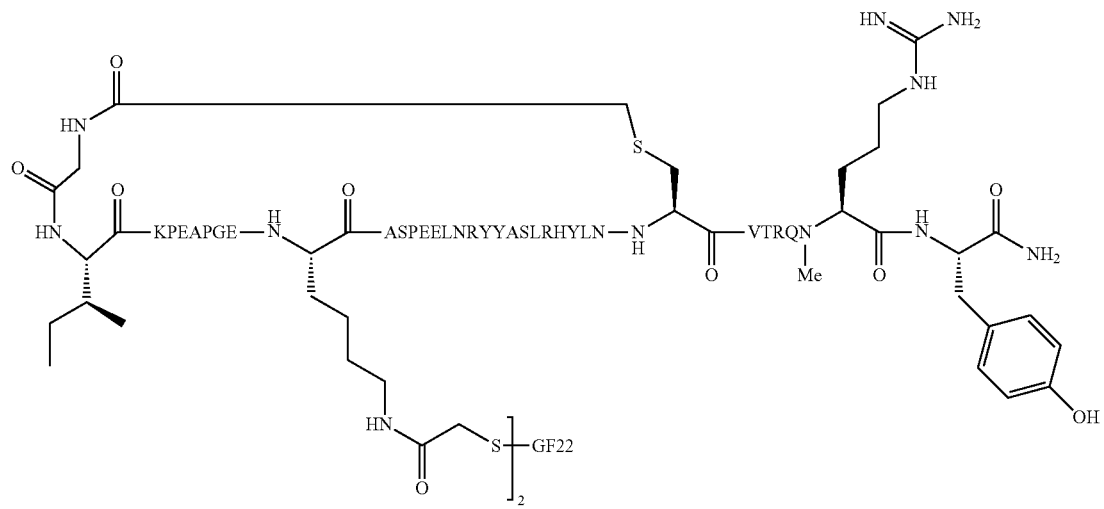
SEQ ID NO: 243
Name: GLP-1 fusion-[Cyclo-(G2-COCH₂-C30), K(Ac)11, N-Me-R35]-PYY2-36 homodimer conjugate
Structure:
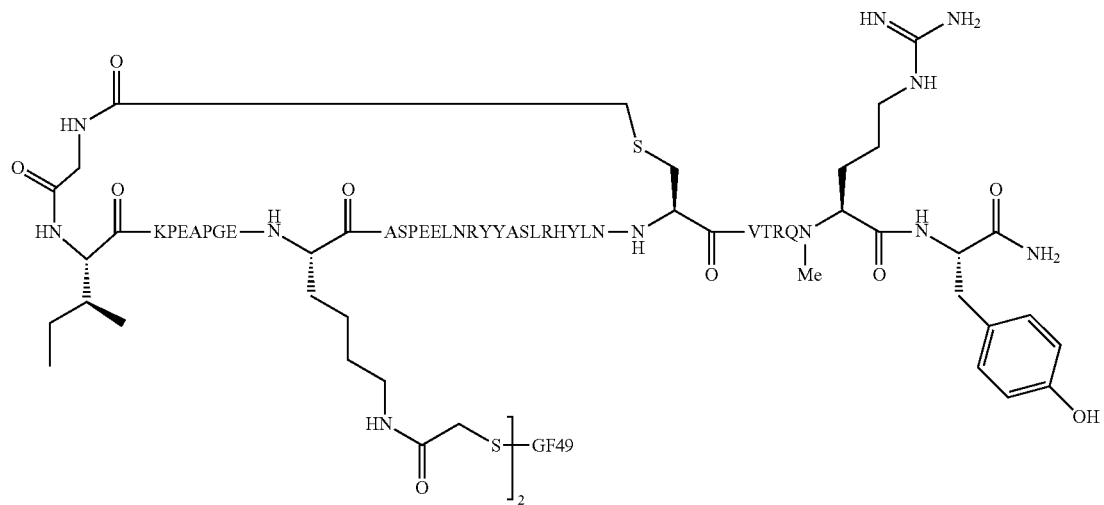

SEQ ID NO: 244
Name: GLP-1 fusion-[Cyclo-(G2-COCH₂-hC31), K(PEG24Ac)11, N-Me-R35]-PYY2-36 homodimer conjugate
Structure:
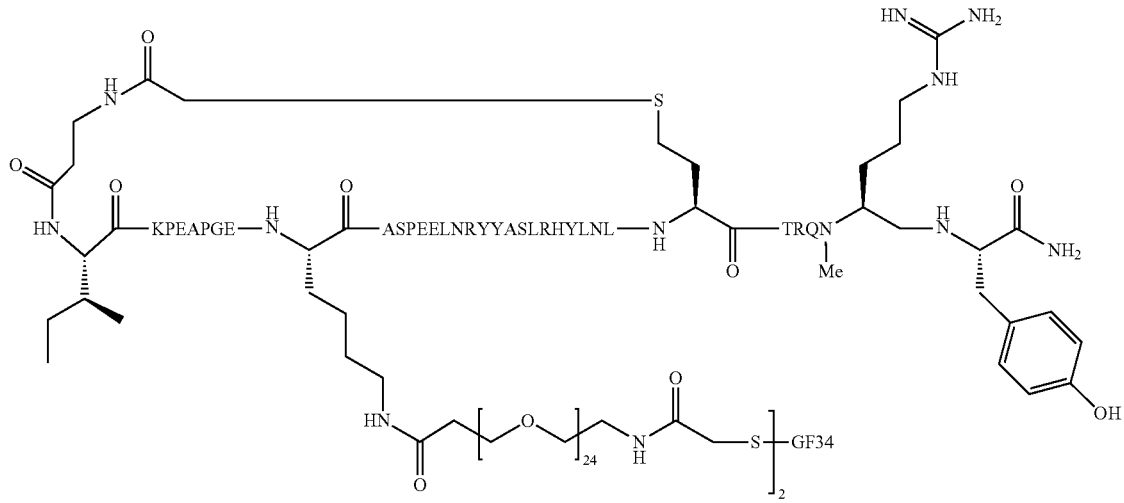
SEQ ID NO: 245
Name: GLP-1 fusion-[Cyclo-(G2-COCH₂-C30), K(Ac)11, N-Me-R35]-PYY2-36 homodimer conjugate
Structure:
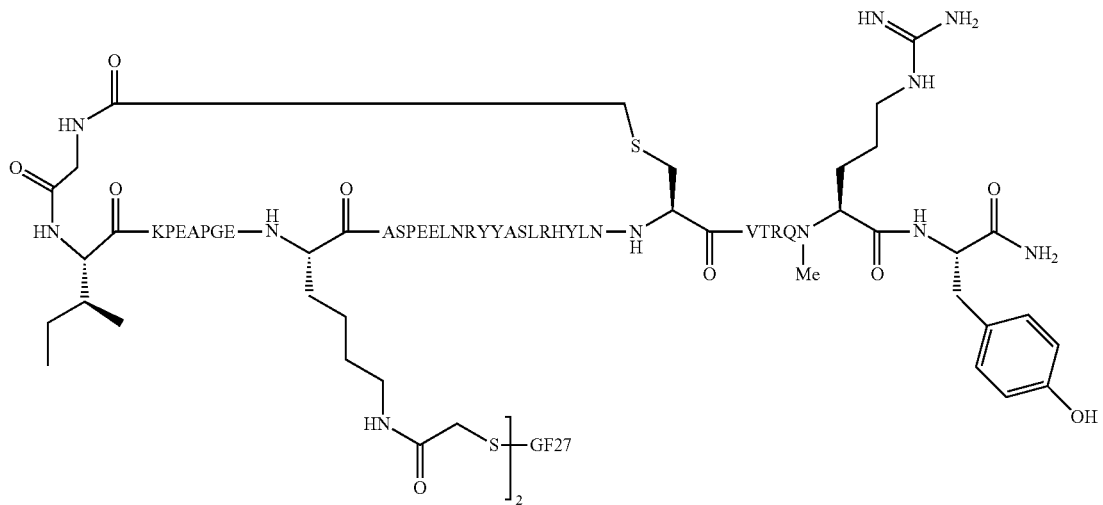

SEQ ID NO: 246
Name: GLP-1 fusion-[Cyclo-(G2-COCH₂-C30), K(Ac)11, N-Me-R35]-PYY2-36 homodimer conjugate
Structure:
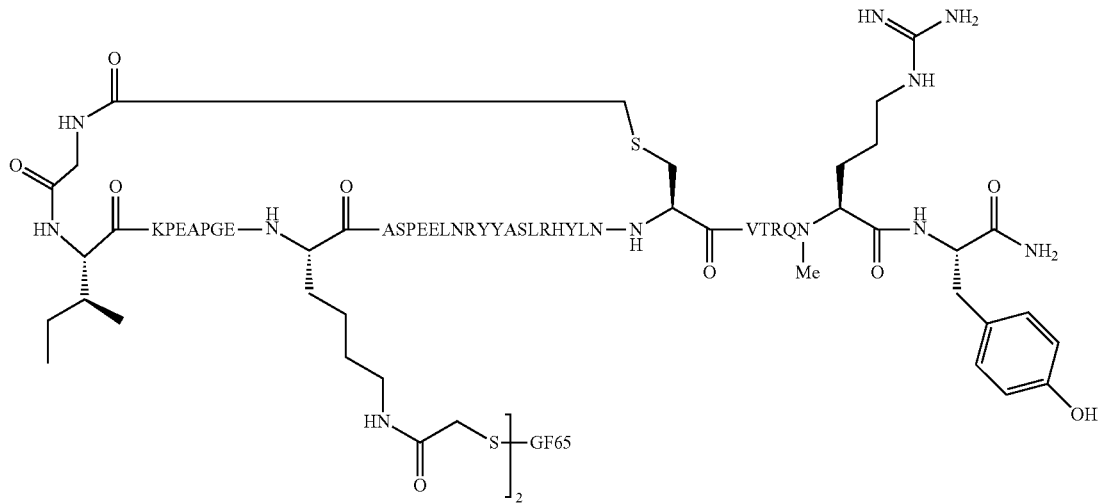
SEQ ID NO: 247
Name: GLP-1 fusion-[Cyclo-(G2-COCH₂-C30), K(Ac)11, N-Me-R35]-PYY2-36 homodimer conjugate
Structure:
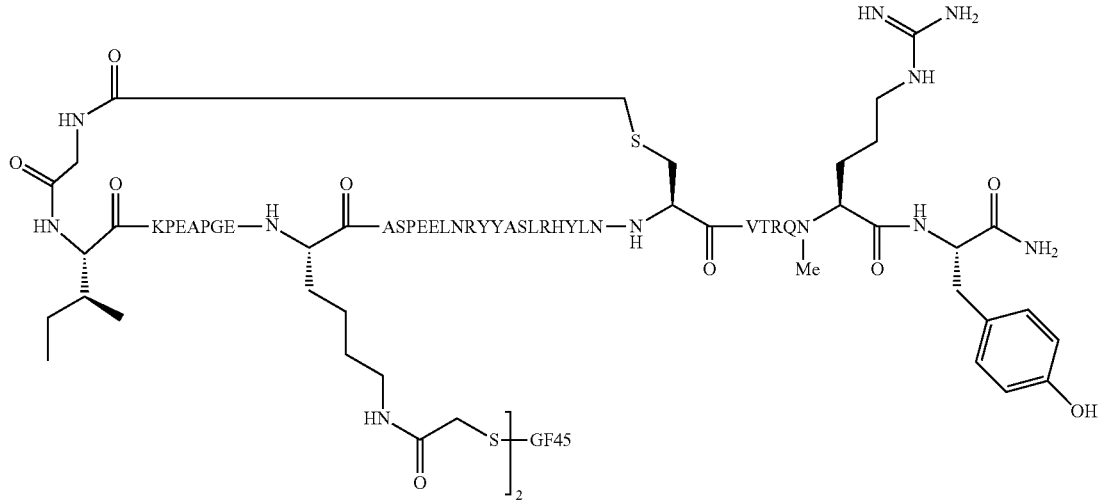

SEQ ID NO: 248
Name: GLP-1 fusion-[Cyclo-(G2-COCH₂-C30), K(Ac)11, N-Me-R35]-PYY2-36 homodimer conjugate
Structure:
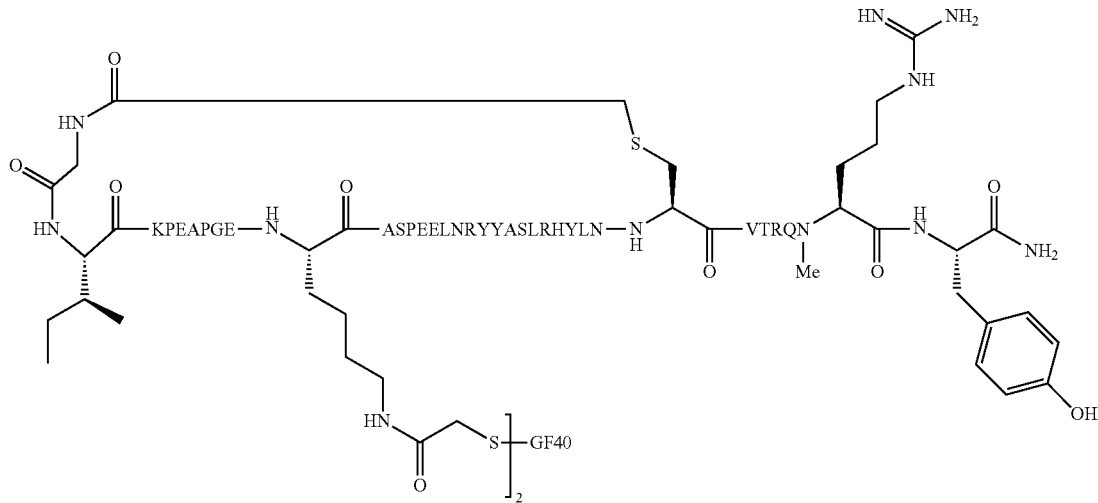
SEQ ID NO: 249
Name: GLP-1 fusion-[Cyclo-(G2-E30), S4, K(Ac)11, N-Me-R35]-PYY2-36 homodimer conjugate
Structure:
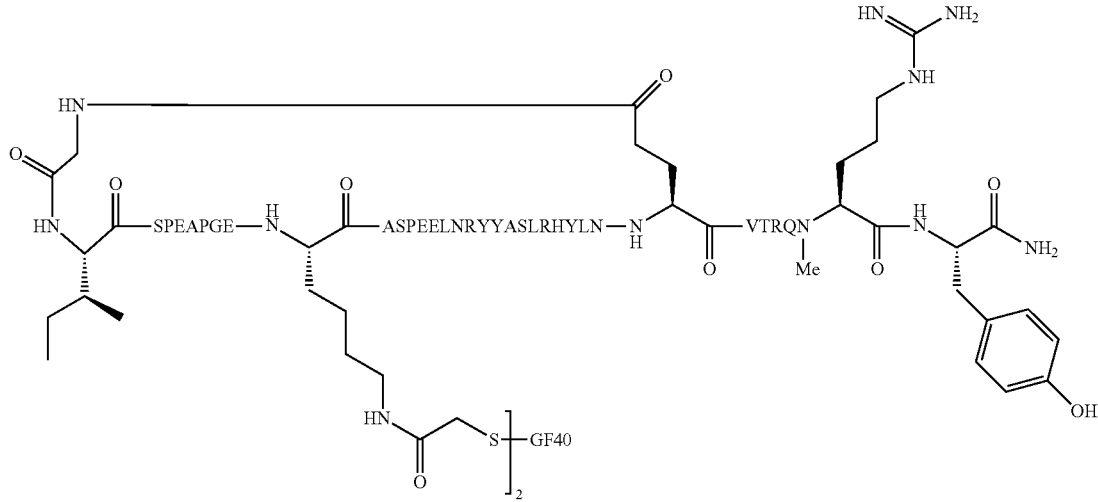

SEQ ID NO: 250
Name: GLP-1 fusion-[Cyclo-(G2-E30), S4, K(Ac)11, psi-(R35, Y36)]-PYY2-36 homodimer conjugate
Structure:
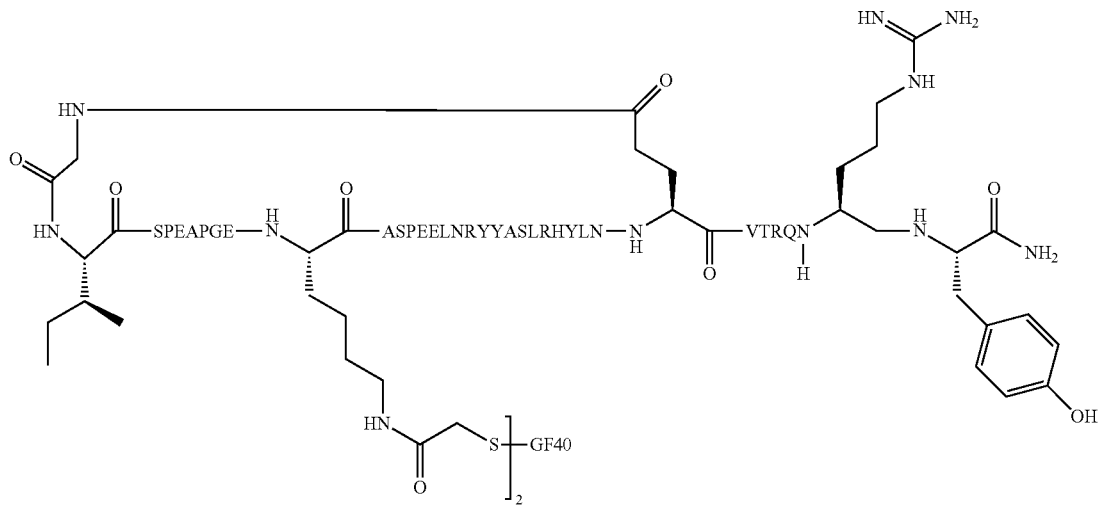
SEQ ID NO: 251
Name: GLP-1 fusion-[Cyclo-(G2-COCH2-C30), K(Ac)11, N-Me-R35]-PYY2-36 homodimer conjugate
Structure:
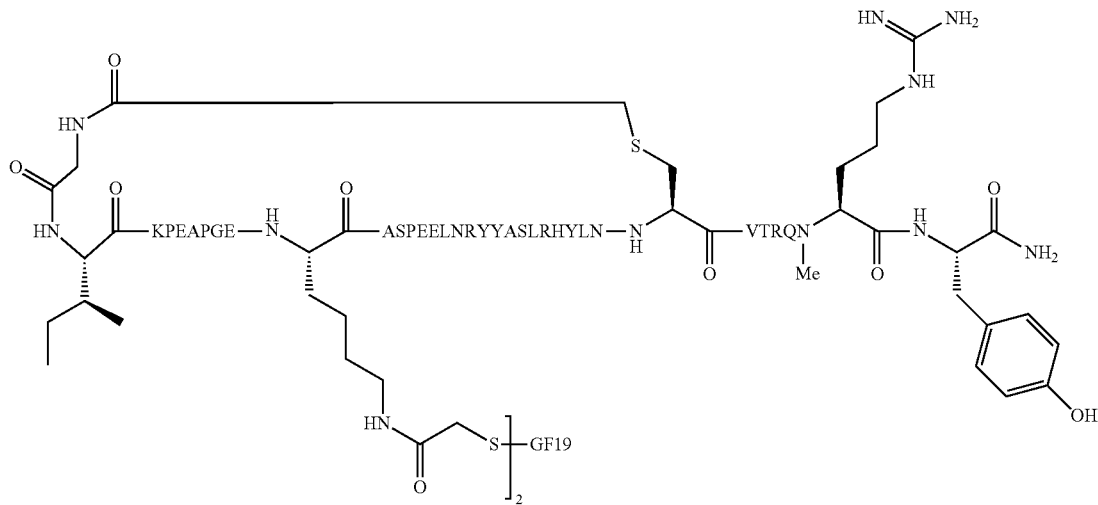

SEQ ID NO: 252
Name: GLP-1 fusion-[Cyclo-(G2-COCH₂-C30), K(Ac)11, N-Me-R35]-PYY2-36 homodimer conjugate
Structure:
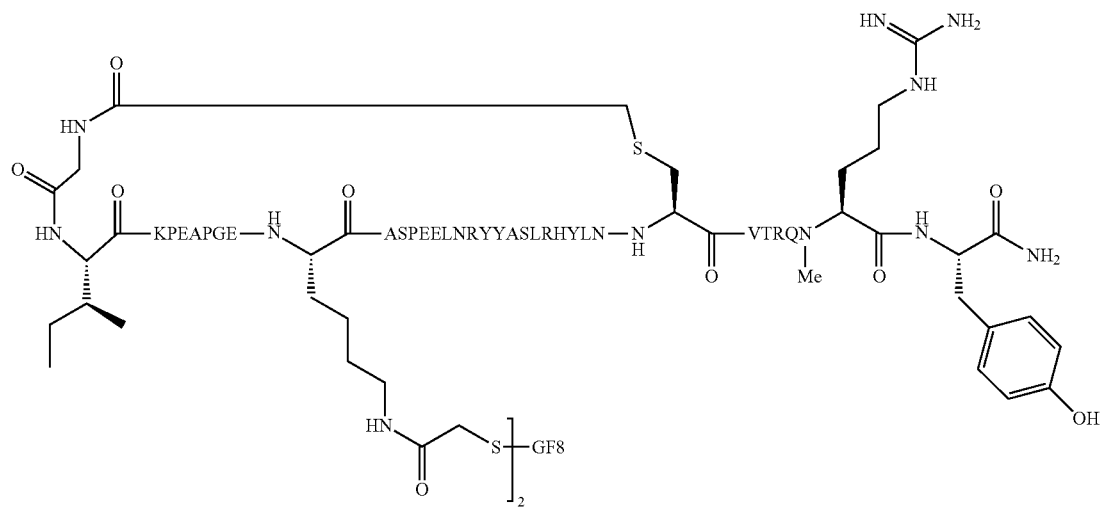
SEQ ID NO: 253
Name: GLP-1 fusion-[Cyclo-(gAba2-COCH₂-hC30), K(Ac)11, N-Me-R35]-PYY2-36 homodimer conjugate
Structure:
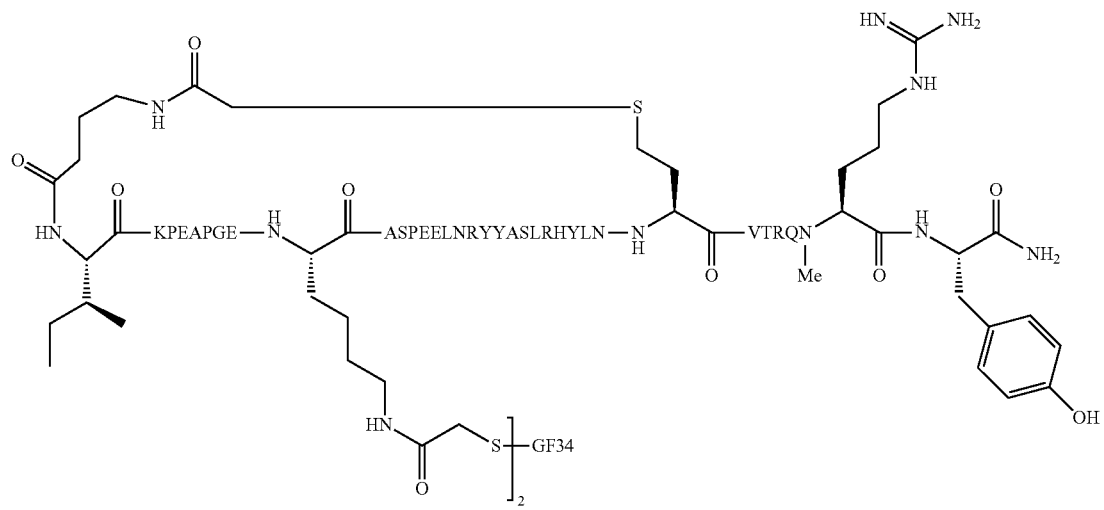

SEQ ID NO: 254
Name: GLP-1 fusion-[Cyclo-(G2-COCH₂-C30), K(Ac)11, N-Me-R35]-PYY2-36 homodimer conjugate
Structure:
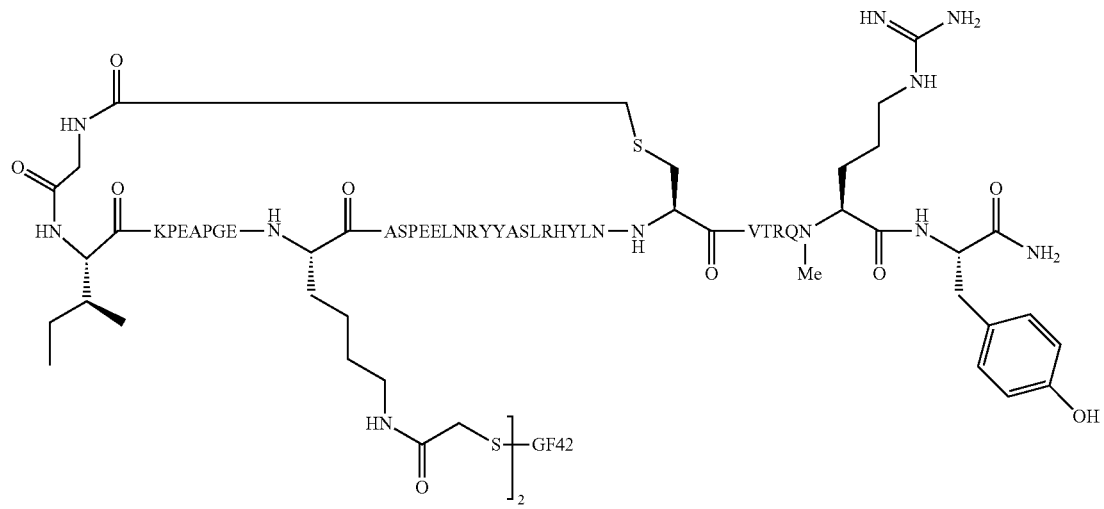
SEQ ID NO: 255
Name: GLP-1 fusion-[Cyclo-(G2-COCH₂-C30), K(Ac)11, N-Me-R35]-PYY2-36 homodimer conjugate
Structure:
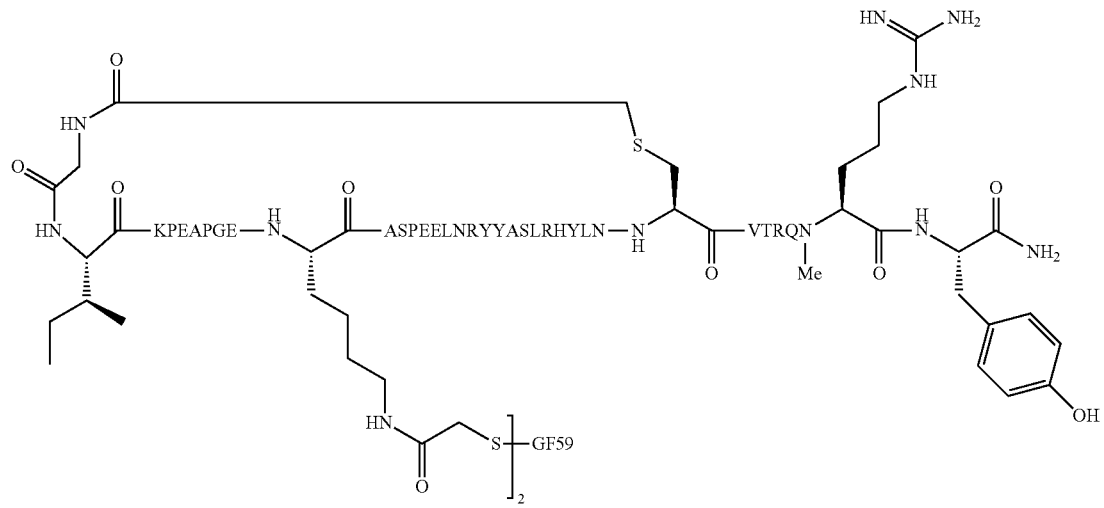

SEQ ID NO: 256
Name: GLP-1 fusion-[Cyclo-(G2-COCH₂-C30), K(Ac)11, N-Me-R35]-PYY2-36 homodimer conjugate
Structure:
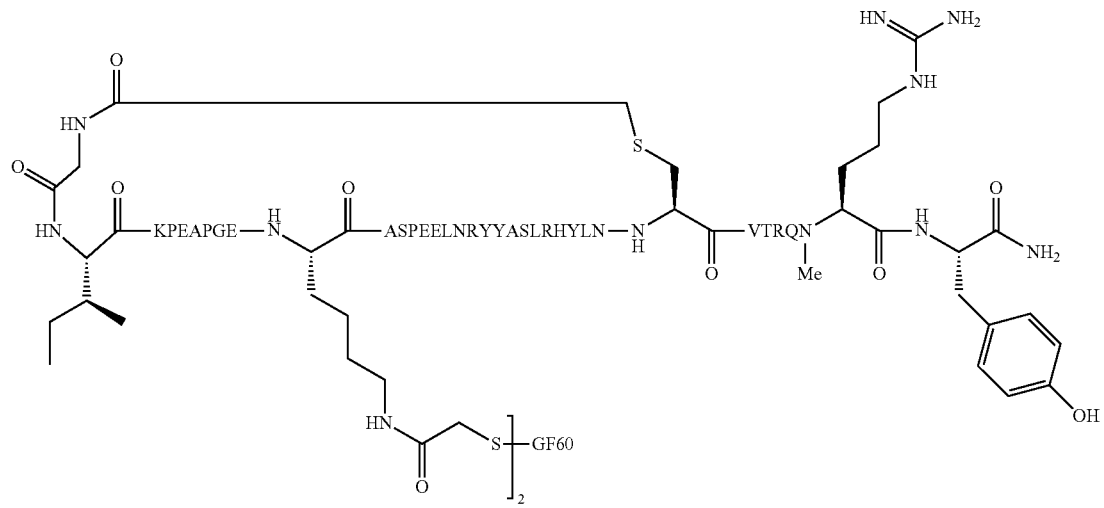
SEQ ID NO: 257
Name: GLP-1 fusion-[Cyclo-(G2-COCH₂-C30), K(Ac)11, N-Me-R35]-PYY2-36 homodimer conjugate
Structure:
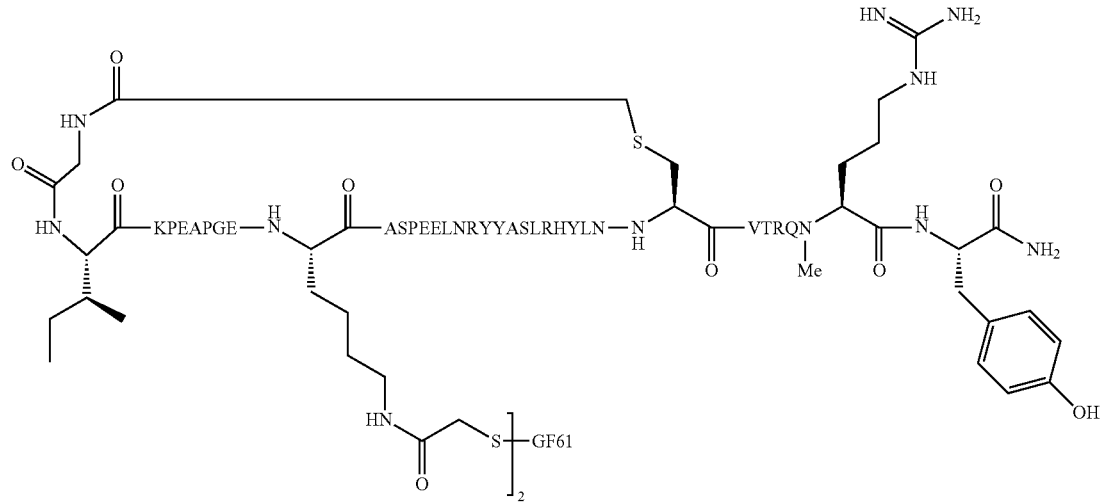

SEQ ID NO: 258
Name: GLP-1 fusion-[Cyclo-(βA2-COCH₂-C30), K(Ac)11, N-Me-R35]-PYY2-36 homodimer conjugate
Structure:
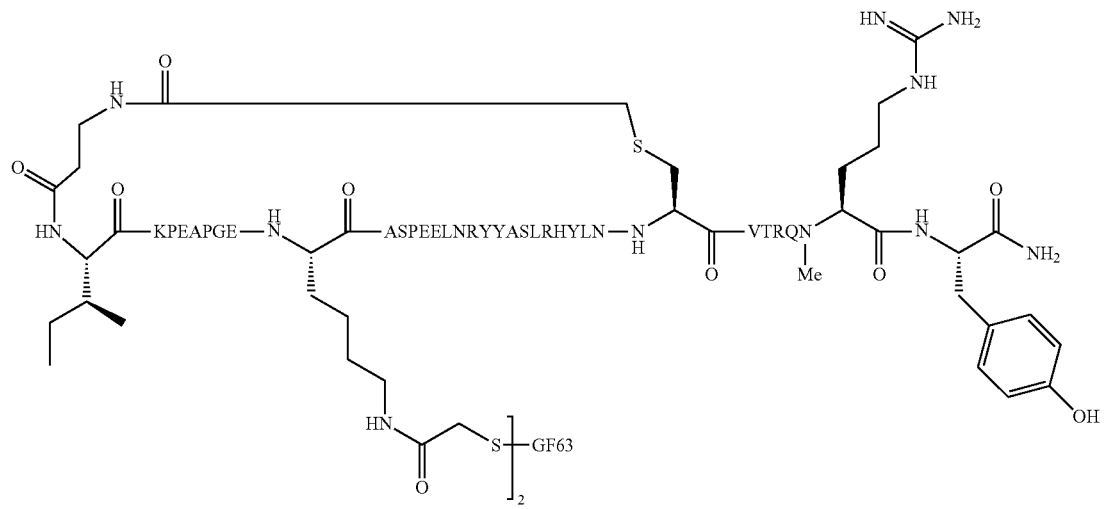
SEQ ID NO: 259
Name: GLP-1 fusion-[Cyclo-(βA2-COCH₂-C30), K(Ac)11, psi-(R35, Y36)]-PYY2-36 homodimer conjugate
Structure:
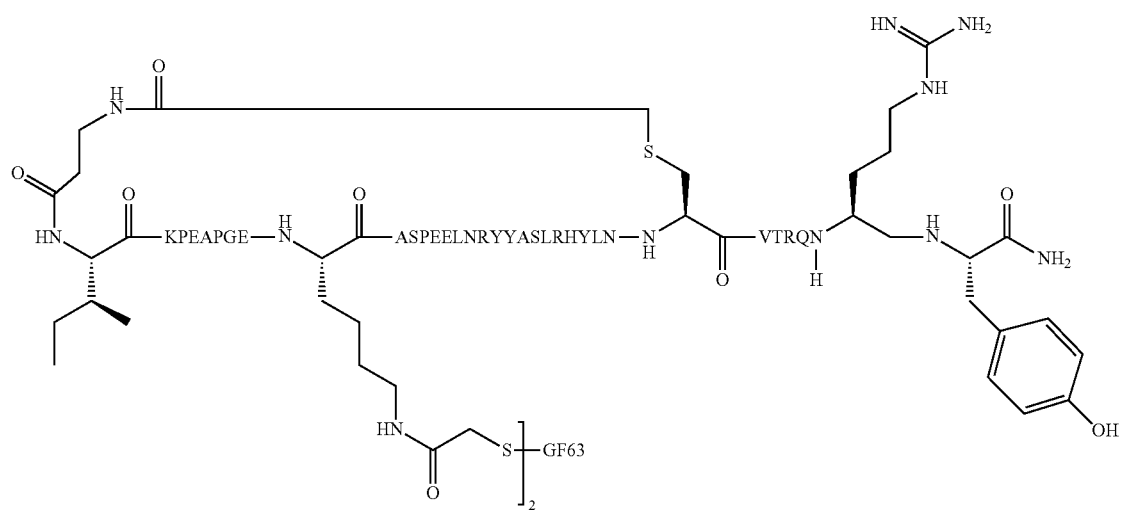

SEQ ID NO: 260
Name: GLP-1 fusion-[Cyclo-(βA2-COCH₂-C30), K(Ac)11, N-Me-R35]-PYY2-36 homodimer conjugate
Structure:
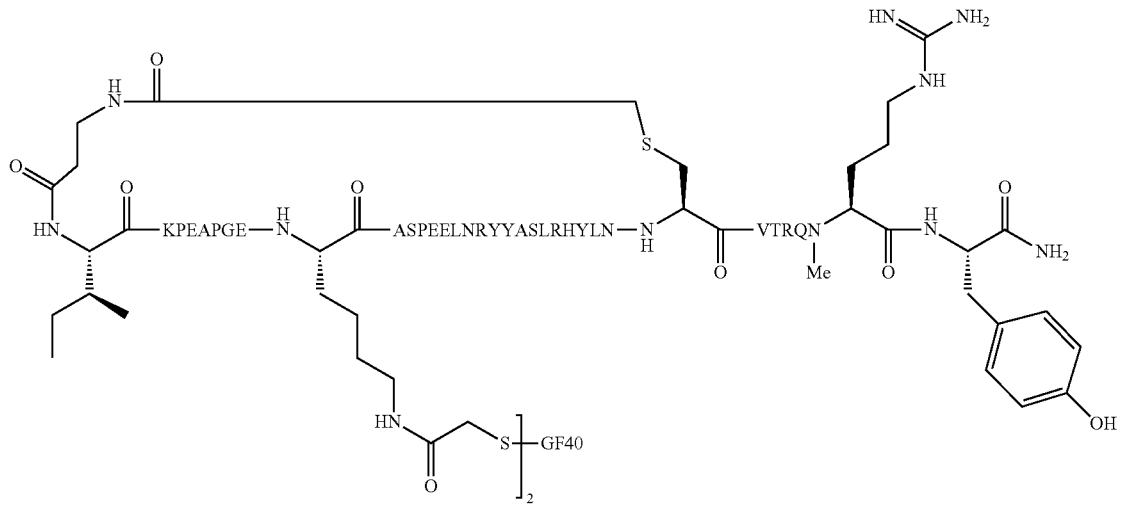
SEQ ID NO: 261
Name: GLP-1 fusion-[Cyclo-(G2-COCH₂-C30), K(Ac)11, N-Me-R35]-PYY2-36 monomer conjugate
Structure:
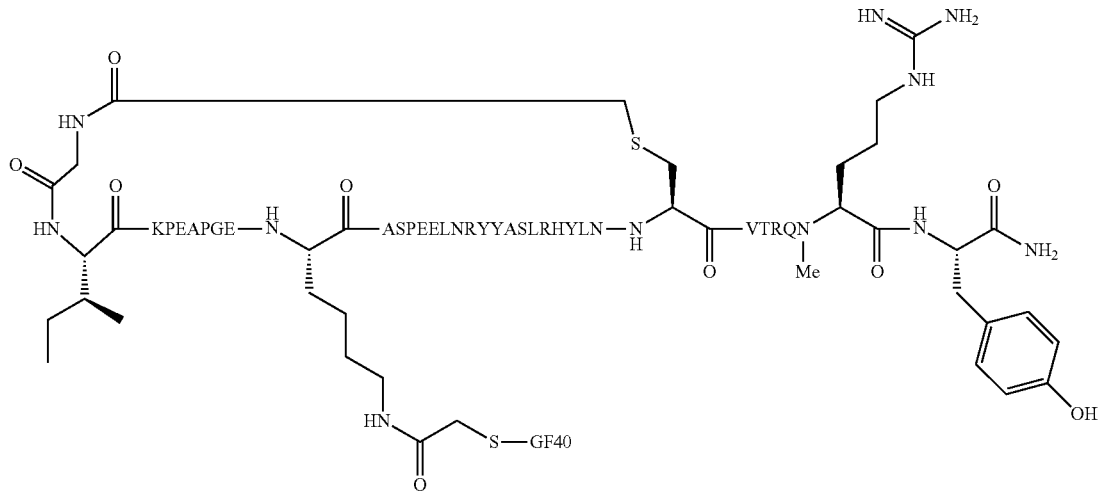

SEQ ID NO: 262

Name: GLP-1 fusion-[Cyclo-(G2-COCH₂-C30), K(Ac)11, N-Me-R35]-PYY2-36
homodimer conjugate Structure:

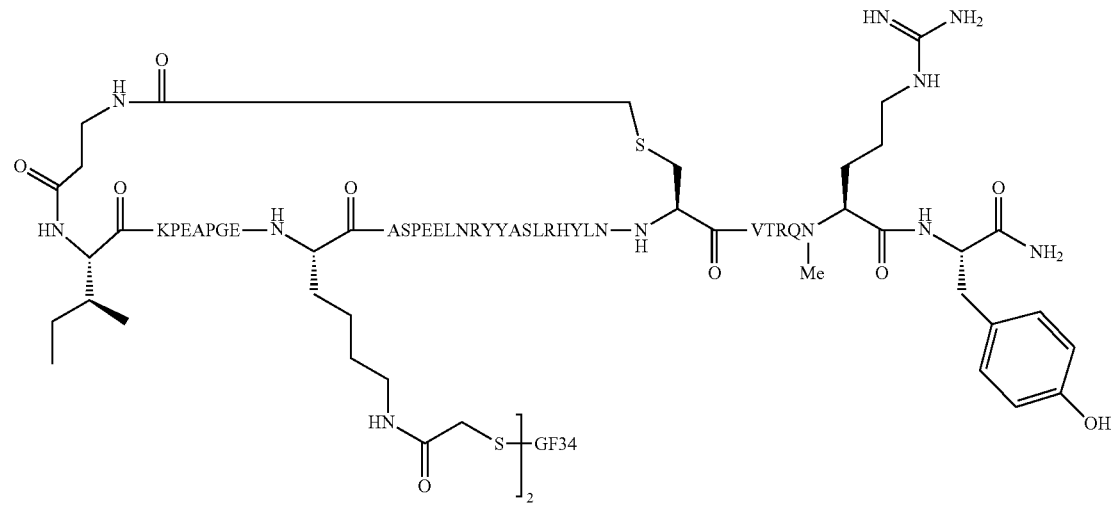

It is claimed:

1. A conjugate comprising a glucagon-like peptide-1 (GLP-1) fusion peptide coupled to a cyclic PYY peptide, wherein the GLP-1 fusion peptide comprises a GLP-1 peptide, an optional first linker peptide, a hinge-Fc region peptide, and a second linker peptide comprising a cysteine residue, wherein the cyclic PYY peptide is represented by Formula I:

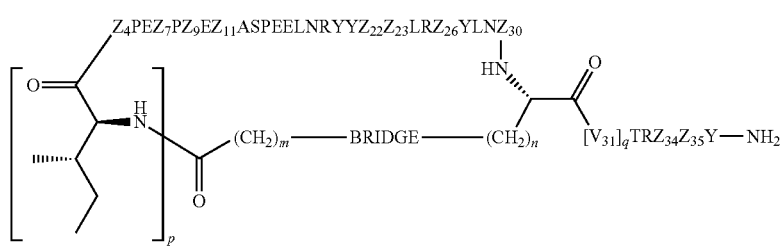

Formula I wherein
p is 0 or 1;
m is 0, 1, 2, 3, 4, or 5;
n is 1, 2, 3, or 4;

q is 0 or 1; provided that q is 1 only when $Z_{30}$ is absent;
BRIDGE is -Ph-$CH_2$—S—, -triazolyl-, —NHC(O)$CH_2$S—, —S$CH_2$C(O)NH—, —(O$CH_2$$CH_2$)$_2$NHC(O)$CH_2$S, —NHC(O)—, or —$CH_2$S—;
$Z_4$ is K, A, E, S, or R;
$Z_7$ is A or K;
$Z_9$ is G or K;
$Z_{11}$ is D or K;
$Z_{22}$ is A or K;
$Z_{23}$ is S or K;
$Z_{26}$ is A or H;
$Z_{30}$ is L, W, or absent, provided that $Z_{30}$ is absent only when q is 1;

$Z_{34}$ is

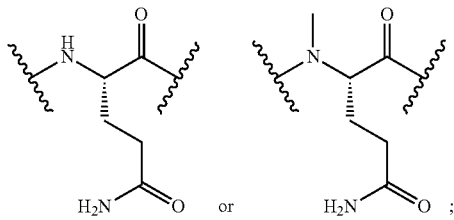 [SMILES: *N[C@@H](CCC(N)=O)C(*)=O ; *C(=O)[C@H](CCC(N)=O)N(*)C]

$Z_{35}$ is

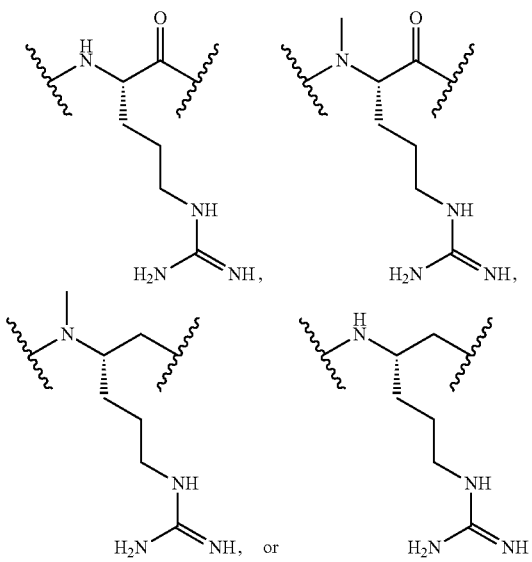

wherein the cyclic PYY peptide is optionally modified by one or more processes selected from the group consisting of amidation, acylation, and pegylation.

2. The conjugate of claim 1, wherein the cyclic PYY peptide of Formula (I) comprises an acylated K residue in at least one of $Z_7$, $Z_9$, $Z_{11}$, $Z_{22}$ or $Z_{23}$, wherein:

$Z_7$ is A or K, wherein the amino side chain of said K is optionally acylated substituted with:

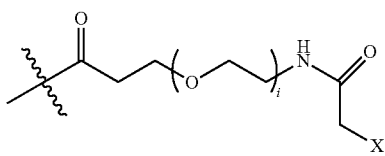

to provide the acylated K residue, wherein i is an integer of 0 to 24, and X=Br, I Cl, —C(O)CH$_2$Br, —C(O)CH$_2$I, or —C(O)CH$_2$Cl;

$Z_9$ is G or K, wherein the amino side chain of said K is optionally acylated with:

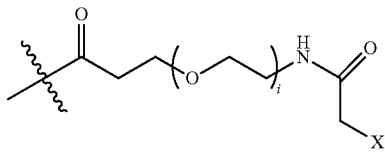

to provide the acylated K residue, wherein i is an integer of 0 to 24, and X=Br, I Cl, —C(O)CH$_2$Br, —C(O)CH$_2$I, or —C(O)CH$_2$Cl;

$Z_{11}$ is D or K, wherein the amino side chain of said K is optionally acylated with:

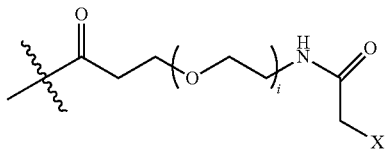

to provide the acylated K residue, wherein i is an integer of 0 to 24, and X=Br, I Cl, —C(O)CH$_2$Br, —C(O)CH$_2$I, or —C(O)CH$_2$Cl;

$Z_{22}$ is A or K, wherein the amino side chain of said K is optionally acylated with the acylated K residue:

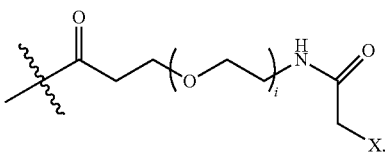

wherein i is an integer of 0 to 24, and X=Br, I, Cl, —C(O)CH$_2$Br, —C(O)CH$_2$I, or —C(O)CH$_2$Cl;

$Z_{23}$ is S or K, wherein the amino side chain of said K is optionally acylated with:

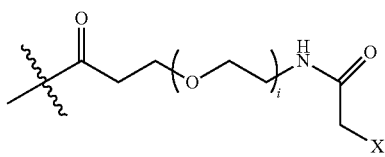

to provide the acylated K residue, wherein i is an integer of 0 to 24, and X=Br, I, Cl, —C(O)CH$_2$Br, —C(O)CH$_2$I, or —C(O)CH$_2$Cl;

$Z_{30}$ is L;

wherein the cysteine residue of the second linker peptide is reactively coupled to the K residue of the at least one of $Z_7$, $Z_9$, $Z_{11}$, $Z_{22}$ or $Z_{23}$.

3. The conjugate of claim 1, wherein the cyclic PYY peptide of Formula (I) comprises an acylated K residue in at least one of $Z_7$, $Z_9$, $Z_{11}$, $Z_{22}$ or $Z_{23}$, wherein:

$Z_7$ is A or K, wherein the amino side chain of said K is optionally acylated with —C(O)CH$_2$Br to provide the acylated K residue, $Z_9$ is G or K, wherein the amino side chain of said K is optionally acylated with —C(O)CH$_2$Br to provide the acylated K residue, $Z_{11}$ is D or K, wherein the amino side chain of said K is optionally acylated with —C(O)CH$_2$Br to provide the acylated K residue, $Z_{22}$ is A or K, wherein the amino side chain of said K is optionally acylated with —C(O)CH$_2$Br to provide the acylated K residue, $Z_{23}$ is S or K, wherein the amino side chain of said K is optionally acylated with —C(O)CH$_2$Br to provide the acylated K residue, $Z_{30}$ is L;

wherein the cysteine residue of the second linker peptide is reactively coupled to the K residue of the at least one of $Z_7$, $Z_9$, $Z_{11}$, $Z_{22}$ or $Z_{23}$.

4. The conjugate of claim 1, wherein the cyclic PYY peptide is selected from the group consisting of SEQ ID NOs:1-54, or a pharmaceutically acceptable salt thereof.

5. The conjugate of claim 4, wherein the cyclic PYY peptide is selected from SEQ ID NO:24, 25, 27, 28, 29, 30, 33, or 34, or a pharmaceutically acceptable salt thereof.

6. The conjugate of claim 1, wherein the GLP-1 fusion peptide is covalently linked to the cyclic PYY peptide at a K residue of the cyclic PYY peptide.

7. The conjugate of claim 6, wherein only one of $Z_7$, $Z_9$, $Z_{11}$, $Z_{22}$ and $Z_{23}$ in Formula I is K, and the K is covalently linked to a cysteine residue in the second linker peptide of the GLP-1 fusion peptide.

8. The conjugate of claim 7, wherein $Z_{11}$ in Formula I is K.

9. The conjugate of claim 1, wherein the GLP-1 peptide comprises an amino acid sequence selected from the group consisting of SEQ ID NOs:56-59.

10. The conjugate of claim 1, wherein the first linker peptide is present and comprises an amino acid sequence selected from the group consisting of SEQ ID NOs:60-83.

11. The conjugate of claim 1, wherein the hinge-Fc region peptide comprises an amino acid sequence selected from the group consisting of SEQ ID NOs:84-90.

12. The conjugate of claim 1, wherein the second linker peptide comprises an amino acid sequence selected from the group consisting of SEQ ID NOs:93-112.

13. The conjugate of claim 1, wherein the second linker peptide comprises the amino acid sequence of SEQ ID NO:93, 94, 95, 106, or 111.

14. A method of producing the conjugate of claim 1, comprising reacting an electrophile introduced onto a side-chain of the cyclic PYY peptide with the sulfhydryl group of a cysteine residue of the second linker peptide of the GLP-1 fusion peptide, thereby creating a covalent linkage between the cyclic PYY peptide and the GLP-1 fusion peptide.

15. The method of claim 14, wherein the cysteine residue of the second linker peptide of the GLP-1 fusion peptide is reduced by contacting the GLP-1 fusion peptide with an excess of an azaphosphine reducing agent, and the reduced cysteine residue is reacted with the electrophile.

16. The method of claim 15, wherein the azaphosphine reducing agent is 1,3,5-triaza-7-phosphatricyclo[3.3.1.1]decane (PTA) or a derivative thereof.

17. A pharmaceutical composition comprising the conjugate of claim 1 and a pharmaceutically acceptable carrier.

18. A method for treating a disease or disorder in a subject in need thereof, wherein said disease or disorder is obesity, type I or type II diabetes, metabolic syndrome, insulin resistance, impaired glucose tolerance, hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and/or eczema, the method comprising administering to the subject in need thereof an effective amount of the pharmaceutical composition of claim 17.

19. The method of claim 18, wherein the pharmaceutical composition is administered via an injection.

20. A method of reducing at least one of food intake or body weight in a subject in need thereof, the method comprising administering to the subject in need thereof an effective amount of the pharmaceutical composition of claim 17.

21. A method of modulating Y2 receptor activity and/or GLP-1 receptor activity in a subject in need thereof, the method comprising administering to the subject in need thereof an effective amount of the pharmaceutical composition of claim 17.

22. A kit comprising the conjugate of claim 1, further comprising a device for injection.

23. A method of producing a pharmaceutical composition comprising the conjugate of claim 1, comprising combining the conjugate with a pharmaceutically acceptable carrier to obtain the pharmaceutical composition.

24. A conjugate comprising a glucagon-like peptide-1 (GLP-1) fusion peptide coupled to a cyclic PYY peptide, wherein the GLP-1 fusion peptide comprises an amino acid sequence selected from the group consisting of SEQ ID NOs:113-224 and 267-274, and wherein the cyclic PYY peptide comprises an amino acid sequence of selected from SEQ ID NO:24, 25, 27, 28, 29, 30, 33, or 34, or a pharmaceutically acceptable salt thereof.

25. The conjugate of claim 24, wherein a cysteine residue between amino acid residues 287 to 289 of the GLP-1 fusion peptide is covalently linked to a lysine residue at residue 7, 9, 11, 22 or 23 of the cyclic PYY peptide via a chemical linker.

26. The conjugate of claim 25, wherein the GLP-1 fusion peptide is covalently linked at cysteine residue 288 to the cyclic PYY peptide at lysine residue 11 via a chemical linker.

27. A conjugate comprising a glucagon-like peptide 1 (GLP-1) fusion peptide coupled to a cyclic PYY peptide, wherein the conjugate comprises an amino acid sequence selected from the group consisting of SEQ ID NOs:225-262 or a pharmaceutically acceptable salt thereof.

* * * * *

SEQUENCE LISTING

<160> NUMBER OF SEQ ID NOS: 274

<210> SEQ ID NO 1
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the Ala is a beta-alanine with a
      cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein Cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 1

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 2

```
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a AcBr chemical modification
<220> FEATURE:
<221> NAME/KEY: Leu
<222> LOCATION: (29)..(29)
<223> OTHER INFORMATION: Leu, wherien Leu is a norleucine with a cyclic
      modification
<220> FEATURE:
<221> NAME/KEY: Arg
<222> LOCATION: (33)..(33)
<223> OTHER INFORMATION: Arg with a N-Me chemical modification

<400> SEQUENCE: 2

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Tyr

<210> SEQ ID NO 3
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a AcBr chemical modification
<220> FEATURE:
<221> NAME/KEY: Leu
<222> LOCATION: (29)..(29)
<223> OTHER INFORMATION: Leu, wherein leu is a norleucine with a cyclic
      modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 3

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Tyr

<210> SEQ ID NO 4
<211> LENGTH: 35
<212> TYPE: PRT
<213> ORGANISM: Artificial Sequence
<220> FEATURE:
<223> OTHER INFORMATION: Cyclic PYY Peptide Compound
```

```
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Glu
<222> LOCATION: (30)..(30)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 4

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Glu Thr Arg
            20                  25                  30

Gln Arg Tyr
        35

<210> SEQ ID NO 5
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a PEG6-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 5

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 6
<211> LENGTH: 35
<212> TYPE: PRT
<213> ORGANISM: Artificial Sequence
<220> FEATURE:
```

```
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 6

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 7
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 7

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 8
<211> LENGTH: 35
<212> TYPE: PRT
<213> ORGANISM: Artificial Sequence
<220> FEATURE:
```

```
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Gln
<222> LOCATION: (33)..(33)
<223> OTHER INFORMATION: Gln with a N-Me chemical modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 8

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 9
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me and a psi-(R35, Y36) chemical
      modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 9

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
```

-continued

```
                35

<210> SEQ ID NO 10
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 10

Ala Ile Arg Pro Glu Ala Pro Gly Glu Lys Ala Ser Pro Glu Glu Leu
1               5                   10                  15

Asn Arg Tyr Tyr Ala Ser Leu Arg His Tyr Leu Asn Trp Cys Thr Arg
            20                  25                  30

Gln Arg Tyr
        35

<210> SEQ ID NO 11
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 11

Ile Arg Pro Glu Ala Pro Gly Glu Lys Ala Ser Pro Glu Glu Leu Asn
1               5                   10                  15

Arg Tyr Tyr Ala Ser Leu Arg His Tyr Leu Asn Trp Cys Thr Arg Gln
            20                  25                  30
```

Arg Tyr

```
<210> SEQ ID NO 12
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (8)..(8)
<223> OTHER INFORMATION: Lys with a PEG12-AcBr chemical modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 12

Lys Pro Glu Ala Pro Gly Glu Lys Ala Ser Pro Glu Glu Leu Asn Arg
1               5                   10                  15

Tyr Tyr Ala Ser Leu Arg His Tyr Leu Asn Leu Cys Thr Arg Gln Arg
            20                  25                  30

Tyr

<210> SEQ ID NO 13
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG12-AcBr chemical modification
<220> FEATURE:
<221> NAME/KEY: Leu
<222> LOCATION: (29)..(29)
<223> OTHER INFORMATION: Leu, wherein the leu is a norleucine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 13

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Leu Val Thr Arg
            20                  25                  30

Gln Arg Tyr
        35
```

```
<210> SEQ ID NO 14
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG-8-triazolyl-CH2CH2CO-PEG4-AcBr
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a (R35, Y36) chemical modification
<220> FEATURE:
<221> NAME/KEY: Tyr
<222> LOCATION: (34)..(34)
<223> OTHER INFORMATION: Tyr with a (R35, Y36) chemical modification

<400> SEQUENCE: 14

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Val Thr Arg
            20                  25                  30

Gln Arg Tyr
        35

<210> SEQ ID NO 15
<211> LENGTH: 36
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (22)..(22)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 15

Ala Ile Lys Pro Glu Ala Pro Gly Glu Asp Ala Ser Pro Glu Glu Leu
1               5                   10                  15

Asn Arg Tyr Tyr Ala Lys Leu Arg His Tyr Leu Asn Leu Cys Val Thr
            20                  25                  30
```

```
Arg Gln Arg Tyr
        35

<210> SEQ ID NO 16
<211> LENGTH: 36
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (21)..(21)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 16

Ala Ile Lys Pro Glu Ala Pro Gly Glu Asp Ala Ser Pro Glu Glu Leu
1               5                   10                  15

Asn Arg Tyr Tyr Lys Ser Leu Arg His Tyr Leu Asn Leu Cys Val Thr
            20                  25                  30

Arg Gln Arg Tyr
        35

<210> SEQ ID NO 17
<211> LENGTH: 36
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (6)..(6)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 17

Ala Ile Lys Pro Glu Lys Pro Gly Glu Asp Ala Ser Pro Glu Glu Leu
1               5                   10                  15
```

```
Asn Arg Tyr Tyr Ala Ser Leu Arg His Tyr Leu Asn Leu Cys Val Thr
            20                  25                  30

Arg Gln Arg Tyr
        35

<210> SEQ ID NO 18
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 18

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 19
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 19

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
```

<210> SEQ ID NO 20
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 20

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 21
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 21

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 22
<211> LENGTH: 35
<212> TYPE: PRT
<213> ORGANISM: Artificial Sequence

```
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 22

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 23
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 23

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 24
<211> LENGTH: 35
<212> TYPE: PRT
<213> ORGANISM: Artificial Sequence
<220> FEATURE:
<223> OTHER INFORMATION: Cyclic PYY Peptide Compound
```

-continued

```
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 24

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 25
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a PEG24-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 25

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 26
<211> LENGTH: 35
<212> TYPE: PRT
<213> ORGANISM: Artificial Sequence
<220> FEATURE:
```

```
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 26

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 27
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 27

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 28
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
```

```
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 28

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 29
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 29

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 30
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
```

```
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 30

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 31
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 31

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 32
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine
      with a cyclic modification
```

```
<220> FEATURE:
<221> NAME/KEY: Lys
<222> LOCATION: (10)..(10)
<223> OTHER INFORMATION: Lys with an AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 32

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 33
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 33

Gly Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 34
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Xaa
<222> LOCATION: (1)..(1)
<223> OTHER INFORMATION: Xaa is a gamma amino-butyric acid with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
```

```
<223> OTHER INFORMATION: Cys, wherein cys is a homocysteine with a
      cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 34

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 35
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a AcBr chemical modification
<220> FEATURE:
<221> NAME/KEY: Cys
<222> LOCATION: (28)..(28)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a N-Me chemical modification

<400> SEQUENCE: 35

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Cys Val Thr Arg Gln
            20                  25                  30

Arg Tyr

<210> SEQ ID NO 36
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a AcBr chemical modification
<220> FEATURE:
<221> NAME/KEY: Cys
<222> LOCATION: (28)..(28)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
```

-continued

```
<222> LOCATION: (34)..(34)
<223> OTHER INFORMATION: Tyr with a psi-(R35, Y36) chemical modification

<400> SEQUENCE: 36

Ile Lys Pro Glu Ala Pro Gly Glu Lys Ala Ser Pro Glu Glu Leu Asn
1               5                   10                  15
Arg Tyr Tyr Ala Ser Leu Arg His Tyr Leu Asn Cys Val Thr Arg Gln
            20                  25                  30
Arg Tyr

<210> SEQ ID NO 37
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a AcBr chemical modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (33)..(33)
<223> OTHER INFORMATION: Arg with a N-Me chemical modification

<400> SEQUENCE: 37

Ile Lys Pro Glu Ala Pro Gly Glu Lys Ala Ser Pro Glu Glu Leu Asn
1               5                   10                  15
Arg Tyr Tyr Ala Ser Leu Arg His Tyr Leu Asn Cys Val Thr Arg Gln
            20                  25                  30
Arg Tyr

<210> SEQ ID NO 38
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a AcBr chemical modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 38

Ile Lys Pro Glu Ala Pro Gly Glu Lys Ala Ser Pro Glu Glu Leu Asn
1               5                   10                  15
```

-continued

```
Arg Tyr Tyr Ala Ser Leu Arg His Tyr Leu Asn Cys Val Thr Arg Gln
            20                  25                  30

Arg Tyr

<210> SEQ ID NO 39
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a AcBr chemical modification
<220> FEATURE:
<221> NAME/KEY: Cys
<222> LOCATION: (28)..(28)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 39

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Cys Val Thr Arg Gln
            20                  25                  30

Arg Tyr

<210> SEQ ID NO 40
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 40

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
```

<210> SEQ ID NO 41
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 41

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 42
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Xaa
<222> LOCATION: (1)..(1)
<223> OTHER INFORMATION: Xaa is a gamma amino butyric acid with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 42

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

-continued

```
<210> SEQ ID NO 43
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Xaa
<222> LOCATION: (1)..(1)
<223> OTHER INFORMATION: Xaa is a gamma amino butyric acid with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 43

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 44
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Xaa
<222> LOCATION: (1)..(1)
<223> OTHER INFORMATION: Xaa is a gamma amino butyric acid with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 44

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 45
<211> LENGTH: 35
```

```
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Xaa
<222> LOCATION: (1)..(1)
<223> OTHER INFORMATION: Xaa is a gamma amino butyric acid with a
      cyclic modification
<220> FEATURE:
<221> NAME/KEY: Lys
<222> LOCATION: (10)..(10)
<223> OTHER INFORMATION: Lys is a AcBr chemical modification
<220> FEATURE:
<221> NAME/KEY: Cys
<222> LOCATION: (30)..(30)
<223> OTHER INFORMATION: Cys, wherein the cys is a homocysteine is a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 45

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 46
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Xaa
<222> LOCATION: (1)..(1)
<223> OTHER INFORMATION: Xaa is a gamma amino butyric acid with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 46

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 47
<211> LENGTH: 35
<212> TYPE: PRT
<213> ORGANISM: Artificial Sequence
```

```
<220> FEATURE:
<223> OTHER INFORMATION: Cyclic PYY Peptide Compound
<220> FEATURE:
<221> NAME/KEY: Xaa
<222> LOCATION: (1)..(1)
<223> OTHER INFORMATION: Xaa is a gamma amino butyric acid with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 47

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 48
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Xaa
<222> LOCATION: (1)..(1)
<223> OTHER INFORMATION: Xaa is a delta-amino valeric acid with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 48

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 49
<211> LENGTH: 35
<212> TYPE: PRT
<213> ORGANISM: Artificial Sequence
<220> FEATURE:
<223> OTHER INFORMATION: Cyclic PYY Peptide Compound
```

```
<220> FEATURE:
<221> NAME/KEY: Xaa
<222> LOCATION: (1)..(1)
<223> OTHER INFORMATION: Xaa is a delta-amino valeric acid with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35,Y36) chemical modification
<220> FEATURE:
<221> NAME/KEY: Tyr
<222> LOCATION: (35)..(35)
<223> OTHER INFORMATION: Tyr with a psi-(R35,Y36) chemical modification

<400> SEQUENCE: 49

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 50
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Xaa
<222> LOCATION: (1)..(1)
<223> OTHER INFORMATION: Xaa is a delta-amino valeric acid with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 50

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 51
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Xaa
```

```
<222> LOCATION: (1)..(1)
<223> OTHER INFORMATION: Xaa is a delta-amino valeric acid with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 51

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 52
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the ala is a beta-alanine with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 52

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 53
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the ala is a beta-alanine with a
      cyclic modification
```

-continued

```
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 53

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 54
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Xaa
<222> LOCATION: (1)..(1)
<223> OTHER INFORMATION: Xaa is a gamma amino butyric acid with a
      cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 54

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 55
<211> LENGTH: 34
<212> TYPE: PRT
<213> ORGANISM: Homo sapiens

<400> SEQUENCE: 55

Ile Lys Pro Glu Ala Pro Gly Glu Asp Ala Ser Pro Glu Glu Leu Asn
1               5                   10                  15
```

```
Arg Tyr Tyr Ala Ser Leu Arg His Tyr Leu Asn Leu Val Thr Arg Gln
            20                  25                  30

Arg Tyr

<210> SEQ ID NO 56
<211> LENGTH: 30
<212> TYPE: PRT
<213> ORGANISM: Artificial Sequence
<220> FEATURE:
<223> OTHER INFORMATION: GLP-1 (7-36)

<400> SEQUENCE: 56

His Ser Glu Gly Thr Phe Thr Ser Asp Val Ser Tyr Leu Glu Gly
1               5                   10                  15

Gln Ala Ala Lys Glu Phe Ile Glu Trp Leu Val Lys Gly Arg
            20                  25                  30

<210> SEQ ID NO 57
<211> LENGTH: 31
<212> TYPE: PRT
<213> ORGANISM: Artificial Sequence
<220> FEATURE:
<223> OTHER INFORMATION: GLP-1 (7-37)

<400> SEQUENCE: 57

His Gly Glu Gly Thr Phe Thr Ser Asp Val Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 58
<211> LENGTH: 39
<212> TYPE: PRT
<213> ORGANISM: Artificial Sequence
<220> FEATURE:
<223> OTHER INFORMATION: Extendin 4 (1-39)

<400> SEQUENCE: 58

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 59
<211> LENGTH: 28
<212> TYPE: PRT
<213> ORGANISM: Artificial Sequence
<220> FEATURE:
<223> OTHER INFORMATION: Extendin 4 (1-28)

<400> SEQUENCE: 59

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 60
<211> LENGTH: 16
<212> TYPE: PRT
<213> ORGANISM: Artificial Sequence
<220> FEATURE:
```

<223> OTHER INFORMATION: Linker 1-1

<400> SEQUENCE: 60

Gly Gly Gly Gly Ala Gly Gly Gly Ala Gly Gly Gly Gly Ala Ala
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Linker 1-2

<400> SEQUENCE: 61

Gly Gly Gly Gly Gly Gly Gly Gly Gly Gly Gly Gly Gly Gly Gly Ala
1               5                   10                  15

<210> SEQ ID NO 62
<211> LENGTH: 21
<212> TYPE: PRT
<213> ORGANISM: Artificial Sequence
<220> FEATURE:
<223> OTHER INFORMATION: Linker 1-3

<400> SEQUENCE: 62

Ala Pro Ala Pro Ala Pro Ala Pro Ala Pro Ala Pro Ala Pro Ala Pro
1               5                   10                  15

Ala Pro Ala Pro Ala
            20

<210> SEQ ID NO 63
<211> LENGTH: 25
<212> TYPE: PRT
<213> ORGANISM: Artificial Sequence
<220> FEATURE:
<223> OTHER INFORMATION: Linker 1-4

<400> SEQUENCE: 63

Ala Pro Ala Pro Ala Pro Ala Pro Ala Pro Ala Pro Ala Pro Ala Pro
1               5                   10                  15

Ala Pro Ala Pro Ala Pro Ala Pro Ala
            20                  25

<210> SEQ ID NO 64
<211> LENGTH: 6
<212> TYPE: PRT
<213> ORGANISM: Artificial Sequence
<220> FEATURE:
<223> OTHER INFORMATION: Linker 1-5

<400> SEQUENCE: 64

Ala Pro Ala Pro Ala Pro
1               5

<210> SEQ ID NO 65
<211> LENGTH: 14
<212> TYPE: PRT
<213> ORGANISM: Artificial Sequence
<220> FEATURE:
<223> OTHER INFORMATION: Linker 1-6

<400> SEQUENCE: 65

Ala Ser Ala Pro Ala Pro Ala Pro Ala Pro Ala Pro Gly Ser
1               5                   10

<210> SEQ ID NO 66
<211> LENGTH: 24
<212> TYPE: PRT
<213> ORGANISM: Artificial Sequence
<220> FEATURE:
<223> OTHER INFORMATION: Linker 1-7

<400> SEQUENCE: 66

Ala Ser Ala Pro Ala Pro Ala Pro Ala Pro Ala Pro Ala Pro Ala Pro
1               5                   10                  15

Ala Pro Ala Pro Ala Pro Gly Ser
            20

<210> SEQ ID NO 67
<211> LENGTH: 12
<212> TYPE: PRT
<213> ORGANISM: Artificial Sequence
<220> FEATURE:
<223> OTHER INFORMATION: Linker 1-8

<400> SEQUENCE: 67

Ala Ser Gly Gly Gly Gly Ser Gly Gly Gly Gly Ser
1               5                   10

<210> SEQ ID NO 68
<211> LENGTH: 22
<212> TYPE: PRT
<213> ORGANISM: Artificial Sequence
<220> FEATURE:
<223> OTHER INFORMATION: Linker 1-9

<400> SEQUENCE: 68

Ala Ser Gly Gly Gly Gly Ser Gly Gly Gly Gly Ser Gly Gly Gly Gly
1               5                   10                  15

Ser Gly Gly Gly Gly Ser
            20

<210> SEQ ID NO 69
<211> LENGTH: 42
<212> TYPE: PRT
<213> ORGANISM: Artificial Sequence
<220> FEATURE:
<223> OTHER INFORMATION: Linker 1-10

<400> SEQUENCE: 69

Ala Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser
        35                  40

<210> SEQ ID NO 70
<211> LENGTH: 15
<212> TYPE: PRT
<213> ORGANISM: Artificial Sequence
<220> FEATURE:
<223> OTHER INFORMATION: Linker 1-11

<400> SEQUENCE: 70

Gly Gly Gly Gly Ala Gly Gly Gly Gly Ala Gly Gly Gly Gly Ala
1               5                   10                  15

<210> SEQ ID NO 71
<211> LENGTH: 20

```
<212> TYPE: PRT
<213> ORGANISM: Artificial Sequence
<220> FEATURE:
<223> OTHER INFORMATION: Linker 1-12

<400> SEQUENCE: 71

Gly Gly Gly Gly Ala Gly Gly Gly Ala Gly Gly Gly Ala Gly
1               5                   10                  15

Gly Gly Gly Ala
            20

<210> SEQ ID NO 72
<211> LENGTH: 21
<212> TYPE: PRT
<213> ORGANISM: Artificial Sequence
<220> FEATURE:
<223> OTHER INFORMATION: Linker 1-13

<400> SEQUENCE: 72

Gly Gly Gly Gly Ala Gly Gly Gly Ala Gly Gly Gly Ala Gly
1               5                   10                  15

Gly Gly Gly Ala Ala
            20

<210> SEQ ID NO 73
<211> LENGTH: 26
<212> TYPE: PRT
<213> ORGANISM: Artificial Sequence
<220> FEATURE:
<223> OTHER INFORMATION: Linker 1-14

<400> SEQUENCE: 73

Gly Gly Gly Gly Ala Gly Gly Gly Ala Gly Gly Gly Ala Gly
1               5                   10                  15

Gly Gly Gly Ala Gly Gly Gly Gly Ala Ala
            20                  25

<210> SEQ ID NO 74
<211> LENGTH: 6
<212> TYPE: PRT
<213> ORGANISM: Artificial Sequence
<220> FEATURE:
<223> OTHER INFORMATION: Linker 1-15

<400> SEQUENCE: 74

Gly Gly Gly Gly Gly Gly
1               5

<210> SEQ ID NO 75
<211> LENGTH: 16
<212> TYPE: PRT
<213> ORGANISM: Artificial Sequence
<220> FEATURE:
<223> OTHER INFORMATION: Linker 1-16

<400> SEQUENCE: 75

Gly Gly Gly Gly His Gly Gly Gly His Gly Gly Gly Gly His Ala
1               5                   10                  15

<210> SEQ ID NO 76
<211> LENGTH: 21
<212> TYPE: PRT
<213> ORGANISM: Artificial Sequence
<220> FEATURE:
<223> OTHER INFORMATION: Linker 1-17
```

```
<400> SEQUENCE: 76

Gly Gly Gly Gly His Gly Gly Gly His Gly Gly Gly Gly His Gly
1               5                   10                  15

Gly Gly Gly His Ala
            20

<210> SEQ ID NO 77
<211> LENGTH: 26
<212> TYPE: PRT
<213> ORGANISM: Artificial Sequence
<220> FEATURE:
<223> OTHER INFORMATION: Linker 1-18

<400> SEQUENCE: 77

Gly Gly Gly Gly His Gly Gly Gly His Gly Gly Gly Gly His Gly
1               5                   10                  15

Gly Gly Gly His Gly Gly Gly Gly His Ala
            20                  25

<210> SEQ ID NO 78
<211> LENGTH: 16
<212> TYPE: PRT
<213> ORGANISM: Artificial Sequence
<220> FEATURE:
<223> OTHER INFORMATION: Linker 1-19

<400> SEQUENCE: 78

Gly Gly Gly Gly Pro Gly Gly Gly Pro Gly Gly Gly Gly Pro Ala
1               5                   10                  15

<210> SEQ ID NO 79
<211> LENGTH: 21
<212> TYPE: PRT
<213> ORGANISM: Artificial Sequence
<220> FEATURE:
<223> OTHER INFORMATION: Linker 1-20

<400> SEQUENCE: 79

Gly Gly Gly Gly Pro Gly Gly Gly Pro Gly Gly Gly Gly Pro Gly
1               5                   10                  15

Gly Gly Gly Pro Ala
            20

<210> SEQ ID NO 80
<211> LENGTH: 26
<212> TYPE: PRT
<213> ORGANISM: Artificial Sequence
<220> FEATURE:
<223> OTHER INFORMATION: Linker 1-21

<400> SEQUENCE: 80

Gly Gly Gly Gly Pro Gly Gly Gly Pro Gly Gly Gly Gly Pro Gly
1               5                   10                  15

Gly Gly Gly Pro Gly Gly Gly Gly Pro Ala
            20                  25

<210> SEQ ID NO 81
<211> LENGTH: 16
<212> TYPE: PRT
<213> ORGANISM: Artificial Sequence
<220> FEATURE:
<223> OTHER INFORMATION: Linker 1-22

<400> SEQUENCE: 81
```

```
Gly Gly Gly Gly Ser Gly Gly Gly Ser Gly Gly Gly Ser Ala
1               5                   10                  15
```

<210> SEQ ID NO 82
<211> LENGTH: 21
<212> TYPE: PRT
<213> ORGANISM: Artificial Sequence
<220> FEATURE:
<223> OTHER INFORMATION: Linker 1-23

<400> SEQUENCE: 82

```
Pro Ala Pro Ala Pro Ala Pro Ala Pro Ala Pro Ala Pro Ala Pro Ala
1               5                   10                  15

Pro Ala Pro Ala Pro
            20
```

<210> SEQ ID NO 83
<211> LENGTH: 22
<212> TYPE: PRT
<213> ORGANISM: Artificial Sequence
<220> FEATURE:
<223> OTHER INFORMATION: Linker 1-24

<400> SEQUENCE: 83

```
Pro Ala Pro Ala Pro Ala Pro Ala Pro Ala Pro Ala Pro Ala Pro Ala
1               5                   10                  15

Pro Ala Pro Ala Pro Ala
            20
```

<210> SEQ ID NO 84
<211> LENGTH: 228
<212> TYPE: PRT
<213> ORGANISM: Artificial Sequence
<220> FEATURE:
<223> OTHER INFORMATION: Hinge-Fc Region Peptide 1

<400> SEQUENCE: 84

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
```

```
                    180                 185                 190
Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
    210                 215                 220

Leu Ser Leu Gly
225

<210> SEQ ID NO 85
<211> LENGTH: 224
<212> TYPE: PRT
<213> ORGANISM: Artificial Sequence
<220> FEATURE:
<223> OTHER INFORMATION: Hinge-Fc Region Peptide 2

<400> SEQUENCE: 85

Gly Pro Pro Cys Pro Pro Cys Pro Ala Pro Glu Ala Ala Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser Gln Glu Asp
            35                  40                  45

Pro Glu Val Gln Phe Asn Trp Tyr Val Asp Gly Val Glu Val His Asn
        50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Arg Leu Thr Val Asp Lys
            180                 185                 190

Ser Arg Trp Gln Glu Gly Asn Val Phe Ser Cys Ser Val Met His Glu
        195                 200                 205

Ala Leu His Asn His Tyr Thr Gln Lys Ser Leu Ser Leu Ser Leu Gly
    210                 215                 220

<210> SEQ ID NO 86
<211> LENGTH: 222
<212> TYPE: PRT
<213> ORGANISM: Artificial Sequence
<220> FEATURE:
<223> OTHER INFORMATION: Hinge-Fc Region Peptide 3

<400> SEQUENCE: 86

Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
                20                  25                  30
```

Glu Val Thr Cys Val Val Val Asp Val Ser Gln Glu Asp Pro Glu Val
         35                  40                  45

Gln Phe Asn Trp Tyr Val Asp Gly Val Glu Val His Asn Ala Lys Thr
 50                  55                  60

Lys Pro Arg Glu Glu Gln Phe Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Gly Leu Pro Ser Ser Ile Glu Lys Thr Ile Ser
                100                 105                 110

Lys Ala Lys Gly Gln Pro Arg Glu Pro Gln Val Tyr Thr Leu Pro Pro
                115                 120                 125

Ser Gln Glu Glu Met Thr Lys Asn Gln Val Ser Leu Thr Cys Leu Val
 130                 135                 140

Lys Gly Phe Tyr Pro Ser Asp Ile Ala Val Glu Trp Glu Ser Asn Gly
 145                 150                 155                 160

Gln Pro Glu Asn Asn Tyr Lys Thr Thr Pro Pro Val Leu Asp Ser Asp
                 165                 170                 175

Gly Ser Phe Phe Leu Tyr Ser Arg Leu Thr Val Asp Lys Ser Arg Trp
                 180                 185                 190

Gln Glu Gly Asn Val Phe Ser Cys Ser Val Met His Glu Ala Leu His
                 195                 200                 205

Asn His Tyr Thr Gln Lys Ser Leu Ser Leu Ser Leu Gly Lys
                 210                 215                 220

<210> SEQ ID NO 87
<211> LENGTH: 221
<212> TYPE: PRT
<213> ORGANISM: Artificial Sequence
<220> FEATURE:
<223> OTHER INFORMATION: Hinge-Fc Region Peptide 4

<400> SEQUENCE: 87

Cys Pro Pro Cys Pro Ala Pro Glu Ala Ala Gly Gly Pro Ser Val Phe
 1                5                  10                  15

Leu Phe Pro Pro Lys Pro Lys Asp Thr Leu Met Ile Ser Arg Thr Pro
                 20                  25                  30

Glu Val Thr Cys Val Val Val Asp Val Ser Gln Glu Asp Pro Glu Val
                 35                  40                  45

Gln Phe Asn Trp Tyr Val Asp Gly Val Glu Val His Asn Ala Lys Thr
 50                  55                  60

Lys Pro Arg Glu Glu Gln Phe Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Gly Leu Pro Ser Ser Ile Glu Lys Thr Ile Ser
                100                 105                 110

Lys Ala Lys Gly Gln Pro Arg Glu Pro Gln Val Tyr Thr Leu Pro Pro
                115                 120                 125

Ser Gln Glu Glu Met Thr Lys Asn Gln Val Ser Leu Thr Cys Leu Val
 130                 135                 140

Lys Gly Phe Tyr Pro Ser Asp Ile Ala Val Glu Trp Glu Ser Asn Gly
 145                 150                 155                 160

Gln Pro Glu Asn Asn Tyr Lys Thr Thr Pro Pro Val Leu Asp Ser Asp
                 165                 170                 175

```
Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly
        210                 215                 220

<210> SEQ ID NO 88
<211> LENGTH: 225
<212> TYPE: PRT
<213> ORGANISM: Artificial Sequence
<220> FEATURE:
<223> OTHER INFORMATION: Hinge-Fc Region Peptide 5

<400> SEQUENCE: 88

Gly Pro Pro Cys Pro Pro Cys Pro Ala Pro Glu Ala Ala Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser Gln Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Arg Leu Thr Val Asp Lys
            180                 185                 190

Ser Arg Trp Gln Glu Gly Asn Val Phe Ser Cys Ser Val Met His Glu
        195                 200                 205

Ala Leu His Asn His Tyr Thr Gln Lys Ser Leu Ser Leu Ser Leu Gly
    210                 215                 220

Lys
225

<210> SEQ ID NO 89
<211> LENGTH: 229
<212> TYPE: PRT
<213> ORGANISM: Artificial Sequence
<220> FEATURE:
<223> OTHER INFORMATION: Hinge-Fc Region Peptide 6

<400> SEQUENCE: 89

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30
```

```
Leu Met Ile Ser Arg Thr Pro Glu Val Thr Cys Val Val Asp Val
        35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 90
<211> LENGTH: 228
<212> TYPE: PRT
<213> ORGANISM: Artificial Sequence
<220> FEATURE:
<223> OTHER INFORMATION: Hinge-Fc Region Peptide 7

<400> SEQUENCE: 90

Glu Arg Lys Cys Cys Val Glu Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160
```

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 91
<211> LENGTH: 16
<212> TYPE: PRT
<213> ORGANISM: Artificial Sequence
<220> FEATURE:
<223> OTHER INFORMATION: Linker 2-1

<400> SEQUENCE: 91

Ala Ser Gly Ser Ala Pro Ala Pro Ala Pro Glu Glu Glu Pro Cys Ala
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Linker 2-2

<400> SEQUENCE: 92

Gly Gly Gly Ala Pro Ala Pro Ala Pro Glu Glu Glu Pro Cys Ala
1               5                   10                  15

<210> SEQ ID NO 93
<211> LENGTH: 17
<212> TYPE: PRT
<213> ORGANISM: Artificial Sequence
<220> FEATURE:
<223> OTHER INFORMATION: Linker 2-3

<400> SEQUENCE: 93

Ala Pro Ala Pro Ala Pro Ala Pro Ala Pro Ala Pro Cys Pro Glu Glu
1               5                   10                  15

Pro

<210> SEQ ID NO 94
<211> LENGTH: 14
<212> TYPE: PRT
<213> ORGANISM: Artificial Sequence
<220> FEATURE:
<223> OTHER INFORMATION: Linker 2-4

<400> SEQUENCE: 94

Ala Pro Ala Pro Ala Pro Ala Pro Ala Pro Ala Pro Cys Pro
1               5                   10

<210> SEQ ID NO 95
<211> LENGTH: 17
<212> TYPE: PRT
<213> ORGANISM: Artificial Sequence
<220> FEATURE:
<223> OTHER INFORMATION: Linker 2-5

<400> SEQUENCE: 95

```
Gly Gly Gly Gly Ala Gly Gly Gly Ala Gly Gly Gly Ala Cys
1               5                   10                  15

Ala
```

<210> SEQ ID NO 96
<211> LENGTH: 22
<212> TYPE: PRT
<213> ORGANISM: Artificial Sequence
<220> FEATURE:
<223> OTHER INFORMATION: Linker 2-6

<400> SEQUENCE: 96

```
Gly Gly Gly Gly Ala Tyr Cys Ala Lys Tyr Asp Gly Cys Tyr Gly Glu
1               5                   10                  15

Leu Asp Phe Trp Cys Gln
            20
```

<210> SEQ ID NO 97
<211> LENGTH: 22
<212> TYPE: PRT
<213> ORGANISM: Artificial Sequence
<220> FEATURE:
<223> OTHER INFORMATION: Linker 2-7

<400> SEQUENCE: 97

```
Gly Gly Gly Gly Ala Tyr Ser Ala Lys Tyr Asp Gly Cys Tyr Gly Glu
1               5                   10                  15

Leu Asp Phe Trp Gly Gln
            20
```

<210> SEQ ID NO 98
<211> LENGTH: 8
<212> TYPE: PRT
<213> ORGANISM: Artificial Sequence
<220> FEATURE:
<223> OTHER INFORMATION: Linker 2-8

<400> SEQUENCE: 98

```
Ala Ala Ala Cys Pro Glu Glu Glu
1               5
```

<210> SEQ ID NO 99
<211> LENGTH: 8
<212> TYPE: PRT
<213> ORGANISM: Artificial Sequence
<220> FEATURE:
<223> OTHER INFORMATION: Linker 2-9

<400> SEQUENCE: 99

```
Ala Ala Ala Glu Glu Pro Cys Ala
1               5
```

<210> SEQ ID NO 100
<211> LENGTH: 14
<212> TYPE: PRT
<213> ORGANISM: Artificial Sequence
<220> FEATURE:
<223> OTHER INFORMATION: Linker 2-10

<400> SEQUENCE: 100

```
Ala Pro Ala Pro Ala Pro Ala Pro Cys Ala Pro Arg Arg Arg
1               5                   10
```

<210> SEQ ID NO 101

```
<211> LENGTH: 9
<212> TYPE: PRT
<213> ORGANISM: Artificial Sequence
<220> FEATURE:
<223> OTHER INFORMATION: Linker 2-11

<400> SEQUENCE: 101

Ala Pro Ala Pro Glu Glu Pro Cys Ala
1               5

<210> SEQ ID NO 102
<211> LENGTH: 16
<212> TYPE: PRT
<213> ORGANISM: Artificial Sequence
<220> FEATURE:
<223> OTHER INFORMATION: Linker 2-12

<400> SEQUENCE: 102

Ala Ser Gly Ser Ala Pro Ala Pro Ala Pro Cys Glu Glu Glu
1               5                   10                  15

<210> SEQ ID NO 103
<211> LENGTH: 17
<212> TYPE: PRT
<213> ORGANISM: Artificial Sequence
<220> FEATURE:
<223> OTHER INFORMATION: Linker 2-13

<400> SEQUENCE: 103

Ala Ser Gly Ser Ala Pro Ala Pro Ala Pro Cys Pro Glu Glu
1               5                   10                  15

Pro

<210> SEQ ID NO 104
<211> LENGTH: 14
<212> TYPE: PRT
<213> ORGANISM: Artificial Sequence
<220> FEATURE:
<223> OTHER INFORMATION: Linker 2-14

<400> SEQUENCE: 104

Ala Ser Gly Ser Gly Gly Gly Ser Gly Gly Gly Ser Cys Ala
1               5                   10

<210> SEQ ID NO 105
<211> LENGTH: 17
<212> TYPE: PRT
<213> ORGANISM: Artificial Sequence
<220> FEATURE:
<223> OTHER INFORMATION: Linker 2-15

<400> SEQUENCE: 105

Gly Gly Gly Gly Gly Gly Gly Gly Gly Gly Gly Gly Gly Gly Cys
1               5                   10                  15

Ala

<210> SEQ ID NO 106
<211> LENGTH: 12
<212> TYPE: PRT
<213> ORGANISM: Artificial Sequence
<220> FEATURE:
<223> OTHER INFORMATION: Linker 2-16

<400> SEQUENCE: 106

Gly Gly Gly Gly Ser Gly Gly Gly Gly Ser Cys Ala
1               5                   10
```

<210> SEQ ID NO 107
<211> LENGTH: 16
<212> TYPE: PRT
<213> ORGANISM: Artificial Sequence
<220> FEATURE:
<223> OTHER INFORMATION: Linker 2-17

<400> SEQUENCE: 107

Ala Ser Gly Ser Pro Pro Pro Pro Pro Glu Pro Glu Pro Cys Ala
1               5                   10                  15

<210> SEQ ID NO 108
<211> LENGTH: 17
<212> TYPE: PRT
<213> ORGANISM: Artificial Sequence
<220> FEATURE:
<223> OTHER INFORMATION: Linker 2-18

<400> SEQUENCE: 108

Ala Ser Gly Ser Ala Pro Ala Pro Ala Pro Ala Pro Cys Pro Glu Pro
1               5                   10                  15

Glu

<210> SEQ ID NO 109
<211> LENGTH: 16
<212> TYPE: PRT
<213> ORGANISM: Artificial Sequence
<220> FEATURE:
<223> OTHER INFORMATION: Linker 2-19

<400> SEQUENCE: 109

Ala Ser Gly Ser Gly Gly Gly Gly Ser Gly Gly Gly Ser Cys Ala
1               5                   10                  15

<210> SEQ ID NO 110
<211> LENGTH: 19
<212> TYPE: PRT
<213> ORGANISM: Artificial Sequence
<220> FEATURE:
<223> OTHER INFORMATION: Linker 2-20

<400> SEQUENCE: 110

Ala Ser Gly Ser Ala Pro Ala Pro Ala Pro Ala Pro Ala Glu Glu Glu
1               5                   10                  15

Pro Cys Ala

<210> SEQ ID NO 111
<211> LENGTH: 17
<212> TYPE: PRT
<213> ORGANISM: Artificial Sequence
<220> FEATURE:
<223> OTHER INFORMATION: Linker 2-21

<400> SEQUENCE: 111

Gly Gly Gly Gly Ser Gly Gly Gly Ser Gly Gly Gly Gly Ser Cys
1               5                   10                  15

Ala

<210> SEQ ID NO 112
<211> LENGTH: 20
<212> TYPE: PRT
<213> ORGANISM: Artificial Sequence
<220> FEATURE:
<223> OTHER INFORMATION: Linker 2-22

<400> SEQUENCE: 112

Ala Ser Gly Ser Gly Gly Gly Ser Gly Gly Gly Ser Glu Glu
1               5                   10                  15

Glu Ala Cys Ala
            20

<210> SEQ ID NO 113
<211> LENGTH: 289
<212> TYPE: PRT
<213> ORGANISM: Artificial Sequence
<220> FEATURE:
<223> OTHER INFORMATION: GLP-1 fusion 1

<400> SEQUENCE: 113

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ala Gly Gly Gly Ala Gly Gly Gly Ala Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Asp Val Ser
            85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Ala Pro Ala Pro Ala Pro Ala Pro Ala Pro Ala Pro Cys
        275                 280                 285

Pro

<210> SEQ ID NO 114
<211> LENGTH: 289
<212> TYPE: PRT

<213> ORGANISM: Artificial Sequence
<220> FEATURE:
<223> OTHER INFORMATION: GLP-1 fusion 2

<400> SEQUENCE: 114

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Gly Gly Gly Gly Gly Gly Gly Gly Gly Gly Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Ala Pro Ala Pro Ala Pro Ala Pro Ala Pro Ala Pro Cys
        275                 280                 285

Pro

<210> SEQ ID NO 115
<211> LENGTH: 294
<212> TYPE: PRT
<213> ORGANISM: Artificial Sequence
<220> FEATURE:
<223> OTHER INFORMATION: GLP-1 fusion 3

<400> SEQUENCE: 115

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
            20                  25                  30

Pro Ala Pro Ala Pro Ala Pro Ala Pro Ala Pro Ala Pro Ala Pro Ala

```
                35                  40                  45
Pro Ala Pro Ala Pro Ala Pro Ala Gly Pro Pro Cys Pro Pro Cys Pro
 50                  55                  60
Ala Pro Glu Ala Ala Gly Gly Pro Ser Val Phe Leu Phe Pro Pro Lys
 65                  70                  75                  80
Pro Lys Asp Thr Leu Met Ile Ser Arg Thr Pro Glu Val Thr Cys Val
                 85                  90                  95
Val Val Asp Val Ser Gln Glu Asp Pro Glu Val Gln Phe Asn Trp Tyr
            100                 105                 110
Val Asp Gly Val Glu Val His Asn Ala Lys Thr Lys Pro Arg Glu Glu
            115                 120                 125
Gln Phe Asn Ser Thr Tyr Arg Val Val Ser Val Leu Thr Val Leu His
            130                 135                 140
Gln Asp Trp Leu Asn Gly Lys Glu Tyr Lys Cys Lys Val Ser Asn Lys
145                 150                 155                 160
Gly Leu Pro Ser Ser Ile Glu Lys Thr Ile Ser Lys Ala Lys Gly Gln
                165                 170                 175
Pro Arg Glu Pro Gln Val Tyr Thr Leu Pro Pro Ser Gln Glu Glu Met
            180                 185                 190
Thr Lys Asn Gln Val Ser Leu Thr Cys Leu Val Lys Gly Phe Tyr Pro
            195                 200                 205
Ser Asp Ile Ala Val Glu Trp Glu Ser Asn Gly Gln Pro Glu Asn Asn
210                 215                 220
Tyr Lys Thr Thr Pro Pro Val Leu Asp Ser Asp Gly Ser Phe Phe Leu
225                 230                 235                 240
Tyr Ser Arg Leu Thr Val Asp Lys Ser Arg Trp Gln Glu Gly Asn Val
                245                 250                 255
Phe Ser Cys Ser Val Met His Glu Ala Leu His Asn His Tyr Thr Gln
                260                 265                 270
Lys Ser Leu Ser Leu Ser Leu Gly Ala Pro Ala Pro Ala Pro Ala Pro
                275                 280                 285
Ala Pro Ala Pro Cys Pro
    290

<210> SEQ ID NO 116
<211> LENGTH: 286
<212> TYPE: PRT
<213> ORGANISM: Artificial Sequence
<220> FEATURE:
<223> OTHER INFORMATION: GLP-1 fusion 4

<400> SEQUENCE: 116

His Gly Glu Gly Thr Phe Thr Ser Asp Leu Ser Lys Gln Met Glu Glu
 1               5                  10                  15
Glu Ala Val Arg Leu Phe Ile Glu Trp Leu Lys Asn Gly Gly Gly Gly
                20                  25                  30
Ala Gly Gly Gly Gly Ala Gly Gly Gly Gly Ala Ala Glu Ser Lys Tyr
            35                  40                  45
Gly Pro Pro Cys Pro Pro Cys Pro Ala Pro Glu Ala Ala Gly Gly Pro
 50                  55                  60
Ser Val Phe Leu Phe Pro Pro Lys Pro Lys Asp Thr Leu Met Ile Ser
 65                  70                  75                  80
Arg Thr Pro Glu Val Thr Cys Val Val Val Asp Val Ser Gln Glu Asp
                 85                  90                  95
Pro Glu Val Gln Phe Asn Trp Tyr Val Asp Gly Val Glu Val His Asn
```

```
            100                 105                 110
Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Ala Pro Ala Pro Ala Pro Ala Pro Ala Pro Cys Pro
        275                 280                 285

<210> SEQ ID NO 117
<211> LENGTH: 286
<212> TYPE: PRT
<213> ORGANISM: Artificial Sequence
<220> FEATURE:
<223> OTHER INFORMATION: GLP-1 fusion 5

<400> SEQUENCE: 117

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
                20                  25                  30

Gly Gly Gly Gly Gly Gly Gly Gly Gly Gly Ala Glu Ser Lys Tyr
            35                  40                  45

Gly Pro Pro Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
```

```
              180                 185                 190
Cys Leu Val Lys Gly Phe Tyr Pro Ser Asp Ile Ala Val Glu Trp Glu
            195                 200                 205

Ser Asn Gly Gln Pro Glu Asn Asn Tyr Lys Thr Thr Pro Pro Val Leu
        210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Ala Pro Ala Pro Ala Pro Ala Pro Ala Pro Ala Pro Cys Pro
        275                 280                 285

<210> SEQ ID NO 118
<211> LENGTH: 291
<212> TYPE: PRT
<213> ORGANISM: Artificial Sequence
<220> FEATURE:
<223> OTHER INFORMATION: GLP-1 fusion 6

<400> SEQUENCE: 118

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Pro Ala Pro
            20                  25                  30

Ala Pro Ala Pro Ala Pro Ala Pro Ala Pro Ala Pro Ala Pro Ala Pro
        35                  40                  45

Ala Glu Ser Lys Tyr Gly Pro Pro Cys Pro Pro Cys Pro Ala Pro Glu
    50                  55                  60

Ala Ala Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser Gln Glu Asp Pro Glu Val Gln Phe Asn Trp Tyr Val Asp Gly
            100                 105                 110

Val Glu Val His Asn Ala Lys Thr Lys Pro Arg Glu Glu Gln Phe Asn
        115                 120                 125

Ser Thr Tyr Arg Val Val Ser Val Leu Thr Val Leu His Gln Asp Trp
    130                 135                 140

Leu Asn Gly Lys Glu Tyr Lys Cys Lys Val Ser Asn Lys Gly Leu Pro
145                 150                 155                 160

Ser Ser Ile Glu Lys Thr Ile Ser Lys Ala Lys Gly Gln Pro Arg Glu
                165                 170                 175

Pro Gln Val Tyr Thr Leu Pro Pro Ser Gln Glu Glu Met Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Arg
225                 230                 235                 240

Leu Thr Val Asp Lys Ser Arg Trp Gln Glu Gly Asn Val Phe Ser Cys
                245                 250                 255

Ser Val Met His Glu Ala Leu His Asn His Tyr Thr Gln Lys Ser Leu
```

```
                    260                 265                 270
Ser Leu Ser Leu Gly Ala Pro Ala Pro Ala Pro Ala Pro Ala
            275                 280                 285

Pro Cys Pro
    290

<210> SEQ ID NO 119
<211> LENGTH: 291
<212> TYPE: PRT
<213> ORGANISM: Artificial Sequence
<220> FEATURE:
<223> OTHER INFORMATION: GLP-1 fusion 7

<400> SEQUENCE: 119

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Pro Ala Pro
            20                  25                  30

Ala Pro Ala Pro Ala Pro Ala Pro Ala Pro Ala Pro Ala Pro Ala Pro
        35                  40                  45

Ala Pro Ala Pro Ala Gly Pro Pro Cys Pro Pro Cys Pro Ala Pro Glu
    50                  55                  60

Ala Ala Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser Gln Glu Asp Pro Glu Val Gln Phe Asn Trp Tyr Val Asp Gly
            100                 105                 110

Val Glu Val His Asn Ala Lys Thr Lys Pro Arg Glu Glu Gln Phe Asn
        115                 120                 125

Ser Thr Tyr Arg Val Val Ser Val Leu Thr Val Leu His Gln Asp Trp
    130                 135                 140

Leu Asn Gly Lys Glu Tyr Lys Cys Lys Val Ser Asn Lys Gly Leu Pro
145                 150                 155                 160

Ser Ser Ile Glu Lys Thr Ile Ser Lys Ala Lys Gly Gln Pro Arg Glu
                165                 170                 175

Pro Gln Val Tyr Thr Leu Pro Pro Ser Gln Glu Glu Met Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Arg
225                 230                 235                 240

Leu Thr Val Asp Lys Ser Arg Trp Gln Glu Gly Asn Val Phe Ser Cys
                245                 250                 255

Ser Val Met His Glu Ala Leu His Asn His Tyr Thr Gln Lys Ser Leu
            260                 265                 270

Ser Leu Ser Leu Gly Ala Pro Ala Pro Ala Pro Ala Pro Ala Pro Ala
        275                 280                 285

Pro Cys Pro
    290

<210> SEQ ID NO 120
<211> LENGTH: 292
<212> TYPE: PRT
```

<213> ORGANISM: Artificial Sequence
<220> FEATURE:
<223> OTHER INFORMATION: GLP-1 fusion 8

<400> SEQUENCE: 120

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ala Gly Gly Gly Ala Gly Gly Gly Ala Ala Glu
            35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
                100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly Gly Gly Gly Gly Ala Gly Gly Gly Ala Gly Gly
            275                 280                 285

Gly Ala Cys Ala
    290

<210> SEQ ID NO 121
<211> LENGTH: 292
<212> TYPE: PRT
<213> ORGANISM: Artificial Sequence
<220> FEATURE:
<223> OTHER INFORMATION: GLP-1 fusion 9

<400> SEQUENCE: 121

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Gly Gly Gly Gly Gly Gly Gly Gly Ala Glu
        35                  40                  45

Ser Lys Tyr Gly Pro Pro Cys Pro Pro Cys Pro Ala Pro Glu Ala Ala
 50                  55                  60

Gly Gly Pro Ser Val Phe Leu Phe Pro Pro Lys Pro Lys Asp Thr Leu
 65                  70                  75                  80

Met Ile Ser Arg Thr Pro Glu Val Thr Cys Val Val Asp Val Ser
                 85                  90                  95

Gln Glu Asp Pro Glu Val Gln Phe Asn Trp Tyr Val Asp Gly Val Glu
                100                 105                 110

Val His Asn Ala Lys Thr Lys Pro Arg Glu Glu Gln Phe Asn Ser Thr
                115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
                180                 185                 190

Ser Leu Thr Cys Leu Val Lys Gly Phe Tyr Pro Ser Asp Ile Ala Val
                195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly Gly Gly Gly Ala Gly Gly Gly Ala Gly Gly
                275                 280                 285

Gly Ala Cys Ala
    290

<210> SEQ ID NO 122
<211> LENGTH: 297
<212> TYPE: PRT
<213> ORGANISM: Artificial Sequence
<220> FEATURE:
<223> OTHER INFORMATION: GLP-1 fusion 10

<400> SEQUENCE: 122

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
                20                  25                  30

Pro Ala Pro Ala Pro Ala Pro Ala Pro Ala Pro Ala Pro Ala Pro Ala
                35                  40                  45

Pro Ala Pro Ala Pro Ala Pro Ala Gly Pro Pro Cys Pro Pro Cys Pro
                50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
        115                 120                 125

Gln Phe Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Gly Gly Gly Gly Ala Gly Gly Gly
        275                 280                 285

Gly Ala Gly Gly Gly Gly Ala Cys Ala
    290                 295

<210> SEQ ID NO 123
<211> LENGTH: 289
<212> TYPE: PRT
<213> ORGANISM: Artificial Sequence
<220> FEATURE:
<223> OTHER INFORMATION: GLP-1 fusion 11

<400> SEQUENCE: 123

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
            20                  25                  30

Ala Gly Gly Gly Gly Ala Gly Gly Gly Ala Ala Glu Ser Lys Tyr
        35                  40                  45

Gly Pro Pro Cys Pro Pro Cys Pro Ala Pro Glu Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

```
Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Gly Gly Gly Gly Ala Gly Gly Gly Gly Ala Gly Gly Gly Ala Cys
        275                 280                 285

Ala

<210> SEQ ID NO 124
<211> LENGTH: 289
<212> TYPE: PRT
<213> ORGANISM: Artificial Sequence
<220> FEATURE:
<223> OTHER INFORMATION: GLP-1 fusion 12

<400> SEQUENCE: 124

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
                20                  25                  30

Gly Gly Gly Gly Gly Gly Gly Gly Gly Ala Glu Ser Lys Tyr
        35                  40                  45

Gly Pro Pro Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
```

```
                225                 230                 235                 240
Ser Arg Trp Gln Glu Gly Asn Val Phe Ser Cys Ser Val Met His Glu
            245                 250                 255

Ala Leu His Asn His Tyr Thr Gln Lys Ser Leu Ser Leu Ser Leu Gly
            260                 265                 270

Gly Gly Gly Gly Ala Gly Gly Gly Ala Gly Gly Gly Ala Cys
            275                 280                 285

Ala

<210> SEQ ID NO 125
<211> LENGTH: 294
<212> TYPE: PRT
<213> ORGANISM: Artificial Sequence
<220> FEATURE:
<223> OTHER INFORMATION: GLP-1 fusion 13

<400> SEQUENCE: 125

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Pro Ala Pro
            20                  25                  30

Ala Pro Ala Pro Ala Pro Ala Pro Ala Pro Ala Pro Ala Pro Ala Pro
            35                  40                  45

Ala Glu Ser Lys Tyr Gly Pro Pro Cys Pro Pro Cys Pro Ala Pro Glu
50                  55                  60

Ala Ala Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser Gln Glu Asp Pro Glu Val Gln Phe Asn Trp Tyr Val Asp Gly
            100                 105                 110

Val Glu Val His Asn Ala Lys Thr Lys Pro Arg Glu Glu Gln Phe Asn
        115                 120                 125

Ser Thr Tyr Arg Val Val Ser Val Leu Thr Val Leu His Gln Asp Trp
    130                 135                 140

Leu Asn Gly Lys Glu Tyr Lys Cys Lys Val Ser Asn Lys Gly Leu Pro
145                 150                 155                 160

Ser Ser Ile Glu Lys Thr Ile Ser Lys Ala Lys Gly Gln Pro Arg Glu
                165                 170                 175

Pro Gln Val Tyr Thr Leu Pro Pro Ser Gln Glu Glu Met Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Arg
225                 230                 235                 240

Leu Thr Val Asp Lys Ser Arg Trp Gln Glu Gly Asn Val Phe Ser Cys
                245                 250                 255

Ser Val Met His Glu Ala Leu His Asn His Tyr Thr Gln Lys Ser Leu
            260                 265                 270

Ser Leu Ser Leu Gly Gly Gly Gly Ala Gly Gly Gly Ala Gly
        275                 280                 285

Gly Gly Gly Ala Cys Ala
    290
```

```
<210> SEQ ID NO 126
<211> LENGTH: 294
<212> TYPE: PRT
<213> ORGANISM: Artificial Sequence
<220> FEATURE:
<223> OTHER INFORMATION: GLP-1 fusion 14

<400> SEQUENCE: 126
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Pro Ala Pro
            20                  25                  30

Ala Pro Ala Pro Ala Pro Ala Pro Ala Pro Ala Pro Ala Pro Ala Pro
        35                  40                  45

Ala Pro Ala Pro Ala Gly Pro Pro Cys Pro Pro Cys Pro Ala Pro Glu
    50                  55                  60

Ala Ala Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser Gln Glu Asp Pro Glu Val Gln Phe Asn Trp Tyr Val Asp Gly
            100                 105                 110

Val Glu Val His Asn Ala Lys Thr Lys Pro Arg Glu Glu Gln Phe Asn
        115                 120                 125

Ser Thr Tyr Arg Val Val Ser Val Leu Thr Val Leu His Gln Asp Trp
    130                 135                 140

Leu Asn Gly Lys Glu Tyr Lys Cys Lys Val Ser Asn Lys Gly Leu Pro
145                 150                 155                 160

Ser Ser Ile Glu Lys Thr Ile Ser Lys Ala Lys Gly Gln Pro Arg Glu
                165                 170                 175

Pro Gln Val Tyr Thr Leu Pro Pro Ser Gln Glu Glu Met Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Arg
225                 230                 235                 240

Leu Thr Val Asp Lys Ser Arg Trp Gln Glu Gly Asn Val Phe Ser Cys
                245                 250                 255

Ser Val Met His Glu Ala Leu His Asn His Tyr Thr Gln Lys Ser Leu
            260                 265                 270

Ser Leu Ser Leu Gly Gly Gly Gly Ala Gly Gly Gly Ala Gly
        275                 280                 285

Gly Gly Gly Ala Cys Ala
    290

```
<210> SEQ ID NO 127
<211> LENGTH: 297
<212> TYPE: PRT
<213> ORGANISM: Artificial Sequence
<220> FEATURE:
<223> OTHER INFORMATION: GLP-1 fusion 15

<400> SEQUENCE: 127
```

His Gly Glu Gly Thr Phe Thr Ser Asp Val Ser Ser Tyr Leu Glu Glu

```
                1               5                    10                      15
            Gln Ala Ala Lys Glu Phe Ile Ala Trp Leu Val Lys Gly Gly Gly
                         20                  25                  30
            Gly Gly Gly Ala Gly Gly Gly Ala Gly Gly Gly Ala Ala Glu
                         35                  40                  45
            Ser Lys Tyr Gly Pro Pro Cys Pro Cys Pro Ala Pro Glu Ala Ala
             50                  55                  60
            Gly Gly Pro Ser Val Phe Leu Phe Pro Pro Lys Pro Lys Asp Thr Leu
             65                  70                  75                  80
            Met Ile Ser Arg Thr Pro Glu Val Thr Cys Val Val Val Asp Val Ser
                         85                  90                  95
            Gln Glu Asp Pro Glu Val Gln Phe Asn Trp Tyr Val Asp Gly Val Glu
                        100                 105                 110
            Val His Asn Ala Lys Thr Lys Pro Arg Glu Glu Gln Phe Asn Ser Thr
                        115                 120                 125
            Tyr Arg Val Val Ser Val Leu Thr Val Leu His Gln Asp Trp Leu Asn
            130                 135                 140
            Gly Lys Glu Tyr Lys Cys Lys Val Ser Asn Lys Gly Leu Pro Ser Ser
            145                 150                 155                 160
            Ile Glu Lys Thr Ile Ser Lys Ala Lys Gly Gln Pro Arg Glu Pro Gln
                        165                 170                 175
            Val Tyr Thr Leu Pro Pro Ser Gln Glu Glu Met Thr Lys Asn Gln Val
                        180                 185                 190
            Ser Leu Thr Cys Leu Val Lys Gly Phe Tyr Pro Ser Asp Ile Ala Val
                        195                 200                 205
            Glu Trp Glu Ser Asn Gly Gln Pro Glu Asn Asn Tyr Lys Thr Thr Pro
            210                 215                 220
            Pro Val Leu Asp Ser Asp Gly Ser Phe Phe Leu Tyr Ser Arg Leu Thr
            225                 230                 235                 240
            Val Asp Lys Ser Arg Trp Gln Glu Gly Asn Val Phe Ser Cys Ser Val
                        245                 250                 255
            Met His Glu Ala Leu His Asn His Tyr Thr Gln Lys Ser Leu Ser Leu
                        260                 265                 270
            Ser Leu Gly Gly Gly Gly Ala Tyr Cys Ala Lys Tyr Asp Gly Cys
                        275                 280                 285
            Tyr Gly Glu Leu Asp Phe Trp Cys Gln
                        290                 295

<210> SEQ ID NO 128
<211> LENGTH: 299
<212> TYPE: PRT
<213> ORGANISM: Artificial Sequence
<220> FEATURE:
<223> OTHER INFORMATION: GLP-1 fusion 16

<400> SEQUENCE: 128

His Gly Glu Gly Thr Phe Thr Ser Asp Leu Ser Lys Gln Met Glu Glu
            1               5                   10                  15
            Glu Ala Val Arg Leu Phe Ile Glu Trp Leu Lys Asn Ala Pro Ala Pro
                        20                  25                  30
            Ala Pro Ala Pro Ala Pro Ala Pro Ala Pro Ala Pro Ala Pro Ala Pro
                        35                  40                  45
            Ala Pro Ala Pro Ala Gly Pro Pro Cys Pro Cys Pro Ala Pro Glu
             50                  55                  60
            Ala Ala Gly Gly Pro Ser Val Phe Leu Phe Pro Pro Lys Pro Lys Asp
```

```
                   65                  70                  75                  80
Thr Leu Met Ile Ser Arg Thr Pro Glu Val Thr Cys Val Val Val Asp
                    85                  90                  95
Val Ser Gln Glu Asp Pro Glu Val Gln Phe Asn Trp Tyr Val Asp Gly
                100                 105                 110
Val Glu Val His Asn Ala Lys Thr Lys Pro Arg Glu Glu Gln Phe Asn
            115                 120                 125
Ser Thr Tyr Arg Val Val Ser Val Leu Thr Val Leu His Gln Asp Trp
        130                 135                 140
Leu Asn Gly Lys Glu Tyr Lys Cys Lys Val Ser Asn Lys Gly Leu Pro
145                 150                 155                 160
Ser Ser Ile Glu Lys Thr Ile Ser Lys Ala Lys Gly Gln Pro Arg Glu
                165                 170                 175
Pro Gln Val Tyr Thr Leu Pro Pro Ser Gln Glu Glu Met Thr Lys Asn
            180                 185                 190
Gln Val Ser Leu Thr Cys Leu Val Lys Gly Phe Tyr Pro Ser Asp Ile
        195                 200                 205
Ala Val Glu Trp Glu Ser Asn Gly Gln Pro Glu Asn Asn Tyr Lys Thr
    210                 215                 220
Thr Pro Pro Val Leu Asp Ser Asp Gly Ser Phe Phe Leu Tyr Ser Arg
225                 230                 235                 240
Leu Thr Val Asp Lys Ser Arg Trp Gln Glu Gly Asn Val Phe Ser Cys
                245                 250                 255
Ser Val Met His Glu Ala Leu His Asn His Tyr Thr Gln Lys Ser Leu
            260                 265                 270
Ser Leu Ser Leu Gly Gly Gly Gly Ala Tyr Cys Ala Lys Tyr Asp
        275                 280                 285
Gly Cys Tyr Gly Glu Leu Asp Phe Trp Cys Gln
    290                 295

<210> SEQ ID NO 129
<211> LENGTH: 297
<212> TYPE: PRT
<213> ORGANISM: Artificial Sequence
<220> FEATURE:
<223> OTHER INFORMATION: GLP-1 fusion 17

<400> SEQUENCE: 129

His Gly Glu Gly Thr Phe Thr Ser Asp Val Ser Ser Tyr Leu Glu Glu
1               5                  10                  15
Gln Ala Ala Lys Glu Phe Ile Ala Trp Leu Val Lys Gly Gly Gly Gly
                20                  25                  30
Gly Gly Gly Ala Gly Gly Gly Ala Gly Gly Gly Ala Ala Glu
            35                  40                  45
Ser Lys Tyr Gly Pro Pro Cys Pro Pro Cys Pro Ala Pro Glu Ala Ala
    50                  55                  60
Gly Gly Pro Ser Val Phe Leu Phe Pro Pro Lys Pro Lys Asp Thr Leu
65                  70                  75                  80
Met Ile Ser Arg Thr Pro Glu Val Thr Cys Val Val Val Asp Val Ser
                85                  90                  95
Gln Glu Asp Pro Glu Val Gln Phe Asn Trp Tyr Val Asp Gly Val Glu
            100                 105                 110
Val His Asn Ala Lys Thr Lys Pro Arg Glu Glu Gln Phe Asn Ser Thr
        115                 120                 125
Tyr Arg Val Val Ser Val Leu Thr Val Leu His Gln Asp Trp Leu Asn
```

```
                130                 135                 140
Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
        210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Gly Gly Gly Gly Ala Tyr Ser Ala Lys Tyr Asp Gly Cys
        275                 280                 285

Tyr Gly Glu Leu Asp Phe Trp Gly Gln
    290                 295

<210> SEQ ID NO 130
<211> LENGTH: 299
<212> TYPE: PRT
<213> ORGANISM: Artificial Sequence
<220> FEATURE:
<223> OTHER INFORMATION: GLP-1 fusion 18

<400> SEQUENCE: 130

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Pro Ala Pro
                20                  25                  30

Ala Pro Ala Pro Ala Pro Ala Pro Ala Pro Ala Pro Ala Pro Ala Pro
            35                  40                  45

Ala Pro Ala Pro Ala Gly Pro Pro Cys Pro Pro Cys Pro Ala Pro Glu
        50                  55                  60

Ala Ala Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser Gln Glu Asp Pro Glu Val Gln Phe Asn Trp Tyr Val Asp Gly
            100                 105                 110

Val Glu Val His Asn Ala Lys Thr Lys Pro Arg Glu Glu Gln Phe Asn
        115                 120                 125

Ser Thr Tyr Arg Val Val Ser Val Leu Thr Val Leu His Gln Asp Trp
    130                 135                 140

Leu Asn Gly Lys Glu Tyr Lys Cys Lys Val Ser Asn Lys Gly Leu Pro
145                 150                 155                 160

Ser Ser Ile Glu Lys Thr Ile Ser Lys Ala Lys Gly Gln Pro Arg Glu
                165                 170                 175

Pro Gln Val Tyr Thr Leu Pro Pro Ser Gln Glu Glu Met Thr Lys Asn
            180                 185                 190

Gln Val Ser Leu Thr Cys Leu Val Lys Gly Phe Tyr Pro Ser Asp Ile
```

195                 200                 205
Ala Val Glu Trp Glu Ser Asn Gly Gln Pro Glu Asn Tyr Lys Thr
210                 215                 220

Thr Pro Pro Val Leu Asp Ser Asp Gly Ser Phe Phe Leu Tyr Ser Arg
225                 230                 235                 240

Leu Thr Val Asp Lys Ser Arg Trp Gln Glu Gly Asn Val Phe Ser Cys
                245                 250                 255

Ser Val Met His Glu Ala Leu His Asn His Tyr Thr Gln Lys Ser Leu
            260                 265                 270

Ser Leu Ser Leu Gly Gly Gly Gly Ala Tyr Ser Ala Lys Tyr Asp
        275                 280                 285

Gly Cys Tyr Gly Glu Leu Asp Phe Trp Gly Gln
290                 295

<210> SEQ ID NO 131
<211> LENGTH: 290
<212> TYPE: PRT
<213> ORGANISM: Artificial Sequence
<220> FEATURE:
<223> OTHER INFORMATION: GLP-1 fusion 19

<400> SEQUENCE: 131

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ala Gly Gly Gly Ala Gly Gly Gly Ala Ala Glu
            35                  40                  45

Ser Lys Tyr Gly Pro Pro Cys Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu

-continued

```
                260                 265                 270
Ser Leu Gly Gly Gly Gly Ala Pro Ala Pro Ala Pro Glu Glu Glu Pro
        275                 280                 285

Cys Ala
    290

<210> SEQ ID NO 132
<211> LENGTH: 290
<212> TYPE: PRT
<213> ORGANISM: Artificial Sequence
<220> FEATURE:
<223> OTHER INFORMATION: GLP-1 fusion 20

<400> SEQUENCE: 132

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Gly Gly Gly Gly Gly Gly Gly Gly Gly Gly Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Gly Gly Gly Ala Pro Ala Pro Ala Pro Glu Glu Glu Pro
        275                 280                 285

Cys Ala
    290

<210> SEQ ID NO 133
<211> LENGTH: 287
<212> TYPE: PRT
```

```
<213> ORGANISM: Artificial Sequence
<220> FEATURE:
<223> OTHER INFORMATION: GLP-1 fusion 21

<400> SEQUENCE: 133

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
                20                  25                  30

Ala Gly Gly Gly Ala Gly Gly Gly Ala Ala Glu Ser Lys Tyr
            35                  40                  45

Gly Pro Pro Cys Pro Pro Cys Pro Ala Pro Glu Ala Ala Gly Gly Pro
        50                  55                  60

Ser Val Phe Leu Phe Pro Pro Lys Pro Lys Asp Thr Leu Met Ile Ser
65              70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Gly Gly Gly Ala Pro Ala Pro Ala Pro Glu Glu Glu Pro Cys Ala
        275                 280                 285

<210> SEQ ID NO 134
<211> LENGTH: 298
<212> TYPE: PRT
<213> ORGANISM: Artificial Sequence
<220> FEATURE:
<223> OTHER INFORMATION: GLP-1 fusion 22

<400> SEQUENCE: 134

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser Gly Gly Gly Ala Gly Gly Gly
        35                  40                  45
```

```
Ala Gly Gly Gly Ala Ala Glu Ser Lys Tyr Gly Pro Cys Pro
 50                  55                  60

Pro Cys Pro Ala Pro Glu Ala Ala Gly Gly Pro Ser Val Phe Leu Phe
 65                  70                  75                  80

Pro Pro Lys Pro Lys Asp Thr Leu Met Ile Ser Arg Thr Pro Glu Val
                 85                  90                  95

Thr Cys Val Val Val Asp Val Ser Gln Glu Asp Pro Glu Val Gln Phe
                100                 105                 110

Asn Trp Tyr Val Asp Gly Val Glu Val His Asn Ala Lys Thr Lys Pro
            115                 120                 125

Arg Glu Glu Gln Phe Asn Ser Thr Tyr Arg Val Val Ser Val Leu Thr
130                 135                 140

Val Leu His Gln Asp Trp Leu Asn Gly Lys Glu Tyr Lys Cys Lys Val
145                 150                 155                 160

Ser Asn Lys Gly Leu Pro Ser Ser Ile Glu Lys Thr Ile Ser Lys Ala
                165                 170                 175

Lys Gly Gln Pro Arg Glu Pro Gln Val Tyr Thr Leu Pro Pro Ser Gln
            180                 185                 190

Glu Glu Met Thr Lys Asn Gln Val Ser Leu Thr Cys Leu Val Lys Gly
            195                 200                 205

Phe Tyr Pro Ser Asp Ile Ala Val Glu Trp Glu Ser Asn Gly Gln Pro
210                 215                 220

Glu Asn Asn Tyr Lys Thr Thr Pro Pro Val Leu Asp Ser Asp Gly Ser
225                 230                 235                 240

Phe Phe Leu Tyr Ser Arg Leu Thr Val Asp Lys Ser Arg Trp Gln Glu
                245                 250                 255

Gly Asn Val Phe Ser Cys Ser Val Met His Glu Ala Leu His Asn His
            260                 265                 270

Tyr Thr Gln Lys Ser Leu Ser Leu Ser Leu Gly Gly Gly Gly Ala Pro
            275                 280                 285

Ala Pro Ala Pro Glu Glu Glu Pro Cys Ala
            290                 295

<210> SEQ ID NO 135
<211> LENGTH: 298
<212> TYPE: PRT
<213> ORGANISM: Artificial Sequence
<220> FEATURE:
<223> OTHER INFORMATION: GLP-1 fusion 23

<400> SEQUENCE: 135

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                 20                  25                  30

Ser Gly Ala Pro Pro Ser Gly Gly Gly Gly Gly Gly Gly Gly Gly Gly
             35                  40                  45

Gly Gly Gly Gly Gly Gly Ala Glu Ser Lys Tyr Gly Pro Pro Cys Pro
 50                  55                  60

Pro Cys Pro Ala Pro Glu Ala Ala Gly Gly Pro Ser Val Phe Leu Phe
 65                  70                  75                  80

Pro Pro Lys Pro Lys Asp Thr Leu Met Ile Ser Arg Thr Pro Glu Val
                 85                  90                  95

Thr Cys Val Val Val Asp Val Ser Gln Glu Asp Pro Glu Val Gln Phe
                100                 105                 110
```

Asn Trp Tyr Val Asp Gly Val Glu Val His Asn Ala Lys Thr Lys Pro
            115                 120                 125

Arg Glu Glu Gln Phe Asn Ser Thr Tyr Arg Val Val Ser Val Leu Thr
130                 135                 140

Val Leu His Gln Asp Trp Leu Asn Gly Lys Glu Tyr Lys Cys Lys Val
145                 150                 155                 160

Ser Asn Lys Gly Leu Pro Ser Ser Ile Glu Lys Thr Ile Ser Lys Ala
                165                 170                 175

Lys Gly Gln Pro Arg Glu Pro Gln Val Tyr Thr Leu Pro Pro Ser Gln
            180                 185                 190

Glu Glu Met Thr Lys Asn Gln Val Ser Leu Thr Cys Leu Val Lys Gly
        195                 200                 205

Phe Tyr Pro Ser Asp Ile Ala Val Glu Trp Glu Ser Asn Gly Gln Pro
    210                 215                 220

Glu Asn Asn Tyr Lys Thr Thr Pro Pro Val Leu Asp Ser Asp Gly Ser
225                 230                 235                 240

Phe Phe Leu Tyr Ser Arg Leu Thr Val Asp Lys Ser Arg Trp Gln Glu
                245                 250                 255

Gly Asn Val Phe Ser Cys Ser Val Met His Glu Ala Leu His Asn His
            260                 265                 270

Tyr Thr Gln Lys Ser Leu Ser Leu Ser Leu Gly Gly Gly Gly Ala Pro
        275                 280                 285

Ala Pro Ala Pro Glu Glu Glu Pro Cys Ala
    290                 295

<210> SEQ ID NO 136
<211> LENGTH: 292
<212> TYPE: PRT
<213> ORGANISM: Artificial Sequence
<220> FEATURE:
<223> OTHER INFORMATION: GLP-1 fusion 24

<400> SEQUENCE: 136

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ala Gly Gly Gly Ala Gly Gly Gly Ala Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

```
Val Tyr Thr Leu Pro Pro Ser Gln Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Ala Pro Ala Pro Ala Pro Ala Pro Ala Pro Ala Pro Cys
        275                 280                 285

Pro Glu Glu Pro
    290

<210> SEQ ID NO 137
<211> LENGTH: 292
<212> TYPE: PRT
<213> ORGANISM: Artificial Sequence
<220> FEATURE:
<223> OTHER INFORMATION: GLP-1 fusion 25

<400> SEQUENCE: 137

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Gly Gly Gly Gly Gly Gly Gly Gly Gly Gly Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240
```

Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
        260                 265                 270

Ser Leu Gly Ala Pro Ala Pro Ala Pro Ala Pro Ala Pro Ala Pro Cys
        275                 280                 285

Pro Glu Glu Pro
    290

<210> SEQ ID NO 138
<211> LENGTH: 297
<212> TYPE: PRT
<213> ORGANISM: Artificial Sequence
<220> FEATURE:
<223> OTHER INFORMATION: GLP-1 fusion 26

<400> SEQUENCE: 138

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
            20                  25                  30

Pro Ala Pro Ala Pro Ala Pro Ala Pro Ala Pro Ala Pro Ala Pro Ala
        35                  40                  45

Pro Ala Pro Ala Glu Ser Lys Tyr Gly Pro Pro Cys Pro Pro Cys Pro
50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
        115                 120                 125

Gln Phe Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Ala Pro Ala Pro Ala Pro Ala Pro
        275                 280                 285

Ala Pro Ala Pro Cys Pro Glu Glu Pro
    290                 295

```
<210> SEQ ID NO 139
<211> LENGTH: 297
<212> TYPE: PRT
<213> ORGANISM: Artificial Sequence
<220> FEATURE:
<223> OTHER INFORMATION: GLP-1 fusion 27

<400> SEQUENCE: 139

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
            20                  25                  30

Pro Ala Pro Ala Pro Ala Pro Ala Pro Ala Pro Ala Pro Ala Pro Ala
        35                  40                  45

Pro Ala Pro Ala Pro Ala Pro Ala Gly Pro Pro Cys Pro Pro Cys Pro
    50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
        115                 120                 125

Gln Phe Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Ala Pro Ala Pro Ala Pro Ala Pro
        275                 280                 285

Ala Pro Ala Pro Cys Pro Glu Glu Pro
    290                 295

<210> SEQ ID NO 140
<211> LENGTH: 289
<212> TYPE: PRT
<213> ORGANISM: Artificial Sequence
<220> FEATURE:
<223> OTHER INFORMATION: GLP-1 fusion 28

<400> SEQUENCE: 140

His Gly Glu Gly Thr Phe Thr Ser Asp Leu Ser Lys Gln Met Glu Glu
1               5                   10                  15
```

Glu Ala Val Arg Leu Phe Ile Glu Trp Leu Lys Asn Gly Gly Gly
            20                  25                  30

Ala Gly Gly Gly Gly Ala Gly Gly Gly Ala Ala Glu Ser Lys Tyr
            35                  40                  45

Gly Pro Pro Cys Pro Pro Cys Pro Ala Pro Glu Ala Ala Gly Gly Pro
            50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
            115                 120                 125

Val Ser Val Leu Thr Val Leu His Gln Asp Trp Leu Asn Gly Lys Glu
130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
            195                 200                 205

Ser Asn Gly Gln Pro Glu Asn Asn Tyr Lys Thr Thr Pro Pro Val Leu
210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Ala Pro Ala Pro Ala Pro Ala Pro Ala Pro Ala Pro Cys Pro Glu Glu
            275                 280                 285

Pro

<210> SEQ ID NO 141
<211> LENGTH: 289
<212> TYPE: PRT
<213> ORGANISM: Artificial Sequence
<220> FEATURE:
<223> OTHER INFORMATION: GLP-1 fusion 29

<400> SEQUENCE: 141

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly
            20                  25                  30

Gly Gly Gly Gly Gly Gly Gly Gly Gly Gly Ala Glu Ser Lys Tyr
            35                  40                  45

Gly Pro Pro Cys Pro Pro Cys Pro Ala Pro Glu Ala Ala Gly Gly Pro
            50                  55                  60

Ser Val Phe Leu Phe Pro Pro Lys Pro Lys Asp Thr Leu Met Ile Ser
65                  70                  75                  80

```
Arg Thr Pro Glu Val Thr Cys Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Ala Pro Ala Pro Ala Pro Ala Pro Ala Pro Ala Pro Cys Pro Glu Glu
        275                 280                 285

Pro

<210> SEQ ID NO 142
<211> LENGTH: 294
<212> TYPE: PRT
<213> ORGANISM: Artificial Sequence
<220> FEATURE:
<223> OTHER INFORMATION: GLP-1 fusion 30

<400> SEQUENCE: 142

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Pro Ala Pro
            20                  25                  30

Ala Pro Ala Pro Ala Pro Ala Pro Ala Pro Ala Pro Ala Pro Ala Pro
        35                  40                  45

Ala Glu Ser Lys Tyr Gly Pro Pro Cys Pro Pro Cys Pro Ala Pro Glu
    50                  55                  60

Ala Ala Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser Gln Glu Asp Pro Glu Val Gln Phe Asn Trp Tyr Val Asp Gly
            100                 105                 110

Val Glu Val His Asn Ala Lys Thr Lys Pro Arg Glu Glu Gln Phe Asn
        115                 120                 125

Ser Thr Tyr Arg Val Val Ser Val Leu Thr Val Leu His Gln Asp Trp
    130                 135                 140

Leu Asn Gly Lys Glu Tyr Lys Cys Lys Val Ser Asn Lys Gly Leu Pro
```

```
145                 150                 155                 160
Ser Ser Ile Glu Lys Thr Ile Ser Lys Ala Lys Gly Gln Pro Arg Glu
                165                 170                 175

Pro Gln Val Tyr Thr Leu Pro Pro Ser Gln Glu Met Thr Lys Asn
            180                 185                 190

Gln Val Ser Leu Thr Cys Leu Val Lys Gly Phe Tyr Pro Ser Asp Ile
            195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Arg
225                 230                 235                 240

Leu Thr Val Asp Lys Ser Arg Trp Gln Glu Gly Asn Val Phe Ser Cys
                245                 250                 255

Ser Val Met His Glu Ala Leu His Asn His Tyr Thr Gln Lys Ser Leu
            260                 265                 270

Ser Leu Ser Leu Gly Ala Pro Ala Pro Ala Pro Ala Pro Ala Pro Ala
            275                 280                 285

Pro Cys Pro Glu Glu Pro
            290

<210> SEQ ID NO 143
<211> LENGTH: 294
<212> TYPE: PRT
<213> ORGANISM: Artificial Sequence
<220> FEATURE:
<223> OTHER INFORMATION: GLP-1 fusion 31

<400> SEQUENCE: 143

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Pro Ala Pro
            20                  25                  30

Ala Pro Ala Pro Ala Pro Ala Pro Ala Pro Ala Pro Ala Pro Ala Pro
        35                  40                  45

Ala Pro Ala Pro Ala Gly Pro Pro Cys Pro Pro Cys Pro Ala Pro Glu
    50                  55                  60

Ala Ala Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser Gln Glu Asp Pro Glu Val Gln Phe Asn Trp Tyr Val Asp Gly
            100                 105                 110

Val Glu Val His Asn Ala Lys Thr Lys Pro Arg Glu Glu Gln Phe Asn
            115                 120                 125

Ser Thr Tyr Arg Val Val Ser Val Leu Thr Val Leu His Gln Asp Trp
        130                 135                 140

Leu Asn Gly Lys Glu Tyr Lys Cys Lys Val Ser Asn Lys Gly Leu Pro
145                 150                 155                 160

Ser Ser Ile Glu Lys Thr Ile Ser Lys Ala Lys Gly Gln Pro Arg Glu
                165                 170                 175

Pro Gln Val Tyr Thr Leu Pro Pro Ser Gln Glu Met Thr Lys Asn
            180                 185                 190

Gln Val Ser Leu Thr Cys Leu Val Lys Gly Phe Tyr Pro Ser Asp Ile
            195                 200                 205

Ala Val Glu Trp Glu Ser Asn Gly Gln Pro Glu Asn Asn Tyr Lys Thr
```

```
                210                 215                 220
Thr Pro Pro Val Leu Asp Ser Asp Gly Ser Phe Phe Leu Tyr Ser Arg
225                 230                 235                 240

Leu Thr Val Asp Lys Ser Arg Trp Gln Glu Gly Asn Val Phe Ser Cys
                245                 250                 255

Ser Val Met His Glu Ala Leu His Asn His Tyr Thr Gln Lys Ser Leu
            260                 265                 270

Ser Leu Ser Leu Gly Ala Pro Ala Pro Ala Pro Ala Pro Ala Pro Ala
        275                 280                 285

Pro Cys Pro Glu Glu Pro
        290

<210> SEQ ID NO 144
<211> LENGTH: 280
<212> TYPE: PRT
<213> ORGANISM: Artificial Sequence
<220> FEATURE:
<223> OTHER INFORMATION: GLP-1 fusion 32

<400> SEQUENCE: 144

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Ala Ser
            20                  25                  30

Gly Gly Gly Gly Ser Gly Gly Gly Ser Cys Pro Pro Cys Pro Ala
        35                  40                  45

Pro Glu Ala Ala Gly Gly Pro Ser Val Phe Leu Phe Pro Pro Lys Pro
50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Ala Ser Gly Ser Ala Pro Ala Pro
            260                 265                 270

Ala Pro Glu Glu Glu Pro Cys Ala
```

<210> SEQ ID NO 145
<211> LENGTH: 282
<212> TYPE: PRT
<213> ORGANISM: Artificial Sequence
<220> FEATURE:
<223> OTHER INFORMATION: GLP-1 fusion 33

<400> SEQUENCE: 145

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Ala Ser
            20                  25                  30

Ala Pro Ala Pro Ala Pro Ala Pro Gly Ser Cys Pro Pro Cys
        35                  40                  45

Pro Ala Pro Glu Ala Ala Gly Gly Pro Ser Val Phe Leu Phe Pro Pro
    50                  55                  60

Lys Pro Lys Asp Thr Leu Met Ile Ser Arg Thr Pro Glu Val Thr Cys
65                  70                  75                  80

Val Val Val Asp Val Ser Gln Glu Asp Pro Glu Val Gln Phe Asn Trp
                85                  90                  95

Tyr Val Asp Gly Val Glu Val His Asn Ala Lys Thr Lys Pro Arg Glu
            100                 105                 110

Glu Gln Phe Asn Ser Thr Tyr Arg Val Val Ser Val Leu Thr Val Leu
        115                 120                 125

His Gln Asp Trp Leu Asn Gly Lys Glu Tyr Lys Cys Lys Val Ser Asn
    130                 135                 140

Lys Gly Leu Pro Ser Ser Ile Glu Lys Thr Ile Ser Lys Ala Lys Gly
145                 150                 155                 160

Gln Pro Arg Glu Pro Gln Val Tyr Thr Leu Pro Pro Ser Gln Glu Glu
                165                 170                 175

Met Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
        195                 200                 205

Asn Tyr Lys Thr Thr Pro Pro Val Leu Asp Ser Asp Gly Ser Phe Phe
    210                 215                 220

Leu Tyr Ser Arg Leu Thr Val Asp Lys Ser Arg Trp Gln Glu Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Leu Gly Lys Ala Ser Gly Ser Ala Pro
            260                 265                 270

Ala Pro Ala Pro Glu Glu Glu Pro Cys Ala
        275                 280

<210> SEQ ID NO 146
<211> LENGTH: 289
<212> TYPE: PRT
<213> ORGANISM: Artificial Sequence
<220> FEATURE:
<223> OTHER INFORMATION: GLP-1 fusion 34

<400> SEQUENCE: 146

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ser Gly Gly Gly Ser Gly Gly
        35                  40                  45

Gly Gly Ser Cys Pro Pro Cys Pro Ala Pro Glu Ala Ala Gly Gly Pro
50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
            85                  90                  95

Pro Glu Val Gln Phe Asn Trp Tyr Val Asp Gly Val Glu Val His Asn
        100                 105                 110

Ala Lys Thr Lys Pro Arg Glu Glu Gln Phe Asn Ser Thr Tyr Arg Val
    115                 120                 125

Val Ser Val Leu Thr Val Leu His Gln Asp Trp Leu Asn Gly Lys Glu
130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
            165                 170                 175

Leu Pro Pro Ser Gln Glu Glu Met Thr Lys Asn Gln Val Ser Leu Thr
        180                 185                 190

Cys Leu Val Lys Gly Phe Tyr Pro Ser Asp Ile Ala Val Glu Trp Glu
    195                 200                 205

Ser Asn Gly Gln Pro Glu Asn Asn Tyr Lys Thr Thr Pro Pro Val Leu
210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
            245                 250                 255

Ala Leu His Asn His Tyr Thr Gln Lys Ser Leu Ser Leu Ser Leu Gly
        260                 265                 270

Lys Ala Ser Gly Ser Ala Pro Ala Pro Ala Pro Glu Glu Glu Pro Cys
    275                 280                 285

Ala

<210> SEQ ID NO 147
<211> LENGTH: 291
<212> TYPE: PRT
<213> ORGANISM: Artificial Sequence
<220> FEATURE:
<223> OTHER INFORMATION: GLP-1 fusion 35

<400> SEQUENCE: 147

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ser Ala Pro Ala Pro Ala Pro Ala
        35                  40                  45

Pro Ala Pro Gly Ser Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln

```
                    85                  90                  95
Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
            115                 120                 125

Arg Val Val Ser Val Leu Thr Val Leu His Gln Asp Trp Leu Asn Gly
        130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Arg Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
            260                 265                 270

Leu Gly Lys Ala Ser Gly Ser Ala Pro Ala Pro Ala Pro Glu Glu Glu
        275                 280                 285

Pro Cys Ala
    290

<210> SEQ ID NO 148
<211> LENGTH: 283
<212> TYPE: PRT
<213> ORGANISM: Artificial Sequence
<220> FEATURE:
<223> OTHER INFORMATION: GLP-1 fusion 36

<400> SEQUENCE: 148

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Ala Ser
            20                  25                  30

Gly Gly Gly Gly Ser Gly Gly Gly Gly Ser Pro Pro Cys Pro Pro
        35                  40                  45

Cys Pro Ala Pro Glu Ala Ala Gly Gly Pro Ser Val Phe Leu Phe Pro
    50                  55                  60

Pro Lys Pro Lys Asp Thr Leu Met Ile Ser Arg Thr Pro Glu Val Thr
65                  70                  75                  80

Cys Val Val Val Asp Val Ser Gln Glu Asp Pro Glu Val Gln Phe Asn
                85                  90                  95

Trp Tyr Val Asp Gly Val Glu Val His Asn Ala Lys Thr Lys Pro Arg
                100                 105                 110

Glu Glu Gln Phe Asn Ser Thr Tyr Arg Val Val Ser Val Leu Thr Val
            115                 120                 125

Leu His Gln Asp Trp Leu Asn Gly Lys Glu Tyr Lys Cys Lys Val Ser
        130                 135                 140

Asn Lys Gly Leu Pro Ser Ser Ile Glu Lys Thr Ile Ser Lys Ala Lys
```

-continued

```
            145                 150                 155                 160
        Gly Gln Pro Arg Glu Pro Gln Val Tyr Thr Leu Pro Pro Ser Gln Glu
                        165                 170                 175
        Glu Met Thr Lys Asn Gln Val Ser Leu Thr Cys Leu Val Lys Gly Phe
                        180                 185                 190
        Tyr Pro Ser Asp Ile Ala Val Glu Trp Glu Ser Asn Gly Gln Pro Glu
                        195                 200                 205
        Asn Asn Tyr Lys Thr Thr Pro Pro Val Leu Asp Ser Asp Gly Ser Phe
                        210                 215                 220
        Phe Leu Tyr Ser Arg Leu Thr Val Asp Lys Ser Arg Trp Gln Glu Gly
        225                 230                 235                 240
        Asn Val Phe Ser Cys Ser Val Met His Glu Ala Leu His Asn His Tyr
                        245                 250                 255
        Thr Gln Lys Ser Leu Ser Leu Ser Leu Gly Lys Ala Ser Gly Ser Ala
                        260                 265                 270
        Pro Ala Pro Ala Pro Glu Glu Glu Pro Cys Ala
                        275                 280

<210> SEQ ID NO 149
<211> LENGTH: 292
<212> TYPE: PRT
<213> ORGANISM: Artificial Sequence
<220> FEATURE:
<223> OTHER INFORMATION: GLP-1 fusion 37

<400> SEQUENCE: 149

His Gly Glu Gly Thr Phe Thr Ser Asp Leu Ser Lys Gln Met Glu Glu
        1               5                   10                  15
        Glu Ala Val Arg Leu Phe Ile Glu Trp Leu Lys Asn Gly Gly Pro Ser
                        20                  25                  30
        Ser Gly Ala Pro Pro Ser Ala Ser Gly Gly Gly Ser Gly Gly
                        35                  40                  45
        Gly Gly Ser Gly Pro Pro Cys Pro Pro Cys Pro Ala Pro Glu Ala Ala
            50                  55                  60
        Gly Gly Pro Ser Val Phe Leu Phe Pro Pro Lys Pro Lys Asp Thr Leu
        65                  70                  75                  80
        Met Ile Ser Arg Thr Pro Glu Val Thr Cys Val Val Val Asp Val Ser
                        85                  90                  95
        Gln Glu Asp Pro Glu Val Gln Phe Asn Trp Tyr Val Asp Gly Val Glu
                        100                 105                 110
        Val His Asn Ala Lys Thr Lys Pro Arg Glu Glu Gln Phe Asn Ser Thr
                        115                 120                 125
        Tyr Arg Val Val Ser Val Leu Thr Val Leu His Gln Asp Trp Leu Asn
                        130                 135                 140
        Gly Lys Glu Tyr Lys Cys Lys Val Ser Asn Lys Gly Leu Pro Ser Ser
        145                 150                 155                 160
        Ile Glu Lys Thr Ile Ser Lys Ala Lys Gly Gln Pro Arg Glu Pro Gln
                        165                 170                 175
        Val Tyr Thr Leu Pro Pro Ser Gln Glu Glu Met Thr Lys Asn Gln Val
                        180                 185                 190
        Ser Leu Thr Cys Leu Val Lys Gly Phe Tyr Pro Ser Asp Ile Ala Val
                        195                 200                 205
        Glu Trp Glu Ser Asn Gly Gln Pro Glu Asn Asn Tyr Lys Thr Thr Pro
                        210                 215                 220
        Pro Val Leu Asp Ser Asp Gly Ser Phe Phe Leu Tyr Ser Arg Leu Thr
```

-continued

```
            225                 230                 235                 240
Val Asp Lys Ser Arg Trp Gln Glu Gly Asn Val Phe Ser Cys Ser Val
                    245                 250                 255

Met His Glu Ala Leu His Asn His Tyr Thr Gln Lys Ser Leu Ser Leu
                260                 265                 270

Ser Leu Gly Lys Ala Ser Gly Ser Ala Pro Ala Pro Ala Pro Glu Glu
            275                 280                 285

Glu Pro Cys Ala
        290

<210> SEQ ID NO 150
<211> LENGTH: 290
<212> TYPE: PRT
<213> ORGANISM: Artificial Sequence
<220> FEATURE:
<223> OTHER INFORMATION: GLP-1 fusion 38

<400> SEQUENCE: 150

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Ala Ser
            20                  25                  30

Gly Gly Gly Gly Ser Gly Gly Gly Ser Gly Gly Gly Ser Gly
        35                  40                  45

Gly Gly Gly Ser Cys Pro Pro Cys Pro Ala Pro Glu Ala Ala Gly Gly
    50                  55                  60

Pro Ser Val Phe Leu Phe Pro Pro Lys Pro Lys Asp Thr Leu Met Ile
65                  70                  75                  80

Ser Arg Thr Pro Glu Val Thr Cys Val Val Val Asp Val Ser Gln Glu
                85                  90                  95

Asp Pro Glu Val Gln Phe Asn Trp Tyr Val Asp Gly Val Glu Val His
            100                 105                 110

Asn Ala Lys Thr Lys Pro Arg Glu Glu Gln Phe Asn Ser Thr Tyr Arg
        115                 120                 125

Val Val Ser Val Leu Thr Val Leu His Gln Asp Trp Leu Asn Gly Lys
    130                 135                 140

Glu Tyr Lys Cys Lys Val Ser Asn Lys Gly Leu Pro Ser Ser Ile Glu
145                 150                 155                 160

Lys Thr Ile Ser Lys Ala Lys Gly Gln Pro Arg Glu Pro Gln Val Tyr
                165                 170                 175

Thr Leu Pro Pro Ser Gln Glu Glu Met Thr Lys Asn Gln Val Ser Leu
            180                 185                 190

Thr Cys Leu Val Lys Gly Phe Tyr Pro Ser Asp Ile Ala Val Glu Trp
        195                 200                 205

Glu Ser Asn Gly Gln Pro Glu Asn Asn Tyr Lys Thr Thr Pro Pro Val
    210                 215                 220

Leu Asp Ser Asp Gly Ser Phe Phe Leu Tyr Ser Arg Leu Thr Val Asp
225                 230                 235                 240

Lys Ser Arg Trp Gln Glu Gly Asn Val Phe Ser Cys Ser Val Met His
                245                 250                 255

Glu Ala Leu His Asn His Tyr Thr Gln Lys Ser Leu Ser Leu Ser Leu
            260                 265                 270

Gly Lys Ala Ser Gly Ser Ala Pro Ala Pro Ala Pro Glu Glu Glu Pro
        275                 280                 285

Cys Ala
```

<210> SEQ ID NO 151
<211> LENGTH: 292
<212> TYPE: PRT
<213> ORGANISM: Artificial Sequence
<220> FEATURE:
<223> OTHER INFORMATION: GLP-1 fusion 39

<400> SEQUENCE: 151

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Ala Ser
            20                  25                  30

Ala Pro Ala Pro Ala Pro Ala Pro Ala Pro Ala Pro Ala Pro Ala Pro
        35                  40                  45

Ala Pro Ala Pro Gly Ser Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Ala Ser Gly Ser Ala Pro Ala Pro Ala Pro Glu Glu
        275                 280                 285

Glu Pro Cys Ala
    290

<210> SEQ ID NO 152
<211> LENGTH: 281
<212> TYPE: PRT
<213> ORGANISM: Artificial Sequence
<220> FEATURE:
<223> OTHER INFORMATION: GLP-1 fusion 40

<400> SEQUENCE: 152

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
                20                  25                  30

Ser Gly Gly Gly Ser Gly Gly Gly Ser Cys Pro Pro Cys Pro
            35                  40                  45

Ala Pro Glu Ala Ala Gly Gly Pro Ser Val Phe Leu Phe Pro Pro Lys
50                  55                  60

Pro Lys Asp Thr Leu Met Ile Ser Arg Thr Pro Glu Val Thr Cys Val
65                  70                  75                  80

Val Val Asp Val Ser Gln Glu Asp Pro Glu Val Gln Phe Asn Trp Tyr
                85                  90                  95

Val Asp Gly Val Glu Val His Asn Ala Lys Thr Lys Pro Arg Glu Glu
                100                 105                 110

Gln Phe Asn Ser Thr Tyr Arg Val Val Ser Val Leu Thr Val Leu His
            115                 120                 125

Gln Asp Trp Leu Asn Gly Lys Glu Tyr Lys Cys Lys Val Ser Asn Lys
            130                 135                 140

Gly Leu Pro Ser Ser Ile Glu Lys Thr Ile Ser Lys Ala Lys Gly Gln
145                 150                 155                 160

Pro Arg Glu Pro Gln Val Tyr Thr Leu Pro Pro Ser Gln Glu Glu Met
                165                 170                 175

Thr Lys Asn Gln Val Ser Leu Thr Cys Leu Val Lys Gly Phe Tyr Pro
                180                 185                 190

Ser Asp Ile Ala Val Glu Trp Glu Ser Asn Gly Gln Pro Glu Asn Asn
            195                 200                 205

Tyr Lys Thr Thr Pro Pro Val Leu Asp Ser Asp Gly Ser Phe Phe Leu
210                 215                 220

Tyr Ser Arg Leu Thr Val Asp Lys Ser Arg Trp Gln Glu Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Leu Gly Lys Ala Ser Gly Ser Ala Pro Ala
                260                 265                 270

Pro Ala Pro Glu Glu Glu Pro Cys Ala
            275                 280

<210> SEQ ID NO 153
<211> LENGTH: 291
<212> TYPE: PRT
<213> ORGANISM: Artificial Sequence
<220> FEATURE:
<223> OTHER INFORMATION: GLP-1 fusion 41

<400> SEQUENCE: 153

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
                20                  25                  30

Ser Gly Gly Gly Ser Gly Gly Gly Ser Gly Gly Gly Ser
            35                  40                  45

Gly Gly Gly Ser Cys Pro Pro Cys Pro Ala Pro Glu Ala Ala Gly
            50                  55                  60

Gly Pro Ser Val Phe Leu Phe Pro Pro Lys Pro Lys Asp Thr Leu Met
65                  70                  75                  80

```
Ile Ser Arg Thr Pro Glu Val Thr Cys Val Val Asp Val Ser Gln
                85                  90                  95

Glu Asp Pro Glu Val Gln Phe Asn Trp Tyr Val Asp Gly Val Glu Val
            100                 105                 110

His Asn Ala Lys Thr Lys Pro Arg Glu Glu Gln Phe Asn Ser Thr Tyr
            115                 120                 125

Arg Val Val Ser Val Leu Thr Val Leu His Gln Asp Trp Leu Asn Gly
        130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
            195                 200                 205

Trp Glu Ser Asn Gly Gln Pro Glu Asn Asn Tyr Lys Thr Thr Pro Pro
        210                 215                 220

Val Leu Asp Ser Asp Gly Ser Phe Phe Leu Tyr Ser Arg Leu Thr Val
225                 230                 235                 240

Asp Lys Ser Arg Trp Gln Gln Gly Asn Val Phe Ser Cys Ser Val Met
                245                 250                 255

His Glu Ala Leu His Asn His Tyr Thr Gln Lys Ser Leu Ser Leu Ser
            260                 265                 270

Leu Gly Lys Ala Ser Gly Ser Ala Pro Ala Pro Ala Pro Glu Glu Glu
        275                 280                 285

Pro Cys Ala
    290

<210> SEQ ID NO 154
<211> LENGTH: 289
<212> TYPE: PRT
<213> ORGANISM: Artificial Sequence
<220> FEATURE:
<223> OTHER INFORMATION: GLP-1 fusion 42

<400> SEQUENCE: 154

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ser Gly Gly Gly Ser Gly Gly
        35                  40                  45

Gly Gly Ser Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140
```

-continued

```
Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
                260                 265                 270

Lys Ala Ser Gly Ser Ala Pro Ala Pro Glu Pro Glu Pro Glu Pro Cys
            275                 280                 285

Ala

<210> SEQ ID NO 155
<211> LENGTH: 291
<212> TYPE: PRT
<213> ORGANISM: Artificial Sequence
<220> FEATURE:
<223> OTHER INFORMATION: GLP-1 fusion 43

<400> SEQUENCE: 155

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser Ala Ser Ala Pro Ala Pro Ala Pro Ala
            35                  40                  45

Pro Ala Pro Gly Ser Cys Pro Pro Cys Pro Ala Pro Glu Ala Ala Gly
        50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
            100                 105                 110

His Asn Ala Lys Thr Lys Pro Arg Glu Glu Gln Phe Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
```

```
            210                 215                 220
Val Leu Asp Ser Asp Gly Ser Phe Phe Leu Tyr Ser Arg Leu Thr Val
225                 230                 235                 240

Asp Lys Ser Arg Trp Gln Glu Gly Asn Val Phe Ser Cys Ser Val Met
            245                 250                 255

His Glu Ala Leu His Asn His Tyr Thr Gln Lys Ser Leu Ser Leu Ser
            260                 265                 270

Leu Gly Lys Ala Ser Gly Ser Ala Pro Ala Pro Glu Pro Glu Pro Glu
            275                 280                 285

Pro Cys Ala
    290

<210> SEQ ID NO 156
<211> LENGTH: 281
<212> TYPE: PRT
<213> ORGANISM: Artificial Sequence
<220> FEATURE:
<223> OTHER INFORMATION: GLP-1 fusion 44

<400> SEQUENCE: 156

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
            20                  25                  30

Ser Gly Gly Gly Ser Gly Gly Gly Ser Cys Pro Pro Cys Pro
            35                  40                  45

Ala Pro Glu Ala Ala Gly Gly Pro Ser Val Phe Leu Phe Pro Pro Lys
50                  55                  60

Pro Lys Asp Thr Leu Met Ile Ser Arg Thr Pro Glu Val Thr Cys Val
65                  70                  75                  80

Val Val Asp Val Ser Gln Glu Asp Pro Glu Val Gln Phe Asn Trp Tyr
            85                  90                  95

Val Asp Gly Val Glu Val His Asn Ala Lys Thr Lys Pro Arg Glu Glu
            100                 105                 110

Gln Phe Asn Ser Thr Tyr Arg Val Val Ser Val Leu Thr Val Leu His
            115                 120                 125

Gln Asp Trp Leu Asn Gly Lys Glu Tyr Lys Cys Lys Val Ser Asn Lys
130                 135                 140

Gly Leu Pro Ser Ser Ile Glu Lys Thr Ile Ser Lys Ala Lys Gly Gln
145                 150                 155                 160

Pro Arg Glu Pro Gln Val Tyr Thr Leu Pro Pro Ser Gln Glu Glu Met
            165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
            195                 200                 205

Tyr Lys Thr Thr Pro Pro Val Leu Asp Ser Asp Gly Ser Phe Phe Leu
            210                 215                 220

Tyr Ser Arg Leu Thr Val Asp Lys Ser Arg Trp Gln Glu Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Leu Gly Lys Ala Ser Gly Ser Ala Pro Ala
            260                 265                 270

Pro Glu Pro Glu Pro Glu Pro Cys Ala
```

<210> SEQ ID NO 157
<211> LENGTH: 289
<212> TYPE: PRT
<213> ORGANISM: Artificial Sequence
<220> FEATURE:
<223> OTHER INFORMATION: GLP-1 fusion 45

<400> SEQUENCE: 157

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ser Gly Gly Gly Ser Gly Gly
        35                  40                  45

Gly Gly Ser Cys Pro Pro Cys Pro Ala Pro Glu Ala Ala Gly Gly Pro
        50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Lys Ala Ser Gly Ser Ala Pro Ala Pro Ala Pro Cys Glu Glu
        275                 280                 285

Glu

<210> SEQ ID NO 158
<211> LENGTH: 291
<212> TYPE: PRT
<213> ORGANISM: Artificial Sequence
<220> FEATURE:
<223> OTHER INFORMATION: GLP-1 fusion 46

<400> SEQUENCE: 158

His Gly Glu Gly Thr Phe Thr Ser Asp Leu Ser Lys Gln Met Glu Glu

```
              1               5                  10                 15
            Glu Ala Val Arg Leu Phe Ile Glu Trp Leu Lys Asn Gly Gly Pro Ser
                             20                 25                 30

Ser Gly Ala Pro Pro Ser Ala Ser Ala Pro Ala Pro Ala Pro Ala
                         35                 40                 45

Pro Ala Pro Gly Ser Cys Pro Cys Pro Ala Pro Glu Ala Ala Gly
                50                 55                 60

Gly Pro Ser Val Phe Leu Phe Pro Pro Lys Pro Lys Asp Thr Leu Met
            65                  70                 75                 80

Ile Ser Arg Thr Pro Glu Val Thr Cys Val Val Val Asp Val Ser Gln
                            85                 90                 95

Glu Asp Pro Glu Val Gln Phe Asn Trp Tyr Val Asp Gly Val Glu Val
                        100                105                110

His Asn Ala Lys Thr Lys Pro Arg Glu Glu Gln Phe Asn Ser Thr Tyr
                        115                120                125

Arg Val Val Ser Val Leu Thr Val Leu His Gln Asp Trp Leu Asn Gly
                        130                135                140

Lys Glu Tyr Lys Cys Lys Val Ser Asn Lys Gly Leu Pro Ser Ser Ile
            145                150                155                160

Glu Lys Thr Ile Ser Lys Ala Lys Gly Gln Pro Arg Glu Pro Gln Val
                            165                170                175

Tyr Thr Leu Pro Pro Ser Gln Glu Glu Met Thr Lys Asn Gln Val Ser
                        180                185                190

Leu Thr Cys Leu Val Lys Gly Phe Tyr Pro Ser Asp Ile Ala Val Glu
                        195                200                205

Trp Glu Ser Asn Gly Gln Pro Glu Asn Asn Tyr Lys Thr Thr Pro Pro
                        210                215                220

Val Leu Asp Ser Asp Gly Ser Phe Phe Leu Tyr Ser Arg Leu Thr Val
            225                230                235                240

Asp Lys Ser Arg Trp Gln Glu Gly Asn Val Phe Ser Cys Ser Val Met
                            245                250                255

His Glu Ala Leu His Asn His Tyr Thr Gln Lys Ser Leu Ser Leu Ser
                        260                265                270

Leu Gly Lys Ala Ser Gly Ser Ala Pro Ala Pro Ala Pro Ala Pro Cys
                        275                280                285

Glu Glu Glu
                290

<210> SEQ ID NO 159
<211> LENGTH: 292
<212> TYPE: PRT
<213> ORGANISM: Artificial Sequence
<220> FEATURE:
<223> OTHER INFORMATION: GLP-1 fusion 47

<400> SEQUENCE: 159

His Gly Glu Gly Thr Phe Thr Ser Asp Leu Ser Lys Gln Met Glu Glu
            1               5                  10                 15

Glu Ala Val Arg Leu Phe Ile Glu Trp Leu Lys Asn Gly Gly Pro Ser
                            20                 25                 30

Ser Gly Ala Pro Pro Ser Ala Ser Gly Gly Gly Ser Gly Gly
                        35                 40                 45

Gly Gly Ser Gly Pro Pro Cys Pro Pro Cys Pro Ala Pro Glu Ala Ala
                50                 55                 60

Gly Gly Pro Ser Val Phe Leu Phe Pro Pro Lys Pro Lys Asp Thr Leu
```

```
                65                  70                  75                  80
Met Ile Ser Arg Thr Pro Glu Val Thr Cys Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
            130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
            210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Ala Ser Gly Ser Ala Pro Ala Pro Ala Pro Ala Pro
            275                 280                 285

Cys Glu Glu Glu
        290

<210> SEQ ID NO 160
<211> LENGTH: 281
<212> TYPE: PRT
<213> ORGANISM: Artificial Sequence
<220> FEATURE:
<223> OTHER INFORMATION: GLP-1 fusion 48

<400> SEQUENCE: 160

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
            20                  25                  30

Ser Gly Gly Gly Gly Ser Gly Gly Gly Gly Ser Cys Pro Pro Cys Pro
            35                  40                  45

Ala Pro Glu Ala Ala Gly Gly Pro Ser Val Phe Leu Phe Pro Pro Lys
        50                  55                  60

Pro Lys Asp Thr Leu Met Ile Ser Arg Thr Pro Glu Val Thr Cys Val
65                  70                  75                  80

Val Val Asp Val Ser Gln Glu Asp Pro Glu Val Gln Phe Asn Trp Tyr
                85                  90                  95

Val Asp Gly Val Glu Val His Asn Ala Lys Thr Lys Pro Arg Glu Glu
            100                 105                 110

Gln Phe Asn Ser Thr Tyr Arg Val Val Ser Val Leu Thr Val Leu His
            115                 120                 125

Gln Asp Trp Leu Asn Gly Lys Glu Tyr Lys Cys Lys Val Ser Asn Lys
```

```
            130                 135                 140
Gly Leu Pro Ser Ser Ile Glu Lys Thr Ile Ser Lys Ala Lys Gly Gln
145                 150                 155                 160

Pro Arg Glu Pro Gln Val Tyr Thr Leu Pro Pro Ser Gln Glu Glu Met
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Arg Leu Thr Val Asp Lys Ser Arg Trp Gln Glu Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Leu Gly Lys Ala Ser Gly Ser Ala Pro Ala
            260                 265                 270

Pro Ala Pro Ala Pro Cys Glu Glu Glu
            275                 280

<210> SEQ ID NO 161
<211> LENGTH: 290
<212> TYPE: PRT
<213> ORGANISM: Artificial Sequence
<220> FEATURE:
<223> OTHER INFORMATION: GLP-1 fusion 49

<400> SEQUENCE: 161

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Ala Ser Gly Gly Gly Ser Gly Gly Gly
        35                  40                  45

Gly Gly Ser Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
```

```
            210                 215                 220
Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
                260                 265                 270

Lys Ala Ser Gly Ser Ala Pro Ala Pro Ala Pro Ala Pro Cys Pro Glu
                275                 280                 285

Glu Pro
    290

<210> SEQ ID NO 162
<211> LENGTH: 292
<212> TYPE: PRT
<213> ORGANISM: Artificial Sequence
<220> FEATURE:
<223> OTHER INFORMATION: GLP-1 fusion 50

<400> SEQUENCE: 162

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Ala Ser Ala Pro Ala Pro Ala Pro Ala Pro
            35                  40                  45

Pro Ala Pro Gly Ser Cys Pro Pro Cys Pro Ala Pro Glu Ala Ala Gly
50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
            115                 120                 125

Arg Val Val Ser Val Leu Thr Val Leu His Gln Asp Trp Leu Asn Gly
            130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
                180                 185                 190

Leu Thr Cys Leu Val Lys Gly Phe Tyr Pro Ser Asp Ile Ala Val Glu
            195                 200                 205

Trp Glu Ser Asn Gly Gln Pro Glu Asn Asn Tyr Lys Thr Thr Pro Pro
            210                 215                 220

Val Leu Asp Ser Asp Gly Ser Phe Phe Leu Tyr Ser Arg Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
                260                 265                 270

Leu Gly Lys Ala Ser Gly Ser Ala Pro Ala Pro Ala Pro Ala Pro Cys
```

-continued

```
                275                 280                 285
Pro Glu Glu Pro
    290

<210> SEQ ID NO 163
<211> LENGTH: 293
<212> TYPE: PRT
<213> ORGANISM: Artificial Sequence
<220> FEATURE:
<223> OTHER INFORMATION: GLP-1 fusion 51

<400> SEQUENCE: 163

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ser Gly Gly Gly Ser Gly Gly
        35                  40                  45

Gly Gly Ser Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Ala Ser Gly Ser Ala Pro Ala Pro Ala Pro Ala Pro
        275                 280                 285

Cys Pro Glu Glu Pro
    290

<210> SEQ ID NO 164
<211> LENGTH: 282
<212> TYPE: PRT
<213> ORGANISM: Artificial Sequence
<220> FEATURE:
<223> OTHER INFORMATION: GLP-1 fusion 52
```

-continued

<400> SEQUENCE: 164

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
            20                  25                  30

Ser Gly Gly Gly Gly Ser Gly Gly Gly Ser Cys Pro Pro Cys Pro
        35                  40                  45

Ala Pro Glu Ala Ala Gly Gly Pro Ser Val Phe Leu Phe Pro Pro Lys
50                  55                  60

Pro Lys Asp Thr Leu Met Ile Ser Arg Thr Pro Glu Val Thr Cys Val
65                  70                  75                  80

Val Val Asp Val Ser Gln Glu Asp Pro Glu Val Gln Phe Asn Trp Tyr
                85                  90                  95

Val Asp Gly Val Glu Val His Asn Ala Lys Thr Lys Pro Arg Glu Glu
            100                 105                 110

Gln Phe Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
130                 135                 140

Gly Leu Pro Ser Ser Ile Glu Lys Thr Ile Ser Lys Ala Lys Gly Gln
145                 150                 155                 160

Pro Arg Glu Pro Gln Val Tyr Thr Leu Pro Pro Ser Gln Glu Glu Met
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
210                 215                 220

Tyr Ser Arg Leu Thr Val Asp Lys Ser Arg Trp Gln Glu Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Leu Gly Lys Ala Ser Gly Ser Ala Pro Ala
            260                 265                 270

Pro Ala Pro Ala Pro Cys Pro Glu Glu Pro
        275                 280
```

<210> SEQ ID NO 165
<211> LENGTH: 283
<212> TYPE: PRT
<213> ORGANISM: Artificial Sequence
<220> FEATURE:
<223> OTHER INFORMATION: GLP-1 fusion 53

<400> SEQUENCE: 165

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
            20                  25                  30

Ser Ala Pro Ala Pro Ala Pro Ala Pro Gly Ser Cys Pro Pro
        35                  40                  45

Cys Pro Ala Pro Glu Ala Ala Gly Gly Pro Ser Val Phe Leu Phe Pro
50                  55                  60
```

Pro Lys Pro Lys Asp Thr Leu Met Ile Ser Arg Thr Pro Glu Val Thr
65                  70                  75                  80

Cys Val Val Asp Val Ser Gln Glu Asp Pro Glu Val Gln Phe Asn
            85                  90                  95

Trp Tyr Val Asp Gly Val Glu Val His Asn Ala Lys Thr Lys Pro Arg
            100                 105                 110

Glu Glu Gln Phe Asn Ser Thr Tyr Arg Val Val Ser Val Leu Thr Val
            115                 120                 125

Leu His Gln Asp Trp Leu Asn Gly Lys Glu Tyr Lys Cys Lys Val Ser
            130                 135                 140

Asn Lys Gly Leu Pro Ser Ser Ile Glu Lys Thr Ile Ser Lys Ala Lys
145                 150                 155                 160

Gly Gln Pro Arg Glu Pro Gln Val Tyr Thr Leu Pro Pro Ser Gln Glu
            165                 170                 175

Glu Met Thr Lys Asn Gln Val Ser Leu Thr Cys Leu Val Lys Gly Phe
            180                 185                 190

Tyr Pro Ser Asp Ile Ala Val Glu Trp Glu Ser Asn Gly Gln Pro Glu
            195                 200                 205

Asn Asn Tyr Lys Thr Thr Pro Pro Val Leu Asp Ser Asp Gly Ser Phe
210                 215                 220

Phe Leu Tyr Ser Arg Leu Thr Val Asp Lys Ser Arg Trp Gln Glu Gly
225                 230                 235                 240

Asn Val Phe Ser Cys Ser Val Met His Glu Ala Leu His Asn His Tyr
            245                 250                 255

Thr Gln Lys Ser Leu Ser Leu Ser Leu Gly Lys Ala Ser Gly Ser Ala
            260                 265                 270

Pro Ala Pro Ala Pro Glu Glu Glu Pro Cys Ala
            275                 280

<210> SEQ ID NO 166
<211> LENGTH: 293
<212> TYPE: PRT
<213> ORGANISM: Artificial Sequence
<220> FEATURE:
<223> OTHER INFORMATION: GLP-1 fusion 54

<400> SEQUENCE: 166

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
            20                  25                  30

Ser Ala Pro Ala Pro Ala Pro Ala Pro Ala Pro Ala Pro Ala Pro Ala
            35                  40                  45

Pro Ala Pro Ala Pro Gly Ser Cys Pro Pro Cys Pro Ala Pro Glu Ala
50                  55                  60

Ala Gly Gly Pro Ser Val Phe Leu Phe Pro Pro Lys Pro Lys Asp Thr
65                  70                  75                  80

Leu Met Ile Ser Arg Thr Pro Glu Val Thr Cys Val Val Val Asp Val
            85                  90                  95

Ser Gln Glu Asp Pro Glu Val Gln Phe Asn Trp Tyr Val Asp Gly Val
            100                 105                 110

Glu Val His Asn Ala Lys Thr Lys Pro Arg Glu Glu Gln Phe Asn Ser
            115                 120                 125

Thr Tyr Arg Val Val Ser Val Leu Thr Val Leu His Gln Asp Trp Leu
            130                 135                 140

```
Asn Gly Lys Glu Tyr Lys Cys Lys Val Ser Asn Lys Gly Leu Pro Ser
145                 150                 155                 160

Ser Ile Glu Lys Thr Ile Ser Lys Ala Lys Gly Gln Pro Arg Glu Pro
                165                 170                 175

Gln Val Tyr Thr Leu Pro Pro Ser Gln Glu Glu Met Thr Lys Asn Gln
            180                 185                 190

Val Ser Leu Thr Cys Leu Val Lys Gly Phe Tyr Pro Ser Asp Ile Ala
        195                 200                 205

Val Glu Trp Glu Ser Asn Gly Gln Pro Glu Asn Asn Tyr Lys Thr Thr
    210                 215                 220

Pro Pro Val Leu Asp Ser Asp Gly Ser Phe Phe Leu Tyr Ser Arg Leu
225                 230                 235                 240

Thr Val Asp Lys Ser Arg Trp Gln Glu Gly Asn Val Phe Ser Cys Ser
                245                 250                 255

Val Met His Glu Ala Leu His Asn His Tyr Thr Gln Lys Ser Leu Ser
            260                 265                 270

Leu Ser Leu Gly Lys Ala Ser Gly Ser Ala Pro Ala Pro Ala Pro Glu
        275                 280                 285

Glu Glu Pro Cys Ala
    290

<210> SEQ ID NO 167
<211> LENGTH: 277
<212> TYPE: PRT
<213> ORGANISM: Artificial Sequence
<220> FEATURE:
<223> OTHER INFORMATION: GLP-1 fusion 55

<400> SEQUENCE: 167

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Cys Pro Pro Cys Pro Ala Pro Glu Ala
        35                  40                  45

Ala Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser Gln Glu Asp Pro Glu Val Gln Phe Asn Trp Tyr Val Asp Gly Val
                85                  90                  95

Glu Val His Asn Ala Lys Thr Lys Pro Arg Glu Glu Gln Phe Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Gly Leu Pro Ser
    130                 135                 140

Ser Ile Glu Lys Thr Ile Ser Lys Ala Lys Gly Gln Pro Arg Glu Pro
145                 150                 155                 160

Gln Val Tyr Thr Leu Pro Pro Ser Gln Glu Glu Met Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205
```

```
Pro Pro Val Leu Asp Ser Asp Gly Ser Phe Phe Leu Tyr Ser Arg Leu
    210                 215                 220

Thr Val Asp Lys Ser Arg Trp Gln Glu Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Leu Gly Lys Ala Ser Gly Ser Ala Pro Ala Pro Ala Pro Glu
            260                 265                 270

Glu Glu Pro Cys Ala
        275
```

<210> SEQ ID NO 168
<211> LENGTH: 283
<212> TYPE: PRT
<213> ORGANISM: Artificial Sequence
<220> FEATURE:
<223> OTHER INFORMATION: GLP-1 fusion 56

<400> SEQUENCE: 168

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Gly Gly Cys Pro Pro
        35                  40                  45

Cys Pro Ala Pro Glu Ala Ala Gly Gly Pro Ser Val Phe Leu Phe Pro
    50                  55                  60

Pro Lys Pro Lys Asp Thr Leu Met Ile Ser Arg Thr Pro Glu Val Thr
65                  70                  75                  80

Cys Val Val Val Asp Val Ser Gln Glu Asp Pro Glu Val Gln Phe Asn
                85                  90                  95

Trp Tyr Val Asp Gly Val Glu Val His Asn Ala Lys Thr Lys Pro Arg
            100                 105                 110

Glu Glu Gln Phe Asn Ser Thr Tyr Arg Val Val Ser Val Leu Thr Val
        115                 120                 125

Leu His Gln Asp Trp Leu Asn Gly Lys Glu Tyr Lys Cys Lys Val Ser
    130                 135                 140

Asn Lys Gly Leu Pro Ser Ser Ile Glu Lys Thr Ile Ser Lys Ala Lys
145                 150                 155                 160

Gly Gln Pro Arg Glu Pro Gln Val Tyr Thr Leu Pro Pro Ser Gln Glu
                165                 170                 175

Glu Met Thr Lys Asn Gln Val Ser Leu Thr Cys Leu Val Lys Gly Phe
            180                 185                 190

Tyr Pro Ser Asp Ile Ala Val Glu Trp Glu Ser Asn Gly Gln Pro Glu
        195                 200                 205

Asn Asn Tyr Lys Thr Thr Pro Pro Val Leu Asp Ser Asp Gly Ser Phe
    210                 215                 220

Phe Leu Tyr Ser Arg Leu Thr Val Asp Lys Ser Arg Trp Gln Glu Gly
225                 230                 235                 240

Asn Val Phe Ser Cys Ser Val Met His Glu Ala Leu His Asn His Tyr
                245                 250                 255

Thr Gln Lys Ser Leu Ser Leu Ser Leu Gly Lys Ala Ser Gly Ser Ala
            260                 265                 270

Pro Ala Pro Ala Pro Glu Glu Glu Pro Cys Ala
        275                 280
```

<210> SEQ ID NO 169
<211> LENGTH: 283
<212> TYPE: PRT
<213> ORGANISM: Artificial Sequence
<220> FEATURE:
<223> OTHER INFORMATION: GLP-1 fusion 57

<400> SEQUENCE: 169

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Pro Ala Pro Cys Pro Pro
        35                  40                  45

Cys Pro Ala Pro Glu Ala Gly Gly Pro Ser Val Phe Leu Phe Pro
    50                  55                  60

Pro Lys Pro Lys Asp Thr Leu Met Ile Ser Arg Thr Pro Glu Val Thr
65                  70                  75                  80

Cys Val Val Val Asp Val Ser Gln Glu Asp Pro Glu Val Gln Phe Asn
                85                  90                  95

Trp Tyr Val Asp Gly Val Glu Val His Asn Ala Lys Thr Lys Pro Arg
            100                 105                 110

Glu Glu Gln Phe Asn Ser Thr Tyr Arg Val Val Ser Val Leu Thr Val
        115                 120                 125

Leu His Gln Asp Trp Leu Asn Gly Lys Glu Tyr Lys Cys Lys Val Ser
130                 135                 140

Asn Lys Gly Leu Pro Ser Ser Ile Glu Lys Thr Ile Ser Lys Ala Lys
145                 150                 155                 160

Gly Gln Pro Arg Glu Pro Gln Val Tyr Thr Leu Pro Pro Ser Gln Glu
                165                 170                 175

Glu Met Thr Lys Asn Gln Val Ser Leu Thr Cys Leu Val Lys Gly Phe
            180                 185                 190

Tyr Pro Ser Asp Ile Ala Val Glu Trp Glu Ser Asn Gly Gln Pro Glu
        195                 200                 205

Asn Asn Tyr Lys Thr Thr Pro Pro Val Leu Asp Ser Asp Gly Ser Phe
    210                 215                 220

Phe Leu Tyr Ser Arg Leu Thr Val Asp Lys Ser Arg Trp Gln Glu Gly
225                 230                 235                 240

Asn Val Phe Ser Cys Ser Val Met His Glu Ala Leu His Asn His Tyr
                245                 250                 255

Thr Gln Lys Ser Leu Ser Leu Ser Leu Gly Lys Ala Ser Gly Ser Ala
            260                 265                 270

Pro Ala Pro Ala Pro Glu Glu Glu Pro Cys Ala
        275                 280
```

<210> SEQ ID NO 170
<211> LENGTH: 282
<212> TYPE: PRT
<213> ORGANISM: Artificial Sequence
<220> FEATURE:
<223> OTHER INFORMATION: GLP-1 fusion 58

<400> SEQUENCE: 170

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

```
Ser Gly Ala Pro Pro Ser Ala Gly Gly Gly Ser Gly Gly
        35                  40                  45

Gly Gly Ser Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Lys Ala Pro Ala Pro Glu Glu Pro Cys Ala
            275                 280

<210> SEQ ID NO 171
<211> LENGTH: 281
<212> TYPE: PRT
<213> ORGANISM: Artificial Sequence
<220> FEATURE:
<223> OTHER INFORMATION: GLP-1 fusion 59

<400> SEQUENCE: 171

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ser Gly Gly Gly Ser Gly Gly
        35                  40                  45

Gly Gly Ser Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110
```

Ala Lys Thr Lys Pro Arg Glu Glu Gln Phe Asn Ser Thr Tyr Arg Val
            115                 120                 125

Val Ser Val Leu Thr Val Leu His Gln Asp Trp Leu Asn Gly Lys Glu
        130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Lys Ala Ala Ala Glu Glu Pro Cys Ala
        275                 280

<210> SEQ ID NO 172
<211> LENGTH: 287
<212> TYPE: PRT
<213> ORGANISM: Artificial Sequence
<220> FEATURE:
<223> OTHER INFORMATION: GLP-1 fusion 60

<400> SEQUENCE: 172

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ser Gly Gly Gly Ser Gly Gly
        35                  40                  45

Gly Gly Ser Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
            195                 200                 205

Ser Asn Gly Gln Pro Glu Asn Asn Tyr Lys Thr Thr Pro Pro Val Leu
        210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Lys Ala Pro Ala Pro Ala Pro Ala Pro Cys Ala Pro Arg Arg Arg
            275                 280                 285

<210> SEQ ID NO 173
<211> LENGTH: 281
<212> TYPE: PRT
<213> ORGANISM: Artificial Sequence
<220> FEATURE:
<223> OTHER INFORMATION: GLP-1 fusion 61

<400> SEQUENCE: 173

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ser Gly Gly Gly Ser Gly Gly
        35                  40                  45

Gly Gly Ser Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Lys Ala Ala Ala Cys Pro Glu Glu Glu
        275                 280

<210> SEQ ID NO 174
<211> LENGTH: 289
<212> TYPE: PRT
<213> ORGANISM: Artificial Sequence
<220> FEATURE:
<223> OTHER INFORMATION: GLP-1 fusion 62

<400> SEQUENCE: 174

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Gly Gly Gly Ser Gly Gly
        35                  40                  45

Gly Gly Ser Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Lys Ala Ser Gly Ser Gly Gly Gly Gly Ser Gly Gly Gly Gly Ser Cys
        275                 280                 285

Ala

<210> SEQ ID NO 175
<211> LENGTH: 297
<212> TYPE: PRT
<213> ORGANISM: Artificial Sequence
<220> FEATURE:
<223> OTHER INFORMATION: GLP-1 fusion 63

<400> SEQUENCE: 175

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
            20                  25                  30

Pro Ala Pro Ala Pro Ala Pro Ala Pro Ala Pro Ala Pro Ala Pro Ala
        35                  40                  45

Pro Ala Pro Ala Glu Ser Lys Tyr Gly Pro Cys Pro Pro Cys Pro
50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
            85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
            115                 120                 125

Gln Phe Asn Ser Thr Tyr Arg Val Val Ser Val Leu Thr Val Leu His
            130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
            195                 200                 205

Ser Asp Ile Ala Val Glu Trp Glu Ser Asn Gly Gln Pro Glu Asn Asn
210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Lys Ala Ser Gly Ser Ala Pro Ala
            275                 280                 285

Pro Ala Pro Glu Glu Glu Pro Cys Ala
            290                 295

<210> SEQ ID NO 176
<211> LENGTH: 305
<212> TYPE: PRT
<213> ORGANISM: Artificial Sequence
<220> FEATURE:
<223> OTHER INFORMATION: GLP-1 fusion 64

<400> SEQUENCE: 176

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Pro Ala Pro Ala Pro Ala Pro Ala
            35                  40                  45

Pro Ala Pro Ala Pro Ala Pro Ala Pro Ala Glu Ser Lys Tyr
50                  55                  60

```
Gly Pro Pro Cys Pro Pro Cys Pro Ala Pro Glu Ala Ala Gly Gly Pro
 65                  70                  75                  80

Ser Val Phe Leu Phe Pro Pro Lys Pro Lys Asp Thr Leu Met Ile Ser
                 85                  90                  95

Arg Thr Pro Glu Val Thr Cys Val Val Val Asp Val Ser Gln Glu Asp
            100                 105                 110

Pro Glu Val Gln Phe Asn Trp Tyr Val Asp Gly Val Glu Val His Asn
        115                 120                 125

Ala Lys Thr Lys Pro Arg Glu Glu Gln Phe Asn Ser Thr Tyr Arg Val
130                 135                 140

Val Ser Val Leu Thr Val Leu His Gln Asp Trp Leu Asn Gly Lys Glu
145                 150                 155                 160

Tyr Lys Cys Lys Val Ser Asn Lys Gly Leu Pro Ser Ser Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Gln Glu Glu Met Thr Lys Asn Gln Val Ser Leu Thr
        195                 200                 205

Cys Leu Val Lys Gly Phe Tyr Pro Ser Asp Ile Ala Val Glu Trp Glu
210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Arg Leu Thr Val Asp Lys
                245                 250                 255

Ser Arg Trp Gln Glu Gly Asn Val Phe Ser Cys Ser Val Met His Glu
            260                 265                 270

Ala Leu His Asn His Tyr Thr Gln Lys Ser Leu Ser Leu Ser Leu Gly
        275                 280                 285

Lys Ala Ser Gly Ser Ala Pro Ala Pro Ala Pro Glu Glu Glu Pro Cys
    290                 295                 300

Ala
305

<210> SEQ ID NO 177
<211> LENGTH: 294
<212> TYPE: PRT
<213> ORGANISM: Artificial Sequence
<220> FEATURE:
<223> OTHER INFORMATION: GLP-1 fusion 65

<400> SEQUENCE: 177

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Pro Ala Pro
            20                  25                  30

Ala Pro Ala Pro Ala Pro Ala Pro Ala Pro Ala Pro Ala Pro Ala Pro
        35                  40                  45

Ala Glu Ser Lys Tyr Gly Pro Pro Cys Pro Pro Cys Pro Ala Pro Glu
    50                  55                  60

Ala Ala Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser Gln Glu Asp Pro Glu Val Gln Phe Asn Trp Tyr Val Asp Gly
            100                 105                 110
```

```
Val Glu Val His Asn Ala Lys Thr Lys Pro Arg Glu Glu Gln Phe Asn
            115                 120                 125

Ser Thr Tyr Arg Val Val Ser Val Leu Thr Val Leu His Gln Asp Trp
130                 135                 140

Leu Asn Gly Lys Glu Tyr Lys Cys Lys Val Ser Asn Lys Gly Leu Pro
145                 150                 155                 160

Ser Ser Ile Glu Lys Thr Ile Ser Lys Ala Lys Gly Gln Pro Arg Glu
                165                 170                 175

Pro Gln Val Tyr Thr Leu Pro Pro Ser Gln Glu Glu Met Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Arg
225                 230                 235                 240

Leu Thr Val Asp Lys Ser Arg Trp Gln Glu Gly Asn Val Phe Ser Cys
                245                 250                 255

Ser Val Met His Glu Ala Leu His Asn His Tyr Thr Gln Lys Ser Leu
            260                 265                 270

Ser Leu Ser Leu Gly Lys Ala Ser Gly Ser Ala Pro Ala Pro Ala Pro
        275                 280                 285

Glu Glu Glu Pro Cys Ala
    290

<210> SEQ ID NO 178
<211> LENGTH: 300
<212> TYPE: PRT
<213> ORGANISM: Artificial Sequence
<220> FEATURE:
<223> OTHER INFORMATION: GLP-1 fusion 66

<400> SEQUENCE: 178

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ser Gly Gly Gly Gly Gly
        35                  40                  45

Ser Gly Gly Gly Gly Ser Ala Glu Ser Lys Tyr Gly Pro Pro Cys Pro
    50                  55                  60

Pro Cys Pro Ala Pro Glu Ala Ala Gly Gly Pro Ser Val Phe Leu Phe
65                  70                  75                  80

Pro Pro Lys Pro Lys Asp Thr Leu Met Ile Ser Arg Thr Pro Glu Val
                85                  90                  95

Thr Cys Val Val Val Asp Val Ser Gln Glu Asp Pro Glu Val Gln Phe
            100                 105                 110

Asn Trp Tyr Val Asp Gly Val Glu Val His Asn Ala Lys Thr Lys Pro
        115                 120                 125

Arg Glu Glu Gln Phe Asn Ser Thr Tyr Arg Val Val Ser Val Leu Thr
    130                 135                 140

Val Leu His Gln Asp Trp Leu Asn Gly Lys Glu Tyr Lys Cys Lys Val
145                 150                 155                 160

Ser Asn Lys Gly Leu Pro Ser Ser Ile Glu Lys Thr Ile Ser Lys Ala
                165                 170                 175
```

```
Lys Gly Gln Pro Arg Glu Pro Gln Val Tyr Thr Leu Pro Pro Ser Gln
            180                 185                 190

Glu Glu Met Thr Lys Asn Gln Val Ser Leu Thr Cys Leu Val Lys Gly
            195                 200                 205

Phe Tyr Pro Ser Asp Ile Ala Val Glu Trp Glu Ser Asn Gly Gln Pro
    210                 215                 220

Glu Asn Asn Tyr Lys Thr Thr Pro Val Leu Asp Ser Asp Gly Ser
225                 230                 235                 240

Phe Phe Leu Tyr Ser Arg Leu Thr Val Asp Lys Ser Arg Trp Gln Glu
                245                 250                 255

Gly Asn Val Phe Ser Cys Ser Val Met His Glu Ala Leu His Asn His
            260                 265                 270

Tyr Thr Gln Lys Ser Leu Ser Leu Ser Leu Gly Lys Ala Ser Gly Ser
            275                 280                 285

Ala Pro Ala Pro Ala Pro Glu Glu Pro Cys Ala
    290                 295                 300

<210> SEQ ID NO 179
<211> LENGTH: 289
<212> TYPE: PRT
<213> ORGANISM: Artificial Sequence
<220> FEATURE:
<223> OTHER INFORMATION: GLP-1 fusion 67

<400> SEQUENCE: 179

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
            20                  25                  30

Ser Gly Gly Gly Gly Ser Gly Gly Gly Ser Ala Glu Ser Lys Tyr
        35                  40                  45

Gly Pro Pro Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Val Leu
    210                 215                 220

Asp Ser Asp Gly Ser Phe Phe Leu Tyr Ser Arg Leu Thr Val Asp Lys
225                 230                 235                 240
```

```
Ser Arg Trp Gln Glu Gly Asn Val Phe Ser Cys Ser Val Met His Glu
            245                 250                 255

Ala Leu His Asn His Tyr Thr Gln Lys Ser Leu Ser Leu Ser Leu Gly
            260                 265                 270

Lys Ala Ser Gly Ser Ala Pro Ala Pro Ala Pro Glu Glu Glu Pro Cys
            275                 280                 285

Ala

<210> SEQ ID NO 180
<211> LENGTH: 290
<212> TYPE: PRT
<213> ORGANISM: Artificial Sequence
<220> FEATURE:
<223> OTHER INFORMATION: GLP-1 fusion 68

<400> SEQUENCE: 180

His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Lys Gly Gly Gly Gly
             20                  25                  30

Gly Gly Gly Gly Gly Gly Gly Gly Gly Gly Gly Gly Gly Gly Ala Glu
         35                  40                  45

Ser Lys Tyr Gly Pro Pro Cys Pro Pro Cys Pro Ala Pro Glu Ala Ala
 50                  55                  60

Gly Gly Pro Ser Val Phe Leu Phe Pro Pro Lys Pro Lys Asp Thr Leu
 65                  70                  75                  80

Met Ile Ser Arg Thr Pro Glu Val Thr Cys Val Val Val Asp Val Ser
             85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Gly Gly Gly Ala Pro Ala Pro Ala Pro Glu Glu Glu Pro
        275                 280                 285

Cys Ala
    290
```

<210> SEQ ID NO 181
<211> LENGTH: 285
<212> TYPE: PRT
<213> ORGANISM: Artificial Sequence
<220> FEATURE:
<223> OTHER INFORMATION: GLP-1 fusion 69

<400> SEQUENCE: 181

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Gly Gly Gly Gly Gly Gly Gly Gly Gly Ala Glu
        35                  40                  45

Ser Lys Tyr Gly Pro Pro Cys Pro Pro Cys Pro Ala Pro Glu Ala Ala
        50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Ala Pro Ala Pro Glu Glu Pro Cys Ala
        275                 280                 285

<210> SEQ ID NO 182
<211> LENGTH: 285
<212> TYPE: PRT
<213> ORGANISM: Artificial Sequence
<220> FEATURE:
<223> OTHER INFORMATION: GLP-1 fusion 70

<400> SEQUENCE: 182

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

```
Gly Gly Gly Ala Gly Gly Gly Ala Gly Gly Gly Ala Ala Glu
        35                  40                  45

Ser Lys Tyr Gly Pro Pro Cys Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Ala Pro Ala Pro Glu Glu Pro Cys Ala
        275                 280                 285

<210> SEQ ID NO 183
<211> LENGTH: 293
<212> TYPE: PRT
<213> ORGANISM: Artificial Sequence
<220> FEATURE:
<223> OTHER INFORMATION: GLP-1 fusion 71

<400> SEQUENCE: 183

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Gly Gly Gly Gly Gly Gly
        35                  40                  45

Gly Gly Gly Gly Gly Gly Ala Glu Ser Lys Tyr Gly Pro Pro Cys Pro
    50                  55                  60

Pro Cys Pro Ala Pro Glu Ala Ala Gly Gly Pro Ser Val Phe Leu Phe
65                  70                  75                  80

Pro Pro Lys Pro Lys Asp Thr Leu Met Ile Ser Arg Thr Pro Glu Val
                85                  90                  95

Thr Cys Val Val Val Asp Val Ser Gln Glu Asp Pro Glu Val Gln Phe
            100                 105                 110
```

```
Asn Trp Tyr Val Asp Gly Val Glu Val His Asn Ala Lys Thr Lys Pro
            115                 120                 125

Arg Glu Glu Gln Phe Asn Ser Thr Tyr Arg Val Val Ser Val Leu Thr
        130                 135                 140

Val Leu His Gln Asp Trp Leu Asn Gly Lys Glu Tyr Lys Cys Lys Val
145                 150                 155                 160

Ser Asn Lys Gly Leu Pro Ser Ser Ile Glu Lys Thr Ile Ser Lys Ala
                165                 170                 175

Lys Gly Gln Pro Arg Glu Pro Gln Val Tyr Thr Leu Pro Pro Ser Gln
            180                 185                 190

Glu Glu Met Thr Lys Asn Gln Val Ser Leu Thr Cys Leu Val Lys Gly
        195                 200                 205

Phe Tyr Pro Ser Asp Ile Ala Val Glu Trp Glu Ser Asn Gly Gln Pro
    210                 215                 220

Glu Asn Asn Tyr Lys Thr Thr Pro Pro Val Leu Asp Ser Asp Gly Ser
225                 230                 235                 240

Phe Phe Leu Tyr Ser Arg Leu Thr Val Asp Lys Ser Arg Trp Gln Glu
                245                 250                 255

Gly Asn Val Phe Ser Cys Ser Val Met His Glu Ala Leu His Asn His
            260                 265                 270

Tyr Thr Gln Lys Ser Leu Ser Leu Ser Leu Gly Lys Ala Pro Ala Pro
        275                 280                 285

Glu Glu Pro Cys Ala
    290

<210> SEQ ID NO 184
<211> LENGTH: 293
<212> TYPE: PRT
<213> ORGANISM: Artificial Sequence
<220> FEATURE:
<223> OTHER INFORMATION: GLP-1 fusion 72

<400> SEQUENCE: 184

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ala Gly Gly Gly Gly Gly
        35                  40                  45

Ala Gly Gly Gly Ala Ala Glu Ser Lys Tyr Gly Pro Pro Cys Pro Pro
    50                  55                  60

Pro Cys Pro Ala Pro Glu Ala Ala Gly Gly Pro Ser Val Phe Leu Phe
65                  70                  75                  80

Pro Pro Lys Pro Lys Asp Thr Leu Met Ile Ser Arg Thr Pro Glu Val
                85                  90                  95

Thr Cys Val Val Val Asp Val Ser Gln Glu Asp Pro Glu Val Gln Phe
            100                 105                 110

Asn Trp Tyr Val Asp Gly Val Glu Val His Asn Ala Lys Thr Lys Pro
        115                 120                 125

Arg Glu Glu Gln Phe Asn Ser Thr Tyr Arg Val Val Ser Val Leu Thr
    130                 135                 140

Val Leu His Gln Asp Trp Leu Asn Gly Lys Glu Tyr Lys Cys Lys Val
145                 150                 155                 160

Ser Asn Lys Gly Leu Pro Ser Ser Ile Glu Lys Thr Ile Ser Lys Ala
                165                 170                 175
```

-continued

```
Lys Gly Gln Pro Arg Glu Pro Gln Val Tyr Thr Leu Pro Pro Ser Gln
            180                 185                 190

Glu Glu Met Thr Lys Asn Gln Val Ser Leu Thr Cys Leu Val Lys Gly
            195                 200                 205

Phe Tyr Pro Ser Asp Ile Ala Val Glu Trp Glu Ser Asn Gly Gln Pro
    210                 215                 220

Glu Asn Asn Tyr Lys Thr Thr Pro Pro Val Leu Asp Ser Asp Gly Ser
225                 230                 235                 240

Phe Phe Leu Tyr Ser Arg Leu Thr Val Asp Lys Ser Arg Trp Gln Glu
                245                 250                 255

Gly Asn Val Phe Ser Cys Ser Val Met His Glu Ala Leu His Asn His
            260                 265                 270

Tyr Thr Gln Lys Ser Leu Ser Leu Ser Leu Gly Lys Ala Pro Ala Pro
        275                 280                 285

Glu Glu Pro Cys Ala
        290

<210> SEQ ID NO 185
<211> LENGTH: 289
<212> TYPE: PRT
<213> ORGANISM: Artificial Sequence
<220> FEATURE:
<223> OTHER INFORMATION: GLP-1 fusion 73

<400> SEQUENCE: 185

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Gly Ser Gly Gly Gly Gly Ser Ala Glu
        35                  40                  45

Arg Lys Cys Cys Val Glu Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240
```

-continued

Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
        260                 265                 270

Ser Leu Gly Ala Pro Ala Pro Ala Pro Ala Pro Ala Pro Ala Pro Cys
        275                 280                 285

Pro

<210> SEQ ID NO 186
<211> LENGTH: 289
<212> TYPE: PRT
<213> ORGANISM: Artificial Sequence
<220> FEATURE:
<223> OTHER INFORMATION: GLP-1 fusion 74

<400> SEQUENCE: 186

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ala Gly Gly Gly Ala Gly Gly Gly Ala Ala Glu
        35                  40                  45

Arg Lys Cys Cys Val Glu Cys Pro Pro Cys Pro Ala Pro Glu Ala Ala
50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Ala Pro Ala Pro Ala Pro Ala Pro Ala Pro Ala Pro Cys
        275                 280                 285

Pro

```
<210> SEQ ID NO 187
<211> LENGTH: 295
<212> TYPE: PRT
<213> ORGANISM: Artificial Sequence
<220> FEATURE:
<223> OTHER INFORMATION: GLP-1 fusion 75

<400> SEQUENCE: 187
```

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ala Gly Gly Gly Ala Gly Gly Gly Ala Gly Gly
        35                  40                  45

Gly Gly Ala Gly Gly Gly Ala Ala Gly Pro Pro Cys Pro Pro Cys
        50                  55                  60

Pro Ala Pro Glu Ala Ala Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser Gln Glu Asp Pro Glu Val Gln Phe Asn Trp
            100                 105                 110

Tyr Val Asp Gly Val Glu Val His Asn Ala Lys Thr Lys Pro Arg Glu
            115                 120                 125

Glu Gln Phe Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Gly Leu Pro Ser Ser Ile Glu Lys Thr Ile Ser Lys Ala Lys Gly
                165                 170                 175

Gln Pro Arg Glu Pro Gln Val Tyr Thr Leu Pro Pro Ser Gln Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
210                 215                 220

Asn Tyr Lys Thr Thr Pro Pro Val Leu Asp Ser Asp Gly Ser Phe Phe
225                 230                 235                 240

Leu Tyr Ser Arg Leu Thr Val Asp Lys Ser Arg Trp Gln Glu Gly Asn
                245                 250                 255

Val Phe Ser Cys Ser Val Met His Glu Ala Leu His Asn His Tyr Thr
            260                 265                 270

Gln Lys Ser Leu Ser Leu Ser Leu Gly Ala Pro Ala Pro Ala Pro Ala
        275                 280                 285

Pro Ala Pro Ala Pro Cys Pro
290                 295

```
<210> SEQ ID NO 188
<211> LENGTH: 294
<212> TYPE: PRT
<213> ORGANISM: Artificial Sequence
<220> FEATURE:
<223> OTHER INFORMATION: GLP-1 fusion 76

<400> SEQUENCE: 188
```

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

Gly Gly Gly Pro Gly Gly Gly Pro Gly Gly Gly Pro Gly Gly
        35                  40                  45

Gly Gly Pro Ala Glu Ser Lys Tyr Gly Pro Cys Pro Cys Pro
50                  55                  60

Ala Pro Glu Ala Ala Gly Gly Pro Ser Val Phe Leu Phe Pro Lys
65                  70                  75                  80

Pro Lys Asp Thr Leu Met Ile Ser Arg Thr Pro Glu Val Thr Cys Val
            85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
            115                 120                 125

Gln Phe Asn Ser Thr Tyr Arg Val Val Ser Val Leu Thr Val Leu His
            130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
            165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
            195                 200                 205

Ser Asp Ile Ala Val Glu Trp Glu Ser Asn Gly Gln Pro Glu Asn Asn
210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
            245                 250                 255

Phe Ser Cys Ser Val Met His Glu Ala Leu His Asn His Tyr Thr Gln
            260                 265                 270

Lys Ser Leu Ser Leu Ser Leu Gly Ala Pro Ala Pro Ala Pro Ala Pro
275                 280                 285

Ala Pro Ala Pro Cys Pro
    290

<210> SEQ ID NO 189
<211> LENGTH: 294
<212> TYPE: PRT
<213> ORGANISM: Artificial Sequence
<220> FEATURE:
<223> OTHER INFORMATION: GLP-1 fusion 77

<400> SEQUENCE: 189

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly His Gly Gly Gly His Gly Gly Gly His Gly Gly
        35                  40                  45

Gly Gly His Ala Glu Ser Lys Tyr Gly Pro Pro Cys Pro Cys Pro
50                  55                  60

Ala Pro Glu Ala Ala Gly Gly Pro Ser Val Phe Leu Phe Pro Pro Lys
65                  70                  75                  80

```
Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
            115                 120                 125

Gln Phe Asn Ser Thr Tyr Arg Val Val Ser Val Leu Thr Val Leu His
            130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
            195                 200                 205

Ser Asp Ile Ala Val Glu Trp Glu Ser Asn Gly Gln Pro Glu Asn Asn
            210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Ala Pro Ala Pro Ala Pro Ala Pro
            275                 280                 285

Ala Pro Ala Pro Cys Pro
    290

<210> SEQ ID NO 190
<211> LENGTH: 294
<212> TYPE: PRT
<213> ORGANISM: Artificial Sequence
<220> FEATURE:
<223> OTHER INFORMATION: GLP-1 fusion 78

<400> SEQUENCE: 190

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ala Gly Gly Gly Ala Gly Gly Gly Ala Gly Gly
            35                  40                  45

Gly Gly Ala Ala Glu Ser Lys Tyr Gly Pro Pro Cys Pro Pro Cys Pro
50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
            115                 120                 125

Gln Phe Asn Ser Thr Tyr Arg Val Val Ser Val Leu Thr Val Leu His
            130                 135                 140
```

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
            165                 170                 175

Pro Arg Glu Pro Gln Val Tyr Thr Leu Pro Pro Ser Gln Glu Glu Met
        180                 185                 190

Thr Lys Asn Gln Val Ser Leu Thr Cys Leu Val Lys Gly Phe Tyr Pro
    195                 200                 205

Ser Asp Ile Ala Val Glu Trp Glu Ser Asn Gly Gln Pro Glu Asn Asn
210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
            245                 250                 255

Phe Ser Cys Ser Val Met His Glu Ala Leu His Asn His Tyr Thr Gln
        260                 265                 270

Lys Ser Leu Ser Leu Ser Leu Gly Ala Pro Ala Pro Ala Pro Ala Pro
    275                 280                 285

Ala Pro Ala Pro Cys Pro
    290

<210> SEQ ID NO 191
<211> LENGTH: 311
<212> TYPE: PRT
<213> ORGANISM: Artificial Sequence
<220> FEATURE:
<223> OTHER INFORMATION: GLP-1 fusion 79

<400> SEQUENCE: 191

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
            20                  25                  30

Ser Gly Gly Gly Gly Ser Gly Gly Gly Gly Ser Gly Gly Gly Gly Ser
        35                  40                  45

Gly Gly Gly Gly Ser Gly Gly Gly Gly Ser Gly Gly Gly Gly Ser Gly
50                  55                  60

Gly Gly Gly Ser Gly Gly Gly Gly Ser Cys Pro Pro Cys Pro Ala Pro
65                  70                  75                  80

Glu Ala Ala Gly Gly Pro Ser Val Phe Leu Phe Pro Pro Lys Pro Lys
            85                  90                  95

Asp Thr Leu Met Ile Ser Arg Thr Pro Glu Val Thr Cys Val Val Val
        100                 105                 110

Asp Val Ser Gln Glu Asp Pro Glu Val Gln Phe Asn Trp Tyr Val Asp
    115                 120                 125

Gly Val Glu Val His Asn Ala Lys Thr Lys Pro Arg Glu Glu Gln Phe
130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Gly Leu
            165                 170                 175

Pro Ser Ser Ile Glu Lys Thr Ile Ser Lys Ala Lys Gly Gln Pro Arg
        180                 185                 190

Glu Pro Gln Val Tyr Thr Leu Pro Pro Ser Gln Glu Glu Met Thr Lys
    195                 200                 205

```
Asn Gln Val Ser Leu Thr Cys Leu Val Lys Gly Phe Tyr Pro Ser Asp
    210                 215                 220
Ile Ala Val Glu Trp Glu Ser Asn Gly Gln Pro Glu Asn Asn Tyr Lys
225                 230                 235                 240
Thr Thr Pro Pro Val Leu Asp Ser Asp Gly Ser Phe Phe Leu Tyr Ser
                245                 250                 255
Arg Leu Thr Val Asp Lys Ser Arg Trp Gln Glu Gly Asn Val Phe Ser
                260                 265                 270
Cys Ser Val Met His Glu Ala Leu His Asn His Tyr Thr Gln Lys Ser
            275                 280                 285
Leu Ser Leu Ser Leu Gly Lys Ala Ser Gly Ser Ala Pro Ala Pro Ala
290                 295                 300
Pro Glu Glu Glu Pro Cys Ala
305                 310

<210> SEQ ID NO 192
<211> LENGTH: 285
<212> TYPE: PRT
<213> ORGANISM: Artificial Sequence
<220> FEATURE:
<223> OTHER INFORMATION: GLP-1 fusion 80

<400> SEQUENCE: 192

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly Gly Pro Ser
                20                  25                  30
Ser Gly Ala Pro Pro Pro Ser Ala Ser Gly Gly Gly Ser Gly Gly
            35                  40                  45
Gly Gly Ser Cys Pro Pro Cys Pro Ala Pro Glu Ala Ala Gly Gly Pro
50                  55                  60
Ser Val Phe Leu Phe Pro Pro Lys Pro Lys Asp Thr Leu Met Ile Ser
65                  70                  75                  80
Arg Thr Pro Glu Val Thr Cys Val Val Val Asp Val Ser Gln Glu Asp
                85                  90                  95
Pro Glu Val Gln Phe Asn Trp Tyr Val Asp Gly Val Glu Val His Asn
                100                 105                 110
Ala Lys Thr Lys Pro Arg Glu Glu Gln Phe Asn Ser Thr Tyr Arg Val
            115                 120                 125
Val Ser Val Leu Thr Val Leu His Gln Asp Trp Leu Asn Gly Lys Glu
130                 135                 140
Tyr Lys Cys Lys Val Ser Asn Lys Gly Leu Pro Ser Ser Ile Glu Lys
145                 150                 155                 160
Thr Ile Ser Lys Ala Lys Gly Gln Pro Arg Glu Pro Gln Val Tyr Thr
                165                 170                 175
Leu Pro Pro Ser Gln Glu Glu Met Thr Lys Asn Gln Val Ser Leu Thr
                180                 185                 190
Cys Leu Val Lys Gly Phe Tyr Pro Ser Asp Ile Ala Val Glu Trp Glu
            195                 200                 205
Ser Asn Gly Gln Pro Glu Asn Asn Tyr Lys Thr Thr Pro Pro Val Leu
210                 215                 220
Asp Ser Asp Gly Ser Phe Phe Leu Tyr Ser Arg Leu Thr Val Asp Lys
225                 230                 235                 240
Ser Arg Trp Gln Glu Gly Asn Val Phe Ser Cys Ser Val Met His Glu
                245                 250                 255
```

```
Ala Leu His Asn His Tyr Thr Gln Lys Ser Leu Ser Leu Gly
            260                 265                 270

Lys Gly Gly Gly Ser Gly Gly Gly Ser Cys Ala
    275                 280             285

<210> SEQ ID NO 193
<211> LENGTH: 291
<212> TYPE: PRT
<213> ORGANISM: Artificial Sequence
<220> FEATURE:
<223> OTHER INFORMATION: GLP-1 fusion 81

<400> SEQUENCE: 193

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ala Gly Gly Gly Ala Gly Gly Gly Ala Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Gly Gly Gly Ala Pro Ala Pro Ala Pro Glu Glu Glu
        275                 280                 285

Pro Cys Ala
    290

<210> SEQ ID NO 194
<211> LENGTH: 292
<212> TYPE: PRT
<213> ORGANISM: Artificial Sequence
<220> FEATURE:
```

<223> OTHER INFORMATION: GLP-1 fusion 82

<400> SEQUENCE: 194

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ala Gly Gly Gly Ala Gly Gly Gly Ala Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Ala Ser Gly Ser Ala Pro Ala Pro Ala Pro Glu Glu
        275                 280                 285

Glu Pro Cys Ala
    290

<210> SEQ ID NO 195
<211> LENGTH: 292
<212> TYPE: PRT
<213> ORGANISM: Artificial Sequence
<220> FEATURE:
<223> OTHER INFORMATION: GLP-1 fusion 83

<400> SEQUENCE: 195

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Gly Gly Gly Gly Gly Gly Gly Gly Gly Ala Glu
        35                  40                  45

Ser Lys Tyr Gly Pro Pro Cys Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Ala Ser Gly Ser Ala Pro Ala Pro Ala Pro Glu Glu
        275                 280                 285

Glu Pro Cys Ala
    290

<210> SEQ ID NO 196
<211> LENGTH: 291
<212> TYPE: PRT
<213> ORGANISM: Artificial Sequence
<220> FEATURE:
<223> OTHER INFORMATION: GLP-1 fusion 84

<400> SEQUENCE: 196

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Gly Gly Gly Gly Gly Gly Gly Gly Gly Gly Ala Glu
        35                  40                  45

Ser Lys Tyr Gly Pro Pro Cys Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
        130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Gly Gly Gly Ala Pro Ala Pro Ala Pro Glu Glu Glu
        275                 280                 285

Pro Cys Ala
    290

<210> SEQ ID NO 197
<211> LENGTH: 289
<212> TYPE: PRT
<213> ORGANISM: Artificial Sequence
<220> FEATURE:
<223> OTHER INFORMATION: GLP-1 fusion 85

<400> SEQUENCE: 197

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Pro Gly Gly Gly Pro Gly Gly Gly Pro Ala Glu
        35                  40                  45

Arg Lys Cys Cys Val Glu Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
        130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

-continued

Val Tyr Thr Leu Pro Pro Ser Gln Glu Glu Met Thr Lys Asn Gln Val
                180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
        210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Ala Pro Ala Pro Ala Pro Ala Pro Ala Pro Ala Pro Cys
            275                 280                 285

Pro

<210> SEQ ID NO 198
<211> LENGTH: 289
<212> TYPE: PRT
<213> ORGANISM: Artificial Sequence
<220> FEATURE:
<223> OTHER INFORMATION: GLP-1 fusion 86

<400> SEQUENCE: 198

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly His Gly Gly Gly His Gly Gly Gly His Ala Glu
            35                  40                  45

Arg Lys Cys Cys Val Glu Cys Pro Pro Cys Pro Ala Pro Glu Ala Ala
        50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

```
Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
        260                 265                 270

Ser Leu Gly Ala Pro Ala Pro Ala Pro Ala Pro Ala Pro Ala Pro Cys
            275                 280                 285

Pro

<210> SEQ ID NO 199
<211> LENGTH: 295
<212> TYPE: PRT
<213> ORGANISM: Artificial Sequence
<220> FEATURE:
<223> OTHER INFORMATION: GLP-1 fusion 87

<400> SEQUENCE: 199

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Pro Gly Gly Gly Pro Gly Gly Gly Pro Gly Gly
        35                  40                  45

Gly Gly Pro Gly Gly Gly Pro Ala Gly Pro Pro Cys Pro Pro Cys
    50                  55                  60

Pro Ala Pro Glu Ala Ala Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser Gln Glu Asp Pro Glu Val Gln Phe Asn Trp
            100                 105                 110

Tyr Val Asp Gly Val Glu Val His Asn Ala Lys Thr Lys Pro Arg Glu
        115                 120                 125

Glu Gln Phe Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Gly Leu Pro Ser Ser Ile Glu Lys Thr Ile Ser Lys Ala Lys Gly
                165                 170                 175

Gln Pro Arg Glu Pro Gln Val Tyr Thr Leu Pro Pro Ser Gln Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Arg Leu Thr Val Asp Lys Ser Arg Trp Gln Glu Gly Asn
                245                 250                 255

Val Phe Ser Cys Ser Val Met His Glu Ala Leu His Asn His Tyr Thr
            260                 265                 270

Gln Lys Ser Leu Ser Leu Ser Leu Gly Ala Pro Ala Pro Ala Pro Ala
        275                 280                 285

Pro Ala Pro Ala Pro Cys Pro
    290                 295
```

```
<210> SEQ ID NO 200
<211> LENGTH: 295
<212> TYPE: PRT
<213> ORGANISM: Artificial Sequence
<220> FEATURE:
<223> OTHER INFORMATION: GLP-1 fusion 88

<400> SEQUENCE: 200

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly His Gly Gly Gly His Gly Gly Gly His Gly Gly
            35                  40                  45

Gly Gly His Gly Gly Gly His Ala Gly Pro Pro Cys Pro Pro Cys
        50                  55                  60

Pro Ala Pro Glu Ala Ala Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser Gln Glu Asp Pro Glu Val Gln Phe Asn Trp
                100                 105                 110

Tyr Val Asp Gly Val Glu Val His Asn Ala Lys Thr Lys Pro Arg Glu
            115                 120                 125

Glu Gln Phe Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Gly Leu Pro Ser Ser Ile Glu Lys Thr Ile Ser Lys Ala Lys Gly
                165                 170                 175

Gln Pro Arg Glu Pro Gln Val Tyr Thr Leu Pro Pro Ser Gln Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
210                 215                 220

Asn Tyr Lys Thr Thr Pro Pro Val Leu Asp Ser Asp Gly Ser Phe Phe
225                 230                 235                 240

Leu Tyr Ser Arg Leu Thr Val Asp Lys Ser Arg Trp Gln Glu Gly Asn
                245                 250                 255

Val Phe Ser Cys Ser Val Met His Glu Ala Leu His Asn His Tyr Thr
            260                 265                 270

Gln Lys Ser Leu Ser Leu Ser Leu Gly Ala Pro Ala Pro Ala Pro Ala
        275                 280                 285

Pro Ala Pro Ala Pro Cys Pro
290                 295

<210> SEQ ID NO 201
<211> LENGTH: 292
<212> TYPE: PRT
<213> ORGANISM: Artificial Sequence
<220> FEATURE:
<223> OTHER INFORMATION: GLP-1 fusion 89

<400> SEQUENCE: 201

His Gly Glu Gly Thr Phe Thr Ser Asp Val Ser Ser Tyr Leu Glu Glu
1               5                   10                  15
```

```
Gln Ala Ala Lys Glu Phe Ile Ala Trp Leu Val Lys Gly Gly Gly
                20                  25                  30

Gly Gly Gly Ser Gly Gly Gly Ser Gly Gly Gly Ser Ala Glu
            35                  40                  45

Arg Lys Cys Cys Val Glu Cys Pro Pro Cys Pro Ala Pro Glu Ala Ala
 50                  55                  60

Gly Gly Pro Ser Val Phe Leu Phe Pro Pro Lys Pro Lys Asp Thr Leu
 65                  70                  75                  80

Met Ile Ser Arg Thr Pro Glu Val Thr Cys Val Val Asp Val Ser
                85                  90                  95

Gln Glu Asp Pro Glu Val Gln Phe Asn Trp Tyr Val Asp Gly Val Glu
                100                 105                 110

Val His Asn Ala Lys Thr Lys Pro Arg Glu Glu Gln Phe Asn Ser Thr
                115                 120                 125

Tyr Arg Val Val Ser Val Leu Thr Val Leu His Gln Asp Trp Leu Asn
        130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
                180                 185                 190

Ser Leu Thr Cys Leu Val Lys Gly Phe Tyr Pro Ser Asp Ile Ala Val
                195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly Ala Pro Ala Pro Ala Pro Ala Pro Ala Pro Ala Pro Cys
            275                 280                 285

Pro Glu Glu Pro
            290

<210> SEQ ID NO 202
<211> LENGTH: 292
<212> TYPE: PRT
<213> ORGANISM: Artificial Sequence
<220> FEATURE:
<223> OTHER INFORMATION: GLP-1 fusion 90

<400> SEQUENCE: 202

His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Lys Gly Gly Gly
                20                  25                  30

Gly Gly Gly Pro Gly Gly Gly Pro Gly Gly Gly Pro Ala Glu
            35                  40                  45

Arg Lys Cys Cys Val Glu Cys Pro Pro Cys Pro Ala Pro Glu Ala Ala
 50                  55                  60

Gly Gly Pro Ser Val Phe Leu Phe Pro Pro Lys Pro Lys Asp Thr Leu
 65                  70                  75                  80
```

```
Met Ile Ser Arg Thr Pro Glu Val Thr Cys Val Val Asp Val Ser
             85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Ala Pro Ala Pro Ala Pro Ala Pro Ala Pro Ala Pro Cys
        275                 280                 285

Pro Glu Glu Pro
    290

<210> SEQ ID NO 203
<211> LENGTH: 292
<212> TYPE: PRT
<213> ORGANISM: Artificial Sequence
<220> FEATURE:
<223> OTHER INFORMATION: GLP-1 fusion 91

<400> SEQUENCE: 203

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly His Gly Gly Gly His Gly Gly Gly His Gly Ala Glu
        35                  40                  45

Arg Lys Cys Cys Val Glu Cys Pro Pro Cys Pro Ala Pro Glu Ala Ala
50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Asp Val Ser
             85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140
```

```
Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
            165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
            210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
            260                 265                 270

Ser Leu Gly Ala Pro Ala Pro Ala Pro Ala Pro Ala Pro Ala Pro Cys
            275                 280                 285

Pro Glu Glu Pro
    290
```

<210> SEQ ID NO 204
<211> LENGTH: 292
<212> TYPE: PRT
<213> ORGANISM: Artificial Sequence
<220> FEATURE:
<223> OTHER INFORMATION: GLP-1 fusion 92

<400> SEQUENCE: 204

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ala Gly Gly Gly Ala Gly Gly Gly Ala Ala Glu
            35                  40                  45

Arg Lys Cys Cys Val Glu Cys Pro Pro Cys Pro Ala Pro Glu Ala Ala
50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
            85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
            165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205
```

```
Glu Trp Glu Ser Asn Gly Gln Pro Glu Asn Asn Tyr Lys Thr Thr Pro
        210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly Ala Pro Ala Pro Ala Pro Ala Pro Ala Pro Ala Pro Cys
            275                 280                 285

Pro Glu Glu Pro
    290

<210> SEQ ID NO 205
<211> LENGTH: 298
<212> TYPE: PRT
<213> ORGANISM: Artificial Sequence
<220> FEATURE:
<223> OTHER INFORMATION: GLP-1 fusion 93

<400> SEQUENCE: 205

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Pro Gly Gly Gly Pro Gly Gly Gly Pro Gly Gly Gly Gly
            35                  40                  45

Gly Gly Pro Gly Gly Gly Pro Ala Gly Pro Cys Pro Pro Cys Pro Cys
        50                  55                  60

Pro Ala Pro Glu Ala Ala Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser Gln Glu Asp Pro Glu Val Gln Phe Asn Trp
                100                 105                 110

Tyr Val Asp Gly Val Glu Val His Asn Ala Lys Thr Lys Pro Arg Glu
            115                 120                 125

Glu Gln Phe Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Gly Leu Pro Ser Ser Ile Glu Lys Thr Ile Ser Lys Ala Lys Gly
                165                 170                 175

Gln Pro Arg Glu Pro Gln Val Tyr Thr Leu Pro Pro Ser Gln Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
210                 215                 220

Asn Tyr Lys Thr Thr Pro Pro Val Leu Asp Ser Asp Gly Ser Phe Phe
225                 230                 235                 240

Leu Tyr Ser Arg Leu Thr Val Asp Lys Ser Arg Trp Gln Glu Gly Asn
                245                 250                 255

Val Phe Ser Cys Ser Val Met His Glu Ala Leu His Asn His Tyr Thr
            260                 265                 270
```

-continued

Gln Lys Ser Leu Ser Leu Ser Leu Gly Ala Pro Ala Pro Ala Pro Ala
            275                 280                 285

Pro Ala Pro Ala Pro Cys Pro Glu Glu Pro
        290                 295

<210> SEQ ID NO 206
<211> LENGTH: 298
<212> TYPE: PRT
<213> ORGANISM: Artificial Sequence
<220> FEATURE:
<223> OTHER INFORMATION: GLP-1 fusion 94

<400> SEQUENCE: 206

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly His Gly Gly Gly His Gly Gly Gly His Gly Gly
        35                  40                  45

Gly Gly His Gly Gly Gly His Ala Gly Pro Pro Cys Pro Pro Cys
    50                  55                  60

Pro Ala Pro Glu Ala Ala Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser Gln Glu Asp Pro Glu Val Gln Phe Asn Trp
            100                 105                 110

Tyr Val Asp Gly Val Glu Val His Asn Ala Lys Thr Lys Pro Arg Glu
        115                 120                 125

Glu Gln Phe Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Gly Leu Pro Ser Ser Ile Glu Lys Thr Ile Ser Lys Ala Lys Gly
                165                 170                 175

Gln Pro Arg Glu Pro Gln Val Tyr Thr Leu Pro Pro Ser Gln Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Arg Leu Thr Val Asp Lys Ser Arg Trp Gln Glu Gly Asn
                245                 250                 255

Val Phe Ser Cys Ser Val Met His Glu Ala Leu His Asn His Tyr Thr
            260                 265                 270

Gln Lys Ser Leu Ser Leu Ser Leu Gly Ala Pro Ala Pro Ala Pro Ala
        275                 280                 285

Pro Ala Pro Ala Pro Cys Pro Glu Glu Pro
    290                 295

<210> SEQ ID NO 207
<211> LENGTH: 298
<212> TYPE: PRT
<213> ORGANISM: Artificial Sequence
<220> FEATURE:

<223> OTHER INFORMATION: GLP-1 fusion 95

<400> SEQUENCE: 207

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ala Gly Gly Gly Ala Gly Gly Gly Ala Gly Gly
        35                  40                  45

Gly Gly Ala Gly Gly Gly Ala Ala Gly Pro Pro Cys Pro Pro Cys
    50                  55                  60

Pro Ala Pro Glu Ala Ala Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser Gln Glu Asp Pro Glu Val Gln Phe Asn Trp
            100                 105                 110

Tyr Val Asp Gly Val Glu Val His Asn Ala Lys Thr Lys Pro Arg Glu
        115                 120                 125

Glu Gln Phe Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Gly Leu Pro Ser Ser Ile Glu Lys Thr Ile Ser Lys Ala Lys Gly
                165                 170                 175

Gln Pro Arg Glu Pro Gln Val Tyr Thr Leu Pro Pro Ser Gln Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Arg Leu Thr Val Asp Lys Ser Arg Trp Gln Glu Gly Asn
                245                 250                 255

Val Phe Ser Cys Ser Val Met His Glu Ala Leu His Asn His Tyr Thr
            260                 265                 270

Gln Lys Ser Leu Ser Leu Ser Leu Gly Ala Pro Ala Pro Ala Pro Ala
        275                 280                 285

Pro Ala Pro Ala Pro Cys Pro Glu Glu Pro
    290                 295
```

<210> SEQ ID NO 208
<211> LENGTH: 297
<212> TYPE: PRT
<213> ORGANISM: Artificial Sequence
<220> FEATURE:
<223> OTHER INFORMATION: GLP-1 fusion 96

<400> SEQUENCE: 208

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Pro Gly Gly Gly Pro Gly Gly Gly Pro Gly Gly
        35                  40                  45
```

Gly Gly Pro Ala Glu Ser Lys Tyr Gly Pro Pro Cys Pro Cys Pro
            50                  55                  60

Ala Pro Glu Ala Ala Gly Gly Pro Ser Val Phe Leu Phe Pro Pro Lys
 65                  70                  75                  80

Pro Lys Asp Thr Leu Met Ile Ser Arg Thr Pro Glu Val Thr Cys Val
                     85                  90                  95

Val Val Asp Val Ser Gln Glu Asp Pro Glu Val Gln Phe Asn Trp Tyr
                100                 105                 110

Val Asp Gly Val Glu Val His Asn Ala Lys Thr Lys Pro Arg Glu Glu
            115                 120                 125

Gln Phe Asn Ser Thr Tyr Arg Val Val Ser Val Leu Thr Val Leu His
130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Ala Pro Ala Pro Ala Pro Ala Pro
        275                 280                 285

Ala Pro Ala Pro Cys Pro Glu Glu Pro
    290                 295

<210> SEQ ID NO 209
<211> LENGTH: 297
<212> TYPE: PRT
<213> ORGANISM: Artificial Sequence
<220> FEATURE:
<223> OTHER INFORMATION: GLP-1 fusion 97

<400> SEQUENCE: 209

His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Lys Gly Gly Gly Gly
                20                  25                  30

Gly Gly Gly His Gly Gly Gly His Gly Gly Gly His Gly Gly
            35                  40                  45

Gly Gly His Ala Glu Ser Lys Tyr Gly Pro Pro Cys Pro Cys Pro
            50                  55                  60

Ala Pro Glu Ala Ala Gly Gly Pro Ser Val Phe Leu Phe Pro Pro Lys
 65                  70                  75                  80

Pro Lys Asp Thr Leu Met Ile Ser Arg Thr Pro Glu Val Thr Cys Val
                     85                  90                  95

Val Val Asp Val Ser Gln Glu Asp Pro Glu Val Gln Phe Asn Trp Tyr
                100                 105                 110

Val Asp Gly Val Glu Val His Asn Ala Lys Thr Lys Pro Arg Glu Glu
         115                 120                 125

Gln Phe Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Ala Pro Ala Pro Ala Pro Ala Pro
        275                 280                 285

Ala Pro Ala Pro Cys Pro Glu Glu Pro
    290                 295

<210> SEQ ID NO 210
<211> LENGTH: 297
<212> TYPE: PRT
<213> ORGANISM: Artificial Sequence
<220> FEATURE:
<223> OTHER INFORMATION: GLP-1 fusion 98

<400> SEQUENCE: 210

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ala Gly Gly Gly Gly Ala Gly Gly Gly Ala Gly Gly
        35                  40                  45

Gly Gly Ala Ala Glu Ser Lys Tyr Gly Pro Pro Cys Pro Pro Cys Pro
    50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
         115                 120                 125

Gln Phe Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

```
Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
            195                 200                 205

Ser Asp Ile Ala Val Glu Trp Glu Ser Asn Gly Gln Pro Glu Asn Asn
            210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
                260                 265                 270

Lys Ser Leu Ser Leu Ser Leu Gly Ala Pro Ala Pro Ala Pro Ala Pro
            275                 280                 285

Ala Pro Ala Pro Cys Pro Glu Glu Pro
            290                 295

<210> SEQ ID NO 211
<211> LENGTH: 294
<212> TYPE: PRT
<213> ORGANISM: Artificial Sequence
<220> FEATURE:
<223> OTHER INFORMATION: GLP-1 fusion 99

<400> SEQUENCE: 211

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Pro
                20                  25                  30

Ala Pro Ala Pro Ala Pro Ala Pro Ala Pro Ala Pro Ala Pro Ala Pro
            35                  40                  45

Ala Pro Ala Pro Glu Ser Lys Tyr Gly Pro Pro Cys Pro Pro Cys Pro
50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
            115                 120                 125

Gln Phe Asn Ser Thr Tyr Arg Val Val Ser Val Leu Thr Val Leu His
            130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
            195                 200                 205

Ser Asp Ile Ala Val Glu Trp Glu Ser Asn Gly Gln Pro Glu Asn Asn
            210                 215                 220

Tyr Lys Thr Thr Pro Pro Val Leu Asp Ser Asp Gly Ser Phe Phe Leu
225                 230                 235                 240
```

```
Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Ala Pro Ala Pro Ala Pro Ala Pro
        275                 280                 285

Ala Pro Ala Pro Cys Pro
    290

<210> SEQ ID NO 212
<211> LENGTH: 297
<212> TYPE: PRT
<213> ORGANISM: Artificial Sequence
<220> FEATURE:
<223> OTHER INFORMATION: GLP-1 fusion 100

<400> SEQUENCE: 212

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Pro
            20                  25                  30

Ala Pro Ala Pro Ala Pro Ala Pro Ala Pro Ala Pro Ala Pro Ala Pro
        35                  40                  45

Ala Pro Ala Ala Glu Ser Lys Tyr Gly Pro Pro Cys Pro Pro Cys Pro
    50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
        115                 120                 125

Gln Phe Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Ala Pro Ala Pro Ala Pro Ala Pro
        275                 280                 285

Ala Pro Ala Pro Cys Pro Glu Glu Pro
    290                 295
```

<210> SEQ ID NO 213
<211> LENGTH: 297
<212> TYPE: PRT
<213> ORGANISM: Artificial Sequence
<220> FEATURE:
<223> OTHER INFORMATION: GLP-1 fusion 101

<400> SEQUENCE: 213

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Pro
            20                  25                  30

Ala Pro Ala Pro Ala Pro Ala Pro Ala Pro Ala Pro Ala Pro Ala Pro
        35                  40                  45

Ala Pro Ala Pro Glu Ser Lys Tyr Gly Pro Pro Cys Pro Pro Cys Pro
    50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
        115                 120                 125

Gln Phe Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Ala Pro Ala Pro Ala Pro Ala Pro
        275                 280                 285

Ala Pro Ala Pro Cys Pro Glu Glu Pro
    290                 295

<210> SEQ ID NO 214
<211> LENGTH: 294
<212> TYPE: PRT
<213> ORGANISM: Artificial Sequence
<220> FEATURE:
<223> OTHER INFORMATION: GLP-1 fusion 102

<400> SEQUENCE: 214

His Gly Glu Gly Thr Phe Thr Ser Asp Val Ser Ser Tyr Leu Glu Glu

```
                1               5                  10                 15
              Gln Ala Ala Lys Glu Phe Ile Ala Trp Leu Val Lys Gly Gly Gly Gly
                              20                  25                 30

Gly Gly Gly Ala Gly Gly Gly Ala Gly Gly Gly Ala Gly Gly
                              35                  40                 45

Gly Gly Ala Glu Ser Lys Tyr Gly Pro Pro Cys Pro Cys Pro Ala
                  50                  55                  60

Pro Glu Ala Ala Gly Gly Pro Ser Val Phe Leu Phe Pro Pro Lys Pro
              65                  70                  75                  80

Lys Asp Thr Leu Met Ile Ser Arg Thr Pro Glu Val Thr Cys Val Val
                              85                  90                  95

Val Asp Val Ser Gln Glu Asp Pro Glu Val Gln Phe Asn Trp Tyr Val
                              100                 105                110

Asp Gly Val Glu Val His Asn Ala Lys Thr Lys Pro Arg Glu Glu Gln
                              115                 120                125

Phe Asn Ser Thr Tyr Arg Val Val Ser Val Leu Thr Val Leu His Gln
                              130                 135                140

Asp Trp Leu Asn Gly Lys Glu Tyr Lys Cys Lys Val Ser Asn Lys Gly
              145                 150                 155                 160

Leu Pro Ser Ser Ile Glu Lys Thr Ile Ser Lys Ala Lys Gly Gln Pro
                              165                 170                 175

Arg Glu Pro Gln Val Tyr Thr Leu Pro Pro Ser Gln Glu Glu Met Thr
                              180                 185                 190

Lys Asn Gln Val Ser Leu Thr Cys Leu Val Lys Gly Phe Tyr Pro Ser
                              195                 200                 205

Asp Ile Ala Val Glu Trp Glu Ser Asn Gly Gln Pro Glu Asn Asn Tyr
                              210                 215                 220

Lys Thr Thr Pro Pro Val Leu Asp Ser Asp Gly Ser Phe Phe Leu Tyr
              225                 230                 235                 240

Ser Arg Leu Thr Val Asp Lys Ser Arg Trp Gln Glu Gly Asn Val Phe
                              245                 250                 255

Ser Cys Ser Val Met His Glu Ala Leu His Asn His Tyr Thr Gln Lys
                              260                 265                 270

Ser Leu Ser Leu Ser Leu Gly Gly Gly Gly Ala Pro Ala Pro Ala Pro
                              275                 280                 285

Glu Glu Glu Pro Cys Ala
                  290

<210> SEQ ID NO 215
<211> LENGTH: 289
<212> TYPE: PRT
<213> ORGANISM: Artificial Sequence
<220> FEATURE:
<223> OTHER INFORMATION: GLP-1 fusion 103

<400> SEQUENCE: 215

His Gly Glu Gly Thr Phe Thr Ser Asp Val Ser Ser Tyr Leu Glu Glu
              1                   5                   10                  15

Gln Ala Ala Lys Glu Phe Ile Ala Trp Leu Val Lys Gly Gly Gly Gly
                              20                  25                  30

Gly Gly Gly Ala Gly Gly Gly Ala Gly Gly Gly Ala Glu Ser
                              35                  40                  45

Lys Tyr Gly Pro Pro Cys Pro Pro Cys Pro Ala Pro Glu Ala Ala Gly
                  50                  55                  60

Gly Pro Ser Val Phe Leu Phe Pro Pro Lys Pro Lys Asp Thr Leu Met
```

```
            65                  70                  75                  80
Ile Ser Arg Thr Pro Glu Val Thr Cys Val Val Asp Val Ser Gln
                    85                  90                  95

Glu Asp Pro Glu Val Gln Phe Asn Trp Tyr Val Asp Gly Val Glu Val
            100                 105                 110

His Asn Ala Lys Thr Lys Pro Arg Glu Glu Gln Phe Asn Ser Thr Tyr
            115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                    165                 170                 175

Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
            195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Arg Leu Thr Val
225                 230                 235                 240

Asp Lys Ser Arg Trp Gln Glu Gly Asn Val Phe Ser Cys Ser Val Met
                    245                 250                 255

His Glu Ala Leu His Asn His Tyr Thr Gln Lys Ser Leu Ser Leu Ser
            260                 265                 270

Leu Gly Gly Gly Gly Ala Pro Ala Pro Ala Pro Glu Glu Pro Cys
            275                 280                 285

Ala

<210> SEQ ID NO 216
<211> LENGTH: 288
<212> TYPE: PRT
<213> ORGANISM: Artificial Sequence
<220> FEATURE:
<223> OTHER INFORMATION: GLP-1 fusion 104

<400> SEQUENCE: 216

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
            20                  25                  30

Ser Gly Gly Gly Gly Ser Gly Gly Gly Ser Ala Glu Ser Lys Tyr
        35                  40                  45

Gly Pro Pro Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                    85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140
```

```
Tyr Lys Cys Lys Val Ser Asn Lys Gly Leu Pro Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
                195                 200                 205

Ser Asn Gly Gln Pro Glu Asn Asn Tyr Lys Thr Thr Pro Pro Val Leu
210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
                260                 265                 270

Lys Gly Gly Gly Ala Pro Ala Pro Ala Pro Glu Glu Pro Cys Ala
                275                 280                 285
```

<210> SEQ ID NO 217
<211> LENGTH: 287
<212> TYPE: PRT
<213> ORGANISM: Artificial Sequence
<220> FEATURE:
<223> OTHER INFORMATION: GLP-1 fusion 105

<400> SEQUENCE: 217

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
                20                  25                  30

Ser Gly Gly Gly Gly Ser Gly Gly Gly Gly Ser Ala Glu Ser Lys Tyr
            35                  40                  45

Gly Pro Pro Cys Pro Pro Cys Pro Ala Pro Glu Ala Ala Gly Gly Pro
50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
130                 135                 140

Tyr Lys Cys Lys Val Ser Asn Lys Gly Leu Pro Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
                195                 200                 205

Ser Asn Gly Gln Pro Glu Asn Asn Tyr Lys Thr Thr Pro Pro Val Leu
210                 215                 220
```

```
Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
            245                 250                 255

Ala Leu His Asn His Tyr Thr Gln Lys Ser Leu Ser Leu Ser Leu Gly
            260                 265                 270

Gly Gly Gly Ala Pro Ala Pro Ala Pro Glu Glu Glu Pro Cys Ala
        275                 280                 285

<210> SEQ ID NO 218
<211> LENGTH: 289
<212> TYPE: PRT
<213> ORGANISM: Artificial Sequence
<220> FEATURE:
<223> OTHER INFORMATION: GLP-1 fusion 106

<400> SEQUENCE: 218

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
            20                  25                  30

Ser Gly Gly Gly Gly Ser Gly Gly Gly Ser Ala Glu Ser Lys Tyr
        35                  40                  45

Gly Pro Pro Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Gly Gly Gly Gly Gly Gly Gly Gly Gly Gly Gly Gly Gly Cys
        275                 280                 285

Ala
```

```
<210> SEQ ID NO 219
<211> LENGTH: 289
<212> TYPE: PRT
<213> ORGANISM: Artificial Sequence
<220> FEATURE:
<223> OTHER INFORMATION: GLP-1 fusion 107

<400> SEQUENCE: 219

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
            20                  25                  30

Ser Gly Gly Gly Ser Gly Gly Gly Ser Ala Glu Ser Lys Tyr
        35                  40                  45

Gly Pro Pro Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Gly Gly Gly Gly Ala Gly Gly Gly Ala Gly Gly Gly Ala Cys
        275                 280                 285

Ala

<210> SEQ ID NO 220
<211> LENGTH: 286
<212> TYPE: PRT
<213> ORGANISM: Artificial Sequence
<220> FEATURE:
<223> OTHER INFORMATION: GLP-1 fusion 108

<400> SEQUENCE: 220

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Gly
                20                  25                  30

Ser Gly Gly Gly Gly Ser Gly Gly Gly Ser Ala Glu Ser Lys Tyr
            35                  40                  45

Gly Pro Pro Cys Pro Pro Cys Pro Ala Pro Glu Ala Ala Gly Gly Pro
        50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Ala Pro Ala Pro Ala Pro Ala Pro Ala Pro Ala Pro Cys Pro
        275                 280                 285

<210> SEQ ID NO 221
<211> LENGTH: 289
<212> TYPE: PRT
<213> ORGANISM: Artificial Sequence
<220> FEATURE:
<223> OTHER INFORMATION: GLP-1 fusion 109

<400> SEQUENCE: 221

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
                20                  25                  30

Ser Gly Gly Gly Gly Ser Gly Gly Gly Ser Ala Glu Ser Lys Tyr
            35                  40                  45

Gly Pro Pro Cys Pro Pro Cys Pro Ala Pro Glu Ala Ala Gly Gly Pro
        50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95
```

```
Pro Glu Val Gln Phe Asn Trp Tyr Val Asp Gly Val Glu Val His Asn
                100                 105                 110

Ala Lys Thr Lys Pro Arg Glu Glu Gln Phe Asn Ser Thr Tyr Arg Val
            115                 120                 125

Val Ser Val Leu Thr Val Leu His Gln Asp Trp Leu Asn Gly Lys Glu
        130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Ala Pro Ala Pro Ala Pro Ala Pro Ala Pro Ala Pro Cys Pro Glu Glu
        275                 280                 285

Pro

<210> SEQ ID NO 222
<211> LENGTH: 288
<212> TYPE: PRT
<213> ORGANISM: Artificial Sequence
<220> FEATURE:
<223> OTHER INFORMATION: GLP-1 fusion 110

<400> SEQUENCE: 222

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
            20                  25                  30

Ala Gly Gly Gly Gly Ala Gly Gly Gly Ala Ala Glu Ser Lys Tyr Gly
        35                  40                  45

Pro Pro Cys Pro Pro Cys Pro Ala Pro Glu Ala Ala Gly Gly Pro Ser
50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser Gln Glu Asp Pro
                85                  90                  95

Glu Val Gln Phe Asn Trp Tyr Val Asp Gly Val Glu Val His Asn Ala
            100                 105                 110

Lys Thr Lys Pro Arg Glu Glu Gln Phe Asn Ser Thr Tyr Arg Val Val
        115                 120                 125

Ser Val Leu Thr Val Leu His Gln Asp Trp Leu Asn Gly Lys Glu Tyr
130                 135                 140

Lys Cys Lys Val Ser Asn Lys Gly Leu Pro Ser Ser Ile Glu Lys Thr
145                 150                 155                 160

Ile Ser Lys Ala Lys Gly Gln Pro Arg Glu Pro Gln Val Tyr Thr
                165                 170                 175
```

```
                    165                 170                 175
Leu Pro Pro Ser Gln Glu Glu Met Thr Lys Asn Gln Val Ser Leu Thr
                180                 185                 190

Cys Leu Val Lys Gly Phe Tyr Pro Ser Asp Ile Ala Val Glu Trp Glu
            195                 200                 205

Ser Asn Gly Gln Pro Glu Asn Asn Tyr Lys Thr Thr Pro Pro Val Leu
        210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Lys Gly Gly Gly Ala Pro Ala Pro Ala Pro Glu Glu Pro Cys Ala
        275                 280                 285

<210> SEQ ID NO 223
<211> LENGTH: 289
<212> TYPE: PRT
<213> ORGANISM: Artificial Sequence
<220> FEATURE:
<223> OTHER INFORMATION: GLP-1 fusion 111

<400> SEQUENCE: 223

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
                20                  25                  30

Ala Gly Gly Gly Gly Ala Gly Gly Gly Ala Ala Glu Ser Lys Tyr
            35                  40                  45

Gly Pro Pro Cys Pro Pro Cys Pro Ala Pro Glu Ala Ala Gly Gly Pro
        50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
```

```
                        245                 250                 255
Ala Leu His Asn His Tyr Thr Gln Lys Ser Leu Ser Leu Gly
            260                 265                 270

Gly Gly Gly Gly Gly Gly Gly Gly Gly Gly Gly Gly Gly Cys
            275                 280                 285

Ala

<210> SEQ ID NO 224
<211> LENGTH: 292
<212> TYPE: PRT
<213> ORGANISM: Artificial Sequence
<220> FEATURE:
<223> OTHER INFORMATION: GLP-1 fusion 112

<400> SEQUENCE: 224

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ala Gly Gly Gly Ala Gly Gly Gly Ala Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Gly Gly Gly Gly Gly Gly Gly Gly Gly Gly Gly Gly Gly
        275                 280                 285

Gly Gly Cys Ala
    290

<210> SEQ ID NO 225
```

```
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 1 chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 225

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 226
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a GLP-1 fusion 1 chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 226

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 227
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
```

```
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a GLP-1 fusion 1 chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 227

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 228
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 1 chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 228

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 229
<211> LENGTH: 35
<212> TYPE: PRT
<213> ORGANISM: Artificial Sequence
<220> FEATURE:
```

```
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 24 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 229

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 230
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Ala
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a GLP-1 fusion 24 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 230

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 231
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Ala
```

```
<222> LOCATION: (1)..(1)
<223> OTHER INFORMATION: Ala, wherein the alanine is a beta-alanine
      with a cyclic modification
<220> FEATURE:
<221> NAME/KEY: Lys
<222> LOCATION: (10)..(10)
<223> OTHER INFORMATION: Lys with a GLP-1 fusion 24 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 231

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 232
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 24 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 232

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 233
<211> LENGTH: 35
<212> TYPE: PRT
<213> ORGANISM: Artificial Sequence
<220> FEATURE:
```

```
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 70 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 233

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 234
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 11 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 234

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 235
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
```

```
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 28 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 235

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 236
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 67 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 236

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 237
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 27 chemical
``` modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 237

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 238
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 23 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 238

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 239
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 54 chemical
      modification
<220> FEATURE:
<221> NAME/KEY: Cys
<222> LOCATION: (29)..(29)
<223> OTHER INFORMATION: Cys with a chemical modification

```
<220> FEATURE:
<221> NAME/KEY: Arg
<222> LOCATION: (34)..(34)
<223> OTHER INFORMATION: Arg with a N-Me chemical modification

<400> SEQUENCE: 239

Gly Ile Ser Pro Glu Ala Pro Gly Glu Lys Ala Ser Pro Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 240
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 63 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 240

Gly Ile Ser Pro Glu Ala Pro Gly Glu Lys Ala Ser Pro Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 241
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 64 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification
```

-continued

<400> SEQUENCE: 241

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 242
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 22 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 242

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 243
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 49 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 243

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 244
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Ala
<222> LOCATION: (1)..(1)
<223> OTHER INFORMATION: Ala, wherein the ala is a beta-alanine with a
      cyclic modification
<220> FEATURE:
<221> NAME/KEY: Lys
<222> LOCATION: (10)..(10)
<223> OTHER INFORMATION: Lys with a PEG24 GLP-1 fusion 34 chemical
      modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 244

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 245
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 35 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 245

Gly Ile Ser Pro Glu Ala Pro Gly Glu Lys Ala Ser Pro Glu Glu Leu
1               5                   10                  15

-continued

```
Asn Arg Tyr Tyr Ala Ser Leu Arg His Tyr Leu Asn Cys Val Thr Arg
            20                  25                  30

Gln Arg Tyr
        35

<210> SEQ ID NO 246
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 65 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 246

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 247
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 45 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 247

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
```

```
<210> SEQ ID NO 248
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 40 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 248

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 249
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 40 chemical
      modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 249

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 250
<211> LENGTH: 35
```

```
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 40 chemical
      modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical
      modification
<220> FEATURE:
<221> NAME/KEY: Tyr
<222> LOCATION: (35)..(35)
<223> OTHER INFORMATION: Tyr with a psi-(R35, Y36) chemical
      modification

<400> SEQUENCE: 250

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 251
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 19 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 251

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 252
```

```
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 8 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 252

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 253
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Xaa
<222> LOCATION: (1)..(1)
<223> OTHER INFORMATION: Xaa is a gamma amino-butyric acid with a
      cyclic modification
<220> FEATURE:
<221> NAME/KEY: Lys
<222> LOCATION: (10)..(10)
<223> OTHER INFORMATION: Lys with a GLP-1 fusion 34 chemical
      modification
<220> FEATURE:
<221> NAME/KEY: Cys
<222> LOCATION: (29)..(29)
<223> OTHER INFORMATION: Cys, wherein cys is a homocysteine with a
      cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 253

Xaa Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 254
<211> LENGTH: 35
<212> TYPE: PRT
<213> ORGANISM: Artificial Sequence
```

```
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 42 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 254

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 255
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 59 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 255

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 256
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
```

```
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 60 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 256

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 257
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 61 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 257

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 258
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Ala
<222> LOCATION: (1)..(1)
<223> OTHER INFORMATION: Ala, wherein the ala is a beta-alanine with a
      cyclic modification
<220> FEATURE:
<221> NAME/KEY: Lys
```

```
<222> LOCATION: (10)..(10)
<223> OTHER INFORMATION: Lys with a GLP-1 fusion 63 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 258

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 259
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Ala
<222> LOCATION: (1)..(1)
<223> OTHER INFORMATION: Ala, wherein the ala is a beta-alanine with a
      cyclic modification
<220> FEATURE:
<221> NAME/KEY: Lys
<222> LOCATION: (10)..(10)
<223> OTHER INFORMATION: Lys with a GLP-1 fusion 63 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 259

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 260
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Ala
<222> LOCATION: (1)..(1)
<223> OTHER INFORMATION: Ala, wherein the ala is a beta-alanine with a
      cyclic modification
<220> FEATURE:
```

```
<221> NAME/KEY: Lys
<222> LOCATION: (10)..(10)
<223> OTHER INFORMATION: Lys with a GLP-1 fusion 40 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 260

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 261
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 40 chemical
      modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 261

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 262
<211> LENGTH: 35
<212> TYPE: PRT
<213> ORGANISM: Artificial Sequence
<220> FEATURE:
<223> OTHER INFORMATION: GLP-1 fusion coupled cyclic PYY peptide
      conjugate
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a GLP-1 fusion 34 chemical
      modification
<220> FEATURE:
```

```
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 262

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 263
<211> LENGTH: 20
<212> TYPE: PRT
<213> ORGANISM: Artificial Sequence
<220> FEATURE:
<223> OTHER INFORMATION: HGE for GLPD30

<400> SEQUENCE: 263

His Gly Glu Gly Thr Phe Thr Ser Asp Val Ser Ser Tyr Leu Glu Glu
1               5                   10                  15

Gln Ala Ala Lys
            20

<210> SEQ ID NO 264
<211> LENGTH: 12
<212> TYPE: PRT
<213> ORGANISM: Artificial Sequence
<220> FEATURE:
<223> OTHER INFORMATION: HGE for GLPD31

<400> SEQUENCE: 264

His Gly Glu Gly Thr Phe Thr Ser Asp Leu Ser Lys
1               5                   10

<210> SEQ ID NO 265
<211> LENGTH: 16
<212> TYPE: PRT
<213> ORGANISM: Artificial Sequence
<220> FEATURE:
<223> OTHER INFORMATION: VVS peptide

<400> SEQUENCE: 265

Val Val Ser Val Leu Thr Val Leu His Gln Asp Trp Leu Asn Gly Lys
1               5                   10                  15

<210> SEQ ID NO 266
<211> LENGTH: 6
<212> TYPE: PRT
<213> ORGANISM: Artificial Sequence
<220> FEATURE:
<223> OTHER INFORMATION: YYA peptide

<400> SEQUENCE: 266

Tyr Tyr Ala Ser Leu Arg
1               5

<210> SEQ ID NO 267
<211> LENGTH: 287
<212> TYPE: PRT
<213> ORGANISM: Artificial Sequence
```

<220> FEATURE:
<223> OTHER INFORMATION: GLP-1 fusion 113

<400> SEQUENCE: 267

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ala Gly Gly Gly Ala Gly Gly Gly Ala Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Gly Gly Gly Gly Ser Gly Gly Gly Ser Cys Ala
        275                 280                 285

<210> SEQ ID NO 268
<211> LENGTH: 284
<212> TYPE: PRT
<213> ORGANISM: Artificial Sequence
<220> FEATURE:
<223> OTHER INFORMATION: GLP-1 fusion 114

<400> SEQUENCE: 268

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
            20                  25                  30

Ala Gly Gly Gly Ala Gly Gly Gly Ala Ala Glu Ser Lys Tyr
        35                  40                  45

Gly Pro Pro Cys Pro Pro Cys Pro Ala Pro Glu Ala Ala Gly Gly Pro

```
                 50                  55                  60
Ser Val Phe Leu Phe Pro Pro Lys Pro Lys Asp Thr Leu Met Ile Ser
 65                  70                  75                  80

Arg Thr Pro Glu Val Thr Cys Val Val Val Asp Val Ser Gln Glu Asp
                 85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Gly Gly Gly Gly Ser Gly Gly Gly Gly Ser Cys Ala
        275                 280

<210> SEQ ID NO 269
<211> LENGTH: 293
<212> TYPE: PRT
<213> ORGANISM: Artificial Sequence
<220> FEATURE:
<223> OTHER INFORMATION: GLP-1 fusion 115

<400> SEQUENCE: 269

His Gly Glu Gly Thr Phe Thr Ser Asp Val Ser Ser Tyr Leu Glu Glu
  1               5                  10                  15

Gln Ala Ala Lys Glu Phe Ile Ala Trp Leu Val Lys Gly Gly Gly Gly
                 20                  25                  30

Gly Gly Gly Ala Gly Gly Gly Ala Gly Gly Gly Ala Ala Glu
             35                  40                  45

Ser Lys Tyr Gly Pro Pro Cys Pro Pro Cys Pro Ala Pro Glu Ala Ala
 50                  55                  60

Gly Gly Pro Ser Val Phe Leu Phe Pro Pro Lys Pro Lys Asp Thr Leu
 65                  70                  75                  80

Met Ile Ser Arg Thr Pro Glu Val Thr Cys Val Val Val Asp Val Ser
                 85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
```

-continued

```
                    130                 135                 140
Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                    165                 170                 175

Val Tyr Thr Leu Pro Pro Ser Gln Glu Glu Met Thr Lys Asn Gln Val
                180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly Gly Gly Gly Ser Gly Gly Gly Ser Gly Gly
            275                 280                 285

Gly Gly Ser Cys Ala
        290
```

<210> SEQ ID NO 270
<211> LENGTH: 290
<212> TYPE: PRT
<213> ORGANISM: Artificial Sequence
<220> FEATURE:
<223> OTHER INFORMATION: GLP-1 fusion 116

<400> SEQUENCE: 270

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
                20                  25                  30

Ala Gly Gly Gly Gly Ala Gly Gly Gly Ala Ala Glu Ser Lys Tyr
            35                  40                  45

Gly Pro Pro Cys Pro Pro Cys Pro Ala Pro Glu Ala Ala Gly Gly Pro
        50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
    130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
```

```
              195                 200                 205
Ser Asn Gly Gln Pro Glu Asn Asn Tyr Lys Thr Thr Pro Val Leu
210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
                260                 265                 270

Gly Gly Gly Gly Ser Gly Gly Gly Ser Gly Gly Gly Gly Ser
            275                 280                 285

Cys Ala
    290

<210> SEQ ID NO 271
<211> LENGTH: 284
<212> TYPE: PRT
<213> ORGANISM: Artificial Sequence
<220> FEATURE:
<223> OTHER INFORMATION: GLP-1 fusion 117

<400> SEQUENCE: 271

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
                20                  25                  30

Ser Gly Gly Gly Gly Ser Gly Gly Gly Ser Ala Glu Ser Lys Tyr
            35                  40                  45

Gly Pro Pro Cys Pro Pro Cys Pro Ala Pro Glu Ala Ala Gly Gly Pro
50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
                100                 105                 110

Ala Lys Thr Lys Pro Arg Glu Glu Gln Phe Asn Ser Thr Tyr Arg Val
            115                 120                 125

Val Ser Val Leu Thr Val Leu His Gln Asp Trp Leu Asn Gly Lys Glu
130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
                180                 185                 190

Cys Leu Val Lys Gly Phe Tyr Pro Ser Asp Ile Ala Val Glu Trp Glu
            195                 200                 205

Ser Asn Gly Gln Pro Glu Asn Asn Tyr Lys Thr Thr Pro Val Leu
210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
```

Gly Gly Gly Gly Ser Gly Gly Gly Gly Ser Cys Ala
        275                 280

<210> SEQ ID NO 272
<211> LENGTH: 295
<212> TYPE: PRT
<213> ORGANISM: Artificial Sequence
<220> FEATURE:
<223> OTHER INFORMATION: GLP-1 fusion 118

<400> SEQUENCE: 272

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Ser Gly Gly Gly Gly
        35                  40                  45

Ser Gly Gly Gly Ser Ala Glu Ser Lys Tyr Gly Pro Pro Cys Pro
    50                  55                  60

Pro Cys Pro Ala Pro Glu Ala Ala Gly Gly Pro Ser Val Phe Leu Phe
65                  70                  75                  80

Pro Pro Lys Pro Lys Asp Thr Leu Met Ile Ser Arg Thr Pro Glu Val
            85                  90                  95

Thr Cys Val Val Val Asp Val Ser Gln Glu Asp Pro Glu Val Gln Phe
        100                 105                 110

Asn Trp Tyr Val Asp Gly Val Glu Val His Asn Ala Lys Thr Lys Pro
    115                 120                 125

Arg Glu Glu Gln Phe Asn Ser Thr Tyr Arg Val Val Ser Val Leu Thr
130                 135                 140

Val Leu His Gln Asp Trp Leu Asn Gly Lys Glu Tyr Lys Cys Lys Val
145                 150                 155                 160

Ser Asn Lys Gly Leu Pro Ser Ser Ile Glu Lys Thr Ile Ser Lys Ala
            165                 170                 175

Lys Gly Gln Pro Arg Glu Pro Gln Val Tyr Thr Leu Pro Pro Ser Gln
        180                 185                 190

Glu Glu Met Thr Lys Asn Gln Val Ser Leu Thr Cys Leu Val Lys Gly
    195                 200                 205

Phe Tyr Pro Ser Asp Ile Ala Val Glu Trp Glu Ser Asn Gly Gln Pro
    210                 215                 220

Glu Asn Asn Tyr Lys Thr Thr Pro Pro Val Leu Asp Ser Asp Gly Ser
225                 230                 235                 240

Phe Phe Leu Tyr Ser Arg Leu Thr Val Asp Lys Ser Arg Trp Gln Glu
            245                 250                 255

Gly Asn Val Phe Ser Cys Ser Val Met His Glu Ala Leu His Asn His
        260                 265                 270

Tyr Thr Gln Lys Ser Leu Ser Leu Ser Leu Gly Gly Gly Gly Ser
    275                 280                 285

Gly Gly Gly Gly Ser Cys Ala
    290                 295

<210> SEQ ID NO 273
<211> LENGTH: 289
<212> TYPE: PRT
<213> ORGANISM: Artificial Sequence
<220> FEATURE:
<223> OTHER INFORMATION: GLP-1 fusion 119

<400> SEQUENCE: 273

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
            20                  25                  30

Ser Gly Gly Gly Gly Ser Gly Gly Gly Ser Ala Glu Ser Lys Tyr
        35                  40                  45

Gly Pro Pro Cys Pro Pro Cys Pro Ala Pro Glu Ala Ala Gly Gly Pro
    50                  55                  60

Ser Val Phe Leu Phe Pro Pro Lys Pro Lys Asp Thr Leu Met Ile Ser
65                  70                  75                  80

Arg Thr Pro Glu Val Thr Cys Val Val Val Asp Val Ser Gln Glu Asp
                85                  90                  95

Pro Glu Val Gln Phe Asn Trp Tyr Val Asp Gly Val Glu Val His Asn
            100                 105                 110

Ala Lys Thr Lys Pro Arg Glu Glu Gln Phe Asn Ser Thr Tyr Arg Val
        115                 120                 125

Val Ser Val Leu Thr Val Leu His Gln Asp Trp Leu Asn Gly Lys Glu
130                 135                 140

Tyr Lys Cys Lys Val Ser Asn Lys Gly Leu Pro Ser Ser Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Gln Glu Glu Met Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
    210                 215                 220

Asp Ser Asp Gly Ser Phe Phe Leu Tyr Ser Arg Leu Thr Val Asp Lys
225                 230                 235                 240

Ser Arg Trp Gln Glu Gly Asn Val Phe Ser Cys Ser Val Met His Glu
                245                 250                 255

Ala Leu His Asn His Tyr Thr Gln Lys Ser Leu Ser Leu Ser Leu Gly
            260                 265                 270

Gly Gly Gly Gly Ser Gly Gly Gly Ser Gly Gly Gly Ser Cys
        275                 280                 285

Ala
```

<210> SEQ ID NO 274
<211> LENGTH: 300
<212> TYPE: PRT
<213> ORGANISM: Artificial Sequence
<220> FEATURE:
<223> OTHER INFORMATION: GLP-1 fusion 120

<400> SEQUENCE: 274

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Ser Gly Gly Gly
        35                  40                  45

Ser Gly Gly Gly Gly Ser Ala Glu Ser Lys Tyr Gly Pro Pro Cys Pro
```

```
                50                  55                  60

Pro Cys Pro Ala Pro Glu Ala Ala Gly Gly Pro Ser Val Phe Leu Phe
65                  70                  75                  80

Pro Pro Lys Pro Lys Asp Thr Leu Met Ile Ser Arg Thr Pro Glu Val
                85                  90                  95

Thr Cys Val Val Val Asp Val Ser Gln Glu Asp Pro Glu Val Gln Phe
                100                 105                 110

Asn Trp Tyr Val Asp Gly Val Glu Val His Asn Ala Lys Thr Lys Pro
                115                 120                 125

Arg Glu Glu Gln Phe Asn Ser Thr Tyr Arg Val Val Ser Val Leu Thr
                130                 135                 140

Val Leu His Gln Asp Trp Leu Asn Gly Lys Glu Tyr Lys Cys Lys Val
145                 150                 155                 160

Ser Asn Lys Gly Leu Pro Ser Ser Ile Glu Lys Thr Ile Ser Lys Ala
                165                 170                 175

Lys Gly Gln Pro Arg Glu Pro Gln Val Tyr Thr Leu Pro Pro Ser Gln
                180                 185                 190

Glu Glu Met Thr Lys Asn Gln Val Ser Leu Thr Cys Leu Val Lys Gly
                195                 200                 205

Phe Tyr Pro Ser Asp Ile Ala Val Glu Trp Glu Ser Asn Gly Gln Pro
                210                 215                 220

Glu Asn Asn Tyr Lys Thr Thr Pro Pro Val Leu Asp Ser Asp Gly Ser
225                 230                 235                 240

Phe Phe Leu Tyr Ser Arg Leu Thr Val Asp Lys Ser Arg Trp Gln Glu
                245                 250                 255

Gly Asn Val Phe Ser Cys Ser Val Met His Glu Ala Leu His Asn His
                260                 265                 270

Tyr Thr Gln Lys Ser Leu Ser Leu Ser Leu Gly Gly Gly Gly Gly Ser
                275                 280                 285

Gly Gly Gly Gly Ser Gly Gly Gly Ser Cys Ala
                290                 295                 300
```